(12) United States Patent
Wang et al.

(10) Patent No.: US 8,202,902 B2
(45) Date of Patent: Jun. 19, 2012

(54) BIVALENT SMAC MIMETICS AND THE USES THEREOF

(75) Inventors: Shaomeng Wang, Saline, MI (US); Haiying Sun, Ann Arbor, MI (US); Dongguang Qin, Ann Arbor, MI (US); Zaneta Nikolovska-Coleska, Ann Arbor, MI (US); Jianfeng Lu, Ann Arbor, MI (US); Su Qiu, Ann Arbor, MI (US); Yuefeng Peng, Ann Arbor, MI (US); Qian Cai, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 735 days.

(21) Appl. No.: 12/270,374

(22) Filed: Nov. 13, 2008

(65) Prior Publication Data

US 2009/0123480 A1   May 14, 2009

Related U.S. Application Data

(63) Continuation-in-part of application No. 11/800,220, filed on May 4, 2007, now Pat. No. 7,960,372.

(60) Provisional application No. 60/923,415, filed on Apr. 13, 2007, provisional application No. 60/798,018, filed on May 5, 2006.

(51) Int. Cl.
*A01N 47/10* (2006.01)
*A61K 31/27* (2006.01)
*C07D 225/00* (2006.01)

(52) U.S. Cl. ........................................ 514/483; 540/483
(58) Field of Classification Search .................. 540/483; 514/183
See application file for complete search history.

(56) References Cited

U.S. PATENT DOCUMENTS

| | | | |
|---|---|---|---|
| 4,415,496 A | 11/1983 | Harris | |
| 6,992,063 B2 | 1/2006 | Shi | |
| 7,309,792 B2 | 12/2007 | Harran | |
| 7,345,081 B2 | 3/2008 | Cohen | |
| 2008/0020986 A1 | 1/2008 | Condon | |
| 2008/0021066 A1 | 1/2008 | Condon | |

FOREIGN PATENT DOCUMENTS

| | | |
|---|---|---|
| EP | 0 629 627 | 12/1994 |
| WO | 01/85196 | 11/2001 |
| WO | 2005/069894 | 8/2005 |
| WO | 2006/010118 | 1/2006 |

OTHER PUBLICATIONS

Yang, Liling8, et al., "Predominant Suppression of Apoptosome by Inhibitor of Apoptosis Protein in Non-Small Cell Lung Cancer H460 Cells: Therapeutic Effect of a Novel Polyarginine-conjugated Smac Peptide," Cancer Research 63, pp. 831-837, Feb. 15, 2003.

Yeh, et al., "Requirement for Casper (c-FLIP) in Regulation of Death Receptor-Induced Apoptosis and Embryonic Development," Immunity, vol. 12, pp. 633-642, Jun. 2000.
Zhang, et al., "Steroselective Bromination—Suzuki Cross-Coupling of Dehydroamino Acids to Form Novel Reverse-Turn Peptidomimetics . . . ," Organic Letters, vol. 4, No. 23, (2002), pp. 4029-4032.
Zhang, Xu Dong, et al., "Relation of TNF-related Apoptosis-inducing Ligand (TRAIL) Reeptor and FLICE-inhibitory Protein Expression to TRAIL-induced Apoptosis of Melanoma," Cancer Research 59, pp. 274u7-2753, Jun. 1, 1999.
Adams, et al., "The Bcl-2 Protein Family: Arbiters of Cell Survival," Science, Aug. 28, 1998, vol. 281, pp. 1322-1326.
Amberger, et al., "Spreading and Migration of Human Glioma and Rat C6 Cells on Central Nervous System Myelin in Vitro is Correlated with Tumor Malignancy and Involves a Metalloproteolytic Activity," Cancer Research 58, pp. 149-158, Jan. 1, 1998.
Arnt, et al., "Synthetic Smac/DIABO Peptides Enhance the Effects of Chemotherapeutic Agents by Binding XIAP and cIAP1 in Situ," The Journal of Biological Chemistry, vol. 277, No. 46, Nov. 15, 2002, pp. 44236-44243.
Ashkenazi et al., "Death Receptors: Signaling and Modulation," Science, vol. 281, Aug. 28, 1998, pp. 1305-1308.
Asselin, et al., "XIAP Regulates Akt Activity and Caspase-3-dependent Cleavage during Cisplatin-induced Apoptosis in Human Ovarian Epithelial Cancer Cells," Cancer Research 61, pp. 1862-1868, Mar. 1, 2001.
Bin, et al., "The short splice form of Casper/c-FLIP is a major cellular inhiitor of TRAIL-induced apoptosis," FEBS Letters 510 (2002) pp. 37-40.
Budihardjo et al., "Biochemical Pathways of Caspase Activation During Apoptosis," Annu. Rev. Cell. Dev. Biol. 1999 15:269-90.
Chai, et al., "Structural Basis of Caspase-7 Inhibition by XIAP," Cell, vol. 104, pp. 769-780, Mar. 9, 2001.
Cheng, et al., Role of X-linked inhibitor of apoptosis protein in chemoresistance in ovarian cancer: possible involvement of the phosphoinositide-3 kinase/Akt pathway, Drug Resistance Updates, 5:131-146 (2002).
Deveraux, et al., "Cleavage of human inhibitor of apoptosis protein XIAP results in fragments with distinct specificities for caspases," The EMBO Journal, vol. 18, No. 19, pp. 5242-5251 (1999).
Deveraux, et al., "IAP family proteins—suppressors of apoptosis," Genes & Development 13:239-252 (1999).
Deveraux, et al., "X-linked IAP is a direct inhibitor of cell-death proteases" Nature, 388:300 (1997).
Du, et al., "Smac, a Mitochondrial Protein that Promotes Cytochrome c-dependent Caspase Activation by Eliminating IAP Inhibition," Cell, vol. 102, pp. 33-42, Jul. 7, 2000.
Duggan, et al., "Synthesis of 5/7-, 5/8- and 5/9-bicyclic lactam templates as constraints for external-turns," Biomolecular Chemistry, 3:2287 (2005).
Ekert, et al., "DIABLO Promotes Apoptosis by Removing MIHA/XIAP from Processed Caspase 9," The Journal of Cell Biology, vol. 152 (2001), pp. 483-490.
French, et al., The TRAIL to selective tumor death, Nature Medicine, vol. 5, No. 2, Feb. 1999, pp. 146-147.

(Continued)

*Primary Examiner* — Paul V. Ward
(74) *Attorney, Agent, or Firm* — Casimir Jones SC

(57) ABSTRACT

The invention relates to bivalent mimetics of Smac which function as inhibitors of Inhibitor of Apoptosis Proteins. The invention also relates to the use of these mimetics for inducing apoptotic cell death and for sensitizing cells to inducers of apoptosis.

4 Claims, 52 Drawing Sheets

OTHER PUBLICATIONS

Fulda, et al., "Smac agonists sensitize for Apo2L/TRAIL- or anticancer drug-induced apoptosis and induce regression of malignant glioma in vivo," Nature Medicine, vol. 8, No. 8, Aug. 2002.

Griffith, et al., Intracellular Regulation of TRAIL-Induced Apoptosis in Human Melanoma Cells, The Journal of Immunology, 161:2833-2840 (1998).

Hofmann, et al., "Expression of inhibitors of apoptosis (IAP) proteins in non-small cell human lung cancer," J. Cancer Res. Clin. Oncol. (2002) 128: 554-560.

Holcik, Martin, et al., "XIAP: Apoptotic brake and promising therapeutic target," Apoptosis 2001; 6, pp. 253-261.

Huang, et al., "Structural Basis of Caspase Inhibition by XIAP: Differential Roles of the Linker versus the BIR Doman," Cell, vol. 104, pp. 781-790, Mar. 9, 2001.

Kataoka, et al., "FLIP Prevents Apoptosis Induced by Death Receptors But Not by Perforin/Granzyme B, Chemotherapeutic Drugs, and Gamma Irradiation," The Journal of Immunology, 161:3936-3942 (1998).

Kim, Kunhong, et al., "Molecular Determinants of Response to TRAIL in Killing of Normal and Cancer Cells," Clinical Cancer Research, vol. 6, pp. 335-346, Feb. 2000.

Kischkel, et al., "Apo2L/TRAIL-Dependent Recruitment of Endogenous FADD and Caspase-8 to Death Receptors 4 and 5," Immunity, vol. 12, pp. 611-620, Jun. 2000.

Kuang, et al., "FADD is Required for DR4- and DR5-mediated Apoptosis," The Journal of Biological Chemistry, vol. 275, No. 33, Aug. 18, 2000, pp. 25065-25068.

Li, et al., "Human Ovarian Cancer and Cisplatin Resistance: Possible Role of Inhibitor of Apoptosis Proteins," Endocrinology, 142:370-380 (2001).

McEleny, et al., "Inhibitors of Apoptosis Proteins in Prostate Cancer Cell Lines," The Prostate 51:133-140 (2002).

Messina, et al., "Resolution of (+/−)-1-Aryl-2-propynylamines via Acyltransfer Catalyzed by *Candida Antarctica* Lipase," J. Org. Chem. (1999), 64, pp. 3767-3769.

Muzio, et al., "An Induced Proximity Model for Caspase-8 Activation," vol. 273, No. 5, Jan. 30, 1998, pp. 2926-2930.

Ng, et al., "X-linked Inhibitor of Apoptosis (XIAP) Blocks Apo2 Ligand/Tumor Necrosis Factor-related Apoptosis-inducing Ligand-mediated Apoptosis of Prostate Cancer Cells . . . ," Molecular Cancer Therapeutics, vol. 1, Oct. 2002, pp. 1051-1058.

Nikolovska-Coleska, Zaneta, et al., "Development and optimization of a binding assay for the XIAP BIR3 domain using fluorescence polarization," Analytical Biochemistry, 332 (2004) pp. 261-273.

Pan, et al., "An Antagonist Decoy Receptor and a Death Domain-Containing Receptor for TRAIL," Science, vol. 277, Aug. 8, 1997.

Pan, Guohua, et al., "The Receptor for the Cytotoxic Ligand TRAIL," Science, vol. 276, Apr. 4, 1997, pp. 111-113.

Polyak, et al., "Rigid Dipeptide Mimics: Synthesis of Enantiopure 5- and 7-Benzyl and 5,7-Dibenzyl Indolizidinone Amino Acids via Enolization and . . . ," J. Org. Chem. (1998), 63, pp. 5937-5949.

Reed, et al., "BCl-2 Family Proteins: Regulators of Cell Death Involved in the Pathogenesis of Cancer and Resistance to Therapy," J. Cell. Biochem. 60:23-32 (1996).

Reed, John C., "Bcl-2 Family Proteins: Strategies for Overcoming Chemoresistance in Cancer," Advances in Pharmacology, vol. 41, (1997), pp. 501-532.

Riedl, Stefan, et al., "Structural Basis for the Inhibition of Caspase-3 by XIAP," Cell, vol. 104, pp. 791-800, Mar. 9, 2001.

Salvesen et al., "IAP Proteins: Blocking the Road to Death's Door," Molecular Cell Biology, vol. 3, Jun. 2002, pp. 401-410.

Srinivasula, et al., "A conserved XIAP-interaction motif in caspase-9 and Smac/DIABLO regulates caspase activity and apoptosis," Nature, vol. 410, Mar. 2001, pp. 112-116.

Srinivasula, et al., "Molecular Determinants of the Caspase-promoting Activity of Smac/DIABLO and Its Role in the Death Receptor Pathway," The Journal of Biological Chemistry, vol. 275, No. 46, Nov. 17, 2000, pp. 36152-36157.

Sun, et al., "Design and synthesis of a potent biotinylated Smac mimetic," Tetrahedron Letters, 46 (2005), pp. 7015-7018.

Sun, et al., "NMR structure and mutagenesis of the inhibitor-of-apoptoisis protein XIAP," Nature, vol. 401, Oct. 21, 1999, pp. 818-822.

Takahash, et al., "A single BIR Domain of XIAP Sufficient for Inhiiting Caspases," The Journal of Biological Chemistry, vol. 273, No. 14, Apr. 3, 1998, pp. 7787-7790.

Tamm, Ingo, et al., "Expression and Prognostic Significance of IAP-Family Genes in Human Cancers and Myeloid Leukemias," Clinical Cancer Research vol. 6, pp. 1796-1803, May 2000.

Teitz, Tal, et al., "Caspase 8 is deleted or silenced preferentially in childhood neuroblastomas with amplification on MYCN," Nature Medicine, vol. 6, No. 5, May 2000, pp. 529-535.

Wagenknecht, Bettina, et al., "Expression and biological activity of X-linked inhibitor of apoptosis (XIAP) in human malignant glioma," Cell Deaeth and Differentiation (1999) 6, pp. 370-376.

Walczak, Henning, "Tumoricidal activity of tumor necrosis factor-related apoptosis-induing ligand in vivo," Nature Medicine, vol. 5, No. 2, Feb. 1999, pp. 157-163.

Walczak, Henning, et al., "TRAIL-R2: a novel apoptosis-mediating receptor for TRAIL," The EMBO Journal vol. 16 No. 17, pp. 5386-5397 (1997).

Wu, Gen Sheng, et al., "KILLER/DR5 is a DNA damage-inducible p53-regulated death receptor gent," Nature Genetics, vol. 17, Oct. 1997, pp. 141-143.

Wu, Geng, et al., "Structural basis of IAP recognition by Smac/DIABLO," Nature, vol. 408, Dec. 2000, pp. 1008-1012.

AU Application No. 2007248473 Search Report dated Oct. 29, 2009.

EP Search Report dated Apr. 29, 2010, EP Patent Application No. 07794581.4.

Roy, S., et al., "Exploring Relationships Between Mimic Configuration, Peptide Conformation and Biological Activity in Indolizidin-2-One Amino Acid Analogs of Gramicidin S" Journal of Peptide Research, Blackwell Publishing Ltd., Oxford: GB, vol. 60, No. 4, Oct. 1, 2002, pp. 198-214.

Wisskirchen, F.M.., et al., "Conformational Restraints Revealing Bioactive Beta-Bend Structures for Halpha CGRP8-37 at the CGRP2 Receptor of the Rat Prostatic Vas Deferens," British Journal of Pharmacology, vol. 126, No. 5, Mar. 1999, pp. 1163-1170.

Peng, Y., et al., "Design and Synthesis of a 1,5-diazabicyclo[6,3,0] dodecane amino acid derivative as a novel dipeptide reverse-turn mimetic," Tetrahedron Letters, Elsevier, Jul. 3, 2006, pp. 4769-4770.

Sun, H., et al., "Structure-Based Design of Potent, Conformationally Constrained SMAC Mimetics," Journal of the American Chemical Society, Jan. 1, 2004, pp. 16686-16687.

Sun, et al., "Supporting Information: Design of Potent, Conformationally Constrained SMAC Mimetics," Journal of American Society, vol. 126, No. 51, Dec. 29, 2004, pp. S1-S20.

Sun, Haiying, et al., "Structure-based Design, Synthesis, and Evaluation of Conformationally Constrained Mimetics of the Second Mitochondria-Derived Activator of Caspase that Target the X-Linked Inhibitor of Apoptosis Protein/Caspase-9 Interaction Site," Journal of Medicinal Chemistry, American Chemical Society, vol. 47, No. 17, Aug. 12, 2004, pp. 4147-4150.

Bach, A.C., "Synthesis and NMR Conformational Analysis of a B-Turn Mimic Incorporated Into Gramicidin S" International Journal of Peptide and Protein Research, vol. 38, No. 4, Oct. 1, 1991, pp. 314-323.

Sun, H., et al., "Design and Synthesis of a Potent Biotinylated SMAC Mimetic," Tetrahedron Letters, vol. 46, No. 41, Oct. 10, 2005, pp. 7015-7018.

Nagai, U., et al., "Bicyclic Turned Dipeptide (BTD) as a Beta-Turn Mimetic: Its Design Synthesis and Incorporation into Bioactive Peptides," Tetrahedron, vol. 49, No. 17, Apr. 23, 1993, pp. 3577-3592.

Lombart, H., et al., "Rigid Dipeptide Mimetics: Efficient Synthesis of Enantiopure Indolizidinone Amino Acids," Journal of Organic Chemistry, vol. 61, No. 26, Dec. 27, 1996, pp. 9437-9446.

Examination Report, NZ Patent Application No. 572531, dated Jun. 3, 2010.

Wolff, M.E., "Burger's Medicinal Chemistry," 5th Ed., Part 1, pp. 975-977 (1995).

Banker, et al., "Modern Pharmaceuticals," 3rd Ed. P. 596 (1996).

TUNEL

BIVALENT SMAC MIMETICS AND THE USES THEREOF

CROSS REFERENCE TO RELATED APPLICATIONS

The present application is a continuation-in-part of pending U.S. patent application Ser. No. 11/800,220 filed May 4, 2007, which claims priority to U.S. Provisional Patent Application No. 60/923,415 filed Apr. 13, 2007 and expired U.S. Provisional Patent Application No. 60/798,018 filed May 5, 2006, each of which are incorporated herein by reference in their entireties.

STATEMENT REGARDING FEDERALLY SPONSORED RESEARCH FOR DEVELOPMENT

This invention was made with government support under W81XWH-04-1-0213 awarded by the Army Medical Research and Material Command. The government has certain rights in the invention.

BACKGROUND OF THE INVENTION

1. Field of the Invention

This invention is in the field of medicinal chemistry. In particular, the invention relates to bivalent mimetics of the N-terminal sequence of Smac which function as inhibitors of inhibitor of apoptosis proteins. The invention also relates to the use of these mimetics for inducing or sensitizing cells to the induction of apoptotic cell death.

2. Related Art

The aggressive cancer cell phenotype is the result of a variety of genetic and epigenetic alterations leading to deregulation of intracellular signaling pathways (Ponder, Nature 411:336 (2001)). The commonality for all cancer cells, however, is their failure to execute an apoptotic program, and lack of appropriate apoptosis due to defects in the normal apoptosis machinery is a hallmark of cancer (Lowe et al., Carcinogenesis 21:485 (2000)). Most current cancer therapies, including chemotherapeutic agents, radiation, and immunotherapy, work by indirectly inducing apoptosis in cancer cells. The inability of cancer cells to execute an apoptotic program due to defects in the normal apoptotic machinery is thus often associated with an increase in resistance to chemotherapy, radiation, or immunotherapy-induced apoptosis. Primary or acquired resistance of human cancer of different origins to current treatment protocols due to apoptosis defects is a major problem in current cancer therapy (Lowe et al., Carcinogenesis 21:485 (2000); Nicholson, Nature 407: 810 (2000)). Accordingly, current and future efforts towards designing and developing new molecular target-specific anticancer therapies to improve survival and quality of life of cancer patients must include strategies that specifically target cancer cell resistance to apoptosis. In this regard, targeting crucial negative regulators that play a central role in directly inhibiting apoptosis in cancer cells represents a highly promising therapeutic strategy for new anticancer drug design.

Two classes of central negative regulators of apoptosis have been identified. The first class of regulators is the Bcl-2 family of proteins, as exemplified by two potent anti-apoptotic molecules, Bcl-2 and Bcl-XL proteins (Adams et al., Science 281:1322 (1998); Reed, Adv. Pharmacol. 41:501 (1997); Reed et al., J. Cell. Biochem. 60:23 (1996)). Therapeutic strategies for targeting Bcl-2 and Bcl-XL in cancer to restore cancer cell sensitivity and overcome resistance of cancer cells to apoptosis have been extensively reviewed (Adams et al., Science 281:1322 (1998); Reed, Adv. Pharmacol. 41:501 (1997); Reed et al., J. Cell. Biochem. 60:23 (1996)). Several laboratories are interested in designing small molecule inhibitors of Bcl-2 and Bcl-XL.

The second class of central negative regulators of apoptosis is the inhibitor of apoptosis proteins (IAPs) (Deveraux et al., Genes Dev. 13:239 (1999); Salvesen et al., Nat. Rev. Mol. Cell. Biol. 3:401 (2002)). This class includes proteins such as XIAP, cIAP-1, cIAP-2, ML-IAP, HIAP, KIAP, TSIAP, NAIP, survivin, livin, ILP-2, apollon, and BRUCE. IAP proteins potently suppress apoptosis induced by a large variety of apoptotic stimuli, including chemotherapeutic agents, radiation, and immunotherapy in cancer cells.

X-linked IAP (XIAP) is the most potent inhibitor in suppressing apoptosis among all of the IAP members (Holcik et al., Apoptosis 6:253 (2001); LaCasse et al., Oncogene 17:3247 (1998); Takahashi et al., J. Biol. Chem. 273:7787 (1998); Deveraux et al., Nature 388:300 (1997); Sun et al., Nature 401:818 (1999); Deveraux et al., EMBO J. 18:5242 (1999); Asselin et al., Cancer Res. 61:1862 (2001)). XIAP plays a key role in the negative regulation of apoptosis in both the death receptor-mediated and the mitochondria-mediated pathways. XIAP functions as a potent endogenous apoptosis inhibitor by directly binding and potently inhibiting three members of the caspase family of enzymes, caspase-3, -7, and -9 (Takahashi et al., J. Biol. Chem. 273:7787 (1998); Deveraux et al., Nature 388:300 (1997); Sun et al., Nature 401:818 (1999); Deveraux et al., EMBO J. 18:5242 (1999); Asselin et al., Cancer Res. 61:1862 (2001); Riedl et al., Cell 104:791 (2001); Chai et al., Cell 104:769 (2001); Huang et al., Cell 104:781 (2001)). XIAP contains three baculovirus inhibitor of apoptosis repeat (BIR) domains as well as a C-terminal RING finger. The third BIR domain (BIR3) selectively targets caspase-9, the initiator caspase in the mitochondrial pathway, whereas the linker region between BIR1 and BIR2 inhibits both caspase-3 and caspase-7 (Salvesen et al., Nat. Rev. Mol. Cell. Biol. 3:401 (2002)). While binding to XIAP prevents the activation of all three caspases, it is apparent that the interaction with caspase-9 is the most critical for its inhibition of apoptosis (Ekert et al., J. Cell Biol. 152:483 (2001); Srinivasula et al., Nature 410:112 (2001)). Because XIAP blocks apoptosis at the down-stream effector phase, a point where multiple signaling pathways converge, strategies targeting XIAP may prove to be especially effective to overcome resistance of cancer cells to apoptosis (Fulda et al., Nature Med. 8:808 (2002); Arnt et al., J. Biol. Chem. 277:44236 (2002)).

Although the precise role of XIAP in each type of cancer is far from completely understood, evidence is mounting to indicate that XIAP is widely overexpressed in many types of cancer and may play an important role in the resistance of cancer cells to a variety of current therapeutic agents (Holcik et al., Apoptosis 6:253 (2001); LaCasse et al., Oncogene 17:3247 (1998)).

XIAP protein was found to be expressed in most of the NCI 60 human cancer cell lines (Tamm et al., Clin. Cancer Res. 6:1796 (2000)). Analysis of tumor samples in 78 previously untreated patients showed that those with lower levels of XIAP had significantly longer survival (Tamm et al., Clin. Cancer Res. 6:1796 (2000)). XIAP was found to be expressed in human malignant glioma (Wagenknecht et al., Cell Death Differ. 6:370 (1999); Fulda et al., Nature Med. 8:808 (2002)). XIAP was found to be expressed in human prostate cancer cells and blocks Apo2 ligand/tumor necrosis factor-related apoptosis inducing ligand-mediated apoptosis of prostate cancer cells in the presence of mitochondrial activation (McEleny et al., Prostate 51:133 (2002); Ng et al., Mol. Cancer. Ther. 1:1051 (2002)). XIAP is overexpressed in non-small cell lung cancer (NSCLC) in patients and has been implicated in pathogenesis of NSCLC (Hofmann et al., *J. Cancer Res. Clin. Oncol.* 128:554 (2002)). Expression of XIAP and lack of down-regulation of XIAP upon treatment with cisplatin have been implicated in cisplatin resistance of human ovarian cancer (Li et al., *Endocrinology* 142:370 (2001); Cheng et al., *Drug Resist. Update* 5:131 (2002)). Taken together, these data suggest that XIAP may play an important role in resistance of several human cancers to current therapeutic agents.

Apoptosis is not a single process, rather, it is involved with a number of different, sometimes interconnected, signaling pathways leading to cell degradation. The pathways involved in a particular form of apoptosis depend on many factors, such as the insult or insults that initiate the process. Other factors include the activation or overactivation of specific receptors, such as the activation of "death" receptors by tumor necrosis factor alpha (TNFα), tumor necrosis factor-related apoptosis-inducing ligand (TRAIL or Apo2L), or FAS ligand. Another determining factor is the type of cell which is involved, since different signaling pathways are shown for so called type I and type II cells after Fas or TNFα receptor activation.

TRAIL (Apo2L) has been shown to be a selective and potent inducer of apoptosis in cancer cells (but not normal cells) upon binding to either of two pro-apoptotic TRAIL receptors, TRAIL-R1 (or DR4) (Pan et al., *Science* 276:111 (1997)) or TRAIL-R2 (KILLER, or DR5) (Wu et al., *Nat. Genet.* 17:141-143 (1997); Pan et al., *Science* 277:815 (1997); Walczak et al., *EMBO J.* 16:5386 (1997)). Activation of the pro-apoptotic death receptors by TRAIL induces the formation of death inducing signaling complex (DISC), which consists of receptor FADD as an adaptor (Kischkel et al., *Immunity* 12:611 (2000); Kuang et al., *J. Biol. Chem.* 275:25065 (2000)), and caspase-8 as an initiator caspase. Once DISC is formed, caspase-8 is auto-processed and activated by induced proximity (Medema et al., *EMBO J.* 16:2794 (1997); Muzio et al., *J. Biol. Chem.* 273:2926 (1998)).

TRAIL has generated significant interest as a potential cancer therapeutic (French et al., *Nat. Med.* 5:146 (1999)) because of its selective targeting of cancer cells, whereas most normal cells appear to be resistant to TRAIL (Ashkenazi et al., *Science* 281:1305 (1998); Walczak et al., *Nat. Med.* 5:157 (1999)). Systemic administration of TRAIL has proven to be safe and effective at killing breast or colon xenografted tumors and prolonging survival in mice (Walczak et al., *Nat. Med.* 5:157 (1999)). Although TRAIL can specifically kill many types of cancer cells, many others display TRAIL-resistance (Kim et al., *Clin. Cancer Res.* 6:335 (2000); Zhang et al., *Cancer Res.* 59:2747 (1999)). In addition, cancer cells have been killed by application of antibodies (monoclonal or polyclonal) that specifically recognize either TRAIL-R1 or TRAIL-R2.

Numerous mechanisms have been identified as potential factors responsible for TRAIL-resistance. Such mechanisms exist at a number of levels, including at the receptor level, mitochondria level, post-mitochondria level, and at the DISC level. For example, loss of caspase-8 expression (Teitz et al., *Nat. Med.* 6:529 (2000); Griffith et al., *J. Immunol.* 161:2833 (1998)), or high expression of the cellular FLICE inhibitor protein (cFLIP) (Kim et al., *Clin. Cancer Res.* 6:335 (2000); Zhang et al., *Cancer Res.* 59:2747 1999; Kataoka et al., *J. Immunol.* 161:3936 (1998)) make cancer cells resistant to TRAIL. Yeh et al. have shown that cFLIP-deficient embryonic mouse fibroblasts are particularly sensitive to receptor-mediated apoptosis (Yeh et al., *Immunity* 12:533 (2000)). Several splice variants of cFLIP are known, including a short splice variant, cFLIP-S, and a longer splice variant, cFLIP-L. It has been shown that cFLIP-deficient embryonic mouse fibroblasts become resistant to TRAIL-induced apoptosis as a result of retroviral-mediated transduction of cFLIP-S (Bin et al., *FEBS Lett.* 510:37 (2002)).

Although TRAIL represents a potentially promising candidate for tumor-selective death receptor activation (i.e., it induces apoptosis preferentially in tumor cells but not in normal tissues), many cancer cells are resistant to apoptosis-inducing drugs, as discussed above. As a result, treatment with such drugs often requires co-treatment with irradiation and/or cytotoxic chemicals to achieve a therapeutic effect. However, both radiation and chemotherapy have significant side effects, and are generally avoided if possible.

Thus, a need exists for an agent that can selectively and efficiently sensitize tumor cells to selective, apoptosis-inducing drugs such as TRAIL or TRAIL receptor antibodies, without also sensitizing surrounding normal cells. Such an agent would also be useful for reducing or preventing the drug resistance commonly associated with the use of receptor-mediated apoptotic cancer drugs, thus improving their effectiveness and eliminating the need for combination therapies.

Recently, Smac/DIABLO (second mitochondria-derived activator of caspases) was identified as a protein released from mitochondria into the cytosol in response to apoptotic stimuli (Budihardjo et al., *Annu. Rev. Cell Dev. Biol.* 15:269 (1999); Du et al., *Cell* 102:33 (2000)). Smac is synthesized with an N-terminal mitochondrial targeting sequence that is proteolytically removed during maturation to the mature polypeptide. Smac was shown to directly interact with XIAP and other IAPs and to disrupt their binding to caspases and facilitate caspase activation. Smac is a potent endogenous inhibitor of XIAP.

High resolution, experimental three-dimensional (3D) structures of the BIR3 domain of XIAP in complex with Smac protein and peptide have recently been determined (Sun et al., *J. Biol. Chem.* 275:36152 (2000); Wu et al., *Nature* 408:1008 (2000)) (FIG. 1). The N-terminal tetrapeptide of Smac (Ala-Val-Pro-Ile, or AVPI (SEQ ID NO:1)) recognizes a surface groove on the BIR3 domain of XIAP through several hydrogen-bonding interactions and van der Waals contacts. The interaction between BIR3 and caspase-9 has also been shown to involve four residues (Ala-Thr-Pro-Phe, or ATPF (SEQ ID NO:2)) on the amino terminus of the small subunit of caspase-9 to the same surface groove on the BIR3 domain. Several recent studies have convincingly demonstrated that Smac promotes the catalytic activity of caspase-9 by competing with caspase-9 for the same binding groove on the surface of the BIR3 domain (Ekert et al., *J. Cell Biol.* 152:483 (2001); Srinivasula et al., *Nature* 410:112 (2001)).

Unlike most protein-protein interactions, the Smac-XIAP interaction is mediated by only four amino acid residues on the Smac protein and a well-defined surface groove on the BIR3 domain of XIAP. The $K_d$ value of Smac peptide AVPI (SEQ ID NO:1) to XIAP ($K_d$=0.4 µM) is essentially the same as the mature Smac protein ($K_d$=0.42 µM). This well-defined interaction site is ideal for the design of non-peptide, drug-like small molecules that mimic the binding of Smac to XIAP.

A cell permeable Smac peptide, which consists of the first four amino acid residues (AVPI (SEQ ID NO:1)) of the N-terminus of Smac tethered to a carrier peptide to facilitate intracellular delivery, was recently shown to sensitize various tumor cells in vitro and malignant glioma cells in vivo to apoptosis induced by death receptor ligation or cytotoxic drugs (Fulda et al., *Nature Med.* 8:808 (2002)). Importantly, this Smac peptide strongly enhanced the anti-tumor activity of Apo2L/TRAIL in an intracranial malignant glioma xenograft model in vivo. Complete eradication of established tumors and survival of mice was only achieved upon combined treatment with Smac peptides and Apo2L/TRAIL. Of significance, Smac peptide does not have detectable toxicity to normal brain tissue.

A second recent independent study also showed that peptides consisting of the first four to eight amino acid residues of the N-terminus of Smac tethered to a different carrier peptide enhanced the induction of apoptosis and the long term antiproliferative effects of diverse chemotherapeutic drugs, including paclitaxel, etoposide, SN-38, and doxorubicin in MCF-7 and other human breast cancer cell lines (Arnt et al., *J. Biol. Chem.* 277:44236 (2002)). This study conclusively showed that XIAP and cIAP-1 are the primary molecular targets for these peptides in cells.

A third study showed that a Smac peptide of the first seven N-terminal residues tethered to polyarginine restored the apoptosome activity and reversed the apoptosis resistance in non-small cell lung cancer H460 cells (Yang et al., *Cancer Res.* 63:831 (2003)). XIAP was shown to be responsible for the defect in apoptosome activity and suppression of caspase activity in H460 cells. When used in combination with chemotherapy, the cell-permeable Smac peptide regressed tumor growth in vivo with little murine toxicity. Taken together, these recent independent studies strongly suggest that a potent, stable, cell-permeable Smac mimetic may have great therapeutic potential for the treatment of human breast cancer and other types of cancer.

Peptide-based inhibitors are useful tools to elucidate the anti-apoptotic function of IAPs and the role of IAPs in response of cancer cells to chemotherapeutic agents. But peptide-based inhibitors in general have intrinsic limitations as potentially useful therapeutic agents. These limitations include their poor cell-permeability and poor in vivo stability. Indeed, in these three published studies using Smac-based peptide inhibitors, the peptides had to be fused to carrier peptides to make them relatively cell-permeable.

U.S. Published Application No. 2005/0197403 discloses dimeric Smac mimetic compounds of formula I:

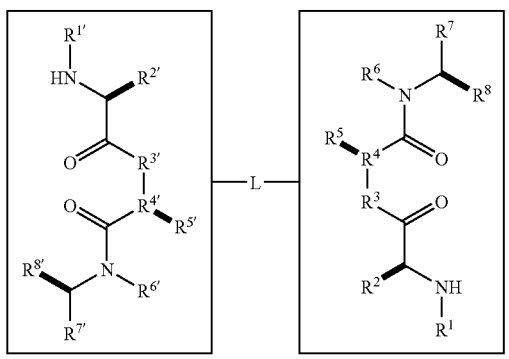

I wherein $R^1$ and $R^{1'}$ are selected from hydrogen, optionally substituted methyl, and hydroxyl;

$R^2$ and $R^{2'}$ are selected from optionally substituted methyl and optionally substituted ethyl;

$R^3$ and $R^{3'}$ are selected from $CH_2$, NH, O and S;

$R_4$ and $R_4'$ are selected from CH and N;

$R^5$-$R^8$, and $R^{5'}$-$R^{8'}$ are selected from hydrogen, optionally hetero-, optionally substituted alkyl, optionally hetero-, optionally substituted alkenyl, optionally hetero-, optionally substituted alkynyl, optionally hetero-, optionally substituted aryl; and L is a linker covalently linking $R^2$, $R^5$, $R^6$ or $R^7$, with $R^{2'}$, $R^{5'}$, $R^{6'}$ or $R^{7'}$, or a pharmaceutically-acceptable salt thereof.

To overcome the intrinsic limitations of peptide-based inhibitors, the present invention involves the design of bivalent conformationally constrained Smac mimetics.

SUMMARY OF THE INVENTION

It is generally accepted that the inability of cancer cells or their supporting cells to undergo apoptosis in response to genetic lesions or exposure to inducers of apoptosis (such as anticancer agents and radiation) is a major factor in the onset and progression of cancer. The induction of apoptosis in cancer cells or their supporting cells (e.g., neovascular cells in the tumor vasculature) is thought to be a universal mechanism of action for virtually all of the effective cancer therapeutic drugs or radiation therapies on the market or in practice today. One reason for the inability of a cell to undergo apoptosis is increased expression and accumulation of IAPs.

The present invention contemplates that exposure of animals suffering from cancer or other hyperproliferative disorders or diseases associated with dysregulation of apoptosis to therapeutically effective amounts of drug(s) (e.g., small molecules) that inhibit the function(s) of IAPs will kill the diseased cells or supporting cells outright (those cells whose continued survival is dependent on the overactivity or overexpression of IAPs) and/or render such cells as a population more susceptible to the cell death-inducing activity of cancer therapeutic drugs or radiation therapies. The present invention contemplates that inhibitors of IAPs satisfy an unmet need for the treatment of multiple cancer types, either when administered as monotherapy to induce apoptosis in cancer cells dependent on IAP function, or when administered in a temporal relationship with other cell death-inducing cancer therapeutic drugs or radiation therapies so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of a compound of the present invention and a course of an anticancer agent or radiation produces a greater tumor response and clinical benefit in such animals compared to those treated with the compound or anticancer drugs/radiation alone. Put another way, because the compounds lower the apoptotic threshold of all cells that express IAPs, the proportion of cells that successfully execute the apoptosis program in response to the apoptosis inducing activity of anticancer drugs/radiation is increased. Alternatively, the compounds of the present invention can be used to allow administration of a lower, and therefore less toxic and more tolerable, dose of an anticancer agent and/or radiation to produce the same tumor response/clinical benefit as the conventional dose of the anticancer agent/radiation alone. Since the doses for all approved anticancer drugs and radiation treatments are known, the present invention contemplates the various combinations of them with the compounds of the present invention. Also, since the compounds of the present invention act at least in part by inhibiting IAPs, the exposure of cancer cells and supporting cells to therapeutically effective amounts of the compounds can be temporally linked to coincide with the attempts of cells to execute the apoptosis program in response to the anticancer agent or radiation therapy. Thus, in some embodiments, administering the compositions of the present invention in connection with certain temporal relationships, provides especially efficacious therapeutic practices.

The present invention relates to Smac mimetics that are useful for inhibiting the activity of IAP proteins and increasing the sensitivity of cells to inducers of apoptosis. In one particular embodiment, the Smac mimetics are compounds of formula II:

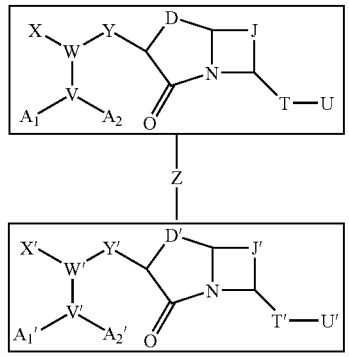

II wherein:

$A_1$ and $A_1'$ are independently selected from the group consisting of hydrogen, optionally substituted alkyl and Z;

$A_2$ and $A_2'$ are independently selected from the group consisting of hydrogen, optionally substituted alkyl and $COR^1$, wherein $A_2$ is absent when V is O and $A_2'$ is absent when V' is O;

V and V' are independently selected from the group consisting of N, CH and O;

W and W' are independently selected from the group consisting of CH and N;

X and X' are independently optionally substituted $C_{1-3}$ alkyl;

Y and Y' are independently selected from the group consisting of $CONR^1$, C(O)O, $(CR^1R^2)_{1-3}$, wherein one or more $CH_2$ groups can be replaced by O, S or $NR^1$, optionally substituted aryl and optionally substituted heteroaryl;

D and D' are independently selected from the group consisting of optionally substituted alkylenyl and $(CR^1R^2)_n$—$R^{5a}$—$(CR^3R^4)_m$;

J and J' are independently selected from the group consisting of optionally substituted alkylenyl and $(CR^1R^2)_p$—$R^{5b}$—$(CR^3R^4)_q$;

T and T' are independently selected from the group consisting of C=O, C=S, C=$NR^1$, S, O, $NR^1$, $CR^1R^2$, optionally substituted carbocyclic, optionally substituted heterocyclic, optionally substituted aryl and optionally substituted heteroaryl;

U and U' are independently selected from the group consisting of hydrogen, $NR^1R^2$, $OR^1$, $SR^1$, optionally substituted alkyl and optionally substituted aryl;

n, m, p and q are independently 0-5;

each $R^1$ is selected from the group consisting of hydrogen, optionally substituted alkyl, optionally substituted carbocyclic, optionally substituted heterocyclic, optionally substituted aryl, optionally substituted heteroaryl and Z;

each $R^2$, $R^3$ and $R^4$ are independently selected from the group consisting of hydrogen, optionally substituted alkyl, optionally substituted carbocyclic, optionally substituted heterocyclic, optionally substituted aryl and optionally substituted heteroaryl;

$R^{5a}$ and $R^{5b}$ are independently selected from the group consisting of C=O, C=S, C=$NR^1$, S, O, $NR^1$ and $CR^1R^2$; and Z is a linker covalently linking one of $A_1$, Y, D, J, T and U with one of $A_1'$, Y', D', J', T' and U';

or pharmaceutically acceptable salts or prodrugs thereof.

In another particular embodiment, the Smac mimetics are compounds of formula III:

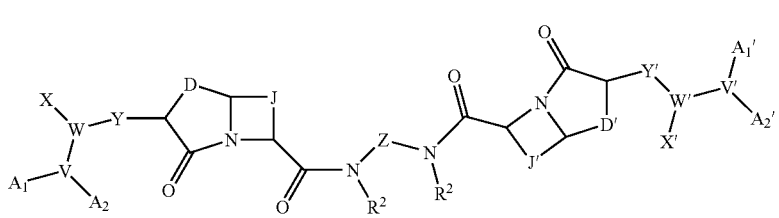

III wherein:

$A_1$ and $A_1'$ are independently selected from the group consisting of hydrogen and optionally substituted alkyl;

$A_2$ and $A_2'$ are independently selected from the group consisting of hydrogen, optionally substituted alkyl and $COR^1$, wherein $A_2$ is absent when V is O and $A_2'$ is absent when V' is O;

V and V' are independently selected from the group consisting of N, CH and O;

W and W' are independently selected from the group consisting of CH and N;

X and X' are independently optionally substituted $C_{1-3}$ alkyl;

Y and Y' are independently selected from the group consisting of $CONR^1$, C(O)O, $(CR^1R^2)_{1-3}$, wherein one or more $CH_2$ groups can be replaced by O, S or $NR^1$, optionally substituted aryl and optionally substituted heteroaryl;

D and D' are independently selected from the group consisting of optionally substituted alkylenyl and $(CR^1R^2)_n$—$R^{5a}$—$(CR^3R^4)_m$;

J and J' are independently selected from the group consisting of optionally substituted alkylenyl and $(CR^1R^2)_p$—$R^{5b}$—$(CR^3R^4)_q$;

n, m, p and q are independently 0-5;

each $R^1$ is selected from the group consisting of hydrogen, optionally substituted alkyl, optionally substituted carbocyclic, optionally substituted heterocyclic, optionally substituted aryl, and optionally substituted heteroaryl;

each $R^2$, $R^3$ and $R^4$ are independently selected from the group consisting of hydrogen, optionally substituted alkyl, optionally substituted carbocyclic, optionally substituted heterocyclic, optionally substituted aryl and optionally substituted heteroaryl;

$R^{5a}$ and $R^{5b}$ are independently selected from the group consisting of C=O, C=S, C=NR$^1$, S, O, NR$^1$ and CR$^1$R$^2$; and Z is a linker; or a pharmaceutically acceptable salt or prodrug thereof.

In another particular embodiment, the Smac mimetics are compounds of formula IV:

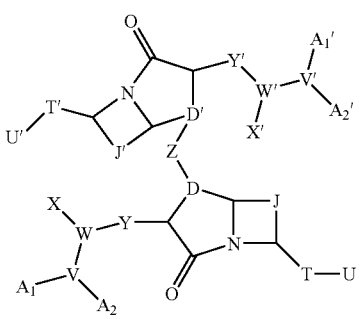

IV wherein:
$A_1$ and $A_1$' are independently selected from the group consisting of hydrogen and optionally substituted alkyl;
$A_2$ and $A_2$' are independently selected from the group consisting of hydrogen, optionally substituted alkyl and COR$^1$, wherein $A_2$ is absent when V is O and $A_2$' is absent when V' is O;
V and V' are independently selected from the group consisting of N, CH and O;
W and W' are independently selected from the group consisting of CH and N;
X and X' are independently optionally substituted $C_{1-3}$ alkyl;
Y and Y' are independently selected from the group consisting of CONR$^1$, C(O)O, $(CR^1R^2)_{1-3}$, wherein one or more CH$_2$ groups can be replaced by O, S or NR$^1$, optionally substituted aryl and optionally substituted heteroaryl;
D and D' are independently selected from the group consisting of optionally substituted alkylenyl and $(CR^1R^2)_n$—$R^{5a}$—$(CR^3R^4)_m$;
J and J' are independently selected from the group consisting of optionally substituted alkylenyl and $(CR^1R^2)_p$—$R^{5b}$—$(CR^3R^4)_q$;
T and T' are independently selected from the group consisting of C=O, C=S, C=NR$^1$, S, O, NR$^1$, CR$^1$R$^2$, optionally substituted carbocyclic, optionally substituted heterocyclic, and optionally substituted aryl;
U and U' are independently selected from the group consisting of hydrogen, NR$^1$R$^2$, OR$^1$, SR$^1$, optionally substituted alkyl and optionally substituted aryl;
n, m, p and q are independently 0-5;
each R$^1$ is selected from the group consisting of hydrogen, optionally substituted alkyl, optionally substituted carbocyclic, optionally substituted heterocyclic, optionally substituted aryl, optionally substituted heteroaryl and Z;
each $R^2$, $R^3$ and $R^4$ are independently selected from the group consisting of hydrogen, optionally substituted alkyl, optionally substituted carbocyclic, optionally substituted heterocyclic, optionally substituted aryl and optionally substituted heteroaryl;

$R^{5a}$ and $R^{5b}$ are independently selected from the group consisting of C=O, C=S, C=NR$^1$, S, O, NR$^1$ and CR$^1$R$^2$; and
Z is a linker; or a pharmaceutically acceptable salt or prodrug thereof.

The invention relates to compounds represented by Formulae II-IV, which are inhibitors of IAP proteins. The invention relates to the use if the compounds of the invention to induce apoptosis in cells. The invention also relates to the use of the compounds of the invention for sensitizing cells to inducers of apoptosis. The compounds are useful for the treatment, amelioration, or prevention of disorders responsive to induction of apoptotic cell death, e.g., disorders characterized by dysregulation of apoptosis, including hyperproliferative diseases such as cancer. In certain embodiments, the compounds can be used to treat, ameliorate, or prevent cancer that is characterized by resistance to cancer therapies (e.g., those which are chemoresistant, radiation resistant, hormone resistant, and the like). In other embodiments, the compounds can be used to treat hyperproliferative diseases characterized by overexpression of IAPs.

The present invention provides pharmaceutical compositions comprising a compound of Formulae II-IV in a therapeutically effective amount to induce apoptosis in cells or to sensitize cells to inducers of apoptosis.

The invention further provides kits comprising a compound of Formulae II-IV and instructions for administering the compound to an animal. The kits may optionally contain other therapeutic agents, e.g., anticancer agents or apoptosis-modulating agents.

DETAILED DESCRIPTION OF THE INVENTION

Figure 1:
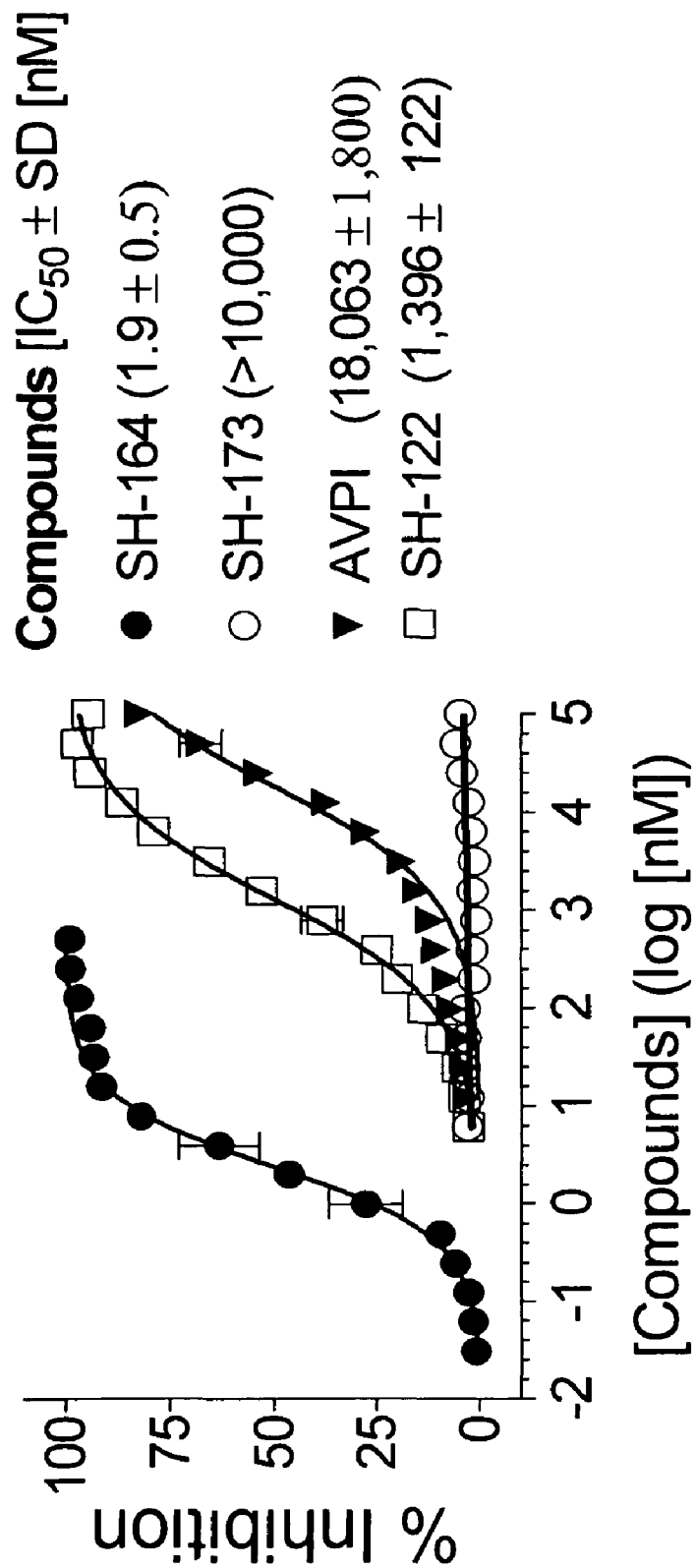
FIG. 1 is a graph showing the competitive binding of Smac mimetics to XIAP BIR3 protein.

The present invention relates to bivalent conformationally constrained compounds represented by Formulae II-IV, which are mimetics of Smac and function as inhibitors of IAPs. These compounds sensitize cells to inducers of apoptosis and, in some instances, themselves induce apoptosis by inhibiting IAPs. Therefore, the invention relates to methods of sensitizing cells to inducers of apoptosis and to methods of inducing apoptosis in cells, comprising contacting the cells with a compound of Formulae II-IV alone or in combination with an inducer of apoptosis. The invention further relates to methods of treating, ameliorating, or preventing disorders in an animal that are responsive to induction of apoptosis comprising administering to the animal a compound of Formulae II-IV and an inducer of apoptosis. Such disorders include those characterized by a dysregulation of apoptosis and those characterized by overexpression of IAPs.

The term "IAP proteins," as used herein, refers to any known member of the Inhibitor of Apoptosis Protein family, including, but not limited to, XIAP, cIAP-1, cIAP-2, ML-IAP, HIAP, TSIAP, KIAP, NAIP, survivin, livin, ILP-2, apollon, and BRUCE.

The term "overexpression of IAPs," as used herein, refers to an elevated level (e.g., aberrant level) of mRNAs encoding for an IAP protein(s), and/or to elevated levels of IAP protein(s) in cells as compared to similar corresponding non-pathological cells expressing basal levels of mRNAs encoding IAP proteins or having basal levels of IAP proteins. Methods for detecting the levels of mRNAs encoding IAP proteins or levels of IAP proteins in a cell include, but are not limited to, Western blotting using IAP protein antibodies, immunohistochemical methods, and methods of nucleic acid amplification or direct RNA detection. As important as the absolute level of IAP proteins in cells is to determining that they overexpress IAP proteins, so also is the relative level of IAP proteins to other pro-apoptotic signaling molecules (e.g., pro-apoptotic Bcl-2 family proteins) within such cells. When the balance of these two are such that, were it not for the levels of the IAP proteins, the pro-apoptotic signaling molecules would be sufficient to cause the cells to execute the apoptosis program and die, said cells would be dependent on the IAP proteins for their survival. In such cells, exposure to an inhibiting effective amount of an IAP protein inhibitor will be sufficient to cause the cells to execute the apoptosis program and die. Thus, the term "overexpression of an IAP protein" also refers to cells that, due to the relative levels of pro-apoptotic signals and anti-apoptotic signals, undergo apoptosis in response to inhibiting effective amounts of compounds that inhibit the function of IAP proteins.

The terms "anticancer agent" and "anticancer drug," as used herein, refer to any therapeutic agents (e.g., chemotherapeutic compounds and/or molecular therapeutic compounds), radiation therapies, or surgical interventions, used in the treatment of hyperproliferative diseases such as cancer (e.g., in mammals).

The term "prodrug," as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, toxicity, lack of specificity, or limited bioavailability. Exemplary prodrugs comprise an active drug molecule itself and a chemical masking group (e.g., a group that reversibly suppresses the activity of the drug). Some preferred prodrugs are variations or derivatives of compounds that have groups cleavable under metabolic conditions. Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol), amides prepared by reaction of the parent acid compound with an amine, or basic groups reacted to form an acylated base derivative (e.g., a lower alkylamide).

The term "pharmaceutically acceptable salt," as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, a therapeutically effective amount preferably refers to the amount of a therapeutic agent that decreases the rate of tumor growth, decreases tumor mass, decreases the number of metastases, increases time to tumor progression, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a compound of Formulae II-IV), an animal or a cell within an animal more susceptible, or more responsive, to the biological effects (e.g., promotion or retardation of an aspect of cellular function including, but not limited to, cell division, cell growth, proliferation, invasion, angiogenesis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least 10%, at least 20%, at least 30%, at least 40%, at least 50%, at least 60%, at least 70%, at least 80%, at least 90%, at least 100%, at least 150%, at least 200%, at least 350%, at least 300%, at least 350%, at least 400%, at least 450%, or at least 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, including for example, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

The term "hyperproliferative disease," as used herein, refers to any condition in which a localized population of proliferating cells in an animal is not governed by the usual limitations of normal growth. Examples of hyperproliferative disorders include, but are not restricted to tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "apoptosis-modulating agents," as used herein, refers to agents which are involved in modulating (e.g., inhibiting, decreasing, increasing, promoting) apoptosis. Examples of apoptosis-modulating agents include proteins which comprise a death domain such as, but not limited to, Fas/CD95, TRAMP, TNF RI, DR1, DR2, DR3, DR4, DR5, DR6, FADD, and RIP. Other examples of apoptotic-modulating agents include, but are not limited to, TNFα, Fas ligand, antibodies to Fas/CD95 and other TNF family receptors, TRAIL (also known as Apo2 Ligand or Apo2L/TRAIL), agonists (e.g., monoclonal or polyclonal agonistic antibodies) of TRAIL-R1 or TRAIL-R2, Bcl-2, p53, BAX, BAD, Akt, CAD, PI3 kinase, PP1, and caspase proteins. Modulating agents broadly include agonists and antagonists of TNF family receptors and TNF family ligands. Apoptosis-modulating agents may be soluble or membrane bound (e.g. ligand or receptor). Preferred apoptosis-modulating agents are inducers of apoptosis, such as TNF or a TNF-related ligand, particularly a TRAMP ligand, a Fas/CD95 ligand, a TNFR-1 ligand, or TRAIL The inhibitors of IAPs of the present invention are compounds having the general Formula II:

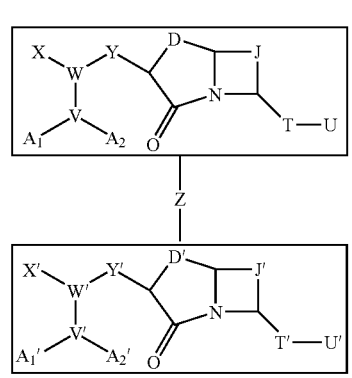

II wherein:

$A_1$ and $A_1'$ are independently selected from the group consisting of hydrogen, optionally substituted alkyl and Z;

$A_2$ and $A_2'$ are independently selected from the group consisting of hydrogen, optionally substituted alkyl and $COR^1$, wherein $A_2$ is absent when V is O and $A_2'$ is absent when V' is O;

V and V' are independently selected from the group consisting of N, CH and O;

W and W' are independently selected from the group consisting of CH and N;

X and X' are independently optionally substituted $C_{1-3}$ alkyl;

Y and Y' are independently selected from the group consisting of $CONR^1$, C(O)O, $(CR^1R^2)_{1-3}$, wherein one or more $CH_2$ groups can be replaced by O, S or $NR^1$, optionally substituted aryl and optionally substituted heteroaryl;

D and D' are independently selected from the group consisting of optionally substituted alkylenyl and $(CR^1R^2)$—$R^{5a}$—$(CR^3R^4)_m$;

J and J' are independently selected from the group consisting of optionally substituted alkylenyl and $(CR^1R^2)_p$—$R^{5b}$—$(CR^3R^4)_q$;

T and T' are independently selected from the group consisting of C=O, C=S, C=$NR^1$, S, O, $NR^1$, $CR^1R^2$, optionally substituted carbocyclic, optionally substituted heterocyclic, optionally substituted aryl and optionally substituted heteroaryl;

U and U' are independently selected from the group consisting of hydrogen, $NR^1R^2$, $OR^1$, $SR^1$, optionally substituted alkyl and optionally substituted aryl;

n, m, p and q are independently 0-5;

each $R^1$ is selected from the group consisting of hydrogen, optionally substituted alkyl, optionally substituted carbocyclic, optionally substituted heterocyclic, optionally substituted aryl, optionally substituted heteroaryl and Z;

each $R^2$, $R^3$ and $R^4$ are independently selected from the group consisting of hydrogen, optionally substituted alkyl, optionally substituted carbocyclic, optionally substituted heterocyclic, optionally substituted aryl and optionally substituted heteroaryl;

$R^{5a}$ and $R^{5b}$ are independently selected from the group consisting of C=O, C=S, C=$NR^1$, S, O, $NR^1$ and $CR^1R^2$; and Z is a linker covalently linking one of $A_1$, Y, D, J, T and U with one of $A_1'$, Y', D', J', T' and U';

or pharmaceutically acceptable salts or prodrugs thereof.

In a further embodiment, Z links D with U'. In a further embodiment, Z links D with D'. In a further embodiment, Z links U with U'. In a further embodiment, n and m are independently selected from 0-4 such that n+m is 3 or 4. In a further embodiment, p and q are independently selected from 0 and 1 such that p+q is 1. In a further embodiment, n and m are independently selected from 0-4 such that n+m is 3 or 4 and p and q are independently selected from 0 and 1 such that p+q is 1. In a further embodiment, T is C=O. In a further embodiment, U is $NR^1R^2$. In a further embodiment, $R^{5b}$ is $CH_2$. In a further embodiment, Y is CONH, W is CH and V is N. In a further embodiment, $A^2$ and $A^{2'}$ are independently selected from the group consisting of hydrogen and optionally substituted alkyl.

In another particular embodiment, the inhibitors of IAPs of the present invention are compounds of formula III:

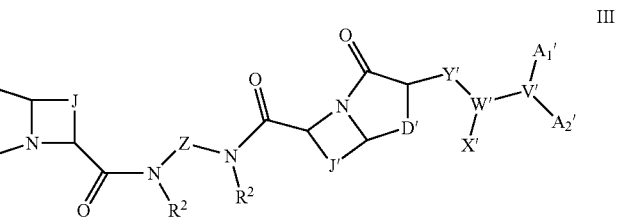

III wherein $A_1$, $A_2$, V, W, X, Y, D, J, Z, $A_1'$, $A_2'$, V', W', X', Y', D', J' and $R^2$ have the meanings as above; or pharmaceutically acceptable salts or prodrugs thereof.

In another particular embodiment, the inhibitors of IAPs of the present invention are compounds of formula XIV:

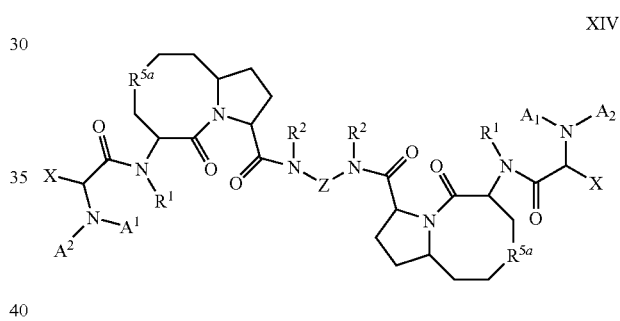

XIV wherein $A_1$, $A_2$, X, $R^1$, $R^2$, $R^{5a}$, and Z have the meanings as above; or pharmaceutically acceptable salts or prodrugs thereof.

In one embodiment, $A_1$, $R^1$, and $R^2$ are hydrogen, $A_2$ and X are optionally substituted alkyl, and $R^{5a}$ is $CH_2$. In another embodiment, $A_2$ and X are methyl.

In another particular embodiment, the inhibitors of IAPs of the present invention are compounds of formula XV:

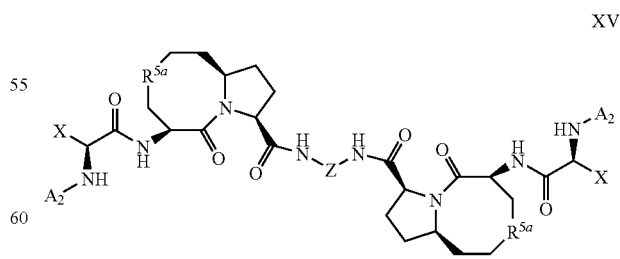

XV wherein $A_2$, X, $R^{5a}$, and Z have the meanings as above; or pharmaceutically acceptable salts or prodrugs thereof. In another embodiment, $A_2$ and X are methyl.

In one embodiment, $A_1$, $R^1$, and $R^2$ are hydrogen, $A_2$ and X are optionally substituted alkyl, and $R^{5a}$ is $CH_2$. In another embodiment, $A_2$ and X are methyl.

In another particular embodiment, the inhibitors of IAPs of the present invention are compounds of formula XVI:

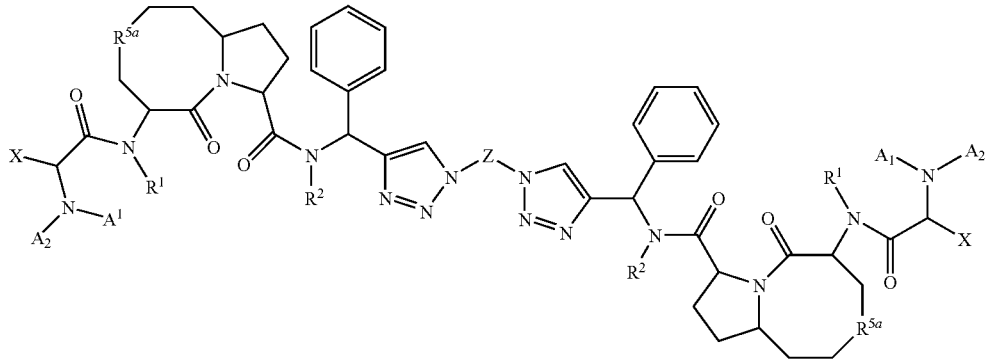

XVI wherein $A_1$, $A_2$, X, $R^1$, $R^2$, $R^{5a}$, and Z have the meanings as above; or pharmaceutically acceptable salts or prodrugs thereof.

In one embodiment, $A_1$, $R^1$, and $R^2$ are hydrogen, $A_2$ and X are optionally substituted alkyl, and $R^{5a}$ is $CH_2$. In another embodiment, $A_2$ and X are methyl. In one embodiment, Z is $-(CH_2)_y-C_6H_4-(CH_2)_y-$ wherein y is 1-10. In another embodiment, y is 2-5. In one embodiment, Z is $-(CH_2)_w-$ wherein w is 2-20. In another embodiment, w is 4-10.

In another particular embodiment, the inhibitors of IAPs of the present invention are compounds of formula XVII:

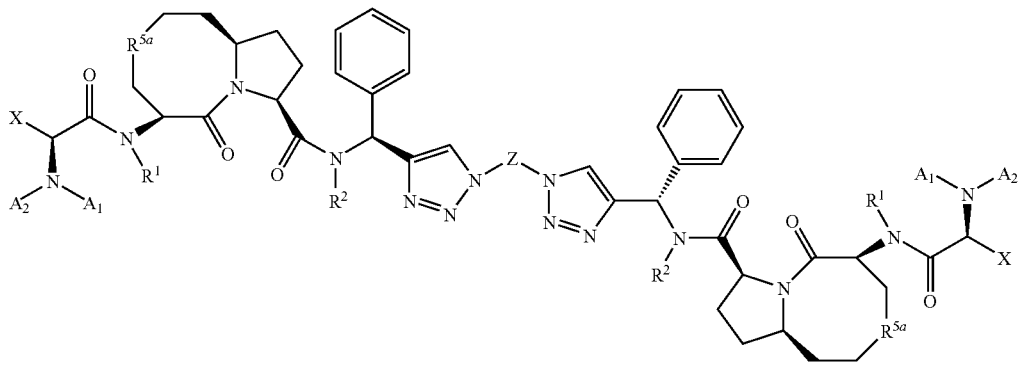

XVII wherein $A_1$, $A_2$, X, $R^1$, $R^2$, $R^{5a}$, and Z have the meanings as above; or pharmaceutically acceptable salts or prodrugs thereof.

In one embodiment, $A_1$, $R^1$, and $R^2$ are hydrogen, $A_2$ and X are optionally substituted alkyl, and $R^{5a}$ is $CH_2$. In another embodiment, $A_2$ and X are methyl. In one embodiment, Z is $-(CH_2)_y-C_6H_4-(CH_2)_y-$ wherein y is 1-10. In another embodiment, y is 2-5. In one embodiment, Z is $-(CH_2)_w-$ wherein w is 2-20. In another embodiment, w is 4-10.

In another particular embodiment, the inhibitors of IAPs of the present invention are compounds of formula XVIII:

XVIII

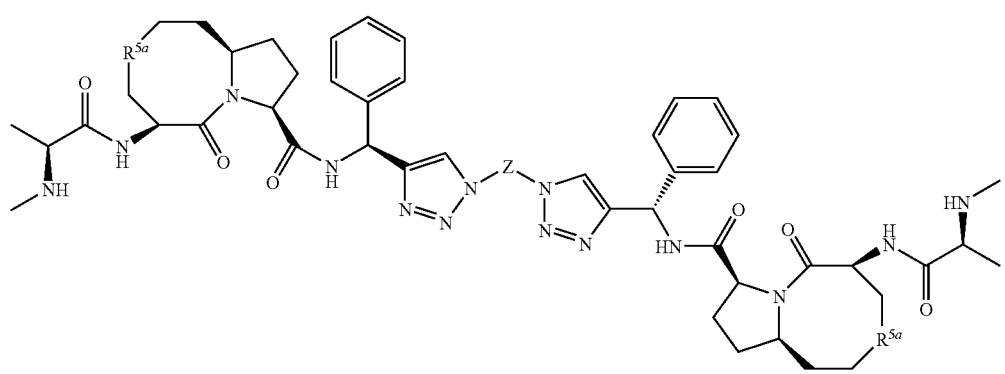

wherein $R^{5a}$ and Z have the meanings as above; or pharmaceutically acceptable salts or prodrugs thereof.

In one embodiment, $R^{5a}$ is $CH_2$. In one embodiment, Z is —$(CH_2)_y$—$C_6H_4$—$(CH_2)_y$—wherein y is 1-10. In another embodiment, y is 2-5. In one embodiment, Z is —$(CH_2)_w$— wherein w is 2-20. In another embodiment, w is 4-10.

In another particular embodiment, the inhibitors of IAPs of the present invention are compounds of formula IV:

IV
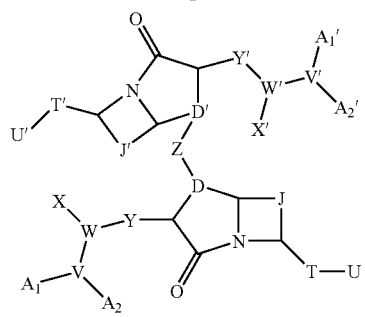

wherein $A_1$, $A_2$, V, W, X, Y, D, J, Z, T, U, $A_1'$, $A_2'$, V', W', X', Y', D', J', T' and U' have the meanings as above; or pharmaceutically acceptable salts or prodrugs thereof.

In another particular embodiment, the inhibitors of IAPs of the present invention are compounds of formula XIX:

XIX
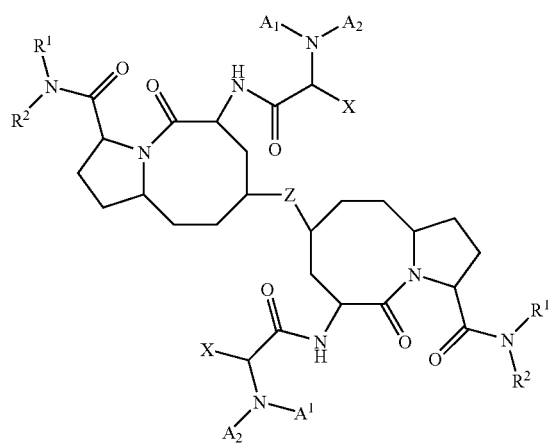

wherein $A_1$, $A_2$, X, $R^1$, $R^2$, and Z have the meanings as above; or pharmaceutically acceptable salts or prodrugs thereof.

In one embodiment, $A_1$ and $R^2$ are hydrogen and $A_2$ and X are optionally substituted alkyl. In another embodiment, $A_2$ and X are methyl. In one embodiment, $R^1$ is —$(CH)Ph_2$.

In another particular embodiment, the inhibitors of IAPs of the present invention are compounds of formula XX:

XX
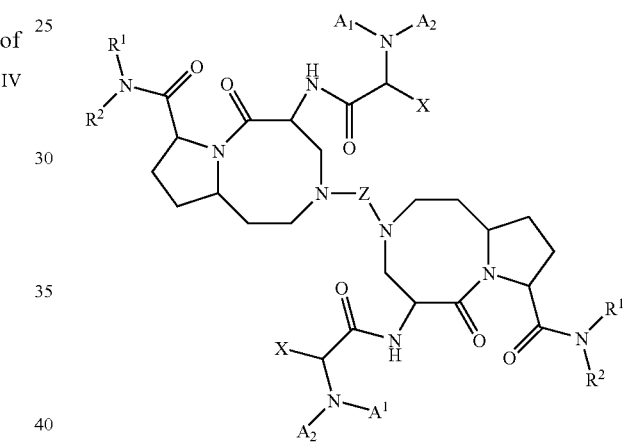

wherein $A_1$, $A_2$, X, $R^1$, $R^2$, and Z have the meanings as above; or pharmaceutically acceptable salts or prodrugs thereof.

In one embodiment, $A_1$ and $R^2$ are hydrogen and $A_2$ and X are optionally substituted alkyl. In another embodiment, $A_2$ and X are methyl. In one embodiment, $R^1$ is —$(CH)Ph_2$.

In another particular embodiment, the inhibitors of IAPs of the present invention are compounds of formula XXI:

XXI
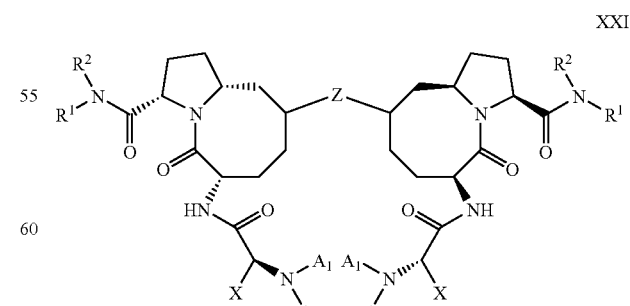

wherein $A_1$, $A_2$, X, $R^1$, $R^2$, and Z have the meanings as above; or pharmaceutically acceptable salts or prodrugs thereof.

In one embodiment, $A_1$ and $R^2$ are hydrogen and $A_2$ and X are optionally substituted alkyl. In another embodiment, $A_2$ and X are methyl. In one embodiment, $R^1$ is —(CH)Ph$_2$.

In another particular embodiment, the inhibitors of IAPs of the present invention are compounds of formula XXII:

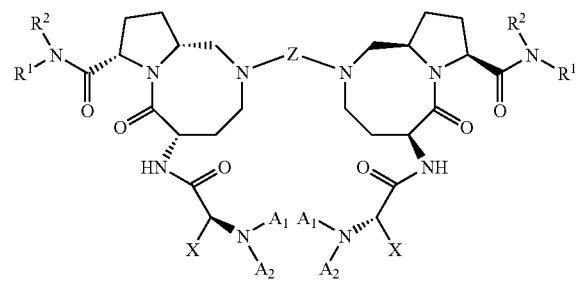

XXII wherein $A_1$, $A_2$, X, $R^1$, $R^2$, and Z have the meanings as above; or pharmaceutically acceptable salts or prodrugs thereof.

In one embodiment, $A_1$ and $R^2$ are hydrogen and $A_2$ and X are optionally substituted alkyl. In another embodiment, $A_2$ and X are methyl. In one embodiment, $R^1$ is —(CH)Ph$_2$.

In another particular embodiment, the inhibitors of IAPs of the present invention are compounds of formula XXIII:

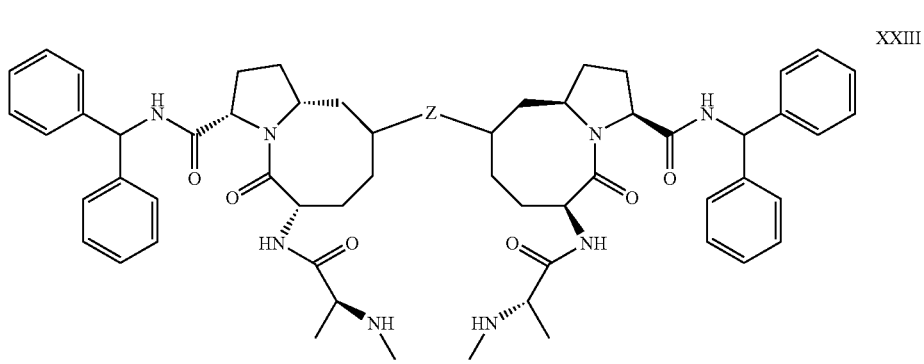

XXIII wherein Z has the meaning as above; or pharmaceutically acceptable salts or prodrugs thereof.

In another particular embodiment, the inhibitors of IAPs of the present invention are compounds of formula XXIV:

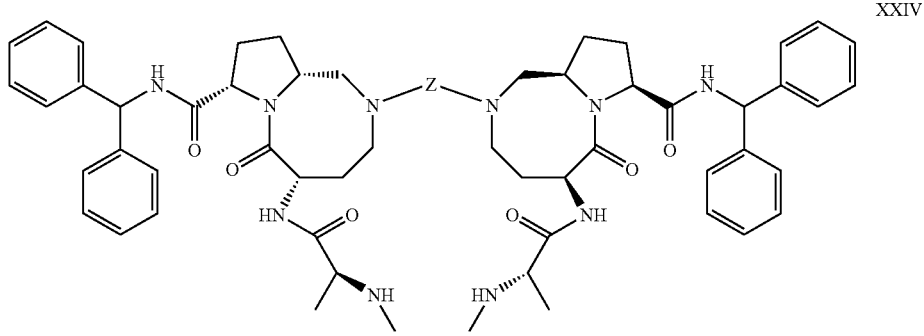

XXIV wherein Z has the meaning as above; or pharmaceutically acceptable salts or prodrugs thereof.

In one embodiment, Z is —CO—(CH$_2$)$_x$—CO— wherein x is 2-20. In another embodiment, x is 4-12. In another embodiment, x is 6-10. In one embodiment, Z is —(CH$_2$)$_y$—C$_6$H$_4$—(CH$_2$)$_y$— wherein y is 1-10. In another embodiment, y is 2-5. In one embodiment, Z is —(CH$_2$)$_w$— wherein w is 2-20. In another embodiment, w is 4-10.

In another particular embodiment, the inhibitors of IAPs of the present invention are compounds of formula V:

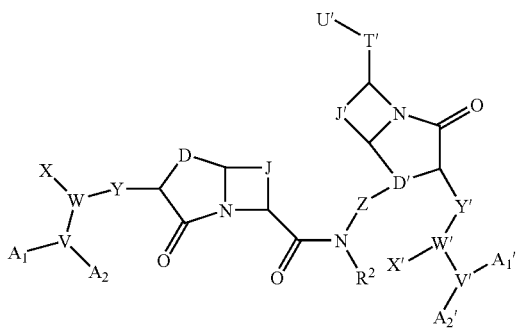

V wherein $A_1$, $A_2$, V, W, X, Y, D, J, Z, $A_1'$, $A_2'$, V', W', X', Y', D', J', T', U' and $R^2$ have the meanings as above; or pharmaceutically acceptable salts or prodrugs thereof.

In another particular embodiment, intermediates useful for making IAPs of the present invention are compounds of formula XIII:

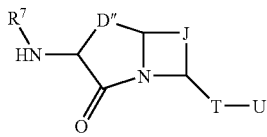

wherein:

D" is $(CR^1R^2)_n-R^{5c}-(CR^3R^4)_m$;

J is selected from the group consisting of optionally substituted alkylenyl and $(CR^1R^2)_n-R^{5b}-(CR^3R^4)_q$;

T is selected from the group consisting of C=O, C=S, C=NR$^1$, S, O, NR$^1$, CR$^1$R$^2$, optionally substituted carbocyclic, optionally substituted heterocyclic, optionally substituted aryl and optionally substituted heteroaryl;

U is selected from the group consisting of hydrogen, NR$^1$R$^2$, OR$^1$, SR$^1$, optionally substituted alkyl and optionally substituted aryl;

n, m, p and q are independently selected from 0-5;

each R$^1$, R$^2$, R$^3$ and R$^4$ are independently selected from the group consisting of hydrogen, optionally substituted alkyl, optionally substituted carbocyclic, optionally substituted heterocyclic, optionally substituted aryl and optionally substituted heteroaryl;

R$^{5c}$ is selected from the group consisting of C=O, C=S, C=NR$^1$, S, O, NR$^1$, CR$^{1a}$R$^{2a}$, NCOR$^8$ and NCO$_2$R$^8$;

R$^{1a}$ and R$^{2a}$ are independently selected from the group consisting of hydrogen, hydroxy, azido, optionally substituted alkyl, optionally substituted carbocyclic, optionally substituted heterocyclic, optionally substituted aryl and optionally substituted heteroaryl;

R$^{5b}$ is selected from the group consisting of O, S, NR$^1$, CR$^1$R$^2$, C=O, C=S and C=NR$^1$;

R$^7$ is selected from the group consisting of hydrogen, CO$_2$R$^{7a}$ and COCH(R$^{7b}$)N(R$^{7c}$)CO$_2$R$^{7a}$;

R$^{7a}$ is selected from the group consisting of optionally substituted alkyl, optionally substituted carbocyclic, optionally substituted heterocyclic, optionally substituted aryl and optionally substituted heteroaryl;

R$^{7b}$ is optionally substituted C$_{1-3}$ alkyl;

R$^{7c}$ is selected from the group consisting of hydrogen and optionally substituted alkyl;

and,

R$^8$ is selected from the group consisting of optionally substituted alkyl, optionally substituted carbocyclic, optionally substituted heterocyclic, optionally substituted aryl and optionally substituted heteroaryl.

In a further embodiment, R$^{7a}$ is t-butyl. In a further embodiment, n is 1, m is 2, R$^{5c}$ is NCO$_2$R$^8$ and R$^8$ is benzyl. In a further embodiment, R$^{5c}$ is CR$^{1a}$R$^{2a}$, R$^{1a}$ is selected from the group consisting of hydroxy, azido and optionally substituted heteroaryl and R$^{2a}$ is hydrogen.

Useful alkyl groups include straight-chained or branched C$_{1-18}$ alkyl groups, especially methyl, ethyl, propyl, isopropyl, t-butyl, sec-butyl, 3-pentyl and 3-hexyl groups. The term "alkylenyl" refers to a divalent alkyl radical containing 1, 2, 3 or 4 joined methylene groups as exemplified by —(CH$_2$)$_4$—.

Useful alkenyl groups include straight-chained or branched C$_{2-18}$ alkyl groups, especially ethenyl, propenyl, isopropenyl, butenyl, isobutenyl, and hexenyl.

The term "alkenylene" as used herein refers to a divalent radical derived from an alkene as exemplified by —CH$_2$CH=CHCH$_2$—.

Useful alkynyl groups are C$_{2-18}$ alkynyl groups, especially ethynyl, propynyl, butynyl, and 2-butynyl groups Useful cycloalkyl groups are C$_{3-8}$ cycloalkyl. Typical cycloalkyl groups include cyclopropyl, cyclobutyl, cyclopentyl, cyclohexyl, cycloheptyl, adamantyl and norbornyl.

Useful aryl groups include C$_{6-14}$ aryl, especially phenyl (abbreviated as "Ph"), naphthyl, phenanthrenyl, anthracenyl, indenyl, azulenyl, biphenyl, biphenylenyl, and fluorenyl groups.

Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthenyl, 2H-pyrrolyl, pyrrolyl, imidazolyl, triazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide, pyrimidinyl N-oxide, and the like.

Optional substituents include one or more alkyl; halo; azido; haloalkyl; hydroxyl; alkynyl; cycloalkyl; heteroalkyl; heteroalkynyl; aryl optionally substituted with one or more lower alkyl, halo, haloalkyl or heteroaryl groups; aryloxy optionally substituted with one or more lower alkyl, haloalkyl, or heteroaryl groups; aralkyl; heteroaryl optionally substituted with one or more lower alkyl, haloalkyl, and aryl groups; heteroaryloxy optionally substituted with one or more lower alkyl, haloalkyl, and aryl groups; alkoxy; alkylthio; arylthio; amido; amino; acyloxy; arylacyloxy optionally substituted with one or more lower alkyl, haloalkyl, and aryl groups; diphenylphosphinyloxy optionally substituted with one or more lower alkyl, halo or haloalkyl groups; heterocyclo optionally substituted with one or more lower alkyl, haloalkyl, and aryl groups; heterocycloalkoxy optionally substituted with one or more lower alkyl, haloalkyl, and aryl groups; partially unsaturated heterocycloalkyl optionally substituted with one or more lower alkyl, haloalkyl, and aryl groups; partially unsaturated heterocycloalkyloxy optionally substituted with one or more lower alkyl, haloalkyl, and aryl groups; and any covalent linker (vide infra).

Useful saturated or partially saturated carbocyclic groups are cycloalkyl groups as defined above, as well as cycloalkenyl groups, such as cyclopentenyl, cycloheptenyl and cyclooctenyl. Carbocyclic groups also include groups having fused optionally substituted aryl groups such as tetralin.

Useful halo or halogen groups include fluorine, chlorine, bromine and iodine.

Useful alkylaryl and alkylheteroaryl groups include any of the above-mentioned C$_{1-18}$ alkyl groups substituted by any of the above-mentioned C$_{6-14}$ aryl groups or heteroaryl groups. Useful values include benzyl, phenethyl and naphthylmethyl.

Useful haloalkyl groups include C$_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful heteroalkyl groups include $C_{1-10}$ alkyl groups containing one or more nitrogen, oxygen or sulfur atoms, e.g., —CH$_2$CH$_2$OCH$_3$, —CH$_2$OH, —CH$_2$CH$_2$NH$_2$ and —CH$_2$CH$_2$NHCH$_3$ groups.

Useful heteroalkynyl groups include $C_{2-18}$ alkynyl groups containing one or more nitrogen, oxygen or sulfur atoms, e.g., —CH$_2$OCH$_2$CCH.

Useful alkoxy groups include oxygen substituted by one of the $C_{1-10}$ alkyl groups mentioned above.

Useful alkylthio groups include sulfur substituted by one of the $C_{1-10}$ alkyl groups mentioned above. Also included are the sulfoxides and sulfones of such alkylthio groups.

Useful amido groups include carbonylamido as well as any $C_{1-6}$ acyl (alkanoyl) attached to an amino nitrogen, e.g., acetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g., formyloxy, acetoxy, propionyloxy, butanoyloxy, pentanoyloxy, hexanoyloxy and the like.

Useful arylacyloxy groups include any of the aryl groups mentioned above substituted on any of the acyloxy groups mentioned above, e.g., 2,6-dichlorobenzoyloxy, 2,6-difluorobenzoyloxy and 2,6-di-(trifluoromethyl)-benzoyloxy groups.

Useful amino groups include —NH$_2$, —NHR$^{11}$, and —NR$^{11}$R$^{11}$, wherein R$^{11}$ and R$^{12}$ are $C_{1-10}$ alkyl or cycloalkyl groups as defined above.

Useful saturated or partially saturated heterocyclic groups include tetrahydrofuranyl, pyranyl, piperidinyl, piperizinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

Useful arylene groups include $C_{6-14}$ arylene, especially phenylene, naphthylene, phenanthrenylene, anthracenylene, indenylene, azulenylene, biphenylene, biphenylenylene, and fluorenylene groups.

Useful heteroarylene groups include disubstituted heteroaryl groups such as 2,5-thienylene, 2,4-imidazolylene, and 1,3-triazolylene.

Throughout the specification, groups an optional substituents thereof are chosen to provide stable moieties and compounds.

Covalent linkers that may be used in the invention include any bivalent covalent linker. In some embodiments, the linker is a contiguous chain of between 5 and 50 atoms. The linker typically has a length of from about 5 angstroms to about 100 angstroms using standard bond lengths and angles. More preferably, the linker has a length of from about 10 angstroms to about 50 angstroms. In certain embodiments, the linker comprises at least one aryl, heteroaryl, or heterocyclic moiety. In other embodiments, the linker is symmetrical. In other embodiments, the linker is non-symmetrical. The linker may be any one of the many known homobifunctional and heterobifunctional linkers. See, e.g., U.S. Pat. Nos. 7,001,989, 6,967,107, 6,921,669, 6,906,182, 6,887,952, 6,759,509, 6,521,431, 6,512,101, 5,880,270, 5,856,571, 5,824,805, 5,262,524, 5,258,498, 5,212,075, 5,165,923, 5,141,648, each if which is incorporated by reference in its entirety In another embodiment, the linker may comprise a —COR$^{9a}$— or —R$^{9a}$CO— group bound to any one of A$_1$, Y, D, J, T or U and any one of A$_1$', Y', D', J', T' or U' wherein R$^{7a}$ is O, S or NR$^{10a}$ and R$^{10a}$ is hydrogen or lower alkyl. In this embodiment, the linker further comprises a group bound to R$^{9a}$— of the first group and CO— of the second group which may include an optionally substituted alkylene group wherein any one of the carbon atoms of the alkylene group may be substituted by one or more O, S, NR$^{10a}$, arylene, and heteroarylene groups. Examples of such linkers include, without limitation:

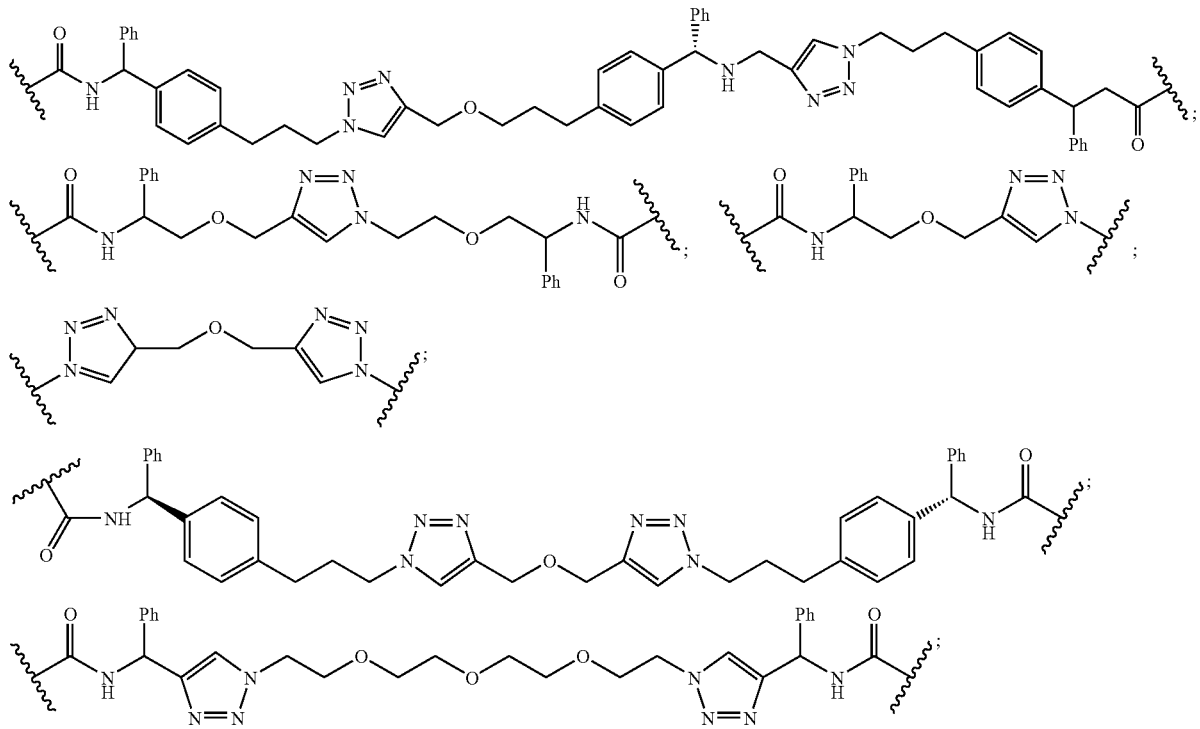

-continued

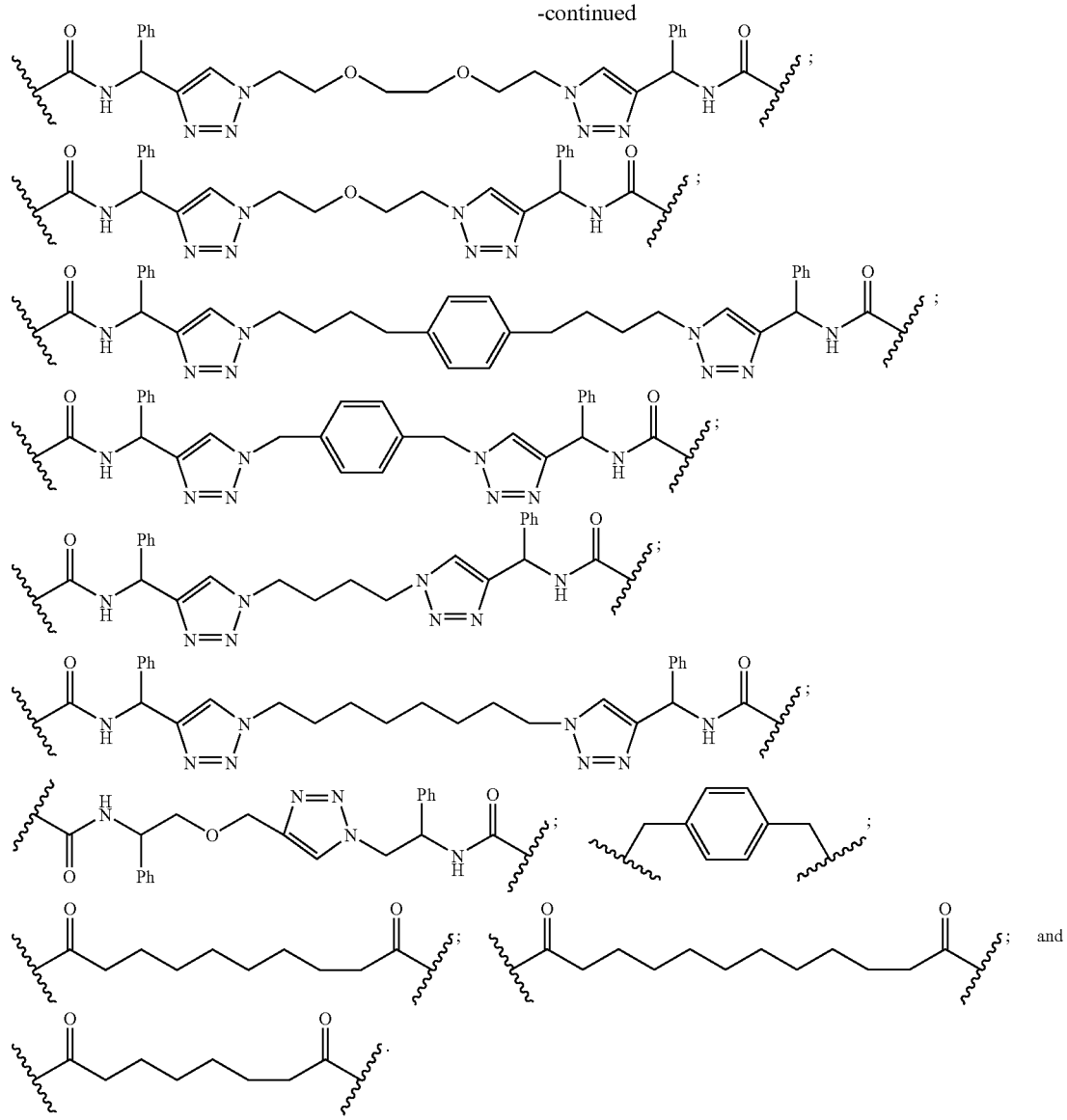

In another embodiment, the linker may comprise a carbonyl group bound to any one of $A_1$, Y, D, J, T or U and any one of $A_1'$, Y', D', J', T' or U', and further comprise an alkylene, polyalkylene or aralkyl glycol group bound to the carbonyl groups. Examples of such glycols include polyoxyethylene, polyoxypropylene, and block copolymers of polyoxyethylene and polyoxypropylene glycol, diethylene glycol, triethylene glycol, tetraethylene glycol, dipropylene glycol, thioethylene glycol, and pentaethylene, hexaethylene, heptaethylene, octaethylene, nonaethylene, and decaethylene glycols. Particular examples of these glycols include ethylene glycol; 1,2-propylene glycol; 1,3-propanediol; 2,4-dimethyl-2-ethylhexane-1,3, diol; 2,2-dimethyl-1,3-propanediol; 2-ethyl-2-butyl-1,3-propanediol; 2-ethyl-2-isobutyl-1,3-propanediol; 1,3-butanediol; 1,4-butanediol: 1,5-pentanediol; 1,6-hexanediol; 2, 2-4-trimethyl-1,6-hexanediol; thiodiethanol. 1,2-cyclohexanedimethanol; 1,3-cyclohexanedimethanol; 1,4-cyclohexanedimethanol; 2,2,4,4-tetramethyl-1,3-cyclobutanediol; p-xylylenediol, 2,3-naphthalenediol and 2,7-naphthalenediol. Examples of diamino compounds include 1,3-bis-(2,4-diaminophenoxy)propane; 2,4-diamino-5-methylphenetol; 2,4-diamino-5-methylphenoxyethanol; 2,4-diaminodiphenylamine; 2,4-diaminophenol; 2,4-diaminophenol; 2,4-diaminophenoxyethanol; 2,6-bis(2-hydroxyethoxy)-3,5-pyridinediamine; 2,6-diaminopyridine; 2,6-dimethoxy-3,5-pyridinediamine, 2-chloro-5-nitro-n-hydroxyethyl p-phenylenediamine, 2-chloro-p-phenylenediamine, 2-aminomethyl-p-aminophenol and 4,5-diamino-1-methylpyrazole. Examples of amino-hydroxy compounds include 2-amino-3-hydroxypyridine; 2-amino-3-nitrophenol; 2-amino-4-hydroxyethylaminoanisole; 2-amino-4-hydroxyethylaminoanisole sulfate; and 2-amino-6-chloro-4-nitrophenol.

In another embodiment, the linker may comprise an oxygen or amino group bound to any one of $A_1$, Y, D, J, T or U and any one of $A_1'$, Y', D', J', T' or U', and further comprise a diacid thereby giving a diester, diamide or ester amide. Examples of such diacids include succinic acid, fumaric acid, adipic acid and the like.

In another embodiment, the linker comprises a 1,2,3-triazol-4,5-ene group which is introduced by cycloaddition of a propargyl group with an azide group.

The linker is used to join two Smac mimetic compounds into a bivalent structure. The Smac mimetic compounds joined together may be the same or different, and may be any Smac mimetic compound known to bind to IAPs and inhibit the interaction of IAPs and caspases. In one embodiment, the Smac mimetics are conformationally constrained. In another embodiment, the Smac mimetics do not contain any naturally occurring amino acids. In a further embodiment, the Smac mimetics do not contain any peptide bonds. Examples of known Smac mimetic compounds that are useful as starting materials in the present invention include the following:

WO 2005/069888 discloses Smac peptidomimetic compounds of formula VI:

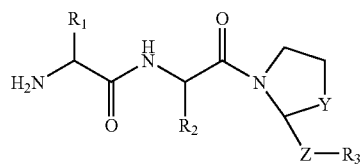

VI or a pharmaceutically acceptable salt or prodrug thereof, wherein:
$R_1$ is $C_{1-2}$ alkyl or $C_{1-2}$ haloalkyl;
$R_2$ is branched or unbranched alkyl or cycloalkyl or substituted or unsubstituted aryl, alkylaryl, heteroaryl, or alkylheteroaryl;
$R_3$ is branched or unbranched alkyl or cycloalkyl or substituted or unsubstituted aryl, alkylaryl, heteroaryl, or alkylheteroaryl;
Y is $(CH_2)_{0-3}$, wherein one or more carbon can be replaced by one or more heteroatoms selected from oxygen, sulfur, and nitrogen, and one or more hydrogens in $CH_2$ groups can be replaced by a branched or unbranched alkyl or cyclic alkyl or substituted or unsubstituted aryl, alkylaryl, heteroaryl, or alkylheteroaryl; and
Z is CONH, $CH_2O$, NHCO, $(CH_2)_{1-4}$, $(CH_2)_{1-3}$CONH $(CH_2)_{0-3}$, $(CH_2)_{1-3}S(CH_2)_{0-3}$, $(CH_2)_{1-3}NH(CH_2)_{0-3}$, $(CH_2)_{1-3}NHCO(CH_2)_{0-3}$, $(CH_2)_{1-3}NHSO_2(CH_2)_{0-3}$, $(CH_2)_{1-3}NHC(O)NH(CH_2)_{0-3}$, $(CH_2)_{1-3}NHC(S)NH(CH_2)_{0-3}$, or $(CH_2)_{1-3}NR'(CH_2)_{0-3}$, wherein R' is branched or unbranched alkyl or cycloalkyl or substituted or unsubstituted aryl, alkylaryl, heteroaryl, or alkylheteroaryl.

WO 2005/069894 discloses Smac mimetic compounds of formula VII:

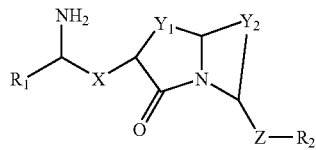

VII or a pharmaceutically acceptable salt or prodrug thereof, wherein:
$R_1$ is $C_{1-2}$ alkyl or $C_{1-2}$ haloalkyl;
$R_2$ is branched or unbranched alkyl or cycloalkyl or substituted or unsubstituted aryl, alkylaryl, heteroaryl, or alkylheteroaryl;
X is CONH, $CH_2O$, $CH_2NH$, $CH_2S$, or $(CH_2)_{1-3}$;
$Y_1$ is $(CH_2)_{1-5}$, wherein one or more carbon can be replaced by one or more heteroatoms selected from oxygen, sulfur, and nitrogen, and one or more hydrogens in $CH_2$ groups can be replaced by a branched or unbranched alkyl or cyclic alkyl or substituted or unsubstituted aryl, alkylaryl, heteroaryl, or alkylheteroaryl;
$Y_2$ is $(CH_2)_{1-5}$, wherein one or more carbon can be replaced by one or more heteroatoms selected from oxygen, sulfur, and nitrogen, and one or more hydrogens in $CH_2$ groups can be replaced by a branched or unbranched alkyl or cyclic alkyl or substituted or unsubstituted aryl, alkylaryl, heteroaryl, or alkylheteroaryl; and
Z is CONH, $CH_2O$, NHCO, $(CH_2)_{1-4}$, $(CH_2)_{1-3}$CONH$(CH_2)_{0-3}$, $(CH_2)_{1-3}S(CH_2)_{0-3}$, $(CH_2)_{1-3}NH(CH_2)_{0-3}$, $(CH_2)_{1-3}NHCO(CH_2)_{0-3}$, $(CH_2)_{1-3}NHSO_2(CH_2)_{0-3}$, $(CH_2)_{1-3}NHC(O)NH(CH_2)_{0-3}$, $(CH_2)_{1-3}NHC(S)NH(CH_2)_{0-3}$, or $(CH_2)_{1-3}NR'(CH_2)_{0-3}$, wherein R' is branched or unbranched alkyl or cycloalkyl or substituted or unsubstituted aryl, alkylaryl, heteroaryl, or alkylheteroaryl WO 2006/010118 discloses Smac mimetics compounds of formula VIII:

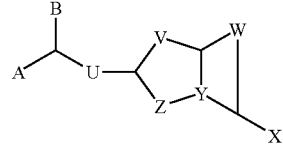

VIII or a pharmaceutically acceptable salt or prodrug thereof, wherein:
A is $NR_1R_2$, or $N^+R_1R_2R_3$;
$R_1$, $R_2$, and $R_3$ are independently hydrogen or optionally substituted $C_{1-8}$ alkyl, $C_{2-8}$ alkenyl, or $C_{2-8}$ alkynyl, in which one or more carbons can be replaced by C=O, C=S, or a heteroatom selected from O, S, and N, and one or more hydrogens in CH, $CH_2$ or $CH_3$ groups can be replaced by fluorine, a branched or unbranched alkyl or cycloalkyl, an optionally substituted aryl, alkylaryl, heteroaryl, or alkylheteroaryl, or $OR_4$, $SR_4$, or $NR_4R_5$;
$R_4$ and $R_5$ are independently hydrogen or optionally substituted $C_{1-4}$ alkyl, $C_{2-5}$ alkenyl, or $C_{2-5}$ alkynyl, in which one or more carbons can be replaced by a heteroatom selected from O, S, and N, or optionally substituted aryl, alkylaryl, heteroaryl, or alkylheteroaryl; or any two of $R_1$, $R_2$, and $R_3$ taken together with the nitrogen to which they are attached form a heterocyclic group, in which one or more carbon atom can be replaced by C=O, C=S, or a heteroatom selected from O, S, and N, with the proviso that the heteroatom is separated from the nitrogen atom by at least two carbons;
B is optionally substituted $C_{1-4}$ alkyl, $C_{2-4}$ alkenyl, or $C_{2-4}$ alkynyl, wherein one or more hydrogens can be replaced by fluorine;
U is CONH, C(O)O, C(S)O, C(S)NH, C(NH)NH, or $(CH_2)_{1-5}$, wherein one or more carbons can be replaced by a heteroatom selected from O, S, and N;
V and W are independently $(CH_2)_{1-5}$, wherein one or more carbons can be replaced by C=O, C=S, or a heteroatom selected from O, S, and N, and one or more hydrogens in $CH_2$ groups can be replaced by a branched or unbranched alkyl or cycloalkyl, an optionally substituted aryl, alkylaryl, heteroaryl, or alkylheteroaryl, or $OR_4$, $SR_4$, or $NR_4R_5$;
X is optionally substituted $C_{1-18}$ alkyl, $C_{2-18}$ alkenyl, $C_{2-18}$ alkynyl, aryl, or heteroaryl, wherein one or more carbons can be replaced by C=O, C=S, or a heteroatom selected from O, S, and N, and one or more hydrogens in CH, CH$_2$ or CH$_3$ groups can be replaced by a branched or unbranched alkyl or cycloalkyl, an optionally substituted aryl, alkylaryl, heteroaryl, or alkylheteroaryl, or OR$_4$, SR$_4$, or NR$_4$R$_5$;

Y is CH or N;

Z is CH$_2$, C=O, C=S, CHSR, CHOR, or CHNR; and

R is hydrogen or optionally substituted C$_{1-4}$ alkyl, C$_{2-4}$ alkenyl, or C$_{2-4}$ alkynyl.

U.S. Published Application No. 2005/0234042 discloses compounds according to formula IX:

<chemical structure IX: R$_1$(R$_2$)N-CH(R$_3$)-C(=O)-NH-CH(R$_4$)-C(=O)-U-R$_5$> wherein R$_1$ is H; C$_1$-C$_4$ alkyl; C$_1$-C$_4$ alkenyl; C$_1$-C$_4$ alkynyl or C$_3$-C$_{10}$ cycloalkyl which are unsubstituted or substituted;

R$_2$ is H; C$_1$-C$_4$ alkyl; C$_1$-C$_4$ alkenyl; C$_1$-C$_4$ alkynyl or C$_3$-C$_{10}$ cycloalkyl which are unsubstituted or substituted;

R$_3$ is H; —CF$_3$; —C$_2$F$_5$; C$_1$-C$_4$ alkyl; C$_1$-C$_4$ alkenyl; C$_1$-C$_4$ alkynyl; —CH$_2$-Z or R$_2$ and R$_3$ together with the nitrogen form a het ring;

Z is H; —OH; F; Cl; —CH$_3$; —CF$_3$; —CH$_2$Cl; —CH$_2$F or —CH$_2$OH;

R$_4$ is C$_1$-C$_{16}$ straight or branched alkyl; C$_1$-C$_{16}$ alkenyl; C$_1$-C$_{16}$ alkynyl; or —C$_3$-C$_{10}$ cycloalkyl; —(CH$_2$)$_{1-6}$-Z$_1$; —(CH$_2$)$_{0-6}$-aryl; and —(CH$_2$)$_{0-6}$-het; wherein alkyl, cycloalkyl and phenyl are unsubstituted or substituted;

Z$_1$ is —N(R$_8$)—C(O)—C$_1$-C$_{10}$ alkyl; —N(R$_8$)—C(O)—(CH$_2$)$_{1-6}$—C$_3$-C$_7$ cycloalkyl; —N(R$_8$)—C(O)—(CH$_2$)$_{0-6}$-phenyl; —N(R$_8$)—C(O)—(CH$_2$)$_{1-6}$-het; —C(O)—N(R$_9$)(R$_{10}$); —C(O)—O—C$_1$-C$_{10}$ alkyl; —C(O)—O—(CH$_2$)$_{1-6}$—C$_3$-C$_7$ cycloalkyl; —C(O)—O—(CH$_2$)$_{0-6}$-phenyl; —C(O)—O—(CH$_2$)$_{1-6}$-het; —O—C(O)—C$_1$-C$_{10}$ alkyl; —O—C(O)—(CH$_2$)$_{1-6}$—C$_3$-C$_7$ cycloalkyl; —O—C(O)—(CH$_2$)$_{0-6}$-phenyl; —O—C(O)—(CH$_2$)$_{1-6}$-het; wherein alkyl, cycloalkyl and phenyl are unsubstituted or substituted;

het is a 5-7 membered heterocyclic ring containing 1-4 heteroatoms selected from N, O and S, or an 8-12 membered fused ring system including at least one 5-7 membered heterocyclic ring containing 1, 2 or 3 heteroatoms selected from N, O, and S, which heterocyclic ring or fused ring system is unsubstituted or substituted on a carbon or nitrogen atom;

R$_8$ is H; —CH$_3$; —CF$_3$; —CH$_2$OH or —CH$_2$Cl;

R$_9$ and R$_{10}$ are each independently H; C$_1$-C$_4$ alkyl; C$_3$-C$_7$ cycloalkyl; —(CH$_2$)$_{1-6}$—C$_3$-C$_7$ cycloalkyl; —(CH$_2$)$_{0-6}$-phenyl; wherein alkyl, cycloalkyl and phenyl are unsubstituted or substituted, or R$_9$ and R$_{10}$ together with the nitrogen form het;

R$_5$ is H; C$_1$-C$_{10}$-alkyl; aryl; phenyl; C$_3$-C$_7$ cycloalkyl; —(CH$_2$)$_{1-6}$—C$_3$-C$_7$ cycloalkyl; —C$_1$-C$_{10}$ alkyl-aryl; —(CH$_2$)$_{0-6}$—C$_3$-C$_7$ cycloalkyl-(CH$_2$)$_{0-6}$-phenyl; —(CH$_2$)$_{0-4}$—CH—((CH$_2$)$_{1-4}$-phenyl)$_2$; —(CH$_2$)$_{0-6}$—CH (phenyl)$_2$; -indanyl; —C(O)—C$_1$-C$_{10}$ alkyl; —C(O)—(CH$_2$)$_{1-6}$—C$_3$-C$_7$-cycloalkyl; —C(O)—(CH$_2$)$_{0-6}$-phenyl; —(CH$_2$)$_{0-6}$—C(O)-phenyl; —(CH$_2$)$_{0-6}$-het; —C(O)—(CH$_2$)$_{1-6}$-het; or R$_5$ is a residue of an amino acid, wherein the alkyl, cycloalkyl, phenyl and aryl substituents are unsubstituted or substituted;

U is as shown in structure X:

<chemical structure X: five-membered ring with X, R$_6$, R$_7$, R'$_6$, R'$_7$, (R$_a$)$_n$—R$_c$, (R$_b$)$_n$—R$_d$> wherein n=0-5;

X is —CH or N;

Ra and Rb are independently an O, S, or N atom or C$_{0-8}$ alkyl wherein one or more of the carbon atoms in the alkyl chain may be replaced by a heteroatom selected from O, S or N, and where the alkyl may be unsubstituted or substituted;

Rd is selected from: (a) —Re-Q-(Rf)$_p$(Rg)$_q$; or (b) Ar$_1$-D-Ar$_2$;

Rc is H or Rc and Rd may together form a cycloalkyl or het; where if Rd and Rc form a cycloalkyl or het, R$_5$ is attached to the formed ring at a C or N atom;

p and q are independently 0 or 1;

Re is C$_{1-8}$ alkyl or alkylidene, and Re which may be unsubstituted or substituted;

Q is N, O, S, S(O), or S(O)$_2$;

Ar$_1$ and Ar$_2$ are substituted or unsubstituted aryl or het;

Rf and Rg are each independently H; —C$_1$-C$_{10}$ alkyl; C$_1$-C$_{10}$ alkylaryl; —OH; —O—C$_1$-C$_{10}$ alkyl; —(CH$_2$)$_{0-6}$—C$_3$-C$_7$ cycloalkyl; —O—(CH$_2$)$_{0-6}$-aryl; phenyl; aryl; phenyl-phenyl; —(CH$_2$)$_{1-6}$-het; —O—(CH$_2$)$_{1-6}$-het; —OR$_{11}$; —C(O)—R$_{11}$; —C(O)—N(R$_{11}$)(R$_{12}$); —N(R$_{11}$)(R$_{12}$); —S—R$_{11}$; —S(O)—R$_{11}$; —S(O)$_2$—R$_{11}$; —S(O)$_2$—NR$_{11}$R$_{12}$; —NR$_{11}$—S(O)$_2$—R$_{12}$; S—C$_1$-C$_{10}$ alkyl; aryl-C$_1$-C$_4$ alkyl; het-C$_1$-C$_4$-alkyl wherein alkyl, cycloalkyl, het and aryl are unsubstituted or substituted; —SO$_2$—C$_1$-C$_2$ alkyl; —SO$_2$—C$_1$-C$_2$ alkylphenyl; —O—C$_1$-C$_4$ alkyl; or Rg and Rf form a ring selected from het or aryl;

D is —CO—; —C(O)—C$_{1-7}$ alkylene or arylene; —CF$_2$—; —O—; —S(O)$_r$ where r is 0-2; 1,3dioxolane; or C$_{1-7}$ alkyl-OH; where alkyl, alkylene or arylene may be unsubstituted or substituted with one or more halogens, OH, —O—C$_1$-C$_6$ alkyl, —S—C$_1$-C$_6$ alkyl or —CF$_3$; or D is —N(Rh) wherein Rh is H; C$_{1-7}$ alkyl (unsubstituted or substituted); aryl; —O(C$_{1-7}$ cycloalkyl) (unsubstituted or substituted); C(O)—C$_1$-C$_{10}$ alkyl; C(O)—C$_0$-C$_{10}$ alkyl-aryl; C—O—C$_1$-C$_{10}$ alkyl; C—O-C$_0$-C$_{10}$ alkyl-aryl or SO$_2$—C$_1$-C$_{10}$-alkyl; SO$_2$—(C$_0$-C$_{10}$-alkylaryl);

R$_6$, R$_7$, R'$_6$ and R'$_7$ are each independently H; —C$_1$-C$_{10}$ alkyl; —C$_1$-C$_{10}$ alkoxy; aryl-C$_1$-C$_{10}$ alkoxy; —OH; —O—C$_1$-C$_{10}$ alkyl; —(CH$_2$)$_{0-6}$—C$_3$-C$_7$ cycloalkyl; —O—(CH$_2$)$_{0-6}$-aryl; phenyl; —(CH$_2$)$_{1-6}$-het; —O—(CH$_2$)$_{1-6}$-het; —OR$_{11}$; —C(O)—R$_{11}$; —C(O)—N(R$_{11}$)(R$_{12}$); —N(R$_{11}$)(R$_{12}$); —S—R$_{11}$; —S(O)—R$_{11}$; —S(O)$_2$—R$_{11}$; —S(O)$_2$—NR$_{11}$R$_{12}$; —NR$_{11}$—S(O)$_2$—R$_{12}$; wherein alkyl, cycloalkyl and aryl are unsubstituted or substituted; and R$_6$, R$_7$, R$_{16}$ and R$_{17}$ can be united to form a ring system;

R$_{11}$ and R$_{12}$ are independently H; C$_1$-C$_{10}$ alkyl; —(CH$_2$)$_{0-6}$—C$_3$-C$_7$ cycloalkyl; —(CH$_2$)$_{0-6}$—(CH)$_{0-1}$ (aryl)$_{1-2}$; —C(O)—C$_1$-C$_{10}$ alkyl; —C(O)—(CH$_2$)$_{1-6}$—C$_3$-C$_7$ cycloalkyl; —C(O)—O—(CH$_2$)$_{0-6}$-aryl; —C(O)—(CH$_2$)$_{0-6}$—O-fluorenyl; —C(O)—NH—(CH$_2$)$_{0-6}$-aryl; —C(O)—(CH$_2$)$_{0-6}$-aryl; —C(O)—(CH$_2$)$_{1-6}$-het; —C(S)—C$_1$-C$_{10}$alkyl; —C(S)—(CH$_2$)$_{1-6}$—C$_3$-C$_7$ cycloalkyl; —C(S)—O—(CH$_2$)$_{0-6}$-aryl; —C(S)—(CH$_2$)$_{0-6}$—O-fluorenyl; —C(S)—NH—(CH$_2$)$_{0-6}$-aryl; —C(S)—(CH$_2$)$_{0-6}$-aryl; —C(S)—(CH$_2$)$_{1-6}$-het;

wherein alkyl, cycloalkyl and aryl are unsubstituted or substituted; or $R_{11}$ and $R_{12}$ are a substituent that facilitates transport of the molecule across a cell membrane; or $R_{11}$ and $R_{12}$ together with the nitrogen atom form het;

wherein the alkyl substituents of $R_{11}$ and $R_{12}$ may be unsubstituted or substituted by one or more substituents selected from $C_1$-$C_{10}$ alkyl, halogen, OH, —O—$C_1$-$C_6$ alkyl, —S—$C_1$-$C_6$ alkyl or —$CF_3$;

substituted cycloalkyl substituents of $R_{11}$ and $R_{12}$ are substituted by one or more substituents selected from a $C_1$-$C_{10}$ alkene; $C_1$-$C_6$ alkyl; halogen; OH; —O—$C_1$-$C_6$ alkyl; —S—$C_1$-$C_6$ alkyl or —$CF_3$; and substituted phenyl or aryl of $R_{11}$ and $R_{12}$ are substituted by one or more substituents selected from halogen; hydroxy; $C_1$-$C_4$ alkyl; $C_1$-$C_4$ alkoxy; nitro; —CN; —O—C(O)—$C_1$-$C_4$ alkyl and —C(O)—O—$C_1$-$C_4$-aryl, or pharmaceutically acceptable salts thereof.

U.S. Published Application No. 2005/0261203 discloses compounds of formula XI:

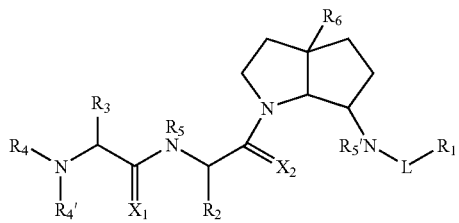

wherein $X_1$ and $X_2$ are independently O or S;
L is a bond, —C($X_3$)—, —C($X_3$)$NR_{12}$ or —C($X_3$)O— wherein $X_3$ is O or S and $R_{12}$ is H or $R_1$;
$R_1$ is alkyl, a carbocycle, carbocycle-substituted alkyl, a heterocycle or heterocycle-substituted alkyl, wherein each is optionally substituted with halogen, hydroxyl, mercapto, carboxyl, alkyl, haloalkyl, alkoxy, alkylsulfonyl, amino, nitro, aryl and heteroaryl;
$R_2$ is alkyl, cycloalkyl, cycloalkylalkyl, aryl, aralkyl, a heterocycle or heterocyclylalkyl;
$R_3$ is H or alkyl;
$R_4$ and $R_{4'}$ are independently H, alkyl, aryl, aralkyl, cycloalkyl, cycloalkylalkyl, heteroaryl, or heteroaralkyl wherein each is optionally substituted with halogen, hydroxyl, mercapto, carboxyl, alkyl, alkoxy, amino and nitro;
$R_5$ and $R_{5'}$ are each independently H or alkyl;
$R_6$ is H or alkyl;
and salts and solvates thereof.

U.S. Published Application No. 2006/0014700 discloses compounds of formula XII:

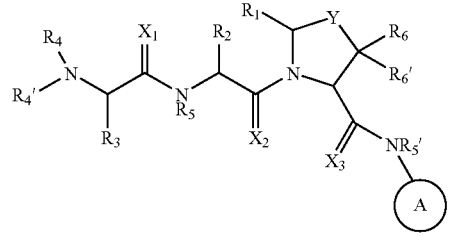

wherein $X_1$, $X_2$ and $X_3$ are independently O or S;
Y is (CHR$_7$)$_n$, O or S; wherein n is 1 or 2 and $R_7$ is H, halogen, alkyl, aryl, aralkyl, amino, arylamino, alkylamino, aralkylamino, alkoxy, aryloxy or aralkyloxy;
A is a 5-member heterocycle comprising 1 to 4 heteroatoms optionally substituted with amino, hydroxyl, mercapto, halogen, carboxyl, amidino, guanidino, alkyl, alkoxy, aryl, aryloxy, acyl, acyloxy, acylamino, alkoxycarbonylamino, cycloalkyl, alkylthio, alkylsulfinyl, alkylsulfonyl, aminosulfonyl, alkylaminosulfonyl, alkylsulfonylamino or a heterocycle; wherein each alkyl, alkoxy, aryl, aryloxy, acyl, acyloxy, acylamino, cycloalkyl and heterocycle substitution is optionally substituted with hydroxyl, halogen, mercapto, carboxyl, alkyl, alkoxy, haloalkyl, amino, nitro, cyano, cycloalkyl, aryl or a heterocycle;
$R_1$ is H or $R_1$ and $R_2$ together form a 5-8 member ring;
$R_2$ is alkyl, cycloalkyl, cycloalkylalkyl, aryl, aralkyl, a heterocycle or heterocyclylalkyl; each optionally substituted with hydroxyl, mercapto, halogen, amino, carboxyl, alkyl, haloalkyl, alkoxy or alkylthio;
$R_3$ is H or alkyl;
$R_4$ and $R_{4'}$ are independently H, hydroxyl, amino, alkyl, aryl, aralkyl, cycloalkyl, cycloalkylalkyl, heteroaryl, or heteroarylalkyl wherein each alkyl, aryl, aralkyl, cycloalkyl, cycloalkylalkyl, heteroaryl and heteroarylalkyl is optionally substituted with halogen, hydroxyl, mercapto, carboxyl, alkyl, alkoxy, amino and nitro;
$R_5$, and $R_{5'}$ are each independently H or alkyl;
$R_6$, and $R_{6'}$ are each independently H, alkyl, aryl or aralkyl;
and salts and solvates thereof.

Certain of the compounds of the present invention may exist as stereoisomers including optical isomers. The invention includes all stereoisomers, both as pure individual stereoisomer preparations and enriched preparations of each, and both the racemic mixtures of such stereoisomers as well as the individual enantiomers that may be separated according to methods that are well known to those of skill in the art.

In certain embodiments of the invention the compound of Formulae II-IV is selected from the group consisting of:

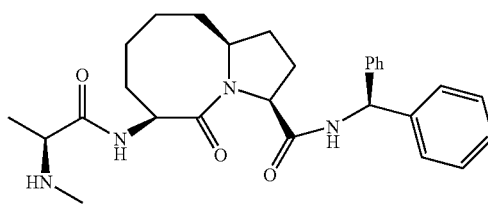

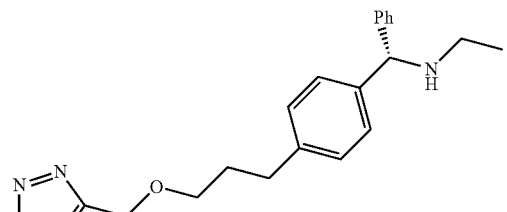

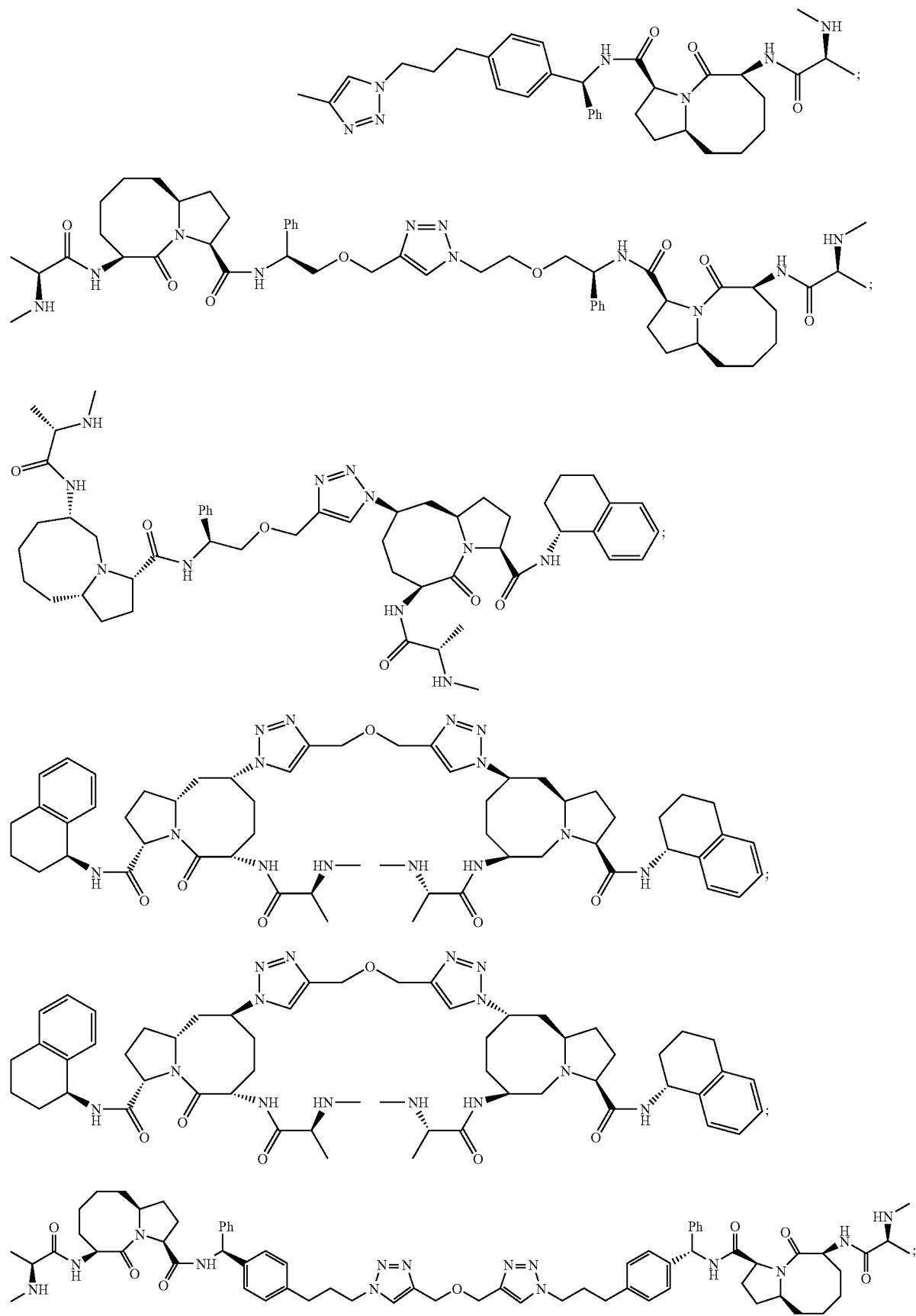

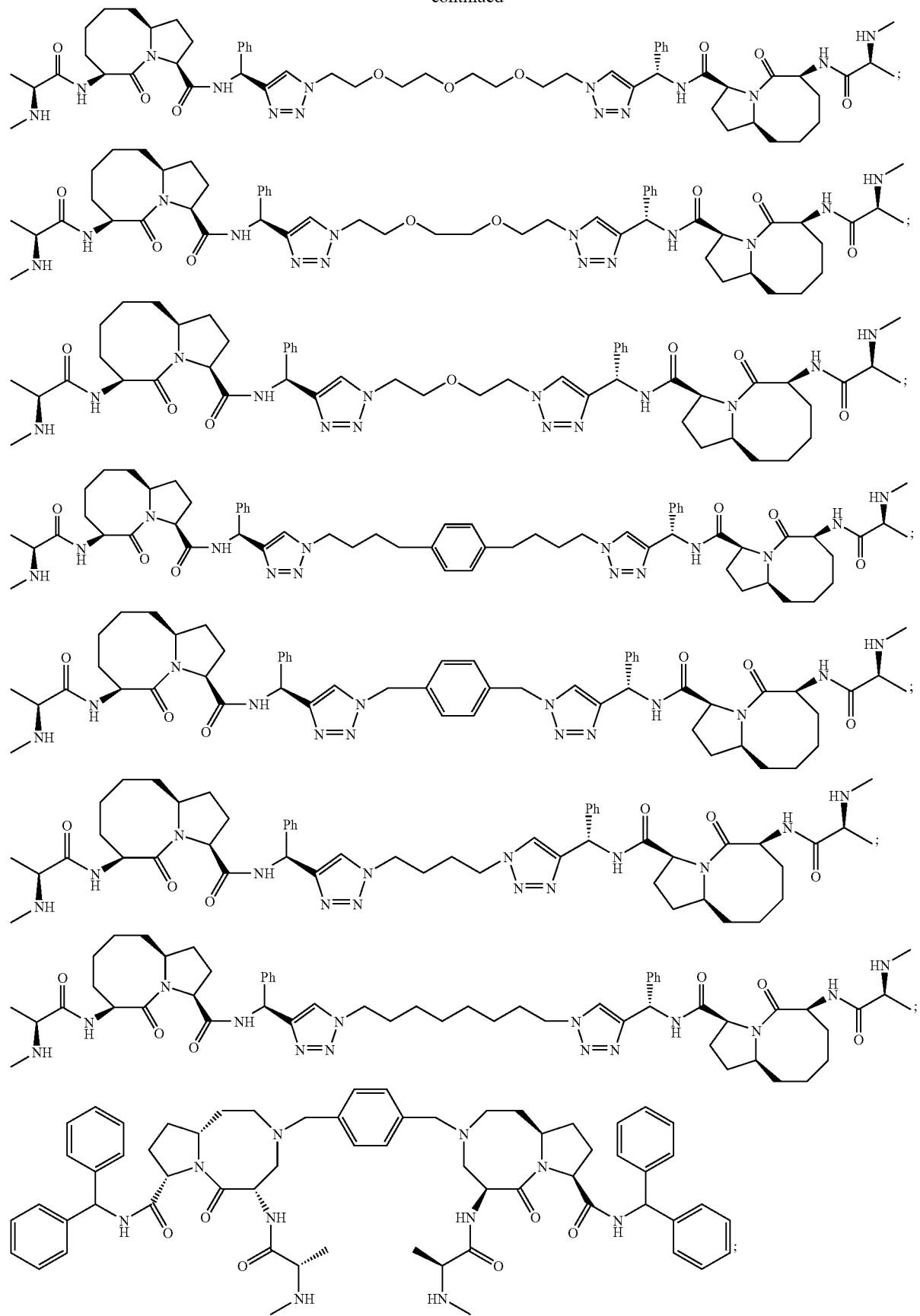

-continued
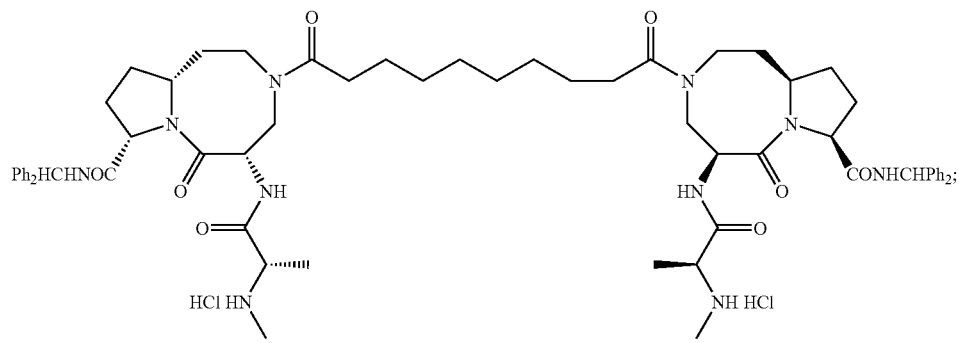
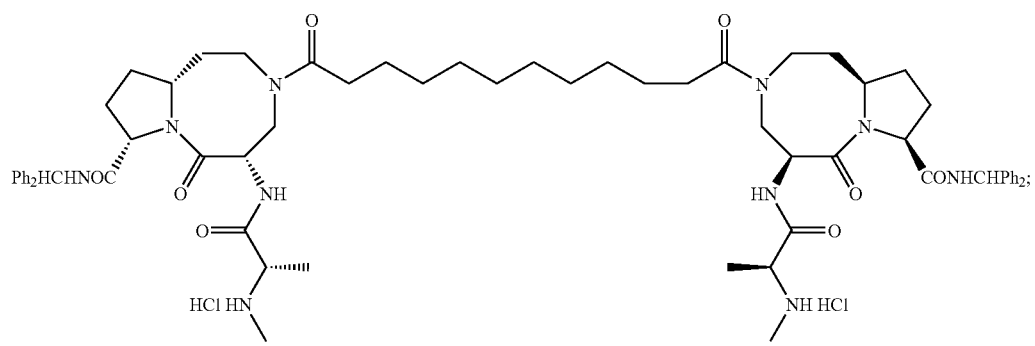
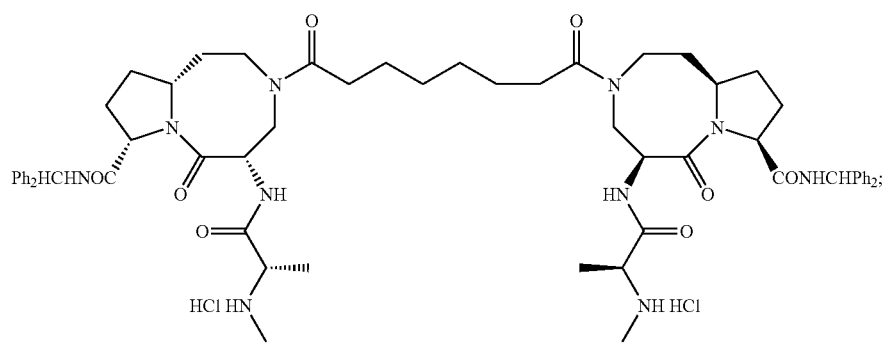
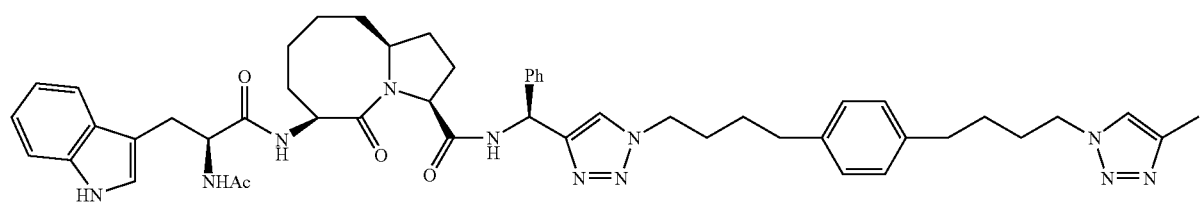
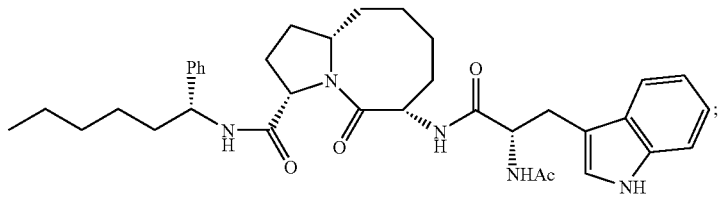
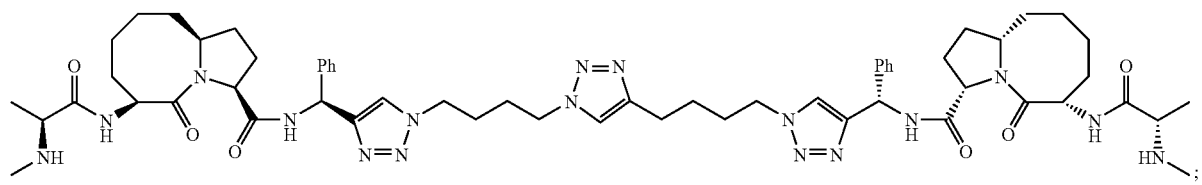

-continued
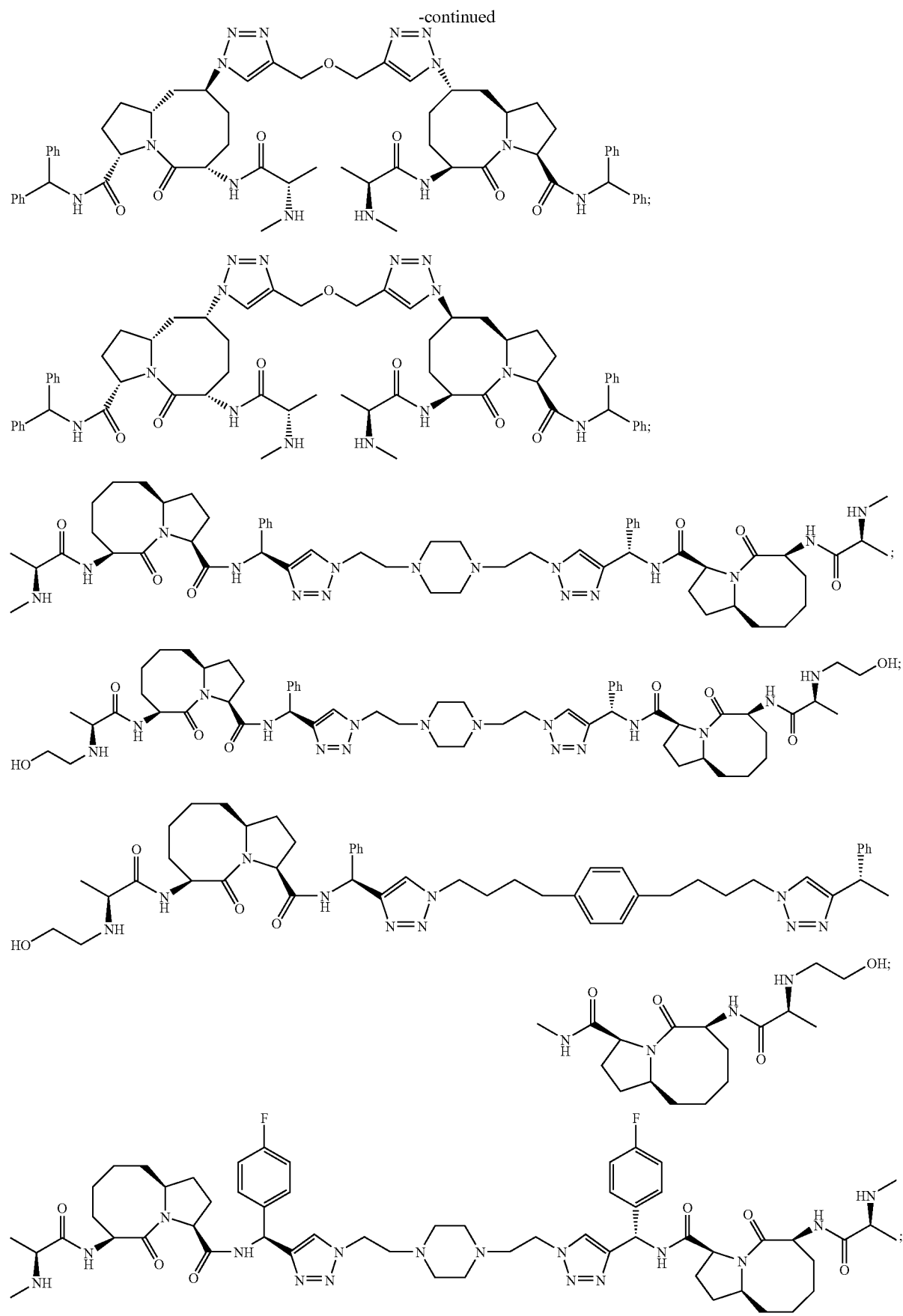

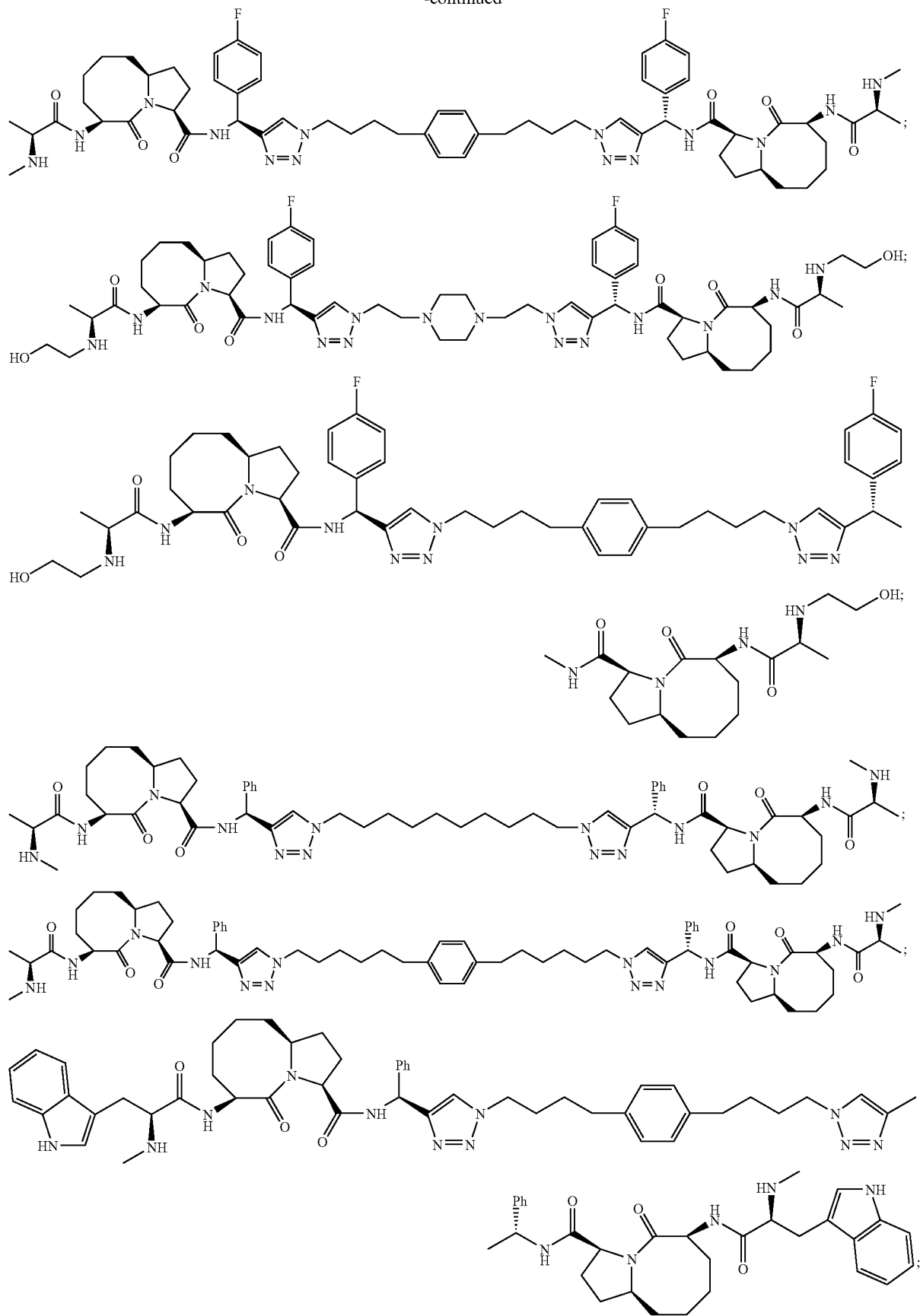

-continued
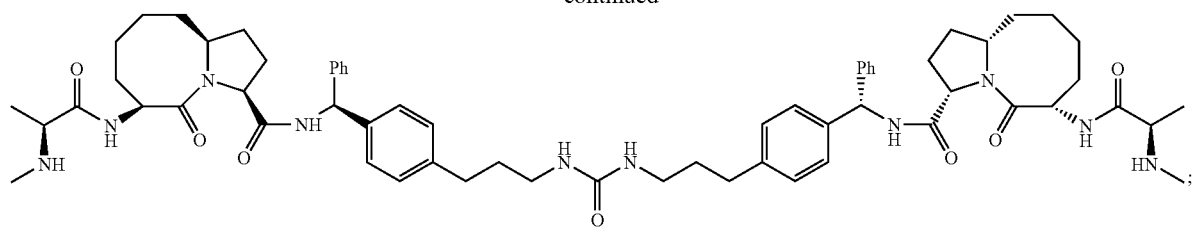
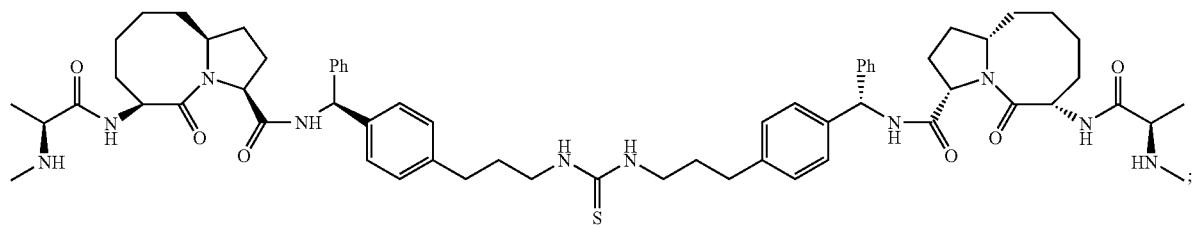
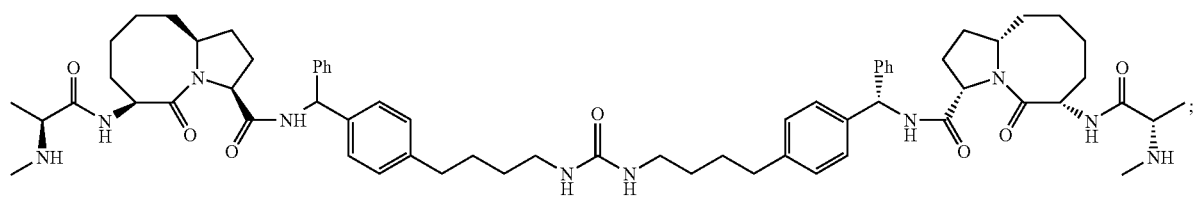
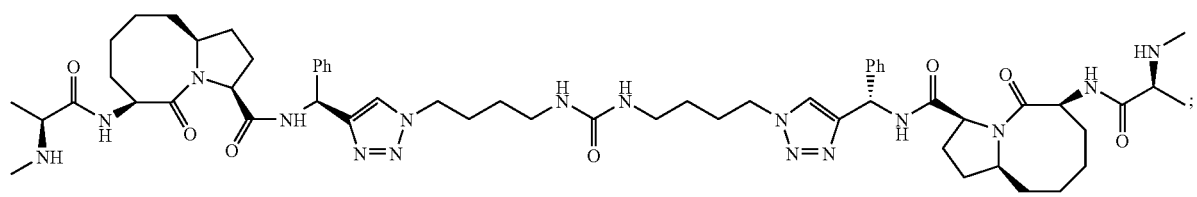
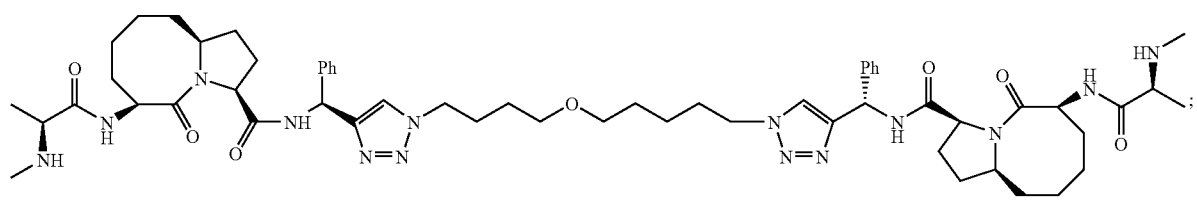
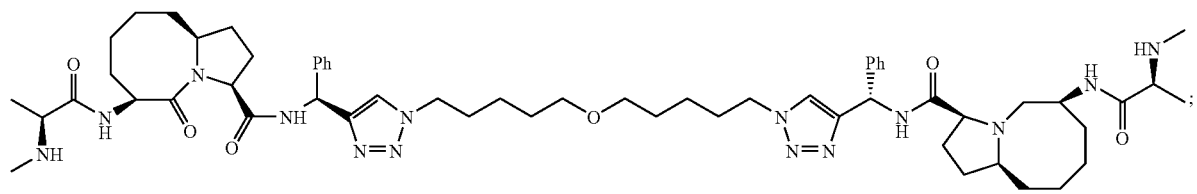
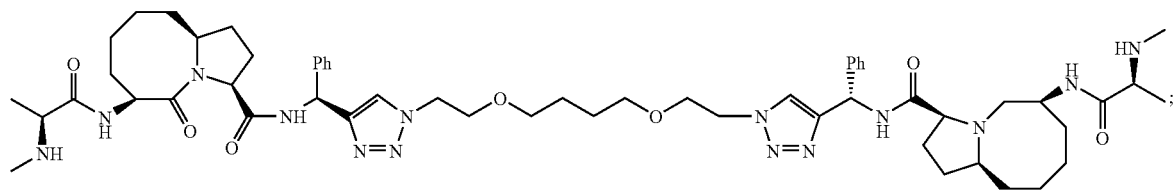
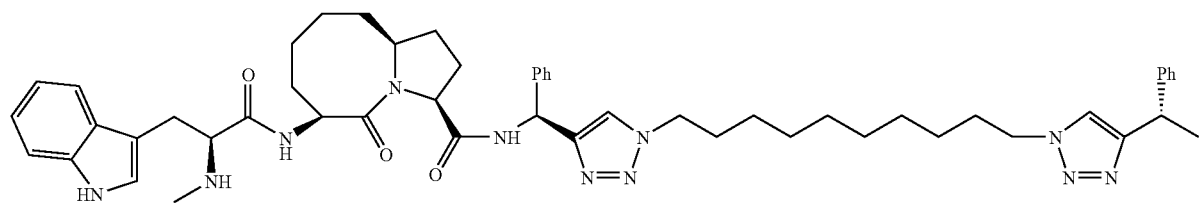
SH-199

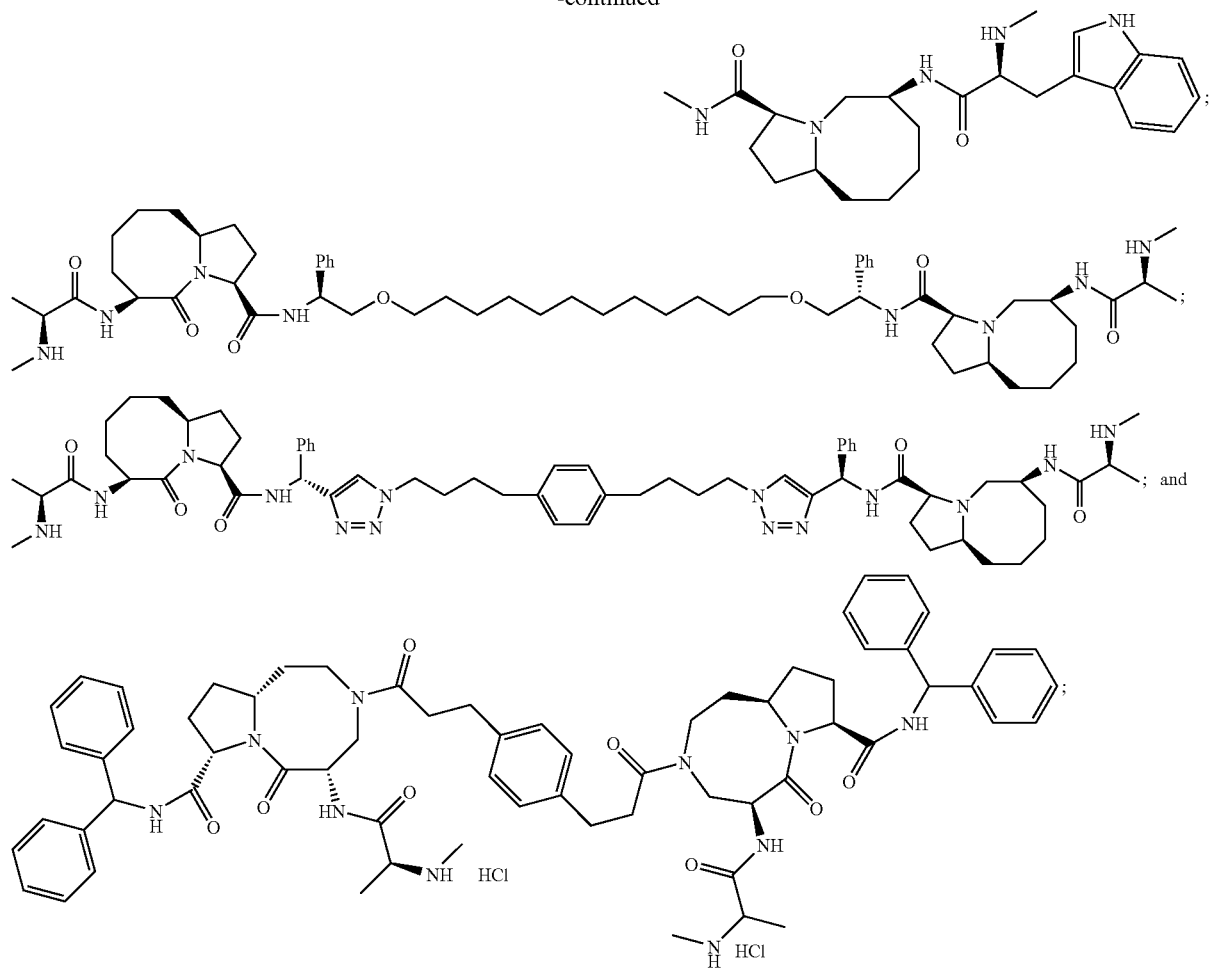

or the free base thereof or another pharmaceutically acceptable salt thereof.

The compounds of this invention may be prepared using methods known to those of skill in the art. Specifically, compounds with Formulae II-IV can be prepared as illustrated by the exemplary reactions in the Examples.

An important aspect of the present invention is that compounds of Formulae II-IV induce apoptosis and also potentiate the induction of apoptosis in response to apoptosis induction signals. Therefore, it is contemplated that these compounds sensitize cells to inducers of apoptosis, including cells that are resistant to such inducers. The IAP inhibitors of the present invention can be used to induce apoptosis in any disorder that can be treated, ameliorated, or prevented by the induction of apoptosis. Thus, the present invention provides compositions and methods for targeting animals characterized as overexpressing an IAP protein. In some of the embodiments, the cells (e.g., cancer cells) show elevated expression levels of IAP proteins as compared to non-pathological samples (e.g., non-cancerous cells). In other embodiments, the cells operationally manifest elevated expression levels of IAP proteins by virtue of executing the apoptosis program and dying in response to an inhibiting effective amount of a compound of Formula I, said response occurring, at least in part, due to the dependence in such cells on IAP protein function for their survival.

In another embodiment, the invention pertains to modulating an apoptosis-associated state which is associated with one or more apoptosis-modulating agents. Examples of apoptosis-modulating agents include, but are not limited to, Fas/CD95, TRAMP, TNF RI, DR1, DR2, DR3, DR4, DR5, DR6, FADD, RIP, TNFα, Fas ligand, TRAIL, antibodies to TRAIL-R1 or TRAIL-R2, Bcl-2, p53, BAX, BAD, Akt, CAD, PI3 kinase, PP1, and caspase proteins. Other agents involved in the initiation, decision and degradation phase of apoptosis are also included. Examples of apoptosis-modulating agents include agents, the activity, presence, or change in concentration of which, can modulate apoptosis in a subject. Preferred apoptosis-modulating agents are inducers of apoptosis, such as TNF or a TNF-related ligand, particularly a TRAMP ligand, a Fas/CD95 ligand, a TNFR-1 ligand, or TRAIL.

In some embodiments, the compositions and methods of the present invention are used to treat diseased cells, tissues, organs, or pathological conditions and/or disease states in an animal (e.g., a mammalian subject including, but not limited to, humans and veterinary animals). In this regard, various diseases and pathologies are amenable to treatment or prophylaxis using the present methods and compositions. A non-limiting exemplary list of these diseases and conditions includes, but is not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to anticancer agents.

In some embodiments, infections suitable for treatment with the compositions and methods of the present invention include, but are not limited to, infections caused by viruses, bacteria, fungi, mycoplasma, prions, and the like.

Some embodiments of the present invention provide methods for administering an effective amount of a compound of Formula I and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies).

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In preferred embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethimide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of Formula II-IV and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyl-triazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-l-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal | DanuoXome | Nexstar Pharmaceuticals, Inc., |

TABLE 1-continued

| | | |
|---|---|---|
| ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | | Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O—(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$•$(C_2H_4O_2)_x$ | Zoladex Implant | AstraZeneca Pharmaceuticals |
| Hydroxyurea | Hydrea | Bristol-Myers Squibb |

TABLE 1-continued

| | | |
|---|---|---|
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino) carbonyloxy]-1H-pyrano[3',4':6,7] indolizino[1,2-b] quinoline-3,14(4H,12H) dione hydrochloride trihydrate) | Camptosar | Pharmacia & Upjohn Company |
| Lenalidomide 3-(4-amino-1-oxo 1,3-dihydro-2H-isoindol-2-yl) piperidine-2,6-dione | Revlimid | Celgene |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl1,4,5,6,7,8-hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Mechlorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |

TABLE 1-continued

| | | |
|---|---|---|
| Paclitaxel ($5\beta$,20-Epoxy-1,2a,4,7$\beta$,10$\beta$,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-$\mu$-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |

TABLE 1-continued

| | | |
|---|---|---|
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity but are not currently approved by the U.S. Food and Drug Administration or other counterpart agencies or are undergoing evaluation for new uses. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9,06-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of Formulae II-IV with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphyrins, cisplatin, mitomycin, tirapazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the patient without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. The dose of radiation is preferably fractionated for maximal target cell exposure and reduced toxicity.

The total dose of radiation administered to an animal preferably is about 0.01 Gray (Gy) to about 100 Gy. More preferably, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), preferably 1-2 Gy (e.g., 1.5-2 Gy). The daily dose of radiation should be sufficient to induce destruction of the targeted cells. If stretched over a period, radiation preferably is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. Preferably, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of Formulae II-IV and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2 3, 4, 5, 10, 12, or 18 hours, 1, 2, 3, 4, 5, or 6 days, 1, 2, 3, or 4 weeks prior to the administration of the therapeutic or anticancer agent. In some embodiments, the compound is administered after the therapeutic or anticancer agent, e.g., 0.5, 1, 2 3, 4, 5, 10, 12, or 18 hours, 1, 2, 3, 4, 5, or 6 days, 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. Preferably, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, and most preferably, from about 0.01 to about 5 mg/kg.

The unit oral dose may comprise from about 0.01 to about 1000 mg, preferably about 0.1 to about 100 mg of the compound. The unit dose may be administered one or more times daily as one or more tablets or capsules each containing from about 0.1 to about 10, conveniently about 0.25 to 50 mg of the compound or its solvates.

In a topical formulation, the compound may be present at a concentration of about 0.01 to 100 mg per gram of carrier. In a preferred embodiment, the compound is present at a concentration of about 0.07-1.0 mg/ml, more preferably, about 0.1-0.5 mg/ml, most preferably, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, preferably from about 0.25 to 75 percent of active compound(s), together with the excipient.

The pharmaceutical compositions of the invention may be administered to any animal which may experience the beneficial effects of the compounds of the invention. Foremost among such animals are mammals, e.g., humans, although the invention is not intended to be so limited. Other animals include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than C12). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

Example 1

Synthesis of Bivalent Smac Mimetics

General Methods: NMR spectra were acquired at a proton frequency of 300 MHz. $^1$H chemical shifts are reported with Me$_4$Si (0.00 ppm), CHCl$_3$ (7.26 ppm), CD$_2$HOD (3.31 ppm), or DHO 04.79 ppm) as internal standards. $^{13}$C chemical shifts are reported with CDCl$_3$ (77.00 ppm), CD$_3$OD (49.00 ppm), or 1,4-dioxane (67.16 ppm) as internal standards. Optical rotations were measured at room temperature.

General Procedure A (Condensation):

To a solution of the two substrates in CH$_2$Cl$_2$ (20 mg/mL for the minor substrate) was added EDC (1.1 eq per amino group), HOBt (1.1 eq per amino group) and N,N-diisopropylethyl amine (4 eq per amino group) at 0° C. with stirring. The mixture was stirred at room temperature for eight hours and then condensed. The residue was purified by chromatography to give the product.

General Procedure B (Click Chemistry):

To a solution of CuSO$_4$ (10 mg/mL) was added (+)-sodium L-ascorbate (2 eq). The mixture was shaken until the color turned to bright yellow. To a solution of the two substrates in acetonitrile or 2-methylpropanol (20 mg/mL for the minor substrate) was added the pre-made mixture of CuSO$_4$-sodium L-ascorbate (0.1 eq of CuSO$_4$ per 1 eq of the minor substrate). The mixture was stirred at room temperature overnight and then extracted with dichloromethane three times. The combined organic layer was washed with brine, dried over Na$_2$SO$_4$ and condensed. The residue was purified by chromatography to give the product.

General Procedure C (Deprotection of Boc):

To a solution of the substrate in methanol (20 mg/mL) was added a solution of HCl in 1,4-dioxane (4 M, 10-20 eq per Boc). The solution was stirred at room temperature overnight and then condensed to give the product.

Example 2

Synthesis of DQ-24, SH-143, SH-155 and SH-142

Compounds DQ-24, SH-143, SH-155 and SH-142 were synthesized according to Scheme I.

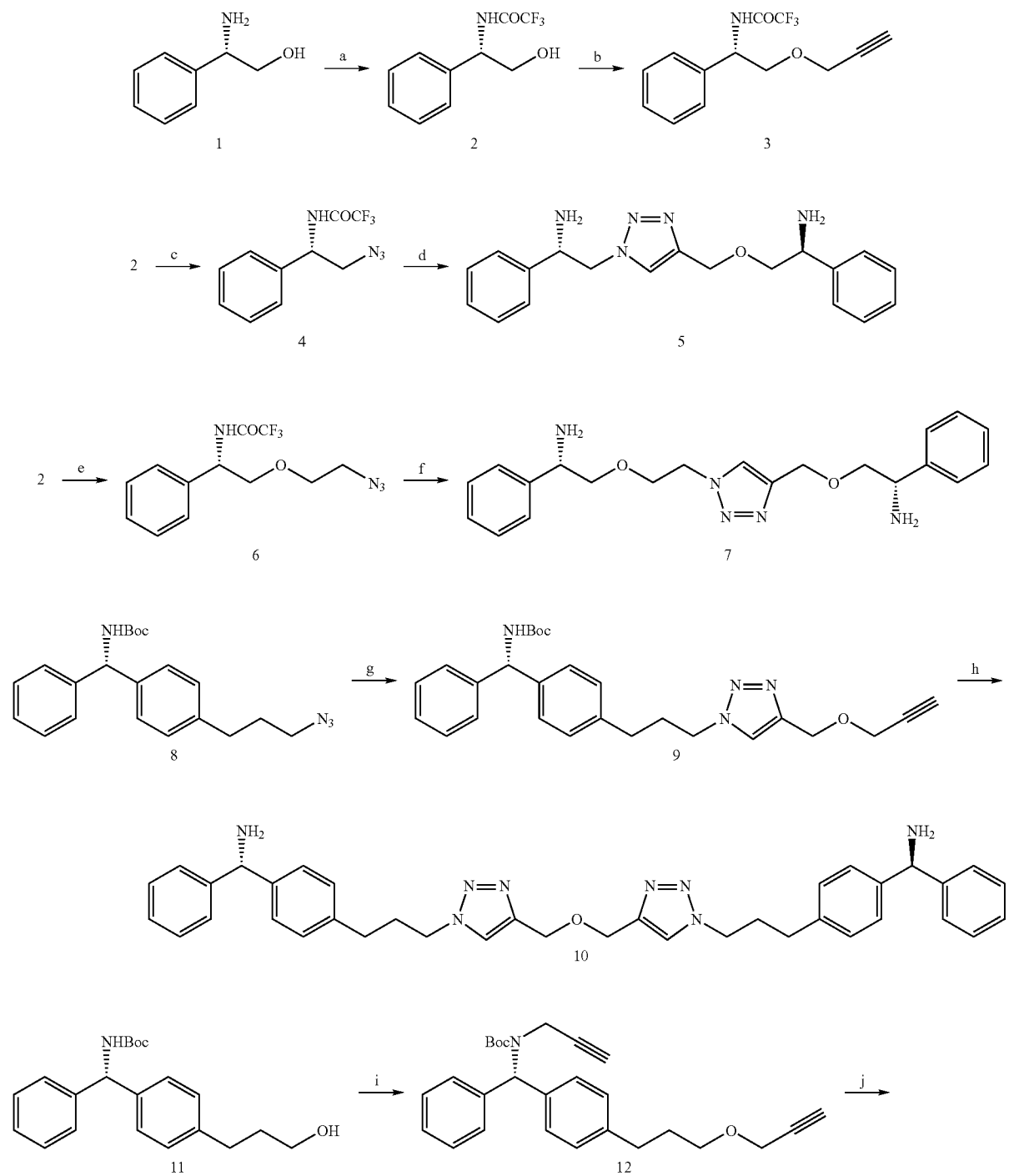

-continued

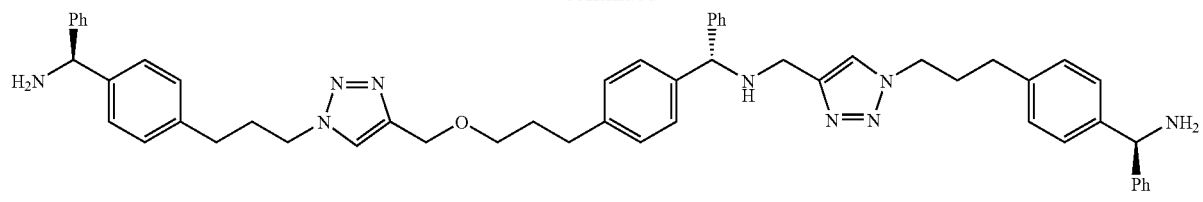

13

Reagents and condititons: (a) i. trifluoroacetic anhydride, Et₃N, CH₂Cl₂, rt; ii. NaHCO₃, MeOH, 95%; (b) NaH, propargyl bromide, DMF, 92%; (c) i. MsCl, Et₃N; ii. NaN₃, DMF, 100° C., 85% over two steps; (d) i. 3, CuSO₄, (+)-sodium L-ascorbate, CH₃CN-H₂O 3:1; ii. 2N LiOH, 1,4-dioxane-H₂O 1:1, 74% over two steps; (e) i. NaH, benzyl 2-bromoethyl ether; ii. 10% Pd-C, H₂, MeOH; iii. MsCl, Et₃N; iv. NaN₃, DMF, 65% over four steps; (f) i. 3, CuSO₄, (+)-sodium L-ascorbate, CH₃CN-H₂O 3:1; ii. 2N LiOH, 1,4-dioxane-H₂O 1:1, 72% over two steps; (g) propargyl ether (5 eq), CuSO₄, (+)-sodium L-ascorbate, CH₃CN-H₂O 3:1, 69%; (h) i. 8, CuSO₄, (+)-sodium L-ascorbate, CH₃CN-H₂O 3:1, ii. 4N HCl in 1,4-dioxane, MeOH, 95%; (i) NaH, propargyl bromide, DMF, 82%; (j) i. 8 (2.2eq), CuSO₄, (+)-sodium L-ascorbate, CH₃CN-H₂O 3:1, ii. 4N HCl in 1,4-dioxane, MeOH, 62% over two steps.

Selective protection of the amino group in L-phenylglycinol 1 with trifluoroacetic anhydride gave an alcohol 2. Alkylation of 2 with propargyl bromide yielded an alkyne 3. Reaction of 2 with methanesulfonyl chloride followed by substitution of the resulted mesylate with NaN₃ furnished an azide 4. Cycloaddition of 3 and 4 under the catalyzation of CuSO₄-(+)-sodium-L-ascorbate followed by removal of the trifluoro acetyl groups afforded a diamine 5.

Alkylation of 2 with benzyl 2-bromoethyl ether followed by hydrolysis of the benzyl protecting group furnished an alcohol. Reaction of this alcohol with methanesulfonyl chloride followed by substitution of the resulted mesylate with NaN₃ furnished azide 6. Cycloaddition of 6 with 3 under the catalyzation of CuSO₄-(+)-sodium-L-ascorbate followed by removal of the trifluoro acetyl groups afforded a diamine 7.

Compound 8 was synthesized according to our previously reported method (Sun et al., *Tetrahedron Letters*, 46:7015 (2005)). Cycloaddition of compound 8 with excessive amount of propargyl ether (5-10 eq) yielded an alkyne 9. Cycloaddition of 9 and 8 under the catalyzation of CuSO₄-(+)-sodium-L-ascorbate followed by removal of the Boc protecting groups afforded a diamine 10.

Compound 11 was synthesized according to our previously reported method (Sun et al., *Tetrahedron Letters*, 46:7015 (2005)). Alkylation of 11 with propargyl bromide yielded an alkyne 12. Cycloaddition of 2.2 eq of 8 with 1 eq of 12 under the catalyzation of CuSO₄-(+)-sodium-L-ascorbate followed by removal of the Boc protecting groups afforded a diamine 13.

Scheme II

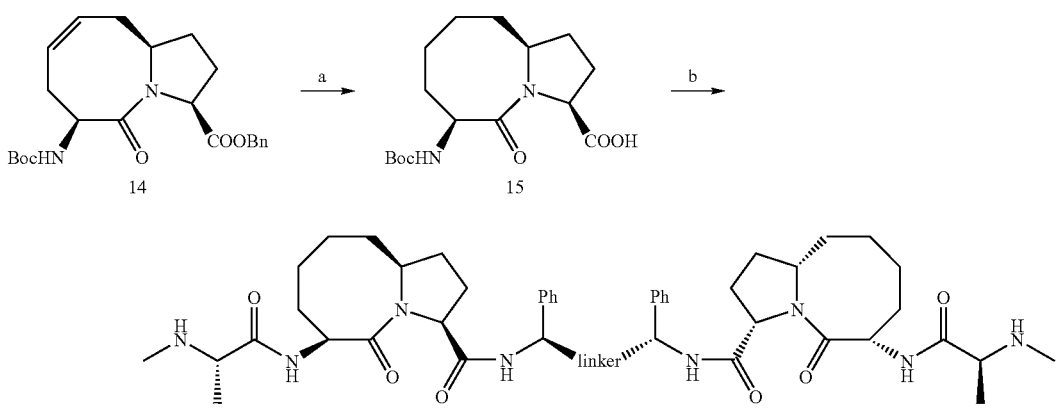

Reagents and conditions: (a) 10% Pd-C, MeOH, H₂, 100%; (b) i. diamine, EDC, HOBt, N,N-diisopropylethyl amine, CH₂Cl₂; ii. 4N HCl in 1,4-dioxane, MeOH; iii. L-N-Boc-N-methyl alanine, EDC, HOBt, N,N-diisopropylethyl amine, CH₂Cl₂; iv. 4N HCl in 1,4-dioxane.

Compound 14 can be synthesized according to literature reported methods (Duggan et al., *Org. Biomol. Chem.*, 3:2287 (2005)) (Scheme II). Reduction of the C—C double bond and hydrolysis of the benzyl ester in compound 14 gave an acid 15. Condensation of 2.2 eq of 15 with the above diamines respectively followed by removal of the Boc protecting groups gave four ammonium salts. Condensation of these salts with L-N-Boc-N-methyl alanine respectively followed by deprotection of the Boc protecting groups afforded the bivalent Smac mimetics DQ-24, SH-143, SH-142 and SH-155. The efficiency of the synthetic scheme for each compound is shown in Table 2.

TABLE 2

| Name | Yield (%, over four steps) |
|---|---|
| DQ-24 | 61 |
| SH-143 | 62 |
| SH-155 | 59 |
| SH-142 | 55 |

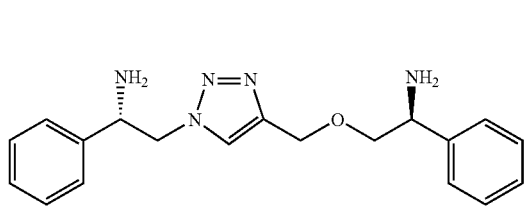
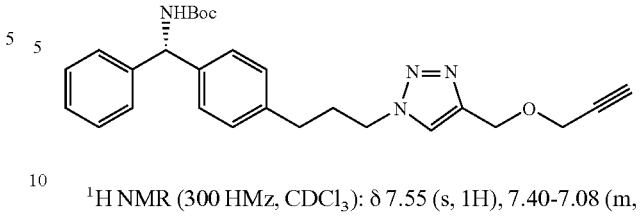
9
¹H NMR (300 HMz, CDCl₃): δ 7.55 (s, 1H), 7.40-7.08 (m, 9H), 5.90 (brs, 1H), 5.24 (brs, 1H), 4.74 (s, 2H), 4.34 (t, J=7.1 Hz, 2H), 4.23 (d, J=2.4 Hz, 1H), 2.96 (t, J=7.3 Hz, 2H), 2.49 (t, J=2.4 Hz, 1H), 2.22 (m, 2H), 1.43 (brs, 9H); ¹³C NMR (75 HMz, CDCl₃): δ 154.93, 144.26, 141.98, 140.15, 139.04, 128.54, 128.50, 127.36, 127.22, 127.07, 122.56, 79.67, 79.16, 74.89, 62.91, 58.06, 57.37, 49.37, 31.94, 31.44, 28.25.
¹H NMR (300 MHz, CDCl₃): δ 7.50 (s, 1H), 7.38-7.20 (m, 3H), 7.28-7.20 (m, 2H), 7.26-7.05 (m, 5H), 4.98-4.75 (m, 2H), 4.23 (s, 2H), 4.36 (m, 2H), 3.50 (m, 2H); ¹³C NMR (75 MHz, CDCl₃): δ 143.78, 133.54, 132.53, 130.26, 129.97, 129.70, 129.62, 127.47, 127.10, 126.40, 69.89, 63.23, 54.67, 54.60, 52.40.
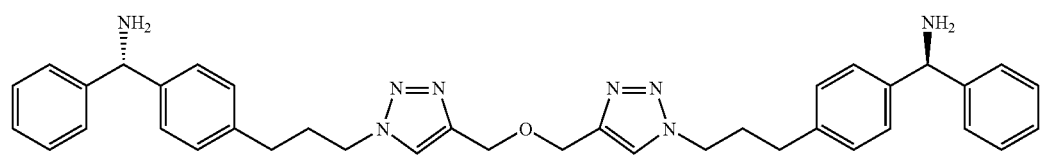
10
¹H NMR (300 MHz, CDCl₃): δ 7.52 (s, 2H), 7.38-7.12 (m, 10H), 7.08-6.99 (m, 4H), 6.92-6.79 (m, 4H), 5.42 (s, 2H), 4.40 (s, 4H), 4.02 (m, 4H), 2.18 (m, 4H), 1.78 (m, 4H); ¹³C NMR (75 MHz, CDCl₃): δ 144.10, 139.59, 137.31, 132.04, 131.80, 131.72, 129.70, 129.64, 127.47, 65.29, 60.60, 52.51, 34.08, 33.18.
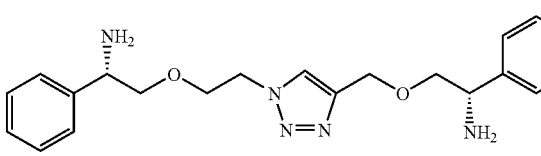
7
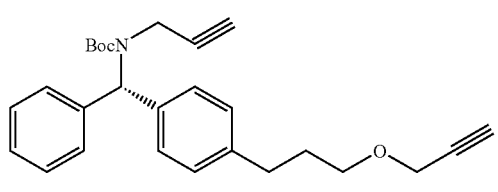
12
¹H NMR (300 MHz, CDCl₃): δ 7.59 (s, 1H), 7.32-7.22 (m, 3H), 7.22-7.13 (m, 5H), 7.12-7.05 (m, 2H), 4.55-4.29 (m, 6H), 3.85-3.75 (m, 1H), 3.75-3.56 (m, 5H); ¹³C NMR (75 MHz, CDCl₃): δ 143.51, 133.88, 133.63, 129.83, 129.61, 129.52, 129.38, 127.36, 127.32, 125.59, 70.89, 70.20, 69.25, 63.42, 54.62, 54.39, 50.49.
¹H NMR (300 MHz, CDCl₃): δ 7.40-7.18 (m, 5H), 7.15 (brs, 4H), 6.45 (brs, 1H), 4.24 (d, J=2.4 Hz, 2H), 3.90 (d, J=1.9 Hz, 2H), 3.55 (t, J=6.3 Hz, 2H), 2.72 (dd, J=8.9, 7.4 Hz, 2H), 2.77 (t, J=2.4 Hz, 1H), 2.04 (t, J=1.9 Hz, 1H), 1.92 (m, 2H), 1.43 (brs, 9H); ¹³C NMR (75 MHz, CDCl₃): δ 155.17, 140.92, 139.85, 136.99, 128.76, 128.53, 128.40, 128.22, 127.22, 80.68, 80.58, 79.86, 74.19, 70.26, 69.16, 58.01, 34.75, 31.79, 30.99, 28.23.

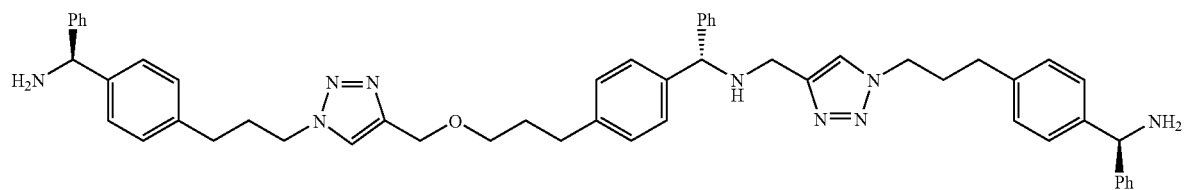
13
¹H NMR (300 MHz, D₂O): δ 7.50 (s, 1H), 7.33 (s, 1H), 7.23-7.03 (m, 17H), 6.99-6.92 (m, 6H), 6.80-6.68 (m, 4H), 5.38 (s, 1H), 5.34 (s, 1H), 5.10 (s, 1H), 4.08 (s, 2H), 4.08 (t, J=6.8 Hz, 1H), 3.99 (s, 2H), 3.92 (t, J=6.8 Hz, 2H), 3.02 (t, J=6.2 Hz, 2H), 2.30 (t, J=7.3 Hz, 2H), 2.17 (t, J=7.3 Hz, 2H), 2.11 (t, J=7.3 Hz, 2H), 1.89-1.80 (m, 2H), 1.78-1.62 (m, 2H), 1.48-1.35 (m, 2H); ¹³C NMR (75 MHz, D₂O): δ 163.46, 162.99, 144.04, 143.16, 141.81, 141.56, 137.61, 137.05, 134.70, 129.75, 129.64, 129.57, 129.54, 129.41, 129.28, 127.64, 127.45, 127.28, 127.16, 126.49, 125.00, 118.54, 114.67, 68.74, 65.33, 62.55, 58.06, 50.20, 49.98, 40.52, 31.70, 31.60, 30.98, 30.67, 30.42, 29.96.
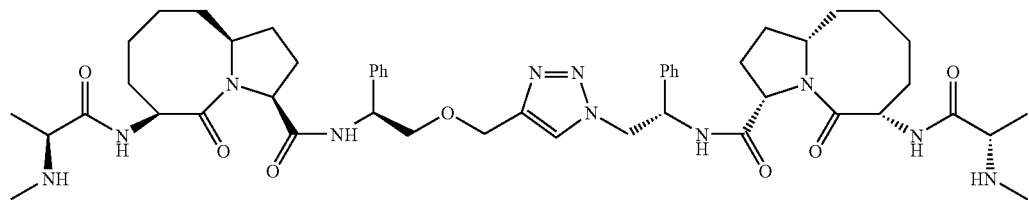
DQ-24
¹H NMR (300 MHz, D₂O): δ 7.77 (s, 1H), 7.78-7.21 (m, 10H), 5.32 (m, 1H), 4.91 (m, 1H), 4.75-4.56 (m, 4H), 4.50 (s, 2H), 4.33 (m, 1H), 4.17 (m, 3H), 3.79 (m, 2H), 3.60 (m, 2H), 2.55 (s, 3H), 2.53 (s, 3H), 2.25-1.80 (m, 4H), 1.79-1.61 (m, 7H), 1.60-1.45 (m, 9H), 1.40-1.38 (m, 4H), 1.37 (d, J=7.5 Hz, 3H), 1.33 (d, J=7.2 Hz, 3H); ¹³C NMR (75 MHz, D₂O): δ 173.82, 173.65, 172.34, 172.29, 144.94, 138.64, 137.46, 129.41, 129.25, 128.87, 128.23, 126.91, 126.88, 125.73, 72.14, 63.14, 62.15, 61.16, 60.96, 57.28, 54.14, 53.64, 53.34, 51.10, 35.94, 32.94, 32.33, 31.31, 27.95, 25.86, 21.99, 15.60.
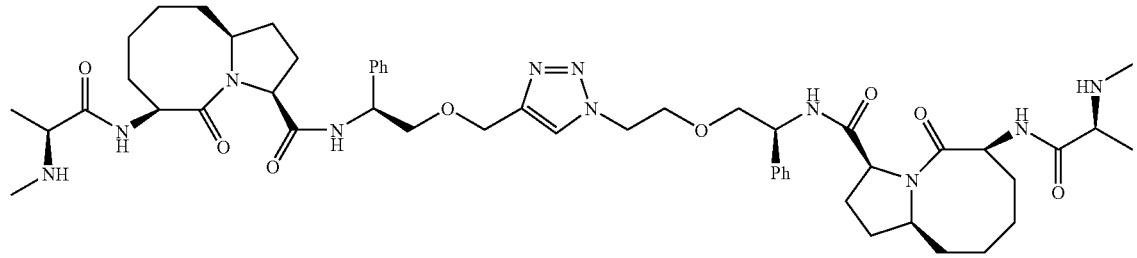
SH-143
¹H NMR (300 MHz, D₂O): δ 7.50 (s, 1H), 7.30-7.08 (m, 10H), 4.95-4.80 (m, 3H), 4.75 (m, 1H), 4.47 (s, 2H), 4.39 (m, 2H), 4.32-4.10 (m, 4H), 4.35-4.08 (m, 4H), 3.66-3.50 (m, 4H), 2.55 (s, 6H), 2.22-1.43 (m, 24H), 1.39 (m, 6H); ¹³C NMR (75 MHz, D₂O): δ 173.71, 172.30, 169.52, 143.92, 138.73, 129.07, 128.18, 126.96, 125.53, 72.87, 72.32, 68.99, 63.36, 62.21, 62.14, 61.05, 57.20, 53.40, 53.24, 51.14, 50.42, 35.96, 32.99, 32.32, 31.32, 27.89, 25.08, 21.94, 15.63.

SH-155
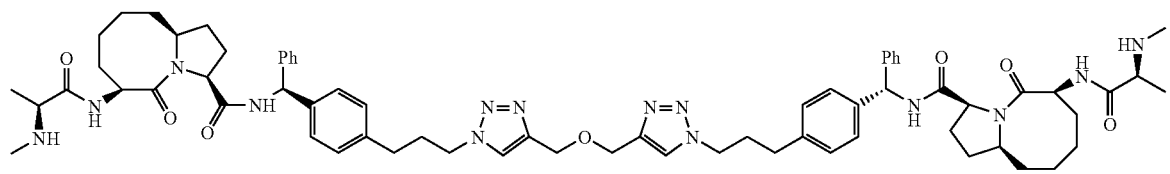
¹H NMR (300 MHz, D₂O): δ 7.29 (s, 2H), 7.10-6.92 (m, 10H), 6.85 (d, J=8.0 Hz, 4H), 6.58 (d, J=8.0 Hz, 4H), 5.78 (s, 2H), 4.65 (m, 2H), 4.38 (s, 4H), 4.22 (m, 2H), 4.08 (m, 2H), 3.95-3.73 (m, 6H), 2.55 (s, 6H), 2.21-1.28 (m, 36H); ¹³C NMR (75 MHz, D₂O): δ 179.33, 172.64, 172.07, 144.32, 141.56, 140.08, 139.74, 129.15, 127.99, 127.69, 127.53, 124.85, 63.13, 62.04, 61.01, 57.48, 57.30, 51.12, 49.98, 36.03, 33.27, 32.47, 31.77, 31.44, 31.22, 27.87, 25.25, 21.99, 15.78.
SH-142
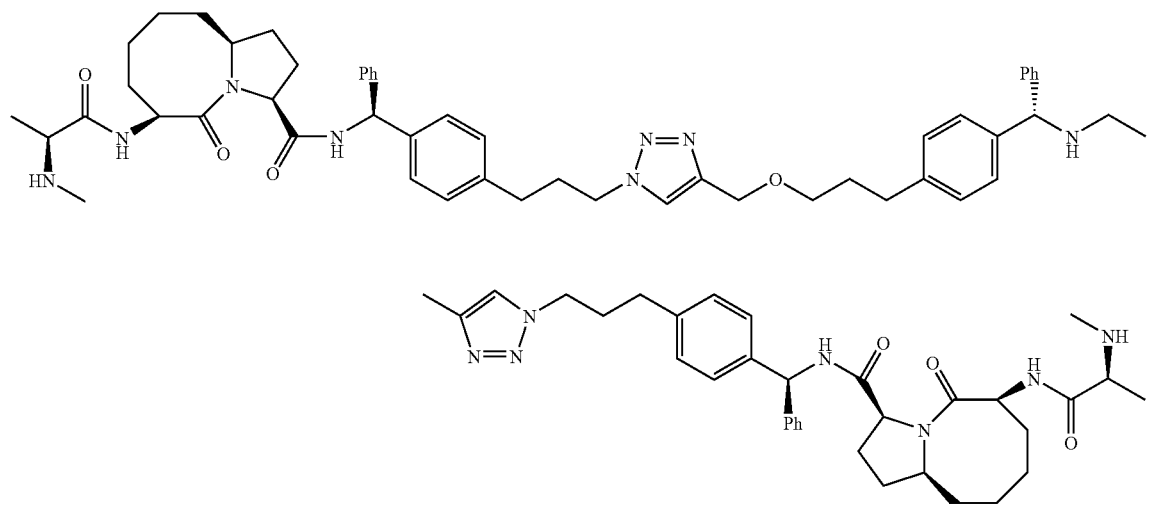
(free amine)
¹H NMR (300 MHz, CDCl₃): δ 7.92 (brd, J=8.4 Hz, 2H), 7.82 (brd, J=8.4 Hz, 2H), 7.49 (s, 1H), 7.45-7.06 (m, 28H), 6.21 (s, 1H), 6.19 (s, 1H), 4.90 (m, 2H), 4.85 (s, 1H), 4.75 (m, 2H), 4.62 (s, 2H), 4.33 (t, J=7.1 Hz, 4H), 4.20 (m, 2H), 3.82 (s, 2H), 3.49 (t, J=7.1 Hz, 2H), 3.06 (m, 2H), 2.70-2.55 (m, 8H), 2.38 (s, 6H), 2.30-1.35 (m, 28H), 1.30 (d, J=6.9 Hz, 6H); ¹³C NMR (75 MHz, CDCl₃): δ 174.16, 172.05, 169.69, 145.37, 141.64, 140.60, 139.70, 139.15, 139.11, 128.60, 128.56, 128.50, 127.59, 127.47, 127.32, 127.29, 127.27, 127.02, 122.22, 121.52, 69.87, 66.39, 64.35, 60.15, 59.75, 59.18, 56.78, 53.41, 49.41, 49.26, 42.65, 36.71, 35.97, 35.12, 32.03, 31.59, 31.55, 31.09, 24.91, 24.06, 23.20, 19.44.
Example 3
Synthesis of SH-156, SH-158, SH-159, SH-164, SH-165, SH-166 and SH-167
Compounds SH-156, SH-158, SH-159, SH-164, SH-165, SH-166 and SH-167 were synthesized according to Scheme III.
Scheme III
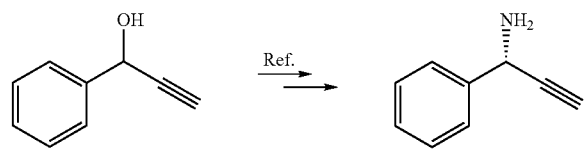

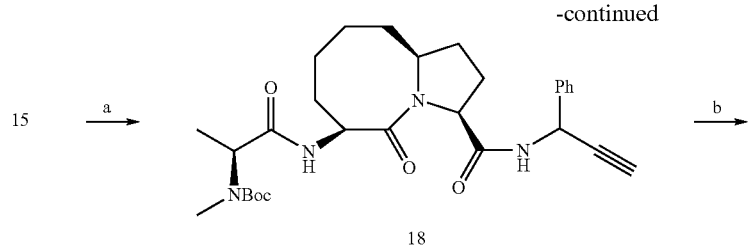

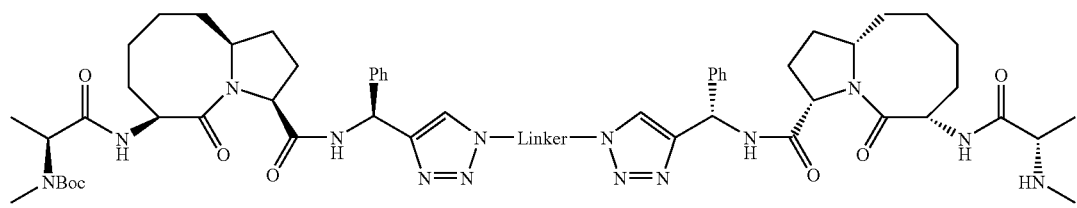

Reagents and conditions: (a) i. 17, EDC, HOBt, N,N-diisopropylethyl amine, CH₂Cl₂; ii. 4 N HCl in 1,4-dioxane, MeOH; iii. L-N-Boc-N-methyl alanine, EDC, HOBt, CH₂Cl₂, 78% over three steps; (b) i. diazide, CuSO₄, (+)-sodium L-ascorbate, t-BuOH--H₂O 3:1, ii. 4N HCl in 1,4-dioxane, MeOH.

The chiral amine 17 can be prepared according to literature reported methods from compound 16 (Messina, et al., *J. Org. Chem.*, 64:3767 (1999)). Condensation of acid 15 with chiral amine 17 followed by deprotection of the Boc protecting group with HCl in methanol yielded an ammonium salt. Condensation of this salt with L-N-Boc-N-methyl alanine furnished intermediate 18. Cycloaddition of 18 with corresponding diazide under the catalyzation of CuSO₄-(+)-sodium-L-ascorbate respectively followed by deprotection of the Boc protecting group gave designed bivalent Smac mimetics SH-156, SH-158, SH-159, SH-164, SH-165, SH-166 and SH-167. The efficiency of the synthetic scheme for each compound is shown in Table 3.

TABLE 3

| Name | Yield (%, over two steps) |
|---|---|
| SH-156 | 63 |
| SH-158 | 65 |
| SH-159 | 61 |
| SH-164 | 62 |
| SH-165 | 59 |
| SH-166 | 58 |
| SH-167 | 59 |

18

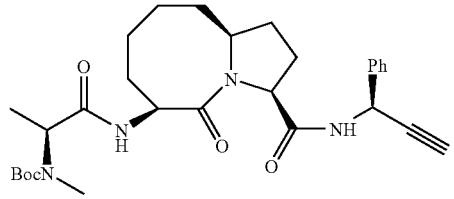

¹H NMR (300 MHz, CDCl₃): δ 7.75 (brd, J=8.5 Hz, 1H), 7.50-7.44 (m, 2H), 7.38-7.23 (m, 3H), 6.90 (brs, 1H), 5.95 (dd, J=8.5, 2.4 Hz, 1H), 4.80 (m, 1H), 4.64 (dd, J=8.4, 6.2 Hz, 1H), 4.60 (brm, 1H), 4.15 (m, 1H), 2.88 (s, 3H), 2.62 (m, 1H), 2.53 (d, J=2.4 Hz, 1H), 2.20-1.70 (m, 5H), 1.51 (brs, 9H), 1.56-1.05 (m, 9H); ¹³C NMR (75 MHz, CDCl₃): δ 171.99, 170.95, 169.73, 138.96, 129.03, 128.55, 127.53, 82.13, 73.25, 60.03, 59.47, 50.32, 45.21, 36.94, 36.30, 32.36, 30.48, 28.80, 25.29, 24.42, 23.45, 14.16.

SH-156

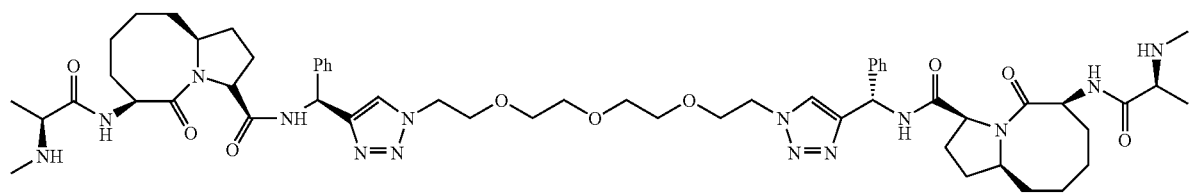

$^1$H NMR (300 MHz, D$_2$O): δ 7.58 (s, 2H), 7.29-7.13 (m, 10H), 6.08 (s, 2H), 4.70 (m, 2H), 4.38 (m, 4H), 4.27 (m, 2H), 4.22 (m, 2H), 3.85 (m, 2H), 3.73 (m, 4H), 3.32 (m, 4H), 3.25 (m, 4H), 2.58 (s, 6H), 2.25-1.48 (m, 22H), 1.40 (d, J=7.0 Hz, 6H), 1.39 (m, 2H); $^{13}$C NMR (75 MHz, D$_2$O): δ 173.36, 172.32, 169.56, 148.12, 139.21, 129.32, 128.54, 127.40, 124.51, 69.98, 69.75, 68.97, 62.07, 61.07, 57.20, 51.13, 50.46, 50.41, 35.94, 33.01, 32.35, 31.31, 27.81, 25.07, 21.92, 15.63.
SH-158
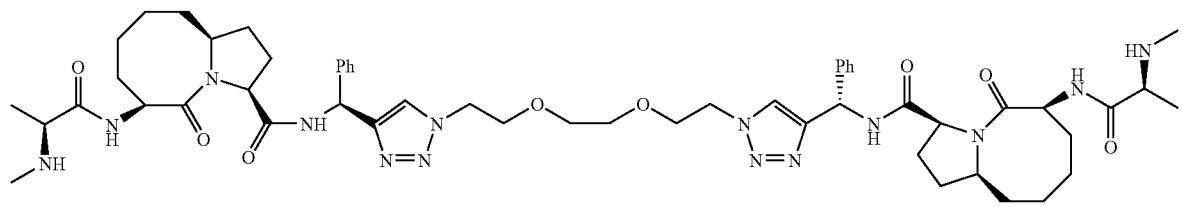
$^1$H NMR (300 MHz, D$_2$O): δ 7.56 (s, 2H), 7.29-7.13 (m, 10H), 6.05 (s, 2H), 4.70 (m, 2H), 4.38-4.14 (m, 8H), 3.85 (m, 2H), 3.63 (m, 4H), 3.35 (s, 4H), 2.55 (s, 6H), 2.22-1.45 (m, 22H), 1.42 (d, J=7.1 Hz, 6H), 1.40 (m, 2H); $^{13}$C NMR (75 MHz, D$_2$O): δ 173.31, 172.28, 169.54, 148.15, 139.23, 129.30, 128.53, 127.38, 124.45, 69.85, 68.90, 62.05, 61.05, 57.20, 51.12, 50.39, 35.93, 33.03, 32.34, 31.32, 27.78, 25.07, 21.93, 15.63.
SH-159
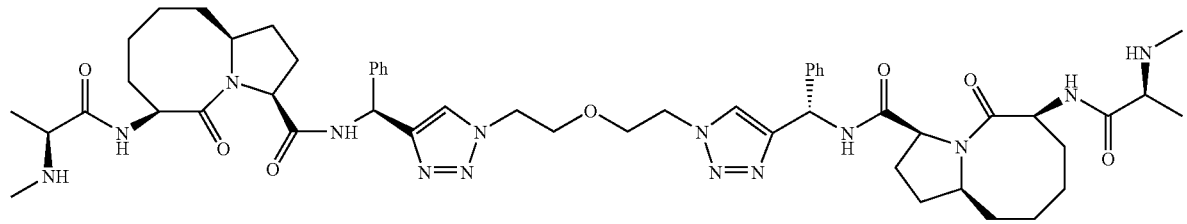
$^1$H NMR (300 MHz, D$_2$O): δ 7.51 (s, 2H), 7.28-7.04 (m, 10H), 6.04 (s, 2H), 4.70 (m, 2H), 4.39-4.15 (m, 8H), 3.82 (m, 2H), 3.70 (m, 4H), 2.56 (s, 6H), 2.20-1.45 (m, 22H), 1.40 (d, J=6.9 Hz, 6H), 1.38 (m, 2H); $^{13}$C NMR (75 MHz, D$_2$O): δ 173.28, 172.22, 169.52, 148.14, 139.30, 129.31, 128.48, 127.33, 124.36, 68.99, 62.04, 61.06, 57.21, 51.10, 50.42, 50.35, 35.93, 33.06, 32.35, 31.32, 27.81, 25.09, 21.93, 15.64.
SH-164
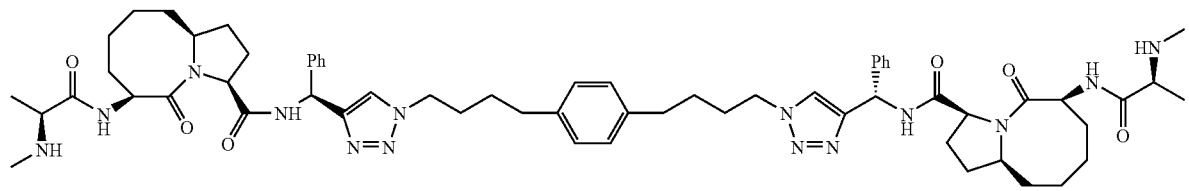

$^1$H NMR (300 MHz, D$_2$O): δ 7.40 (s, 2H), 7.15-6.85 (m, 10H), 6.65 (s, 4H), 6.08 (s, 2H), 4.65 (m, 2H), 4.32 (m, 2H), 4.08 (m, 2H), 3.92-3.74 (m, 6H), 2.84 (m, 4H), 2.54 (s, 6H), 2.28-1.04 (m, 38H); $^{13}$C NMR (75 MHz, D$_2$O): δ 172.24, 171.83, 169.34, 148.50, 139.56, 139.41, 129.07, 128.53, 127.43, 122.92, 61.70, 60.72, 57.20, 51.23, 50.86, 50.15, 36.08, 34.96, 34.64, 31.34, 29.61, 28.63, 28.57, 28.20, 27.60, 25.20, 15.71.
SH-165
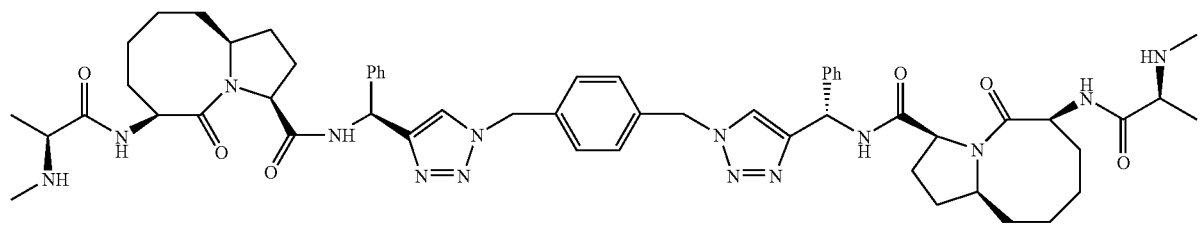
$^1$H NMR (300 MHz, D$_2$O): δ 7.55 (s, 2H), 7.19-7.05 (m, 10H), 6.85 (s, 4H), 5.98 (s, 2H), 5.15 (s, 4H), 4.65 (m, 2H), 4.25 (t, J=7.2 Hz, 2H), 4.10 (m, 2H), 3.82 (m, 2H), 2.54 (s, 6H), 2.12-1.20 (m, 30H); $^{13}$C NMR (75 MHz, D$_2$O): δ 173.04, 172.16, 169.49, 148.55, 139.08, 135.38, 129.27, 128.82, 128.51, 127.40, 123.90, 62.92, 60.92, 57.19, 53.62, 51.05, 50.39, 35.88, 33.05, 32.28, 31.32, 27.66, 25.06, 21.91, 15.64.
SH-166
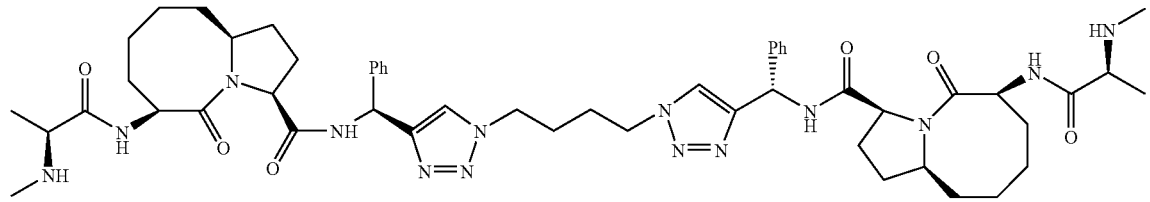
$^1$H NMR (300 MHz, D$_2$O): δ 7.59 (s, 2H), 7.28-7.10 (m, 10H), 6.02 (s, 2H), 4.65 (m, 2H), 4.29 (m, 2H), 4.22-4.08 (m, 6H), 3.82 (m, 2H), 2.53 (s, 6H), 2.20-1.42 (m, 26H), 1.40 (d, J=7.1 Hz, 6H), 1.35 (m, 2H); $^{13}$C NMR (75 MHz, D$_2$O): δ 173.35, 172.29, 169.53, 148.20, 139.07, 129.31, 128.54, 127.36, 124.06, 62.05, 61.03, 57.19, 51.11, 50.32, 50.05, 35.92, 33.02, 32.33, 31.31, 27.76, 26.68, 25.06, 21.93, 15.63.
SH-167
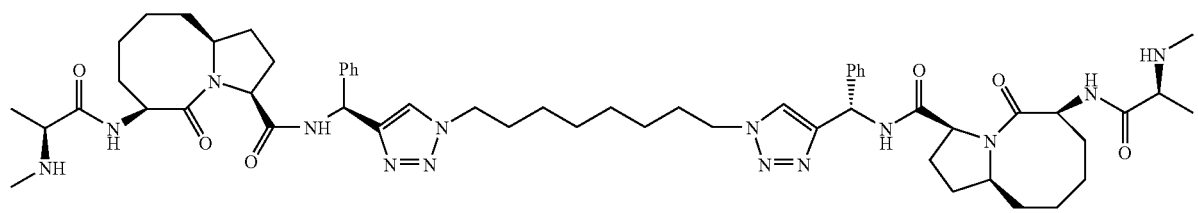

$^1$H NMR (300 MHz, D$_2$O): δ 7.62 (s, 2H), 7.28-7.12 (m, 10H), 6.07 (s, 2H), 4.65 (m, 2H), 4.30 (t, J=8.8 Hz, 2H), 4.25-4.10 (m, 6H), 3.84 (m, 2H), 2.55 (s, 6H), 2.23-1.95 (m, 4H), 1.95-1.45 (m, 22H), 1.40 (d, J=7.0 Hz, 6H), 1.35 (m, 2H), 1.05-0.85 (m, 8H); $^{13}$C NMR (75 MHz, D$_2$O): δ 173.33, 172.28, 169.55, 148.22, 139.18, 129.30, 128.54, 127.43, 123.96, 62.04, 61.02, 57.18, 51.10, 50.72, 50.44, 35.94, 33.03, 32.34, 31.32, 29.35, 27.86, 25.40, 25.09, 21.90, 15.64.

Example 4

Synthesis of SH-153 and SH-172

Compounds SH-153 and SH-172 were synthesized according to Schemes IV and V.

Scheme IV

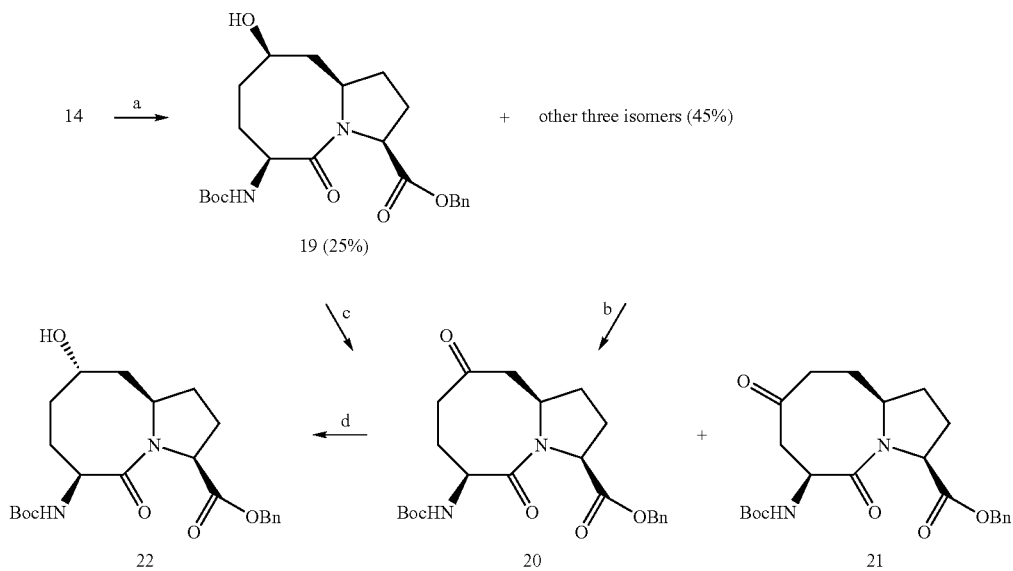

Reagents and coditions: (a) 9-BBN, THF, then H$_2$O$_2$ (35% in water), 3 N NaOH; (b) Dess-Martin periodinane, CH$_2$Cl$_2$, yield for 20 33%, yield for 21 62%; (c) Dess-Martin periodinane, CH$_2$Cl$_2$, 96%; (d) NaBH$_3$CN, MeOH, H$_2$SO$_4$ (cata.), 94%.

Borohydrogenation of the C—C double bond in compound 14 by treatment with 9-BBN followed by oxidation of the resulted borane by alkaline H$_2$O$_2$ gave a mixture of four alcohols. Alcohol 19 can be separated from the other three isomers by chromatography and its structure was confirmed by X-ray analysis. Oxidation of the mixture of the other three isomers by Dess-Martin periodinane yielded two ketones 20 and 21 which can be separated by chromatography. Reduction of ketone 20 by NaBH$_3$CN in the presence of a catalytic amount of H$_2$SO$_4$ furnished alcohol 22 as a single isomer. Oxidation of alcohol 19 by Dess-Martin periodinane also gave ketone 20, so the structure of alcohol 22 was also confirmed.

Scheme V

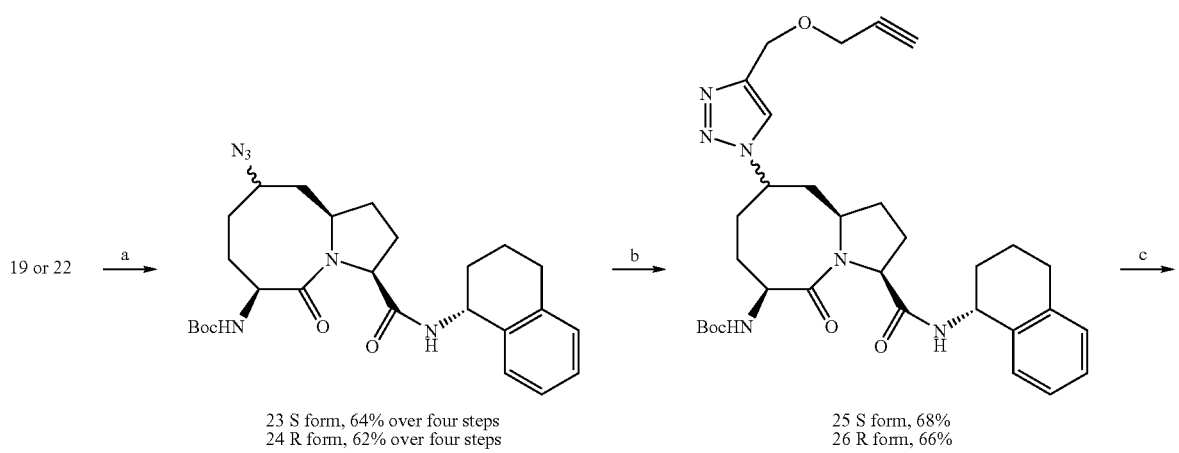

23 S form, 64% over four steps
24 R form, 62% over four steps

25 S form, 68%
26 R form, 66%

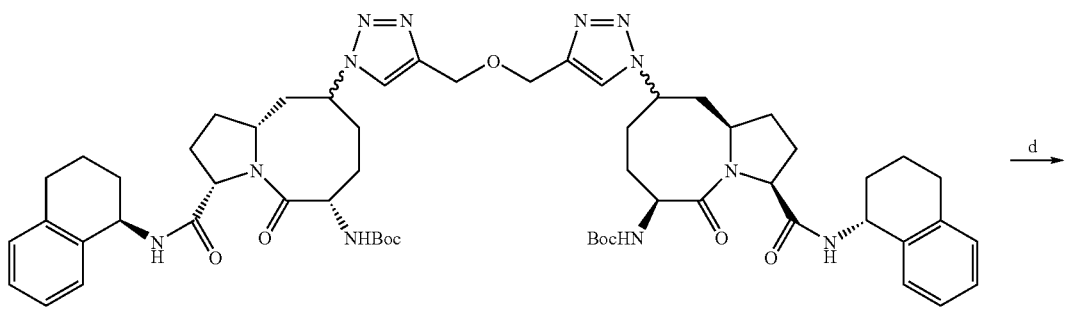

27 (S, S), 79%
28 (R, R), 81%

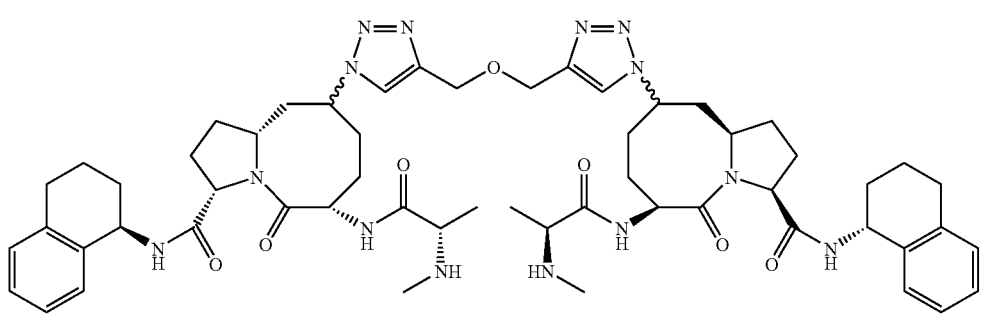

SH-172 (S, S), 74% over three steps
SH-153 (R, R), 72% over three steps

Reagents and conditions: (a) i. 10% Pd-C, H₂, MeOH; ii. (R)-(-)-1,2,3,4-tetrahydro-1-naphthylamine, EDC, HOBt, N,N-diisopropylethyl amine, CH₂Cl₂; iii. MsCl, N,N-diisopropylethyl amine, CH₂Cl₂; iv. NaN₃, DMF; (b) propargyl ether (5 eq), CuSO₄, (+)-sodium L-ascorbate, AcCN:t-BuOH:H₂O 2:2:1, rt; (c) 23 or 24, CuSO₄, (+)-sodium L-ascorbate, t-BuOH:H₂O 1:1, rt; diisopropylethyl amine, CH₂Cl₂; iii. 4 N HCl in 1,4-dioxane, MeOH.

Hydrolysis of the benzyl esters in 19 and 22 followed by condensation of the resulted acid with (R)-(−)-1,2,3,4-tetrahydro-1-naphthylamine yielded two amides (Scheme V). Reaction of these two amides with methanesulfonyl chloride followed by substitution of the resulted two mesylates with NaN₃ furnished two azides 23 and 24. Cycloaddition of these two azides with excessive amount propargyl ether under the catalyzation of CuSO₄-(+)-sodium-L-ascorbate gave two alkynes 25 and 26. Cycloaddition of 23 and 24 with these two alkynes respectively furnished compounds 27 and 28. Removal of the Boc protecting groups in these two compounds followed by condensation with L-N-Boc-N-methyl alanine yielded two amides. Removal of the Boc protecting groups in these two amides gave SH-153 and SH-172, respectively.

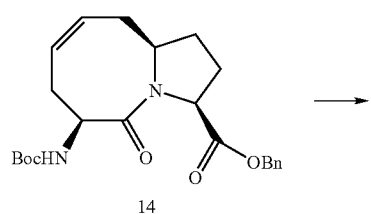

14

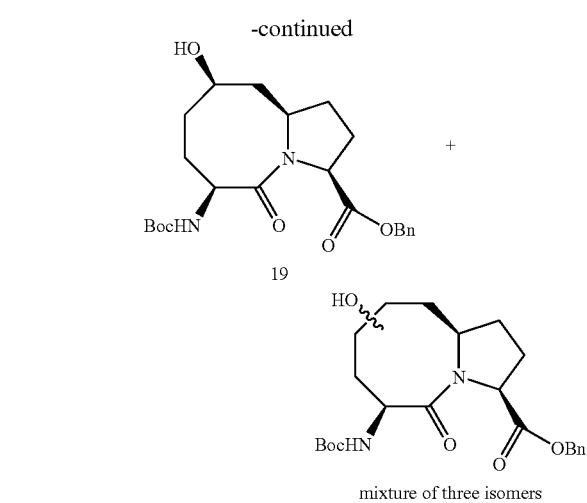

19 mixture of three isomers

To a solution of compound 14 (1.25 g, 3 mmol) in 50 mL of dry THF was added 9 mL of 9-BBN solution (0.5 M in THF, 4.5 mmol). After the solution was refluxed for 12 h, 1.5 mL of 3 M NaOH solution and 2 mL of H₂O₂ solution (35% in water) was added dropwise at 0° C. After warming to room temperature and stirring for 2 h, the mixture was extracted with ethyl acetate by three times. The combined organic layer was dried over Na₂SO₄ and then condensed. The residue was purified by chromatography to give compound 19 (330 mg, 25%) and a mixture of three other isomers (580 mg, 45%).

Chemical data for compound 19: $^1$H NMR (300 MHz, CDCl$_3$): δ 7.40-7.28 (m, 5H), 5.43 (brd, J=7.8 Hz, 1H), 5.28, 5.18 (ABq, J=Hz, 2H), 4.67 (t, J=8.4 Hz, 1H), 4.65 (m, 1H), 4.20 (m, 1H), 3.96 (m, 1H), 2.45-1.60 (m, 10H), 1.38 (brs, 9H); $^{13}$C NMR (75 MHz, CDCl$_3$): δ 172.38, 170.83, 155.13, 135.39, 128.58, 128.40, 128.34, 79.70, 70.63, 67.14, 60.13, 56.16, 50.70, 45.22, 32.67, 31.70, 28.35, 27.34.

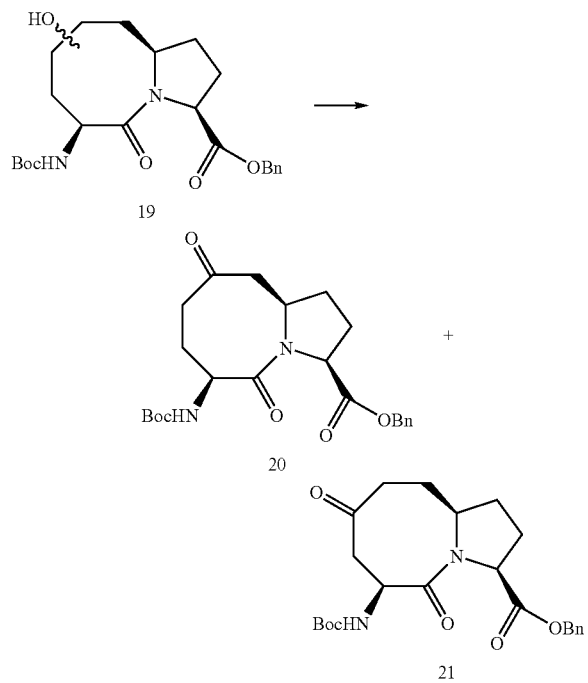

To a solution of the mixture of three isomers obtained above (570 mg, 1.3 mmol) in 15 mL of CH$_2$Cl$_2$ was added Dess-Martin periodinane (660 mmol, 1.56 mmol) at room temperature. The mixture was stirred at the same temperature for 2 h and then condensed. The residue was purified by chromatography to give compound 20 (160 mg, 28%) and 21 (330 mg, 58%). Compound 19 can be oxidized to compound 20 in the same method.

Chemical data for compound 20: $^1$H NMR (300 MHz, CDCl$_3$): δ 7.40-7.28 (m, 5H), 5.42 (brd, J=8.2 Hz, 1H), 5.28, 5.18 (ABq, J=12.2 Hz, 2H), 4.62 (t, J=8.4 Hz, 1H), 4.37 (m, 1H), 3.13 (m, 1H), 3.02 (t, 1H), 2.50-1.98 (m, 8H), 1.83 (m, 1H), 1.60 (m, 1H), 1.38 (brs, 9H); $^{13}$C NMR (75 MHz, CDCl$_3$): δ 211.37, 172.20, 170.94, 154.92, 135.23, 128.56, 128.41, 128.22, 79.81, 67.17, 60.53, 56.06, 53.39, 52.88, 36.79, 32.36, 30.18, 28.22, 27.00.

Chemical data for compound 21: $^1$H NMR (300 MHz, CDCl$_3$): δ 7.40-7.20 (m, 5H), 5.49 (brd, J=7.7 Hz, 1H), 5.17 (s, 2H), 5.09 (m, 1H), 4.52 (t, J=8.5 Hz, 1H), 4.22 (m, 1H), 3.08 (dd, J=12.7, 4.5 Hz, 1H), 2.92 (m, 1H), 2.60 (m, 2H), 2.36-1.72 (m, 6H), 1.43 (brs, 9H); $^{13}$C NMR (75 MHz, CDCl$_3$): δ 207.72, 170.93, 170.15, 154.74, 135.58, 128.37, 128.30, 128.14, 80.00, 66.67, 60.14, 59.74, 52.13, 48.52, 39.65, 34.18, 32.36, 28.21, 26.90.

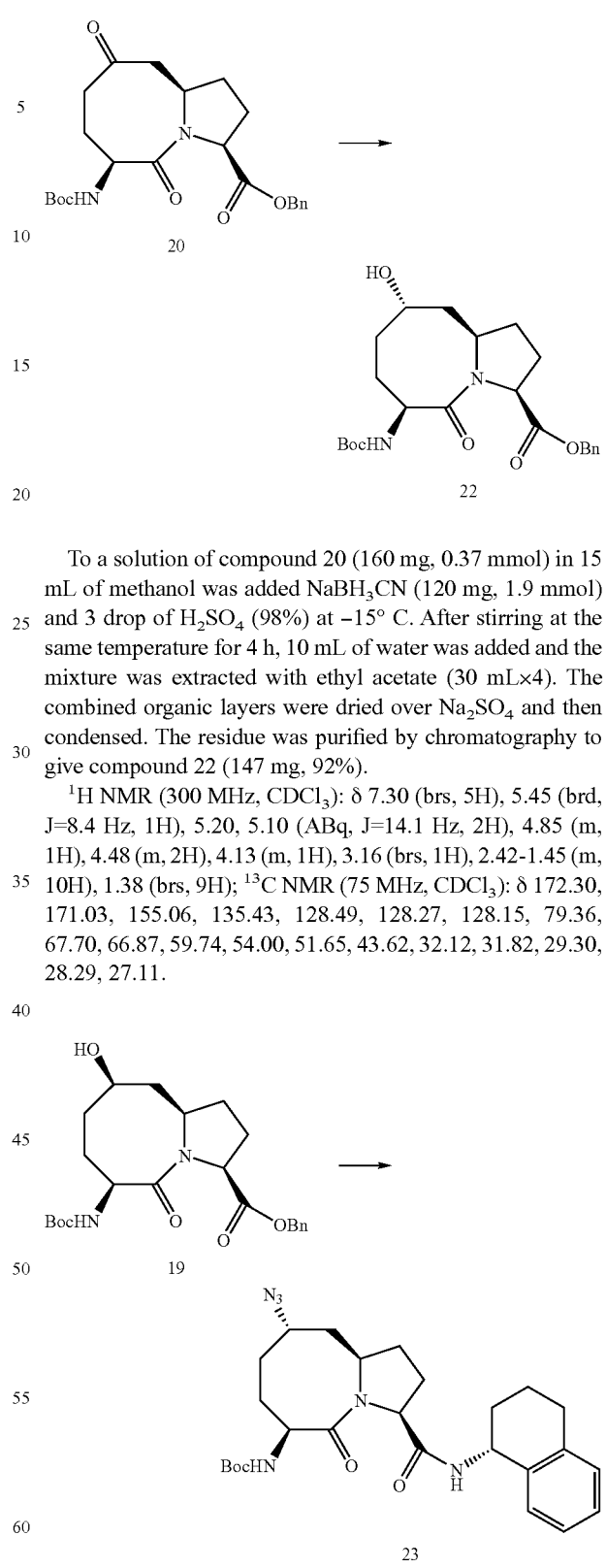

To a solution of compound 20 (160 mg, 0.37 mmol) in 15 mL of methanol was added NaBH$_3$CN (120 mg, 1.9 mmol) and 3 drop of H$_2$SO$_4$ (98%) at −15° C. After stirring at the same temperature for 4 h, 10 mL of water was added and the mixture was extracted with ethyl acetate (30 mL×4). The combined organic layers were dried over Na$_2$SO$_4$ and then condensed. The residue was purified by chromatography to give compound 22 (147 mg, 92%).

$^1$H NMR (300 MHz, CDCl$_3$): δ 7.30 (brs, 5H), 5.45 (brd, J=8.4 Hz, 1H), 5.20, 5.10 (ABq, J=14.1 Hz, 2H), 4.85 (m, 1H), 4.48 (m, 2H), 4.13 (m, 1H), 3.16 (brs, 1H), 2.42-1.45 (m, 10H), 1.38 (brs, 9H); $^{13}$C NMR (75 MHz, CDCl$_3$): δ 172.30, 171.03, 155.06, 135.43, 128.49, 128.27, 128.15, 79.36, 67.70, 66.87, 59.74, 54.00, 51.65, 43.62, 32.12, 31.82, 29.30, 28.29, 27.11.

To a solution of compound 19 (170 mg, 0.39 mmol) in 10 mL of CH$_2$Cl$_2$ was added methanesulfonyl chloride (0.05 mL, 0.6 mmol). The solution was cooled to 0° C. and then 0.2 mL of N,N-diisopropylethylamine was added dropwise. The mixture was stirred at room temperature for 4 h and then condensed. The residue was purified by chromatography to give a mesylate. To a solution of this mesylate in 10 mL of methanol was added 50 mg of 10% Pd—C. After the mixture was stirred at room temperature under H$_2$ for 3 h, the catalyst was filtered off and the filtration was condensed to yield an acid. The acid was dissolved in 10 mL of CH$_2$Cl$_2$. To this solution was added (R)-(−)-1,2,3,4-tetrahydro-1-naphthylamine (60 mg, 0.4 mmol), EDC (77 mg, 0.4 mmol), HOBt (55 mg, 0.4 mmol) and 0.3 mL of N,N-diisopropylethylamine subsequently. The solution was stirred at room temperature overnight and then condensed. The residue was purified by chromatography to furnish an amide. To a solution of this amide in 5 mL of DMF was added 0.2 g of NaN$_3$. The mixture was stirred at 110° C. for 6 h and then partitioned between 60 mL of ethyl acetate and 15 mL of brine. The organic layer was dried over Na$_2$SO$_4$ and then condensed. The residue was purified by chromatography to give compound 23 (132 mg, 68% over four steps).

$^1$H NMR (300 MHz, CDCl$_3$): δ 7.30 (m, 1H), 7.20-7.03 (m, 3H), 6.81 (brd, J=8.2 Hz, 1H), 5.50 (brd, J=8.4 Hz, 1H), 5.18 (m, 1H), 4.65 (m, 1H), 4.48 (m, 1H), 4.35 (m, 1H), 3.84 (m, 1H), 2.80 (m, 2H), 2.45 (m, 1H), 2.30-1.78 (m, 13H), 1.45 (brs, 9H); $^{13}$C NMR (75 MHz, CDCl$_3$): δ 171.19, 170.26, 154.87, 137.18, 136.41, 129.07, 128.73, 127.28, 126.16, 79.56, 60.47, 59.30, 54.47, 50.79, 47.57, 40.40, 33.19, 32.56, 29.83, 29.02, 28.32, 27.82, 25.43, 19.74.

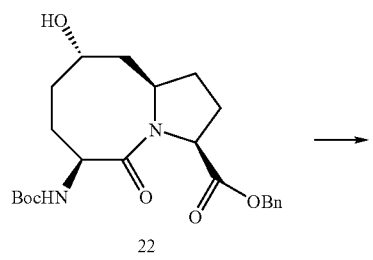

22

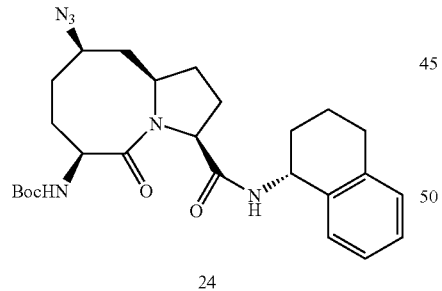

24

Compound 24 was synthesized in the same sequence as that for compound 6 from compound 22 (63% over four steps).

$^1$H NMR (300 MHz, CDCl$_3$): δ 7.32 (m, 1H), 7.15 (m, 2H), 7.06 (m, 1H), 6.77 (brd, J=8.3 Hz, 1H), 5.43 (brd, J=8.2 Hz, 1H), 5.16 (m, 1H), 4.54 (m, 1H), 4.48 (t, J=7.5 Hz, 1H), 4.25 (m, 1H), 3.52 (m, 1H), 2.80 (m, 2H), 2.48-1.50 (m, 14H), 1.42 (brs, 9H); $^{13}$C NMR (75 MHz, CDCl$_3$): δ 171.02, 170.07, 154.94, 137.11, 136.33, 128.98, 128.76, 127.20, 126.23, 79.76, 61.17, 60.35, 56.99, 49.85, 47.47, 42.20, 32.74, 29.84, 29.14, 29.01, 28.25, 26.08, 19.76.

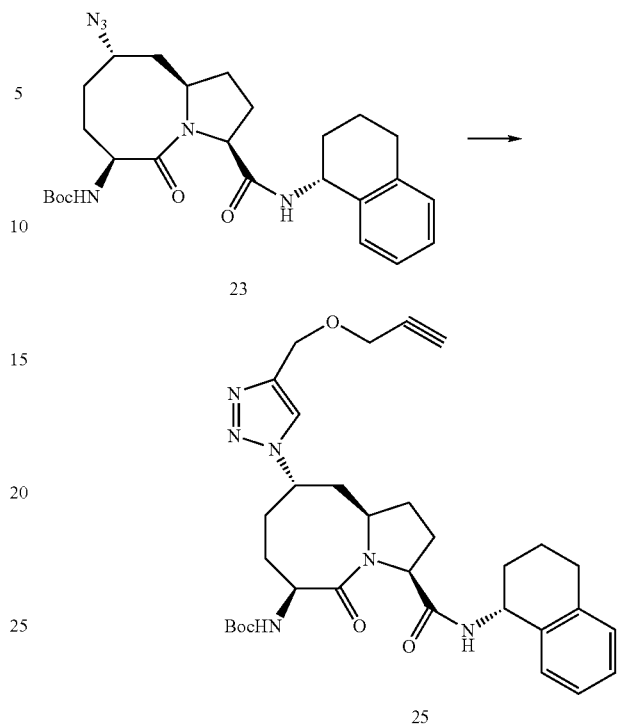

To a solution of 20 mg of CuSO$_4$ in 2 mL of water was added 40 mg of (+)-sodium L-ascorbate. The mixture was shaken until the color turned to bright yellow. This mixture was added dropwise to a solution of compound 23 (120 mg, 0.24 mmol) and 0.2 mL of propargyl ether in 3 mL of acetonitrile and 3 mL of t-BuOH at room temperature. The mixture was stirred at the same temperature overnight and then partitioned between 60 mL of CH$_2$Cl$_2$ and 15 mL of brine. The organic layer was dried over Na$_2$SO$_4$ and then condensed. The residue was purified by chromatography to give compound 25 (105 mg, 74%).

$^1$H NMR (300 MHz, CDCl$_3$): δ 7.64 (s, 1H), 7.39 (m, 1H), 7.18 (m, 2H), 7.07 (m, 1H), 6.50 (brd, J=8.3 Hz, 1H), 5.83 (brd, J=7.1 Hz, 1H), 5.19 (m, 1H), 4.76 (m, 1H), 4.70 (s, 2H), 4.55-4.32 (m, 3H), 4.23 (d, J=2.4 Hz, 2H), 2.80 (m, 2H), 2.50 (t, J=2.4 Hz, 1H), 2.46-1.63 (m, 14H), 1.48 (brs, 9H); $^{13}$C NMR (75 MHz, CDCl$_3$): δ 170.63, 170.48, 154.79, 143.58, 137.35, 136.30, 129.11, 128.59, 127.36, 126.41, 122.65, 79.71, 79.31, 74.87, 62.96, 60.83, 59.13, 57.49, 54.65, 53.29, 47.84, 41.98, 34.53, 32.49, 31.26, 30.15, 29.10, 28.34, 25.81, 20.06.

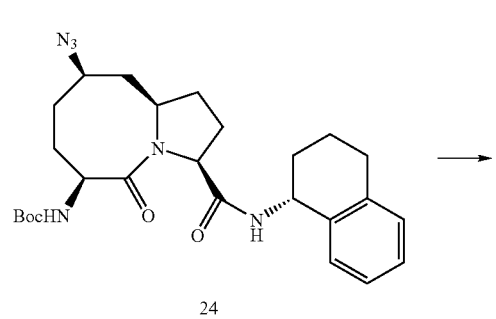

24

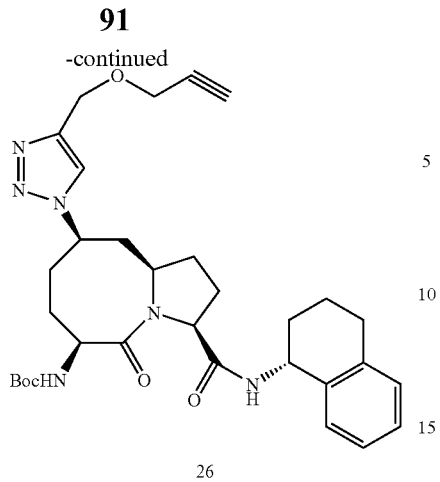

26

Compound 26 was synthesized in the same method as that for compound 25 from compound 24 (yield 73%).

$^1$H NMR (300 MHz, CDCl$_3$): δ 7.59 (s, 1H), 7.36 (m, 1H), 7.13 (m, 2H), 7.04 (m, 1H), 6.68 (brd, J=8.2 Hz, 1H), 5.48 (brd, J=8.3 Hz, 1H), 5.15 (m, 1H), 4.89 (m, 1H), 4.72 (m, 1H), 4.70 (s, 2H), 4.56-4.35 (m, 2H), 4.14 (d, J=2.3 Hz, 1H), 2.80 (m, 2H), 2.58-1.55 (m, 15H), 1.43 (brs, 9H); $^{13}$C NMR (75 MHz, CDCl$_3$): δ 170.83, 170.60, 155.02, 144.76, 137.22, 136.29, 129.03, 128.79, 127.31, 126.32, 120.18, 79.86, 79.18, 74.97, 62.97, 61.36, 60.02, 57.52, 57.22, 49.65, 47.76, 43.81, 32.84, 32.72, 30.50, 29.92, 29.01, 28.29, 26.56, 19.86.

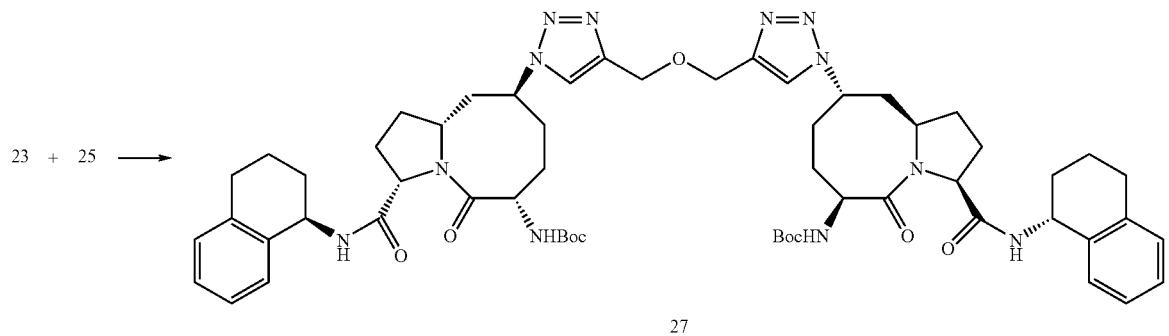

27

To a solution of compound 23 and 25 in 3 mL of acetonitrile and 3 mL of t-BuOH was added a mixture of 20 mg of CuSO$_4$ and 40 mg of (+)-sodium L-ascorbate in 2 mL of water. The mixture was stirred at room temperature overnight and then partitioned between 60 mL of CH$_2$Cl$_2$ and 15 mL of brine. The organic layer was dried over Na$_2$SO$_4$ and then condensed. The residue was purified by chromatography to give compound 27 (79%).

$^1$H NMR (300 MHz, CDCl$_3$): δ 7.70 (s, 2H), 7.40 (m, 2H), 7.19 (m, 4H), 7.11 (m, 2H), 6.54 (brd, J=8.3 Hz, 2H), 5.79 (brd, J=7.1 Hz, 2H), 5.19 (m, 2H), 4.75 (m, 2H), 4.67 (s, 4H), 4.47 (m, 4H), 4.35 (t, J=8.5 Hz, 2H), 2.79 (m, 4H), 2.45-1.60 (m, 28H), 1.43 (brs, 18H); $^{13}$C NMR (75 MHz, CDCl$_3$): δ 170.57, 170.48, 154.78, 143.89, 137.31, 136.32, 129.06, 128.62, 127.31, 126.39, 122.60, 79.66, 63.66, 60.80, 59.06, 54.65, 53.27, 47.80, 41.93, 34.49, 32.49, 30.13, 29.21, 29.09, 28.32, 25.78, 20.03.

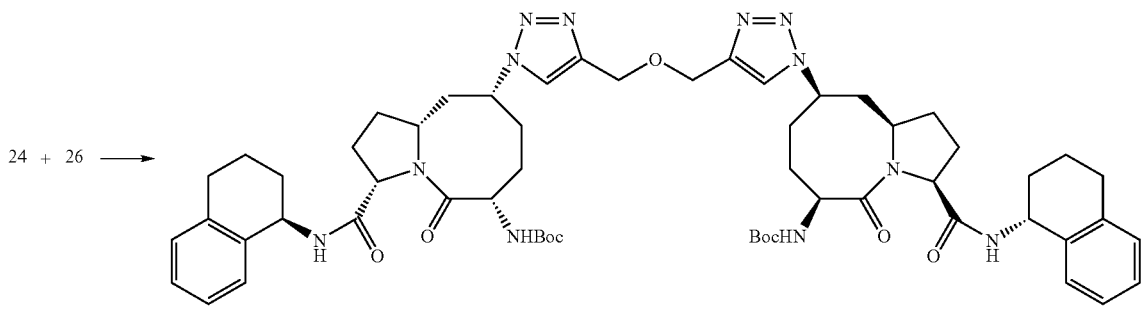

28

Compound 28 was synthesized in the same method as that for compound 27 from compound 24 and 26.

¹H NMR (300 MHz, CDCl₃): δ 7.61 (s, 2H), 7.38 (m, 1H), 7.20-6.99 (m, 6H), 6.60 (brd, J=8.0 Hz, 2H), 5.48 (brd, J=8.1 Hz, 2H), 5.16 (m, 2H), 4.89 (m, 2H), 4.73 (m, 2H), 4.70 (s, 4H), 4.52-4.33 (m, 4H), 2.78 (m, 4H), 2.56-1.58 (m, 28H), 1.43 (brs, 18H); ¹³C NMR (75 MHz, CDCl₃): δ 170.89, 170.51, 155.01, 137.22, 136.25, 129.03, 128.81, 127.33, 126.35, 120.21, 79.87, 63.85, 61.38, 60.03, 57.27, 49.65, 47.75, 43.86, 32.85, 32.73, 30.51, 29.21, 29.03, 28.30, 26.54, 19.84.

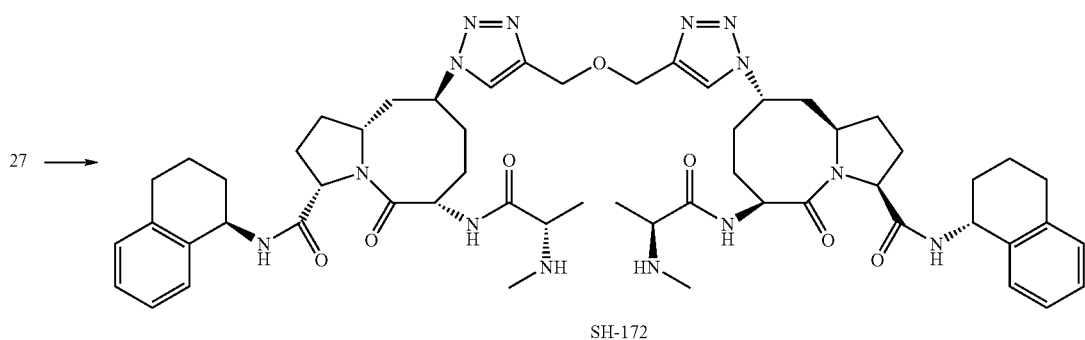

SH-172

To a solution of compound 27 in 5 mL of methanol was added 1 mL of HCl solution (4 N in 1,4-dioxane). The solution was stirred at room temperature overnight and then condensed. The residue was suspended in 5 mL of CH₂Cl₂. To this mixture was added L-N-methyl-N-Boc-alanine, EDC, HOBt and N,N-diisopropylethylamine. The mixture was stirred at room temperature overnight and then condensed. The residue was purified by chromatography to give an amide. To a solution of this amide in 5 mL of methanol was added 1 mL of HCl solution (4 N in 1,4-dioxane). The solution was stirred at room temperature overnight and then condensed to give crude SH-172 as a salt with HCl. This compound was purified by HPLC to give pure product. The gradient ran from 75% of solvent A (water contained 0.1% of TFA) and 25% of solvent B (acetonitrile contained 0.1% of TFA) to 55% of solvent A and 45% of solvent in 25 min. Analytical HPLC showed the purity is over 95%.

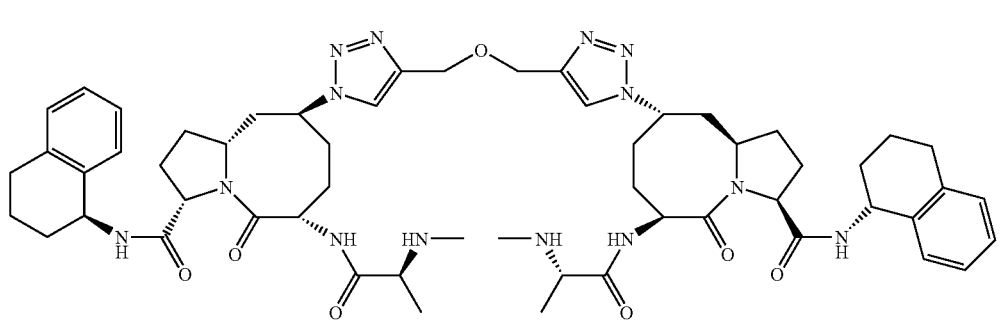

SH-172

$^1$H NMR (300 MHz, D$_2$O): δ 7.85 (s, 2H), 7.22-7.02 (m, 8H), 4.98-4.79 (m, 4H), 4.80-4.60 (m, 4H), 4.52 (s, 4H), 4.28 (t, J=8.7 Hz, 2H), 3.82 (m, 2H), 2.72-2.50 (m, 10H), 2.48-1.55 (m, 28H), 1.45 (d, J=7.0 Hz, 6H); $^{13}$C NMR (75 MHz, D$_2$O): δ 173.57, 171.59, 169.27, 138.30, 136.14, 129.54, 128.56, 127.82, 126.61, 124.46, 62.79, 61.98, 59.66, 57.28, 55.45, 53.24, 48.38, 41.25, 31.93, 31.32, 31.11, 29.86, 28.81, 27.24, 20.27, 15.64.

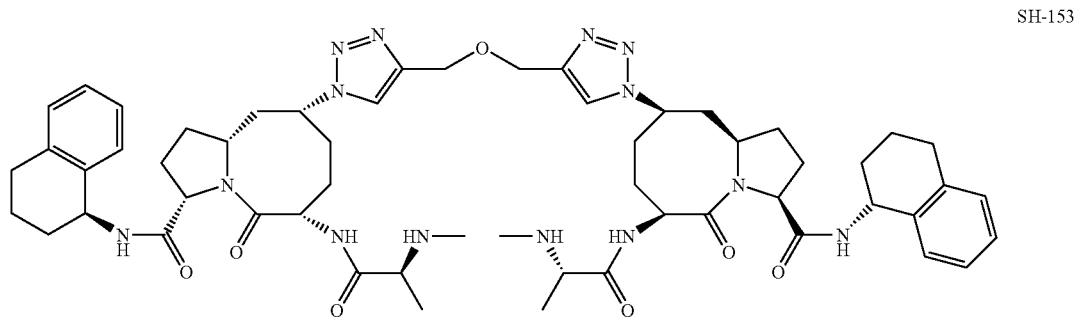

SH-153

SH-153 was synthesized in the same sequence as that for SH-172 from compound 28.

$^1$H NMR (300 MHz, D$_2$O): δ 7.95 (s, 2H), 7.20-6.95 (m, 8H), 4.92-4.74 (m, 6H), 4.59 (s, 4H), 4.55 (m, 2H), 4.27 (m, 2H), 3.86 (m, 2H), 2.78-2.52 (m, 12H), 2.42-2.08 (m, 8H), 1.99-1.55 (m, 18H), 1.45 (d, J=7.0 Hz, 6H); $^{13}$C NMR (75 MHz, D$_2$O): δ 172.99, 171.58, 169.78, 138.23, 136.07, 129.46, 128.57, 127.78, 126.57, 123.39, 62.82, 62.56, 60.59, 58.14, 57.13, 50.49, 48.38, 42.62, 32.49, 31.30, 29.84, 29.53, 28.78, 27.86, 20.20, 15.61.

Example 5

Synthesis of SH-146

Compound SH-146 was synthesized according to Scheme VI.

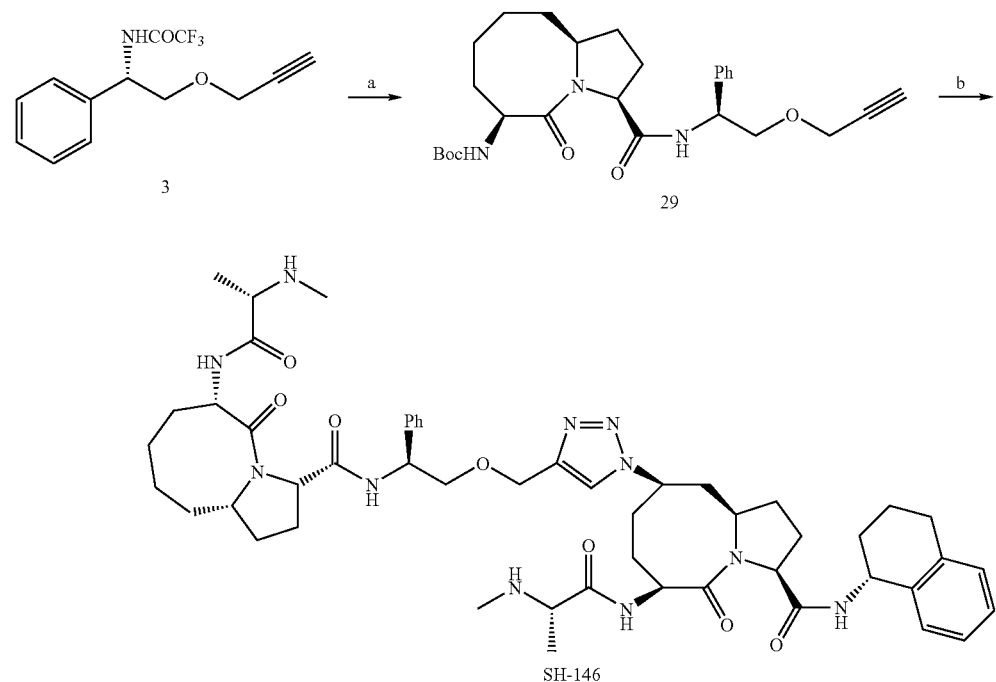

Scheme VI

SH-146

Reagents and conditions: (a) i. 2N LiOH, 1,4-dioxane:H2O 1:1; ii. 15, EDC, HOBt, N,N-diisopropylethyl amine, CH2Cl2, 88% over two steps; (b) i. 24, CuSO$_4$, (+)-sodium L-ascorbate, t-BuOH-H$_2$O 1:1, ii. 4N HCl in 1,4-dioxane, MeOH; iii. L-N-Boc-N-methyl alanine, EDC, HOBt, N,N-diisopropylethyl amine, CH$_2$Cl$_2$; iv. 4N HCl in 1,4-dioxane, MeOH, 55% over four steps.

Removal of the trifluoroacetyl protecting group in compound 3 followed by condensation of the resulted amine with acid 15 gave an amide 29. Cycloaddition of azide 24 with alkyne 29 under the catalyzation of CuSO₄-(+)-sodium-L-ascorbate followed by removal of the Boc protecting groups afforded an ammonium salt. After condensation of this salt with L-N-Boc-N-methyl alanine, the Boc protecting groups were cleaved by treating with HCl in methanol to afford the bivalent Smac mimetic SH-146.

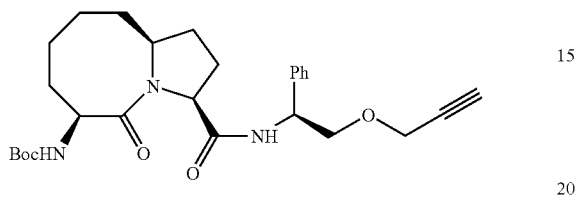

29

¹H NMR (300 MHz, CDCl₃): δ 7.75 (brs, J=7.4 Hz, 1H), 7.32-7.15 (m, 5H), 5.53 (brd, J=7.1 Hz, 1H), 5.08 (m, 1H), 4.73 (t, J=6.6 Hz, 1H), 4.60 (m, 1H), 4.19 (brs, 2H), 4.12 (m, 1H), 3.80 (m, 2H), 2.62 (m, 1H), 2.45 (t, J=2.3 Hz, 1H), 2.23-1.65 (m, 4H), 1.55-1.10 (m, 16H); ¹³C NMR (75 MHz, CDCl₃): δ 172.20, 169.94, 155.03, 139.45, 128.37, 127.46, 127.05, 79.59, 79.23, 74.91, 72.23, 59.76, 59.27, 58.34, 52.96, 51.08, 36.44, 32.00, 28.37, 24.93, 24.12, 23.08.

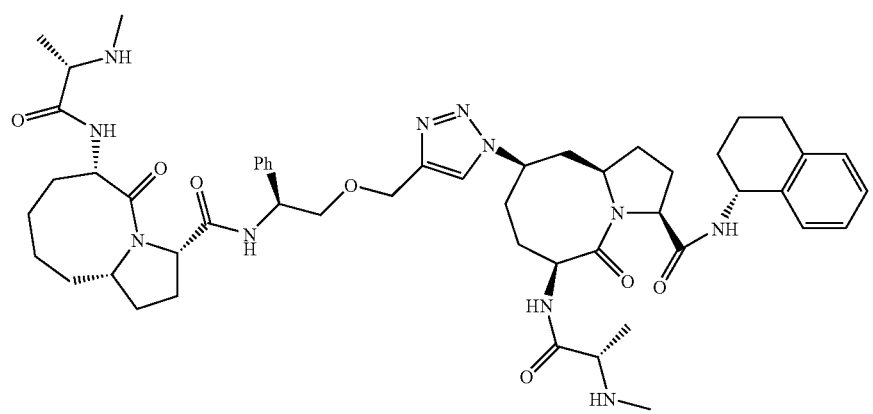

SH-146

¹H NMR (300 MHz, D₂O): δ 7.84 (s, 1H), 7.40-7.25 (m, 6H), 7.24-7.02 (m, 3H), 4.98-4.85 (m, 4H), 4.74 (m, 2H), 4.53 (s, 2H), 4.30 (m, 2H), 4.27 (m, 1H), 3.97-3.80 (m, 2H), 3.78-3.65 (m, 2H), 2.92 (m, 2H), 2.56 (s, 3H), 2.55 (s, 3H), 2.35-1.45 (m, 26H), 1.43 (d, J=7.0 Hz, 3H), 1.38 (d, J=7.0 Hz, 3H); ¹³C NMR (75 MHz, D₂O): δ 173.88, 173.59, 172.24, 171.57, 169.52, 169.26, 143.92, 138.65, 138.31, 136.20, 129.51, 129.12, 128.48, 128.17, 127.80, 126.95, 126.60, 124.24, 72.30, 63.35, 62.21, 61.98, 61.05, 59.61, 57.27, 57.19, 55.46, 53.35, 53.20, 51.12, 48.41, 41.21, 35.95, 33.00, 32.34, 31.30, 29.83, 28.80, 27.94, 25.08, 21.91, 20.30, 15.62.

Example 6

Synthesis of YP-317, YP-381, YP-383 and YP-385

Compound YP-317 was synthesized according to Scheme VII.

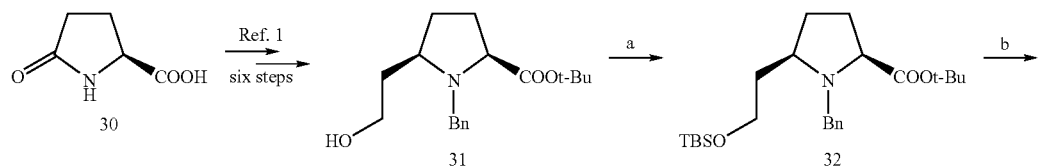

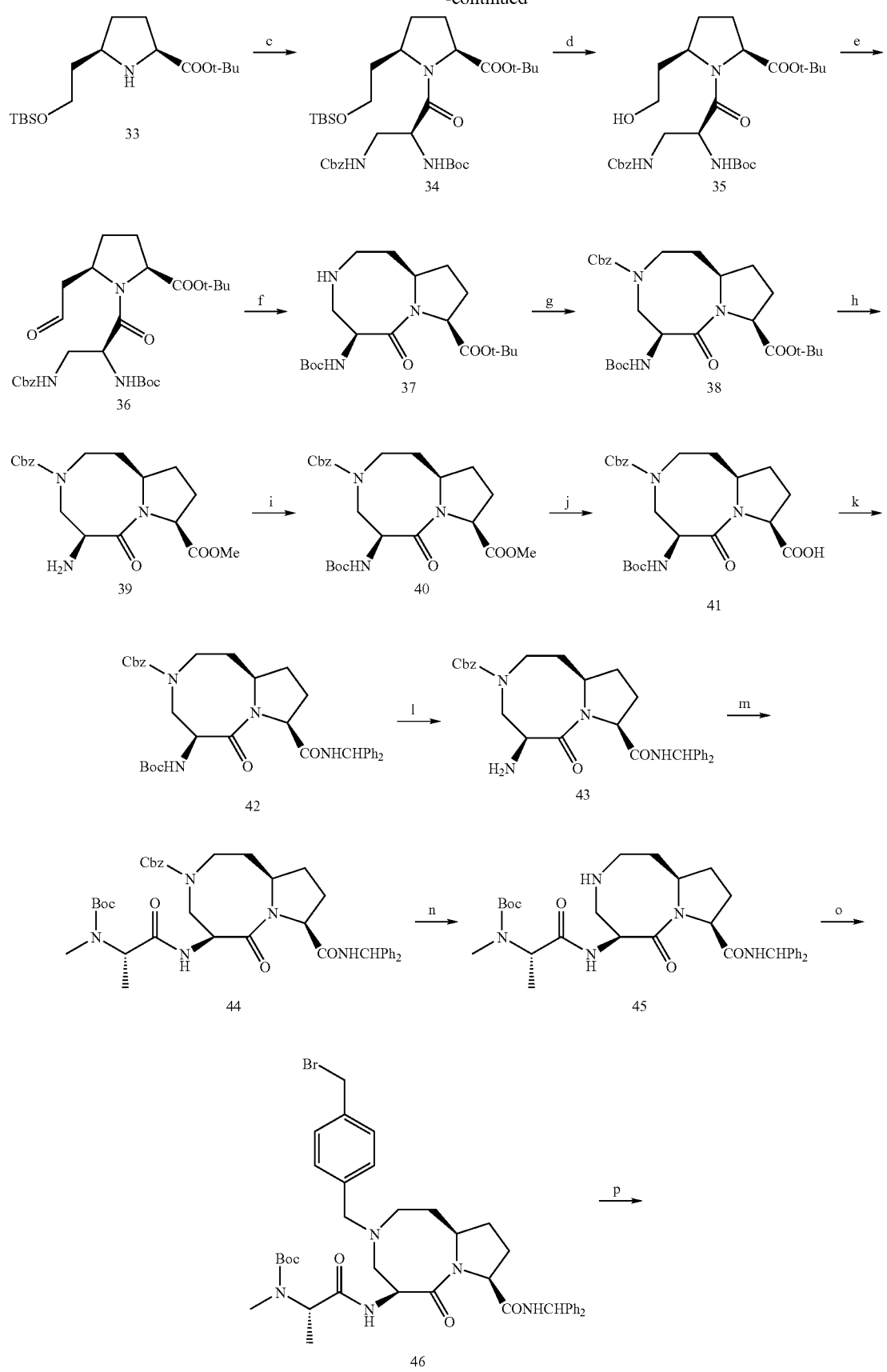

-continued

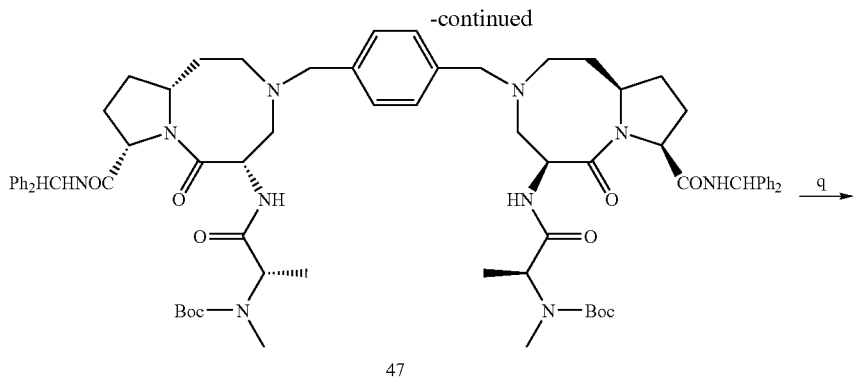

47

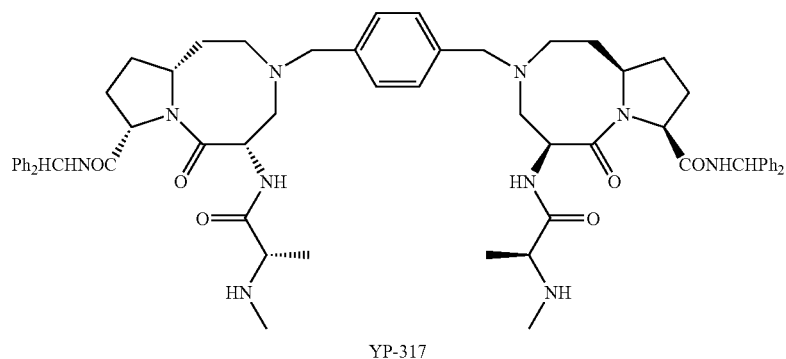

YP-317

Reagents and conditions: (a) tert-Butyldimethylsilyl chloride, N,N-diisopropylethyl amine, Methylene chloride; (b) 10% Pd-C, Methanol, H₂, 88% over two steps; (c) Boc-Dap(Z)-OH, EDC, HOBt, N,N-diisopropylethyl amine, Methylene chloride; (d) 1 Tetrabutylammonium fluoride in tetrahydrofuran, Tetrahydrofuran, 87% over two steps; (e) Dess-Martin periodinane, Methylene chloride, 96%; (f) 10% Pd-C, Methanol, H₂, 64%; (g) Benzyl chloroformate, Sodium bicarbonate, 1,4-dioxane, 95%; (h) Thionyl chloride, Methanol; (i) Boc anhydride, Sodium bicarbonate, 1,4-dioxane, 71% over two steps; (j) 2M Lithium hydroxide in H₂O, 1,4 dioxane-H₂O; (k) Aminodiphenylmethane, EDC, HOBt, N, N-diisopropylethyl amine, Methylene chloride, 74% over two steps; (l) 4M Hydrogen chloride in 1,4-dioxane, Methanol; (m) L-N-Boc-N-methyl alanine, EDC, HOBt, N,N-diisopropylethyl amine, Methylene chloride, 78% over two steps; (n) 10% Pd-C, Methanol, H₂, 90%; (o) α,α'-dibromo-p-xylene, Sodium bicarbonate, 1,4-dioxane; (p) compound 21, Sodium bicarbonate, 1,4-dioxane; (q) 4M Hydrogen chloride in 1,4-dioxane, Methanol, 34% over three steps.

Compound 31 was prepared in six steps from pyroglutamic acid (compound 30) by the published methods (Zhang et al., Org. Lett., 4:4029-4032 (2002); (b) Polyak et al., J. Org. Chem. 63:5937-5949 (1998)). The hydroxyl group in compound 31 was protected with TBS to yield compound 32. The benzyl protective group was removed by catalytic hydrogenation to yield amine 33, which was coupled with Boc-Dap (Z)-OH to give amide 34. The TBS protective group in compound 34 was removed by 1 M tetrabutylammonium fluoride in tetrahydrofuran to yield alcohol 35, which was then oxidized to aldehyde 36 by Dess-Martin Periodinane. Removal of the Cbz protective group in compound 36 by catalytic hydrogenation, intramolecular condensation of the desired amine with the aldehyde and subsequent reduction of the resulted enamine were carried out in one pot to give bicyclic compound 37. Amine 37 was protected with Cbz protective group to yield compound 38. The Boc protective group in compound 38 was removed and tert-butyl ester was converted to methyl ester by treating with thionyl chloride in methanol to give compound 39. The amine group was protected with Boc protective group to yield compound 40. Methyl ester 40 was transformed to carboxylic acid 41, which was condensed with aminodiphenylmethane to form amide 42. The Boc protective group in compound 42 was removed to give free amine 43, which was coupled with L-N-Boc-N-methyl alanine to yield amide 44. The Cbz protective group in compound 44 was removed by catalytic hydrogenation to give amine 45, which was treated with α,α'-dibromo-p-xylene to yield compound 46. Compound 46 was treated with compound 45 and sodium bicarbonate to give the protected dimer 47, whose Boc protective groups were removed to form the desired dimer YP-317.

$^1$H NMR (D₂O) δ 9.23-9.26 (m, 1H), 7.18-7.22 (m, 8H), 7.06-7.08 (m, 4H), 6.02-6.05 (m, 1H), 5.30-5.36 (m, 1H), 4.59 (m, 1H), 4.52 (m, 1H), 4.27 (s, 2H), 3.78-3.86 (m, 2H), 3.53-3.58 (m, 2H), 2.99 (t, J=2 Hz, 1H), 2.56 (s, 3H), 2.32 (m, 1H), 1.84-1.92 (m, 1H), 1.67-1.75 (m, 4H), 1.35-1.37 (d, J=7 Hz, 3H); $^{13}$C NMR (D₂O) δ 173.93, 170.13, 167.90, 163.54, 163.07, 140.74, 140.62, 132.39, 130.59, 129.39, 129.26, 128.40, 128.13, 127.85, 127.58, 118.58, 114.72, 62.98, 61.07, 59.03, 58.25, 57.10, 56.42, 55.26, 54.18, 47.98, 31.65, 31.24, 30.98, 27.01, 15.42; HRMS Found: [M+H]⁺ 1057.6057 (calcd 1057.6028).

YP-381, YP-383 and YP-385 were synthesized in a similar fashion via acylation of compound 45.

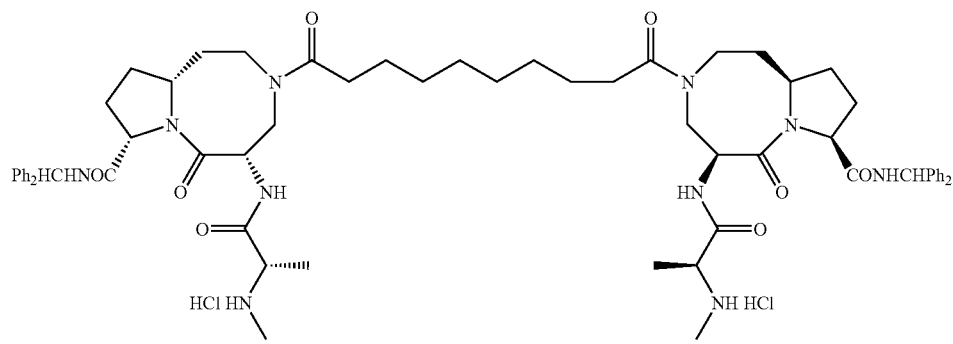
YP-381
¹H NMR (300 MHz, CD₃OD, TMS) δ 8.94-8.91 (d, J=7.9 Hz, 1H), 7.37-7.24 (m, 10H), 6.17-6.14 (d, J=8.2 Hz, 1H), 4.58-4.55 (m, 1H), 4.24 (br, 1H), 3.99-3.90 (m, 2H), 3.50-3.38 (m, 1H), 2.70 (s, 3H), 2.65-2.40 (m, 2H), 2.31 (m, 1H), 2.09-1.78 (m, 6H), 1.61 (m, 2H), 1.56-1.53 (d, J=7.0 Hz, 3H), 1.32 (s, 4H). ¹³CNMR (75 MHz, CD₃OD) δ 176.5, 175.9, 173.2, 169.6, 143.0, 129.6, 128.8, 128.2, 62.7, 58.2, 53.7, 34.4, 33.4, 32.3, 31.8, 30.3, 28.3, 26.1, 16.2. HRMS: calcd. m/z for [M+Na]⁺ 1143.6371; found 1143.6387.
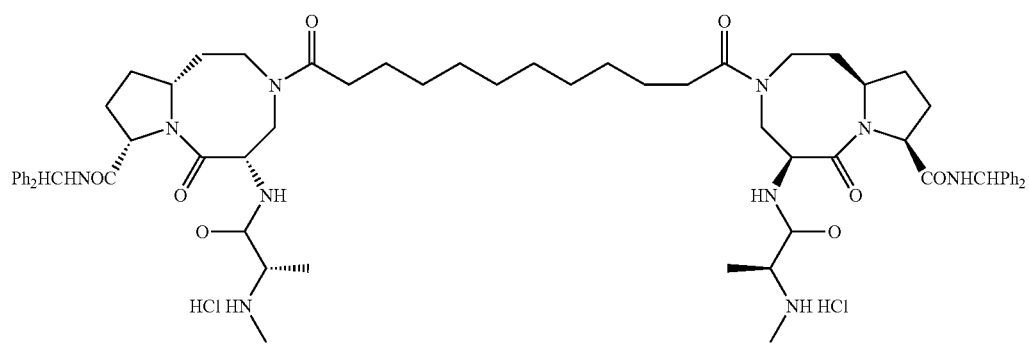
YP-383
¹H NMR (300 MHz, CD₃OD, TMS) δ 7.35-7.27 (m, 10H), 6.16 (s, 1H), 4.59-4.52 (m, 1H), 4.24 (br, 1H), 4.02-3.99 (m, 1H), 3.97-3.92 (m, 1H), 3.90-3.87 (m, 1H), 3.58-3.48 (m, 2H), 2.70 (s, 3H), 2.56-2.34 (m, 2H), 2.34-2.32 (m, 1H), 2.06-1.19 (m, 6H), 1.56-1.53 (d, J=7.0 Hz, 3H), 1.30 (s, 6H).
¹³CNMR (75 MHz, CD₃OD) δ 176.5, 175.9, 173.2, 169.6, 143.0, 129.6, 128.8, 128.2, 62.7, 58.2, 53.7, 34.4, 33.4, 31.7, 30.6, 30.4, 28.3, 26.3, 16.1. HRMS: calcd. m/z for [M+Na]⁺ 1171.6684; found 1171.6680.
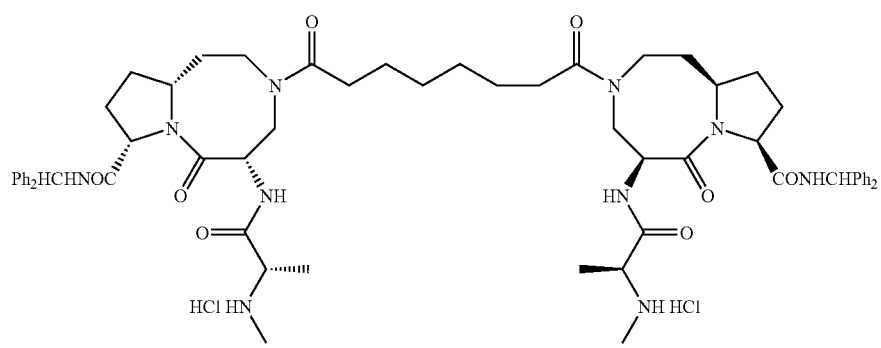
YP-385

$^1$H NMR (300 MHz, CD$_3$OD, TMS) δ 8.95-8.93 (d, J=8.1 Hz, 1H), 7.37-7.24 (m, 10H), 6.17-6.14 (d, J=8.0 Hz, 1H), 4.58-4.56 (m, 1H), 4.24 (br, 1H), 3.99-3.92 (m, 2H), 3.82-3.70 (m, 1H), 2.70 (s, 3H), 2.62-2.40 (m, 2H), 2.33 (m, 1H), 2.04-1.75 (m, 6H), 1.60-1.56 (m, 2H), 1.55-1.52 (d, J=7.0 Hz, 3H), 1.34-1.30 (m, 2H). $^{13}$CNMR (75 MHz, CD$_3$OD) δ 176.5, 175.8, 173.3, 169.7, 143.0, 129.6, 128.8, 128.2, 62.7, 58.2, 53.7, 34.5, 33.4, 31.7, 30.2, 28.3, 26.2, 16.1. HRMS: calcd. m/z for [M+Na]$^+$ 1115.6058; found 1115.6055.

Example 7

Synthesis of Smac Mimetic Intermediates

Scheme VIII

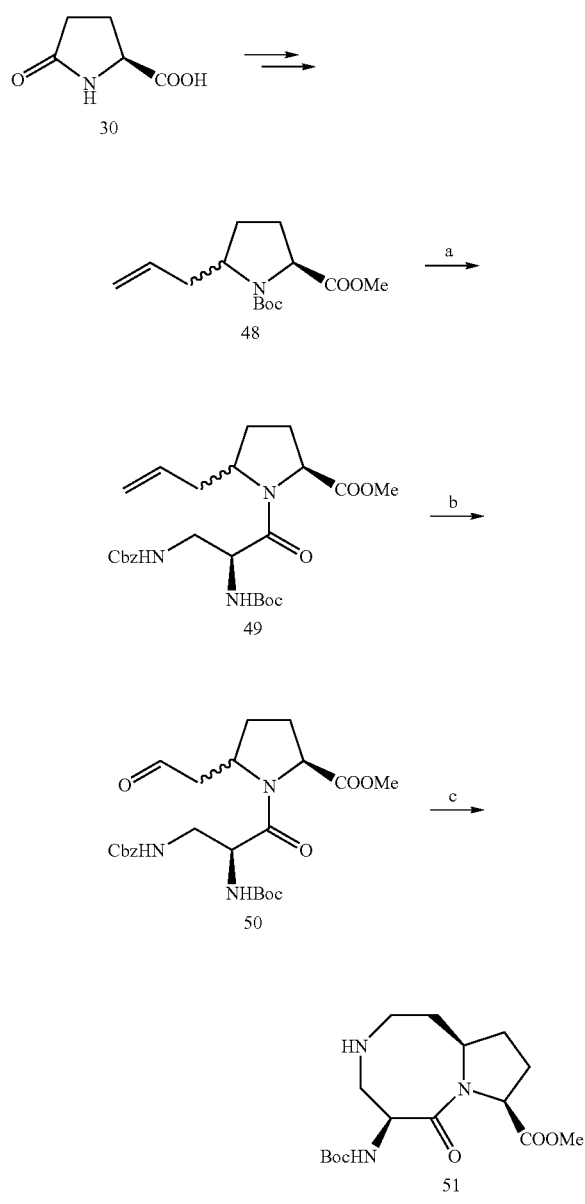

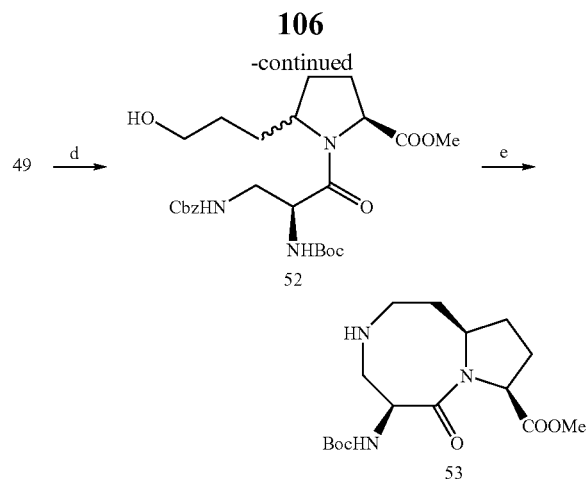

Reagents and conditions: (a) i. 4N HCl in 1,4-dioxane, methanol; ii. Boc-Dap(Z)-OH, EDC, HOBt, N,N-diisopropylethylamine, CH$_2$Cl$_2$, 52% over two steps; (b) O$_3$, then PPh$_3$, CH$_2$Cl$_2$, 90%; (c) H$_2$, 10% Pd-C, i-PrOH, 41%; (d) 9-BBN (2 eq), THF, reflux, 12 h, then 3N NaOH (2 eq), 35% H$_2$O$_2$ (2.5 eq), 0° C.- rt, 85%; (e) i. Dess-Martin periodinane, CH$_2$Cl$_2$; ii. H$_2$, 10% Pd-C, i-PrOH, 50% over two steps.

The synthesis of intermediates 51 and 53 is shown in Scheme VIII. Compound 48 may be prepared in five steps from pyroglutamic acid 30 according to reported methods (see: (1) Zhang, J.; Xiong, C.; Wang, W.; Ying, J.; Hruby, V., J. Org. Lett., 2002, 4 (23), 4029-4032 and (2) Polyak, F. and Lubell, W. D. J. Org, Chem. 1998, 63, 5937-5949) as a mixture of two diastereoisomers with the R form isomer as the major product (ratio is about 4:1). Removal of the Boc group in 48 followed by condensation with N-α-(tert-butoxycarbonyl)-N-β-(benzoxycarbonyl)-L-diamino-propionic acid (Boc-Dap(Z)-OH) gave amide 49. Ozone oxidation of the C—C double bond in 49 yielded aldehyde 50. Cleavage of the Cbz group in 4, intra-molecular condensation of the resulting amine with the aldehyde group and subsequent reduction of the enamine were realized in one pot to give compound 51. In this transformation only compound 51 was obtained and there was no detectable formation of its isomer, suggesting that the amino aldehyde from the minor isomer does not cyclize under these conditions.

Hydroboration of the C—C double bond in 49 with 9-BBN followed by alkaline oxidation of the resulted borane afforded alcohols 52. Oxidation of 52 with Dess-Martin periodinane furnished a mixture of two aldehydes, which was cyclized in the same procedure as that for compound 51 to give compound 53. Similar to 51, during this transformation only one isomer was obtained.

Analytical data for compound 51: [α]$^{20}$$_D$–30.2 (c=1.7, CHCl$_3$); $^1$H NMR (300 MHz, CDCl$_3$, TMS) δ 5.45 (brd, J=8.0 Hz, 1H), 4.67 (m, 1H), 4.52 (t, J=9.0 Hz, 1H), 4.23 (m, 1H), 3.74 (s, 3H), 3.20 (m, 2H), 2.94 (m, 1H), 2.74 (dd, J=13.6, 10.9 Hz, 1), 2.35 (m, 1H), 2.14 (m, 1H), 1.99 (m, 1H), 1.86-1.74 (m, 3H), 1.66 (m, 1H), 1.43 (brs, 9H); $^{13}$C NMR (75 MHz, CDCl$_3$, TMS) δ 173.42, 170.60, 155.16, 79.68, 59.46, 58.39, 54.92, 52.44, 46.72, 37.45, 32.15, 29.64, 28.29, 26.98.

Analytical data for compound 53: [α]$^{20}$$_D$–23.2 (c=1.0, CHCl$_3$); $^1$H NMR (300 MHz, CDCl$_3$, TMS) δ 5.23 (brd, J=8.0 Hz, 1H), 4.79 (m, 1H), 4.65 (dd, J=9.7, 8.2 Hz), 4.22 (m, 1H), 3.74 (s, 3H), 3.02-2.80 (m, 4H), 2.38-1.70 (m, 9H), 1.43 (brs, 9H); $^{13}$C NMR (75 MHz, CDCl$_3$, TMS) δ 173.38, 171.59, 155.09, 79.68, 62.03, 59.82, 53.72, 53.15, 52.48, 50.09, 34.66, 34.55, 29.47, 28.31, 27.33.

Example 8

Synthesis of SH-188, 189 and 190

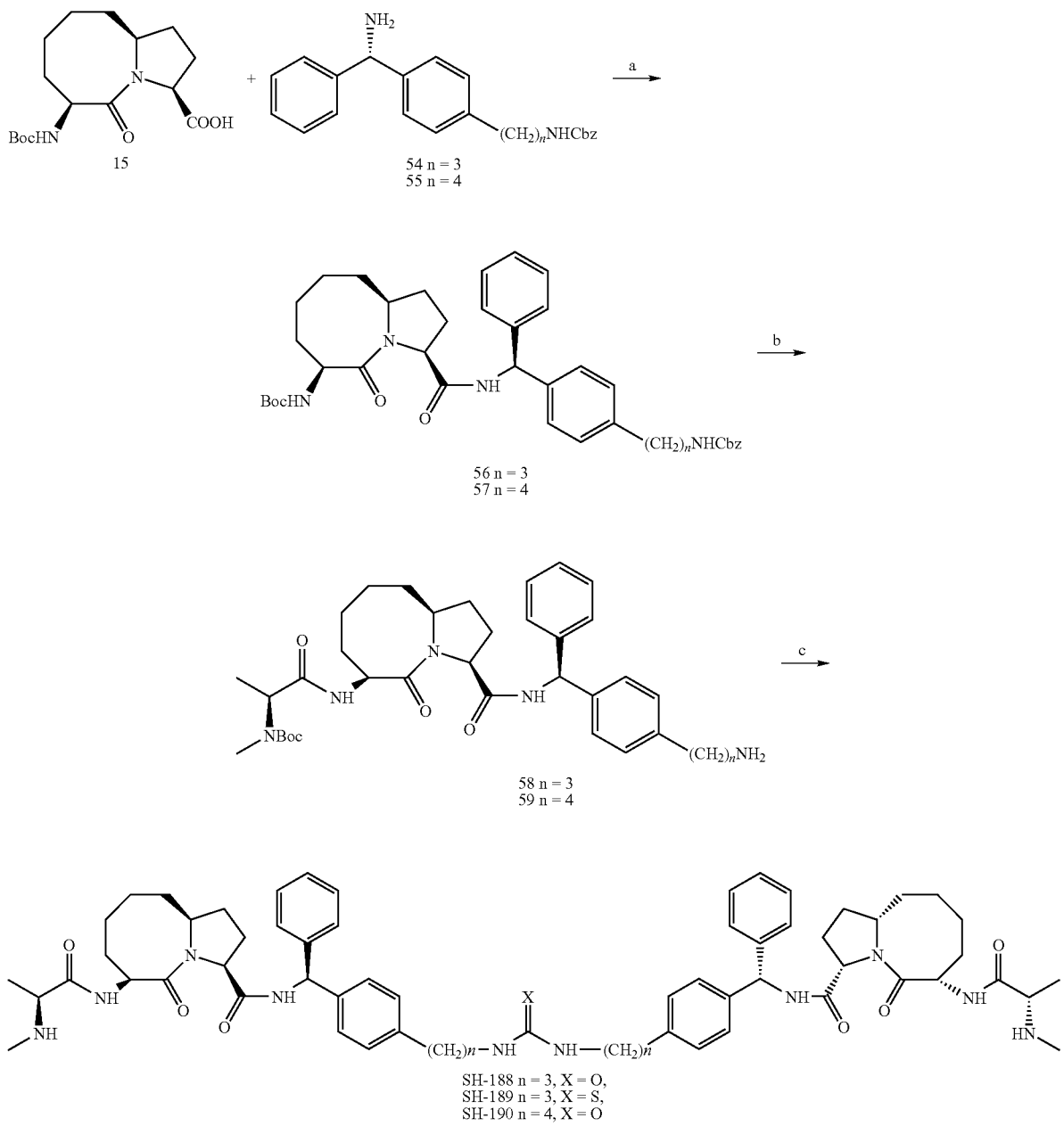

Reagents and conditions: (a) EDC, HOBt, N,N-diisopropylethylamine, $CH_2Cl_2$; (b) i. 4N HCl in 1,4-dioxane, MeOH; ii. (S)-N-Boc-N-methylalanine, EDC, HOBt, N,N-diisopropylethylamine, $CH_2Cl_2$; iii. 10% Pd-C, $H_2$, MeOH; (c) thiophosgene or triphosgene, $CH_2Cl_2$; ii. 4N HCl in 1,4-dioxane, MeOH.

Condensation of acid 15 with amine 54 or 55 gave amides 56 and 57 respectively (Scheme IX). Removal of the Boc protecting group in 56 or 57 followed by condensation of the resulted ammoniums with (S)—N-Boc-N-methyl alanine yielded two amides. Removal of the Cbz protecting groups in these two amides furnished amines 58 and 59. Condensation of 58 or 59 with 0.5 eq of triphosgene afforded two ureas. Removal of the Boc protecting groups in these two ureas provided SH-188 and SH-190, respectively. Condensation of 58 with 0.5 eq of thiophosgene gave a thiourea. Removal of the Boc protecting group in this thiourea yielded SH-189.

Example 9

Synthesis of SH-202

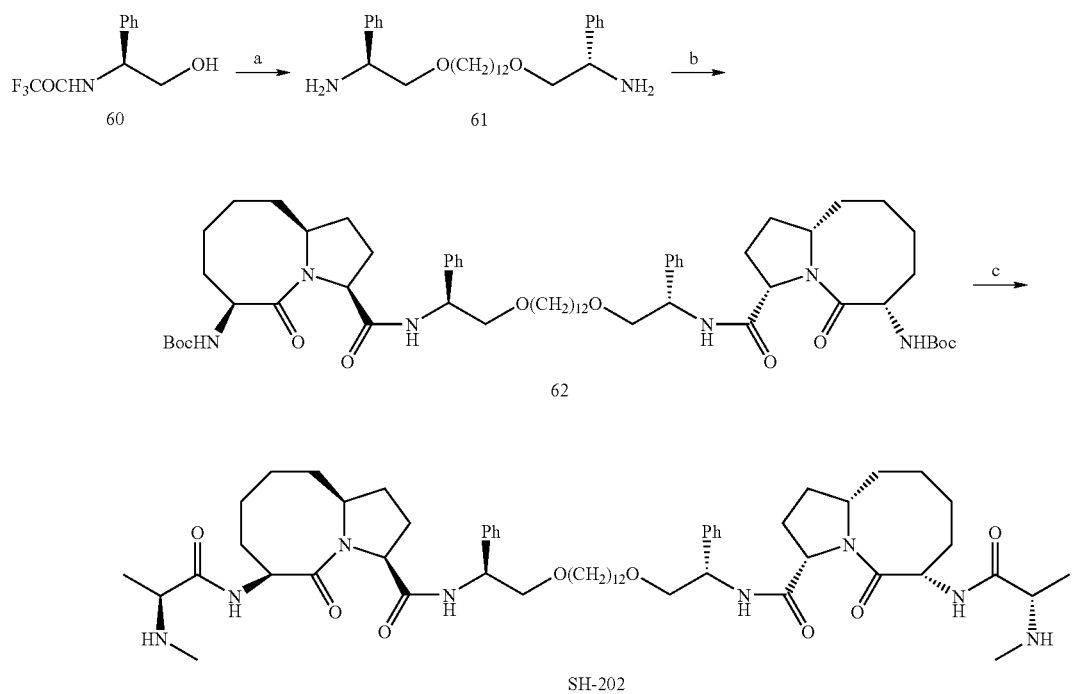

Reagents and conditions: (a). i. NaH (2.5 eq), 1,12-dibromododecane, DMF; ii. 3N LiOH, 1,4-dioxane; (b) acid 15 (2.2 eq), EDC, HOBt, N,N-diisopropylethylamine, $CH_2Cl_2$; (c) i. 4N HCl, 1,4-dioxane, MeOH, ii. (S)-N-Boc-N-methyl alanine, EDC, HOBt, N,N-diisopropylethylamine, $CH_2Cl_2$; iii. 4N HCl, 1,4-dioxane, MeOH.

Substitution of sodium alcoholate derived from compound 60 with 1,12-dibromododecane followed by removal of the trifluoroacetyl group gave diamine 61. Condensation of 61 with 2 eq of acid 15 yielded an amide 62. Removal of the Boc protecting groups in 62 followed by condensation with (S)—N-Boc-N-methyl alanine furnished an amide. Removal of the Boc protecting group in this amide provided SH-202.

Example 10

Synthesis of Smac Mimetic Intermediates

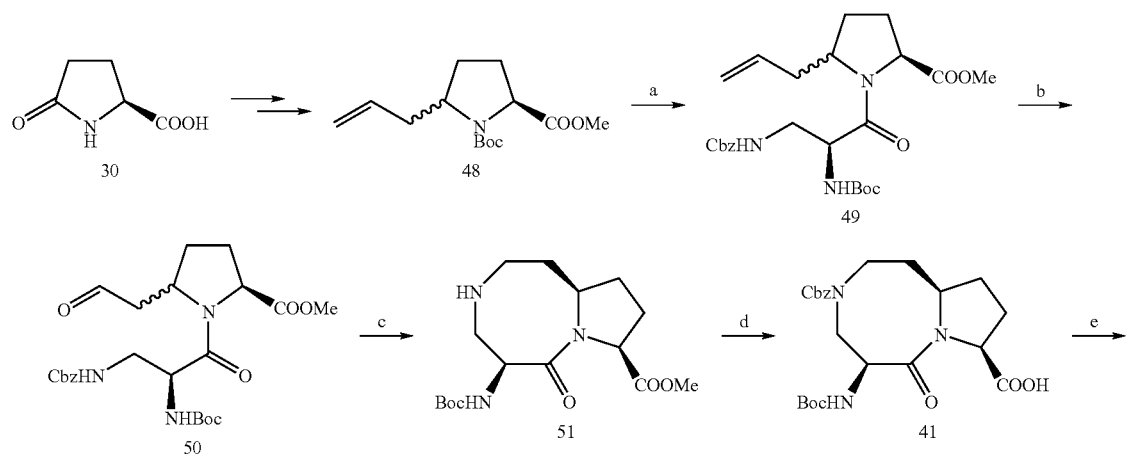

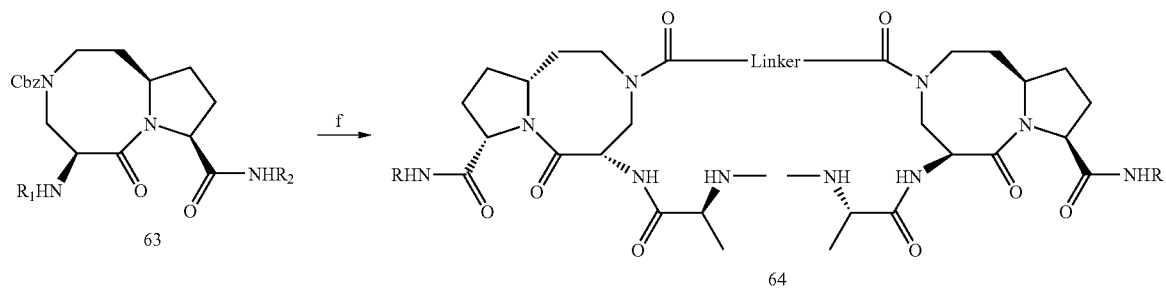

Reagents and conditions: (a) i. 4N HCl in 1,4-dioxane, methanol; ii. Boc-Dap(Z)-OH, EDC, HOBt, N,N-diisopropylethylamine, CH$_2$Cl$_2$; (b) O$_3$, then PPh$_3$, CH$_2$Cl$_2$; (c) H$_2$, 10% Pd-C, i-PrOH; (d) i. CbzCl, NaHCO$_3$, 1,4-dioxane; ii. 3N LiOH, 1,4-dioxane then 1N HCl; (e) i. amine, EDC, HOBt, N,N-diisopropylethylamine, CH$_2$Cl$_2$; ii. 4N HCl in 1,4-dioxane, methanol; iii. (S)-N-protected amino acid, EDC, HOBt, N,N-diisopropylethylamine, CH$_2$Cl$_2$; (f) i. diacid (0.5 eq), EDC, HOBt, N,N-diisopropylethylamine, CH$_2$Cl$_2$; ii. 4N HCl in 1,4-dioxane, methanol.

A novel and efficient method for the synthesis of key intermediate 41 is presented in Scheme XI. Compound 48 may be prepared in five steps from pyroglutamic acid 30 according to reported methods (see: (1) Zhang, J.; Xiong, C.; Wang, W.; Ying, J. and Hruby, V., J. *Org. Lett.*, 2002, 4 (23), 4029-4032 and (2) Polyak, F. and Lubell, W. D. J. *Org. Chem.* 1998, 63, 5937-5949) as a mixture of two diastereoisomers with the R form isomer as the major product (ratio is about 4:1). Removal of the Boc group in 48 followed by condensation with N-α-(tert-butoxycarbonyl)-N-β-(benzoxycarbonyl)-L-diamino-propionic acid (Boc-Dap(Z)-OH) gave amides 49. Ozone oxidation of the C—C double bond in 49 followed by reduction with PPh$_3$ yielded aldehyde 50. Cleavage of the Cbz group in 50, intra-molecular condensation of the resulted amine with the aldehyde group and subsequent reduction of the enamine were realized in one pot to give the desired compound 51. Protection of the amino group followed by hydrolysis of the methyl ester in 51 furnished acid 41.

Condensation of 41 with different diamines gave a series of amides. Removal of the Boc protecting groups in these amides followed by condensation of the resulted ammonium salts with (S)—N-protected amino acids yielded a series of amides 63. Removal of the protecting groups in these amides afforded our designed bivalent Smac mimetics 64.

Example 11

Bivalent Smac Mimetics

SH-173

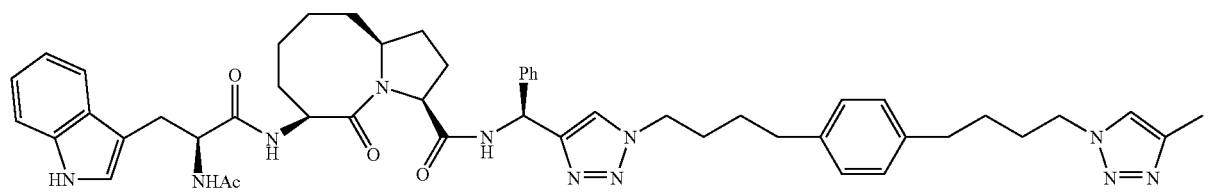

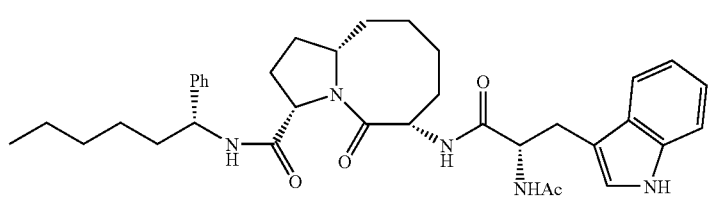

SH-173: ¹H NMR (300 HMz, CDCl₃): δ 8.70 (s, 2H), 8.32 (d, J=8.0 Hz, 2H), 7.60 (d, J=7.4 Hz, 2H), 7.40-6.80 (m, 26H), 6.47 (d, J=7.9 Hz, 2H), 6.25 (d, J=8.0 Hz, 2H), 4.81 (m, 2H), 4.70 (m, 2H), 4.50 (m, 2H), 4.27 (t, J=7.1 Hz, 4H), 3.95 (m, 2H), 3.30-3.08 (m, 4H), 2.60 (t, J=2.61 Hz, 4H), 2.45-2.25 (m, 2H), 2.12-1.20 (m, 36H); ¹³C NMR (75 HMz, CDCl₃): δ 170.78, 170.41, 170.14, 169.88, 148.00, 140.45, 138.98, 136.19, 128.53, 128.44, 127.68, 127.56, 127.28, 123.70, 121.67, 121.55, 119.13, 118.57, 111.29, 110.25, 59.98, 59.06, 54.01, 50.40, 50.20, 50.01, 47.76, 35.93, 34.61, 31.74, 29.53, 29.09, 28.08, 24.83, 23.30, 22.95, 20.82;
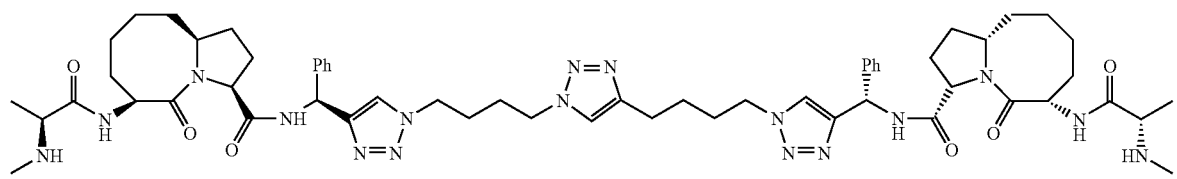
SH-175
SH-175: ¹H NMR (300 HMz, D₂O): δ 7.87 (s, 1H), 7.71 (s, 2H), 7.30-7.11 (m, 10H), 6.05 (s, 2H), 4.64 (m, 2H), 4.35-4.16 (m, 10H), 3.81 (m, 2H), 2.60 (t, J=6.2 Hz, 2H), 2.54 (s, 6H), 2.10 (m, 2H), 1.98 (m, 2H), 1.75-1.42 (m, 34H); ¹³C NMR (75 HMz, D₂O): δ 175.85, 174.79, 172.08, 150.63, 147.37, 141.60, 131.85, 131.09, 129.93, 128.50, 126.79, 64.57, 63.53, 59.73, 54.54, 53.66, 52.90, 52.59, 38.49, 35.57, 34.90, 33.93, 31.29, 30.32, 28.96, 28.65, 27.63, 27.38, 25.24, 24.49, 18.22.
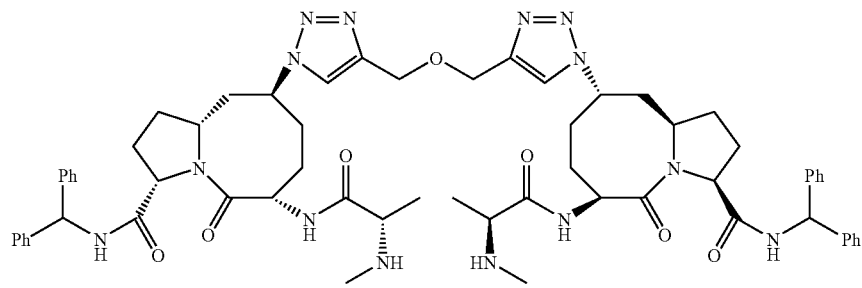
SH-176
SH-176: ¹H NMR (300 MHz, D₂O): δ 7.48 (s, 2H), 7.10-6.67 (20H), 5.84 (s, 2H), 4.65 (m, 2H), 4.55 (m, 2H), 4.42-4.16 (m, 8H), 3.80 (m, 2H), 2.53 (s, 6H), 2.25-1.30 (m, 26H); ¹³C NMR (75 MHz, D₂O): δ 172.72, 171.00, 169.10, 143.67, 141.49, 141.30, 129.07, 127.96, 127.58, 127.39, 124.10, 62.76, 61.24, 59.43, 57.67, 57.27, 55.00, 53.20, 41.26, 32.12, 31.31, 26.98, 24.69, 15.62.
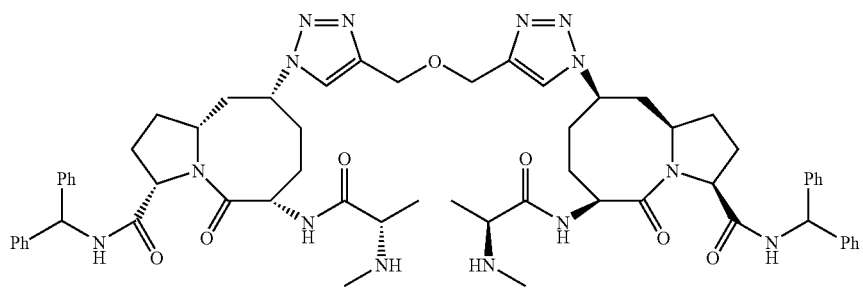
SH-177

SH-177: $^1$H NMR (300 MHz, D$_2$O): δ 7.62 (s, 2H), 7.15-6.90 (20H), 5.90 (s, 2H), 4.75 (m, 4H), 4.43 (s, 4H), 4.39 (m, 4H), 3.83 (m, 2H), 2.80 (s, 6H), 2.46 (m, 2H), 2.22-1.90 (m, 8H), 1.75-1.43 (m, 10H), 1.36 (d, J=8.4 Hz, 6H); $^{13}$C NMR (75 MHz, D$_2$O): δ 175.14, 173.74, 172.25, 146.86, 144.06, 143.66, 131.72, 131.66, 130.55, 130.21, 129.97, 125.60, 65.46, 64.63, 62.98, 60.36, 59.70, 52.87, 45.02, 34.98, 33.87, 32.30, 30.26, 18.17.
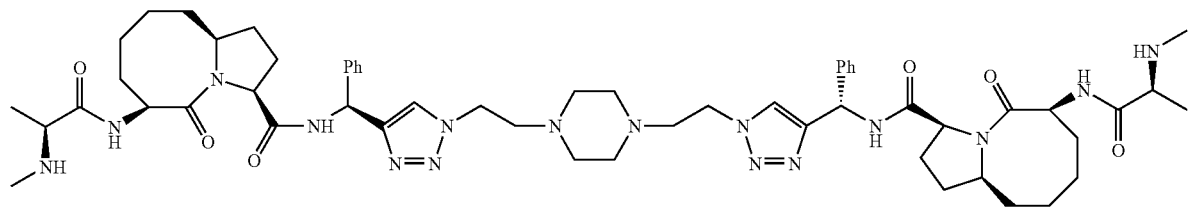
SH-178
SH-178: $^1$H NMR (300 MHz, D$_2$O): δ 7.88 (s, 2H), 7.46-7.30 (m, 10H), 6.19 (s, 2H), 4.78 (m, 6H), 4.42 (m, 2H), 4.30 (m, 2H), 3.90 (m, 2H), 3.74 (m, 4H), 3.60 (m, 4H), 3.52 (m, 2H), 3.28 (m, 2H), 2.64 (s, 6H), 2.40-1.56 (m, 24H), 1.49 (d, J=7.0 Hz, 6H); $^{13}$C NMR (75 MHz, D$_2$O): δ 176.14, 174.90, 172.10, 151.28, 141.51, 131.90, 131.19, 130.01, 127.32, 64.64, 63.61, 59.73, 58.06, 53.68, 52.96, 52.05, 47.49, 38.50, 35.53, 34.90, 33.89, 30.35, 27.61, 24.48, 18.18.
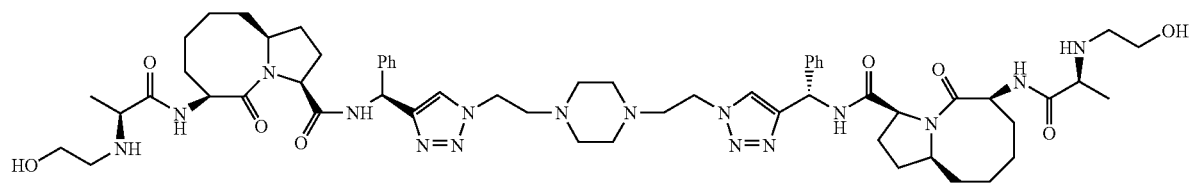
SH-179
SH-179: $^1$H NMR (300 MHz, D$_2$O): δ 7.87 (s, 2H), 7.40-7.22 (m, 10H), 6.19 (s, 2H), 4.74 (m, 6H), 4.42 (m, 2H), 4.30 (m, 2H), 4.05 (m, 2H), 3.79 (t, J=5.1 Hz, 4H), 3.71 (t, J=5.1 Hz, 4H), 3.53 (brs, 8H), 3.10 (m, 4H), 2.40-1.60 (m, 24H), 1.50 (d, J=7.0 Hz, 6H); $^{13}$C NMR (75 MHz, D$_2$O): δ 176.15, 174.92, 172.00, 151.25, 141.51, 131.90, 131.19, 130.07, 127.28, 64.64, 63.60, 59.57, 58.60, 58.06, 53.69, 52.95, 52.14, 50.67, 47.56, 38.49, 35.53, 34.89, 30.34, 27.60, 24.47, 18.46.
SH-180
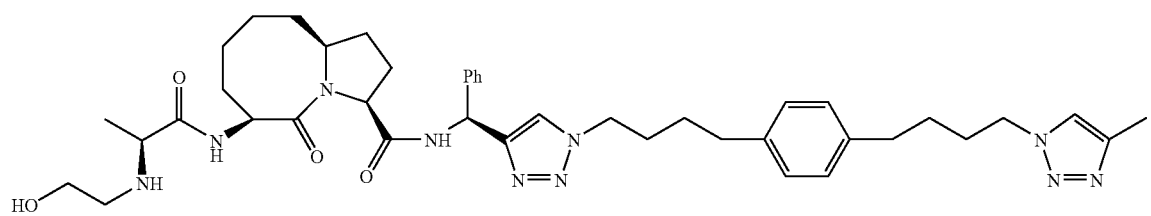
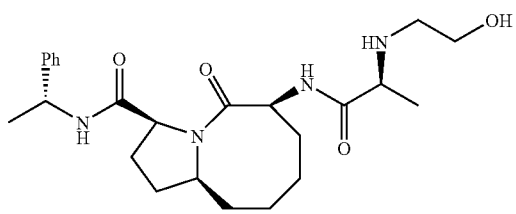

SH-180: $^1$H NMR (300 MHz, D$_2$O): δ 7.60 (s, 2H), 7.30-7.10 (m, 10H), 6.68 (s, 4H), 6.15 (s, 2H), 4.74 (m, 2H), 4.52-4.30 (m, 4H), 4.20 (m, 2H), 4.19-4.02 (m, 8H), 3.80 (m, 2H), 3.13 (m, 2H), 2.40-1.12 (m, 42H); $^{13}$C NMR (75 MHz, D$_2$O): δ 172.79, 170.36, 169.39, 148.33, 139.54, 129.24, 128.55, 127.41, 123.46, 61.91, 60.88, 60.28, 57.02, 56.06, 50.99, 50.38, 49.08, 48.13, 35.98, 34.26, 33.10, 32.32, 29.20, 27.85, 25.11, 21.95, 16.84.
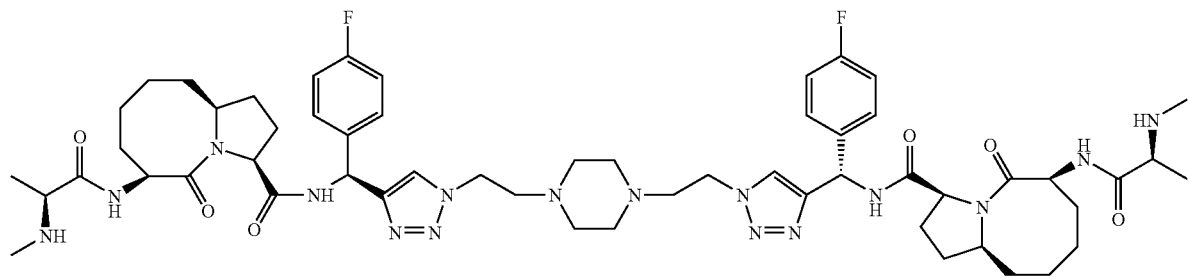
SH-181
SH-181: $^1$H NMR (300 MHz, D$_2$O): δ 7.87 (s, 2H), 7.31 (m, 4H), 7.08 (m, 4H), 6.16 (s, 2H), 4.82-4.72 (m, 6H), 4.50 (m, 2H), 4.26 (m, 2H), 3.88 (m, 2H), 3.78 (m, 4H), 3.68 (brs, 8H), 2.61 (s, 6H), 2.36-1.53 (m, 24H), 1.50 (t, J=7.0 Hz, 6H); $^{13}$C NMR (75 MHz, D$_2$O): δ 176.03, 174.85, 172.05, 163.45, 151.16, 137.40, 131.90, 127.33, 118.51, 64.59, 63.58, 59.73, 58.02, 53.64, 52.30, 51.87, 47.26, 38.48, 35.53, 34.86, 33.85, 30.27, 27.60, 24.47, 18.16.
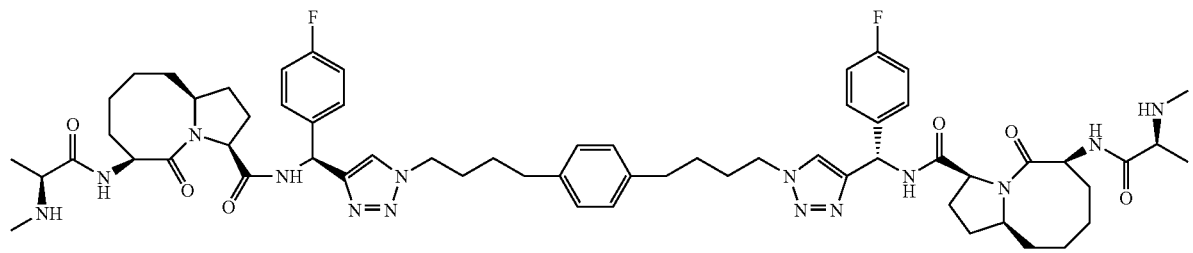
SH-182
SH-182: $^1$H NMR (300 MHz, D$_2$O): δ 7.61 (s, 2H), 7.23 (m, 4H), 6.78 (m, 4H), 6.53 (m, 4H), 6.12 (s, 2H), 4.70 (m, 2H), 4.32 (m, 2H), 4.18 (m, 2H), 4.10-3.83 (m, 6H), 2.61 (s, 6H), 2.22-1.03 (m, 42H); $^{13}$C NMR (75 MHz, D$_2$O): δ 172.53, 171.92, 169.39, 160.60, 148.31, 139.38, 134.84, 129.40, 128.42, 115.60, 61.76, 60.78, 57.20, 50.94, 50.27, 49.59, 35.99, 34.42, 33.22, 32.32, 31.33, 29.41, 27.95, 25.14, 21.99, 15.66.
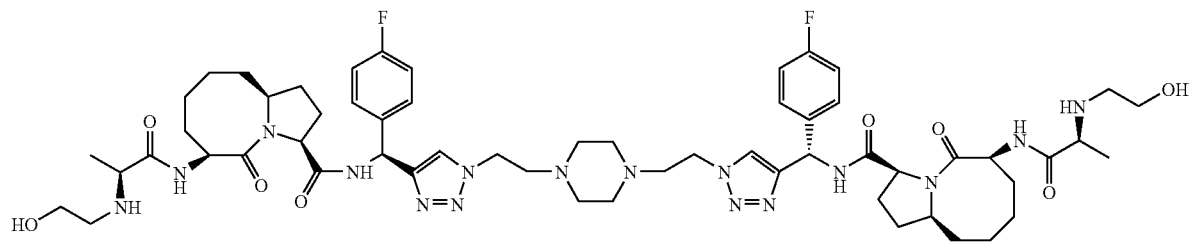
SH-183

SH-183: $^1$H NMR (300 HMz, D$_2$O): δ 7.87 (s, 2H), 7.38-7.22 (m, 4H), 7.12-6.99 (m, 4H), 6.17 (s, 2H), 4.85-4.74 (m, 6H), 4.34 (m, 2H), 4.27 (m, 2H), 3.98 (m, 2H), 3.80-3.65 (m, 8H), 3.55 (s, 8H), 3.10 (m, 2H), 2.37-1.40 (m, 30H).
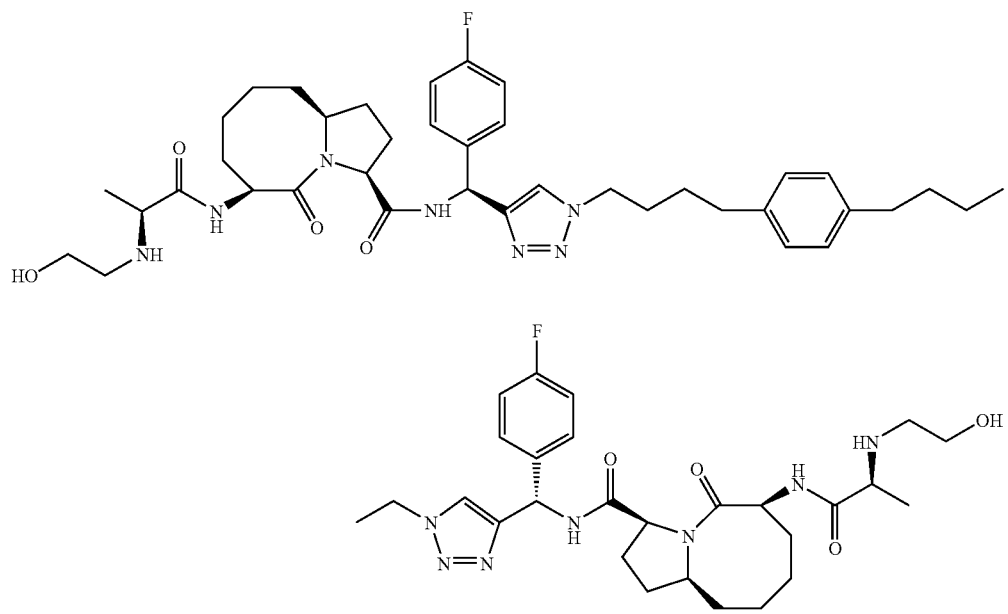
SH-184: $^1$H NMR (300 MHz, D$_2$O): δ 7.62 (s, 2H), 7.20 (m, 4H), 6.90-6.70 (m, 4H), 6.69-6.50 (brs, 4H), 6.19 (s, 2H), 4.72 (m, 2H), 4.50-4.28 (m, 4H), 4.20-3.80 (m, 6H), 3.12 (m, 4H), 2.22-0.98 (m, 42H).
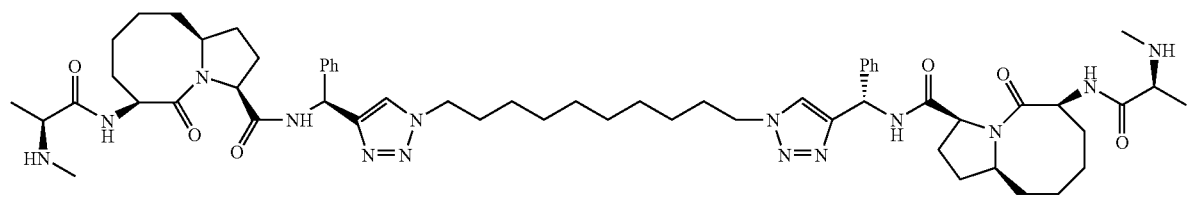
SH-185: $^1$H NMR (300 HMz, D$_2$O): δ 7.67 (s, 2H), 7.26-7.10 (m, 10H), 6.07 (s, 2H), 4.73 (m, 2H), 4.28 (m, 2H), 4.25-4.10 (m, 6H), 3.83 (m, 2H), 2.54 (s, 6H), 2.20-1.92 (m, 4H), 1.86-1.30 (m, 34H), 0.98-0.80 (m, 12H); $^{13}$C NMR (75 HMz, D$_2$O): δ 177.43, 173.05, 172.22, 148.26, 139.29, 129.28, 128.50, 127.43, 123.81, 62.00, 60.99, 57.20, 51.08, 50.76, 50.40, 36.00, 33.06, 32.36, 31.32, 29.52, 28.62, 28.26, 27.77, 25.76, 25.10, 21.93, 15.65.
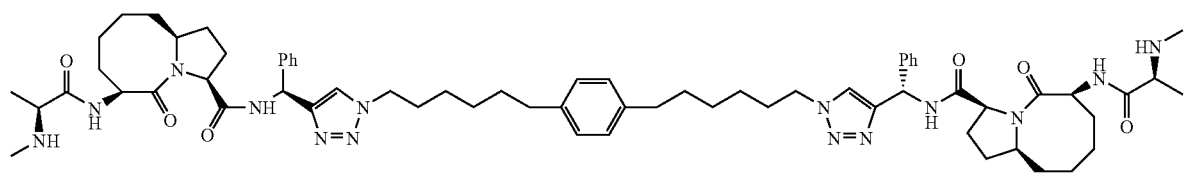

SH-186: ¹H NMR (300 HMz, D$_2$O): δ 7.58 (s, 2H), 7.20-6.90 (m, 10H), 6.61 (s, 4H), 6.08 (s, 2H), 4.72 (m, 2H), 4.30 (m, 2H), 4.10 (m, 2H), 3.95 (m, 4H), 3.80 (m, 2H), 2.52 (s, 6H), 2.25-1.05 (m, 36H), 1.02-0.75 (m, 14H); ¹³C NMR (75 HMz, D$_2$O): δ 174.88, 174.40, 171.91, 151.04, 142.52, 142.31, 131.63, 130.92, 130.00, 125.57, 125.09, 64.30, 63.24, 59.74, 53.42, 52.90, 38.63, 38.20, 35.90, 34.85, 34.28, 33.87, 32.69, 32.05, 31.73, 30.20, 29.07, 27.76, 24.49, 18.23.
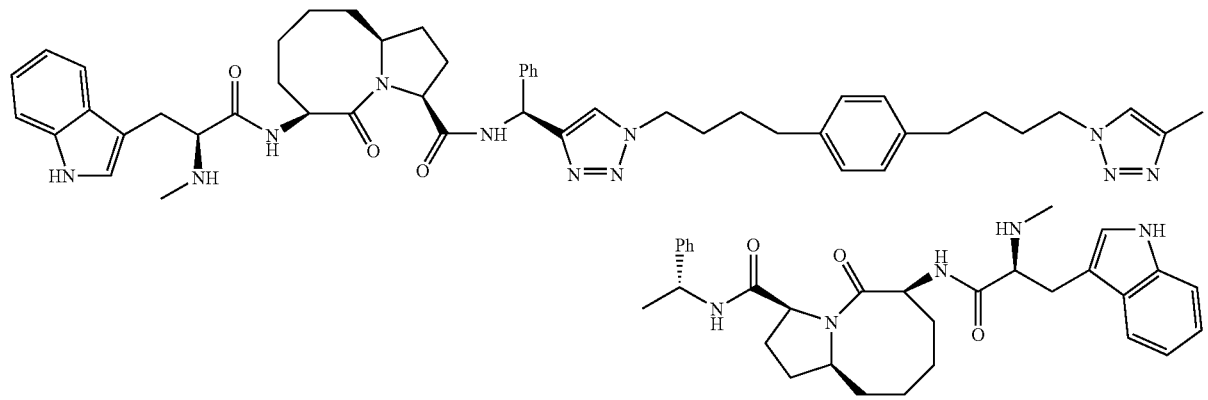
SH-187
SH-187: ¹H NMR (300 HMz, D$_2$O): δ 7.56 (s, 2H), 7.40-7.05 (m, 16H), 7.02 (m, 2H), 6.90 (m, 2H), 6.78 (m, 4H), 6.11 (s, 2H), 4.75 (m, 2H), 4.49 (m, 2H), 4.25 (m, 4H), 4.20 (m, 2H), 3.98 (m, 2H), 3.84 (m, 2H), 2.49 (s, 6H), 2.38 (m, 4H), 2.24-1.22 (m, 36H).
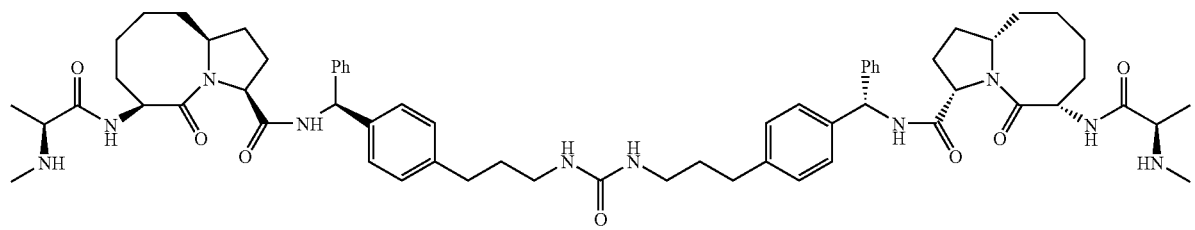
SH-188
SH-188: ¹H NMR (300 HMz, D$_2$O): δ 7.10-6.92 (m, 10H), 6.85 (m, 4H), 6.70 (m, 4H), 5.85 (s, 2H), 4.65 (m, 2H), 4.32 (m, 2H), 4.06 (m, 2H), 3.82 (m, 2H), 2.74 (m, 4H), 2.54 (s, 6H), 2.15 (m, 4H), 2.02-1.20 (m, 34H); ¹³C NMR (75 HMz, D$_2$O): δ 172.36, 171.92, 169.41, 160.17, 141.40, 141.15, 139.27, 129.01, 127.66, 127.46, 61.88, 60.87, 57.18, 50.94, 39.72, 35.99, 33.20, 32.49, 31.60, 31.33, 27.79, 25.19, 21.91, 15.69.
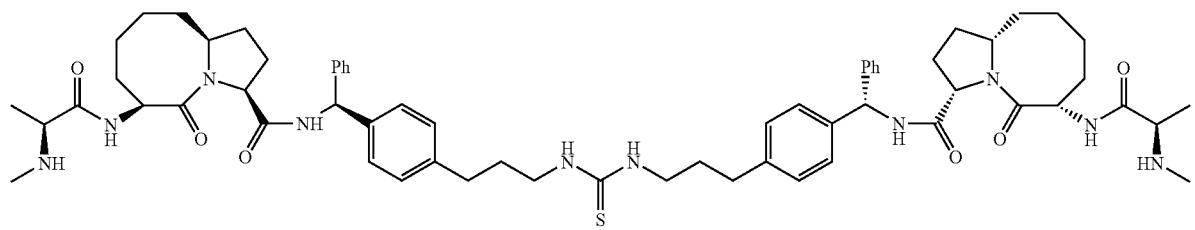
SH-189

SH-189: ¹H NMR (300 HMz, D₂O): δ 7.18-6.99 (m, 10H), 6.95 (m, 4H), 6.80 (m, 4H), 5.90 (s, 2H), 4.72 (m, 2H), 4.36 (m, 2H), 4.13 (m, 2H), 3.89 (m, 2H), 3.30 (brm, 4H), 2.63 (s, 6H), 2.30 (m, 4H), 2.12-1.18 (m, 34H).
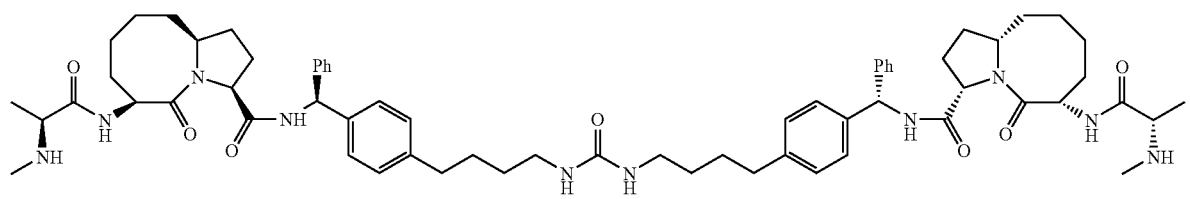
SH-190
SH-190: ¹H NMR (300 HMz, D₂O): 6 ¹³C NMR (75 HMz, D₂O): δ 7.15-6.93 (m, 10H), 6.95 (m, 4H), 6.79 (m, 4H), 6.85 (s, 2H), 4.74 (m, 2H), 4.36 (m, 2H), 4.13 (m, 2H), 3.88 (m, 2H), 2.80 (m, 4H), 2.58 (s, 6H), 2.36-1.08 (m, 42H).
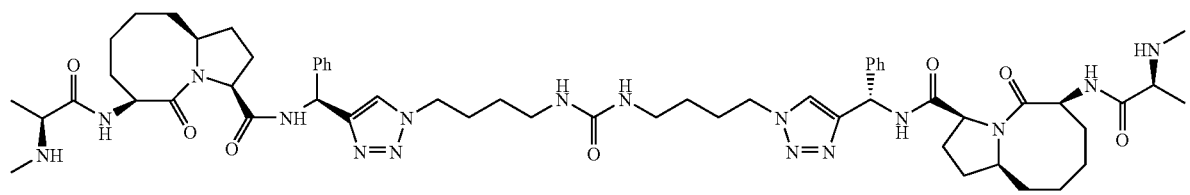
SH-191
SH-191: ¹H NMR (300 HMz, D₂O): δ 7.75 (s, 2H), 7.40-7.20 (m, 10H), 6.16 (s, 2H), 4.74 (m, 2H), 4.36 (m, 2H), 4.32-4.20 (m, 6H), 3.89 (m, 2H), 2.95 (t, J=6.6 Hz, 4H), 2.64 (s, 6H), 2.32-1.20 (m, 38H).
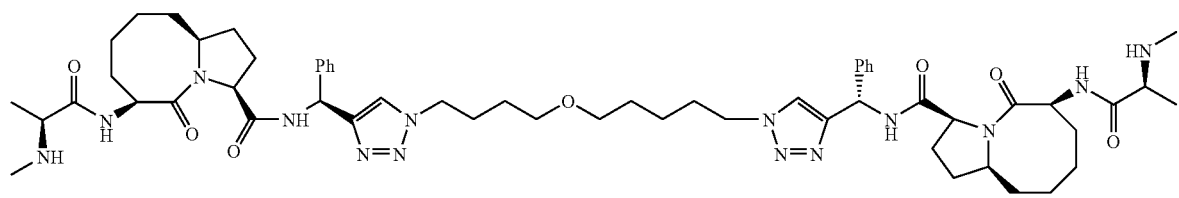
SH-198
SH-198: ¹H NMR (300 HMz, D₂O): δ 7.70 (s, 2H), 7.30-7.12 (m, 10H), 6.07 (s, 2H), 4.65 (m, 2H), 4.32 (m, 2H), 4.25-4.10 (m, 6H), 3.84 (m, 2H), 3.10 (m, 4H), 2.55 (s, 6H), 2.20-1.20 (m, 38H), 0.98 (m, 2H); ¹³C NMR (75 HMz, D₂O): δ 173.17, 172.22, 169.53, 148.15, 139.16, 129.32, 128.54, 127.40, 124.04, 70.20, 69.63, 62.01, 60.98, 57.19, 51.10, 50.82, 50.63, 50.35, 35.97, 33.06, 32.36, 31.37, 29.29, 28.17, 27.77, 26.48, 25.80, 25.10, 22.58, 21.95, 15.67.
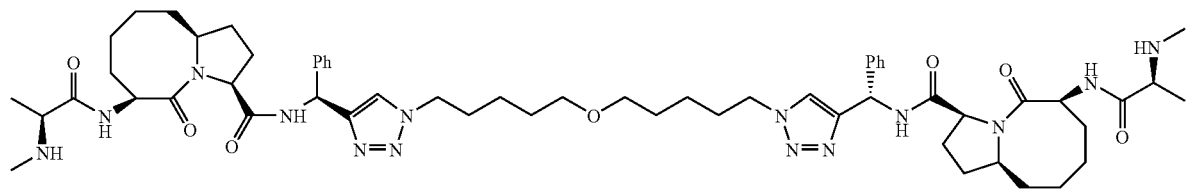
SH-199

SH-199: ¹H NMR (300 HMz, D₂O): δ 7.73 (s, 2H), 7.20-7.02 (m, 10H), 6.05 (s, 2H), 4.65 (m, 2H), 4.30 (m, 2H), 4.22-4.08 (m, 6H), 3.84 (m, 2H), 3.08 (m, 4H), 2.52 (s, 6H), 2.25-0.90 (m, 42H); ¹³C NMR (75 HMz, D₂O): δ 173.02, 172.13, 169.49, 147.91, 139.07, 129.31, 128.55, 127.41, 124.14, 70.25, 66.87, 61.93, 60.90, 57.18, 50.97, 50.22, 36.01, 33.08, 32.37, 31.40, 29.33, 28.23, 27.74, 25.11, 22.62, 21.97, 15.70.
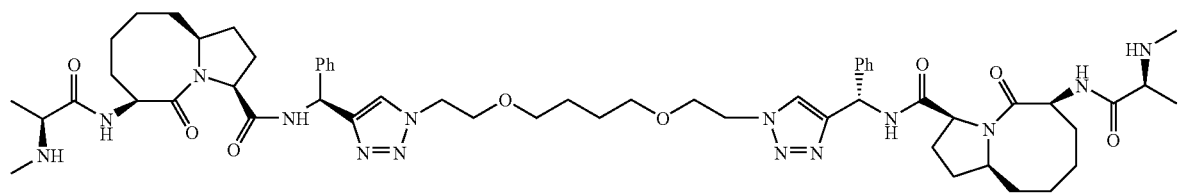
SH-200
SH-200: ¹H NMR (300 HMz, D₂O): δ 7.77 (s, 2H), 7.22-7.08 (m, 10H), 6.05 (s, 2H), 4.65 (m, 2H), 4.37-4.22 (m, 6H), 4.16 (m, 2H), 3.82 (m, 2H), 3.48 (m, 4H), 3.08 (m, 4H), 2.52 (s, 6H), 2.16-1.42 (m, 30H), 1.01 (m, 4H); ¹³C NMR (75 HMz, D₂O): δ 173.11, 172.16, 169.49, 148.01, 139.10, 129.32, 128.56, 127.38, 124.62, 70.59, 68.39, 66.87, 61.96, 60.95, 57.19, 50.73, 50.24, 35.98, 33.09, 32.36, 31.40, 27.77, 25.43, 25.12, 21.96, 15.69.
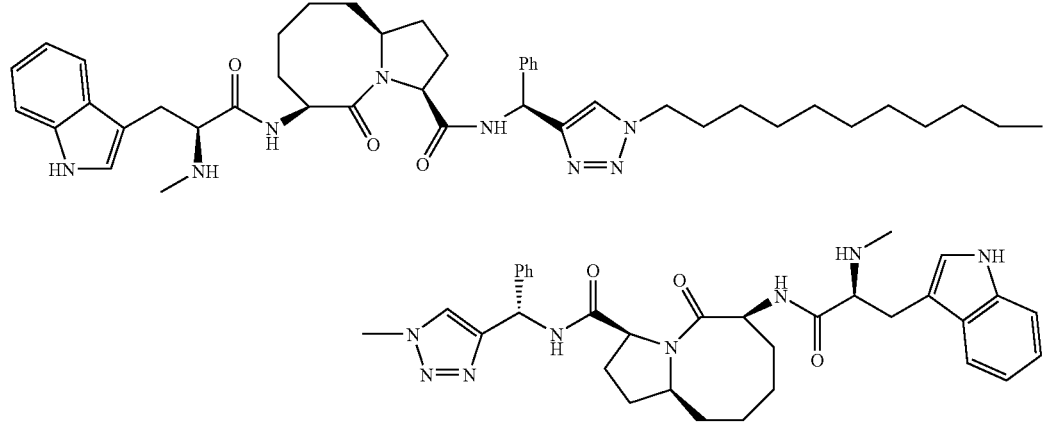
SH-201
SH-201: ¹H NMR (300 HMz, D₂O): δ 7.60 (s, 2H), 7.40-6.70 (m, 20), 6.16 (s, 2H), 4.75 (m, 2H), 4.49 (m, 2H), 4.25 (m, 4H), 4.20 (m, 2H), 3.98 (m, 2H), 3.84 (m, 2H), 2.49 (s, 6H), 2.40-1.20 (m, 48H).
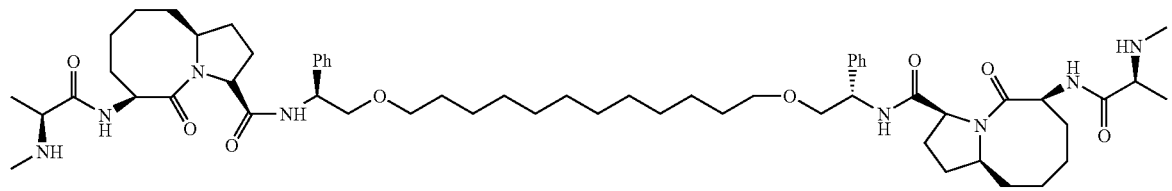
SH-202

SH-202: $^1$H NMR (300 HMz, D$_2$O): δ 7.35-7.16 (m, 10H), 5.02 (m, 2H), 4.74 (m, 2H), 4.39 (m, 2H), 4.27 (m, 2H), 3.92 (m, 2H), 3.55 (m, 4H), 3.34 (m, 4H), 2.64 (s, 6H), 2.28-1.20 (m, 54H); $^{13}$C NMR (75 HMz, D$_2$O): δ 175.35, 174.62, 172.04, 141.98, 131.60, 130.66, 129.70, 75.84, 73.59, 64.68, 63.33, 59.74, 55.57, 53.55, 38.93, 35.65, 35.05, 33.93, 32.55, 32.31, 30.64, 28.86, 27.85, 24.68, 18.29.

(5-Fam)-NH$_2$ (termed SM5F). The K$_d$ value of the binding of SM5F peptide to XIAP BIR3 protein was determined to be 17.92 nM, showing that this peptide binds to the surface pocket of the XIAP protein with high affinity. The recombinant XIAP BIR3 protein of human XIAP (residues 241-356) fused to His-tag was stable and soluble, and was used for the FP based binding assay.

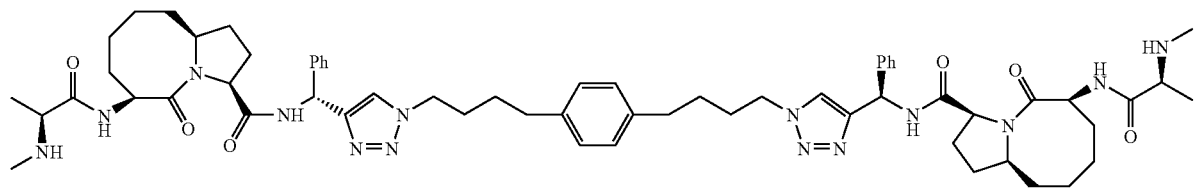

SH-206

SH-206: $^1$H NMR (300 HMz, D$_2$O): δ 7.44 (s, 2H), 7.30-6.80 (m, 10H), 6.49 (s, 4H), 5.99 (s, 2H), 4.63 (m, 2H), 4.28 (m, 2H), 4.06 (m, 2H), 3.92 (m, 2H), 3.80 (m, 4H), 2.55 (s, 6H), 2.28-0.95 (m, 42H); $^{13}$C NMR (75 HMz, D$_2$O): δ 175.04, 174.33, 171.97, 150.65, 143.08, 141.97, 131.63, 131.00, 130.59, 129.60, 126.25, 64.31, 63.33, 59.74, 53.47, 52.92, 38.47, 36.87, 35.85, 34.86, 33.87, 31.85, 30.42, 27.65, 24.52, 18.26.

The dose-dependent binding experiments were carried out with serial dilutions of the tested compounds in DMSO. A 5 μl sample of the tested samples and preincubated XIAP BIR3 protein (30 nM) and SM5F peptide (5 nM) in the assay buffer (100 mM potassium phosphate, pH 7.5; 100 μg/ml bovine gamma globulin; 0.02% sodium azide, purchased from Invitrogen™ Life Technology), were added in Dynex 96-well, black, round-bottom plates (Fisher Scientific) to produce a

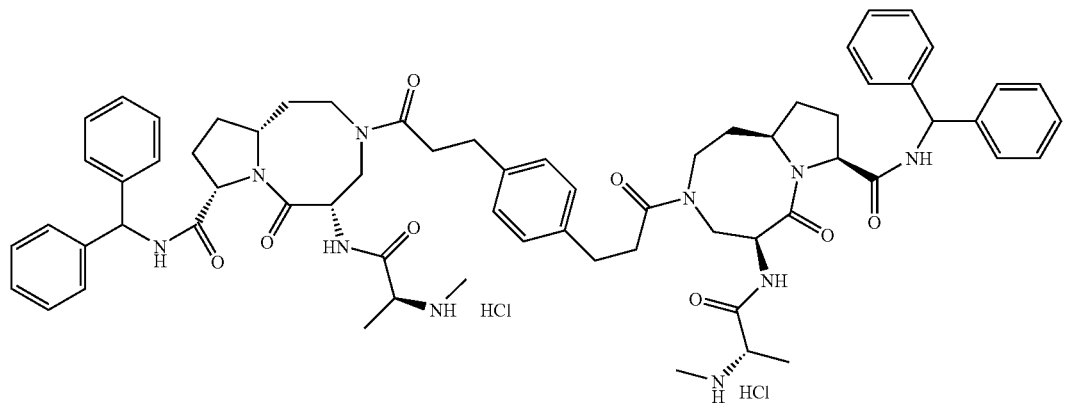

SM-140

SM-410: $^1$H NMR (MeOH-d$_4$, 300 M Hz) δ 8.91 (m, 2H), 7.37-7.13 (m, 24H), 6.16 (m, 2H), 4.73 (m, 2H), 4.53 (m, 2H), 4.06-3.73 (m, 8H), 3.37-3.27 (m, 6H), 2.92 (m, 6H), 2.68 (m, 6H), 2.30 (m, 2H), 2.05-1.81 (m, 10H), 1.55 (m, 6H); $^{13}$C NMR (MeOH-d$_4$, 300 M Hz) δ 174.4, 172.3, 169.3, 168.6, 142.2, 142.0, 139.3, 129.1, 128.7, 128.5, 127.8, 127.5, 127.3, 61.8, 57.3, 52.6, 51.8, 46.6, 34.9, 32.4, 31.4, 30.9, 27.3, 15.3.

Example 12

Binding of Inhibitors to XIAP BIR3

In order to test the binding ability of the bivalent Smac mimetics to IAP proteins, a sensitive and quantitative in vitro binding assay using the fluorescence polarization (FP) based method was developed and used to determine the binding affinity of Smac mimetics to XIAP protein (Nikolovska-Coleska et al., *Anal Biochem.* 332:261-73 (2004)). For this assay, 5-carboxyfluorescein (5-Fam) was coupled to the lysine side chain of the mutated Smac peptide, AbuRPF-K- final volume of 125 μl. For each assay, the bound peptide control containing recombinant XIAP BIR3 protein and SM5F (equivalent to 0% inhibition) and free peptide control containing only free SM5F (equivalent to 100% inhibition) were included. The polarization values were measured after 3 hrs of incubation when the binding reached equilibrium using an ULTRA READER (Tecan U.S. Inc., Research Triangle Park, N.C.). IC$_{50}$ values, the inhibitor concentration at which 50% of bound peptide is displaced, were determined from a plot using nonlinear least-squares analysis. Curve fitting was performed using GRAPHPAD PRISM software (GraphPad Software, Inc., San Diego, Calif.).

Example 13

Fluorescence-Polarization-Based Binding Assay to XIAP Protein

A Smac mimetic was incubated with human XIAP protein (residues 120-356) (10 nM) and a fluorescently tagged, Smac-based bivalent peptide, called Smac2-F (0.5 nM) as the tracer in the assay buffer (100 mM potassium phosphate, pH 7.5; 100 ug/ml bovine gamma globulin; 0.02% sodium azide) in Dynex 96-well, black, round-bottom plates (Fisher Scientific). Smac2-F was determined to bind XIAP with a $K_d$ value of 1.2 nM. For each assay, the controls included XIAP and Smac2-F peptide (equivalent to 0% inhibition), and Smac-2F only (equal to 100% of inhibition). The polarization values were measured after 2 hours incubation, using the Ultra plate reader. The $IC_{50}$ value, the inhibitor concentration at which 50% of bound tracer is displaced, is determined from the plot using nonlinear least-squares analysis. Curve fitting is performed using GraphPad Prism® software.

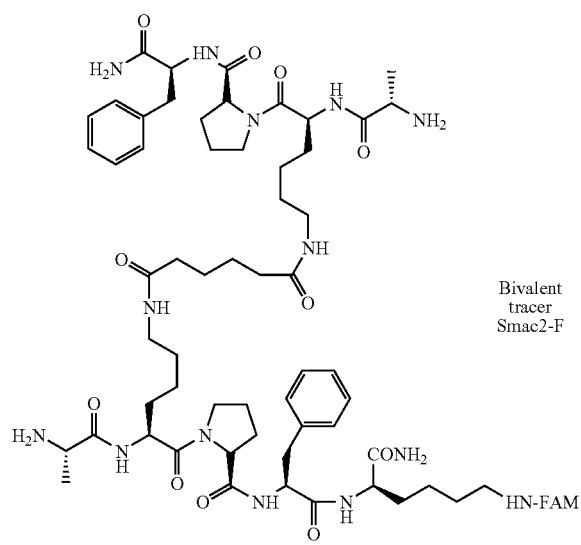

Bivalent tracer Smac2-F

When tested in the binding assay, bivalent Smac mimetic SH-164 had an $IC_{50}$ of 1.9±0.5 nM (FIG. 1). This was more than 500-fold better than the binding affinity of the monovalent Smac mimetic SH-122 and >5000 times more potent than the natural Smac peptide AVPI (SEQ ID NO: 1). These data suggest that bivalent Smac mimetics will act as potent inhibitors of IAP activity. The binding affinities of additional bivalent Smac mimetics are presented in Table 4.

TABLE 4

| Name | Binding Affinities to XIAP BIR3 ($IC_{50}$ [uM]) |
|---|---|
| YP-245P3 | 1-10 |
| YP-246P | 0.1-1 |
| YP-330 | <0.1 |
| YP-337 | <0.1 |
| YP-350 | <0.1 |
| YP-356 | <0.1 |
| YP-376 | <0.1 |
| YP-377 | <0.1 |
| SM-401 | <0.1 |
| SM-402 | <0.1 |
| SM-403 | <0.1 |
| SM-404 | <0.1 |
| SM-405 | <0.1 |
| SM-406 | <0.1 |
| SM-407 | <0.1 |
| SM-408 | <0.1 |
| SM-409 | <0.1 |
| SH-207 | <1 |

Example 14

Cell Growth Inhibition by Bivalent Smac Mimetics

The effect of SH-164 on the growth of various cancer cell lines was tested. Cells were seeded in 96-well flat bottom cell culture plates at a density of 3000 cells/well with a tested compound and incubated at 37° C. in an atmosphere of 95% air and 5% $CO_2$ for 4 days. The rate of cell growth inhibition after treatment with different concentrations of the compound was determined using a WST-8 kit (2-(2-methoxy-4-nitrophenyl)-3-(4-nitrophenyl)-5-(2, 4 disulfophenyl)-2H-tetrazolium monosodium salt; Dojindo Molecular Technologies, Inc., Gaithersburg, Md.). WST-8 was added at a final concentration of 10% to each well, and then the plates were incubated at 37° C. for 2-3 hrs. The absorbance of the samples was measured at 450 nm using a ULTRA Tecan Reader (Molecular Device). The concentration of the tested compound that inhibited cell growth by 50% ($IC_{50}$) was calculated by comparing absorbance in untreated cells and the cells treated with the tested compound.

Figure 2:
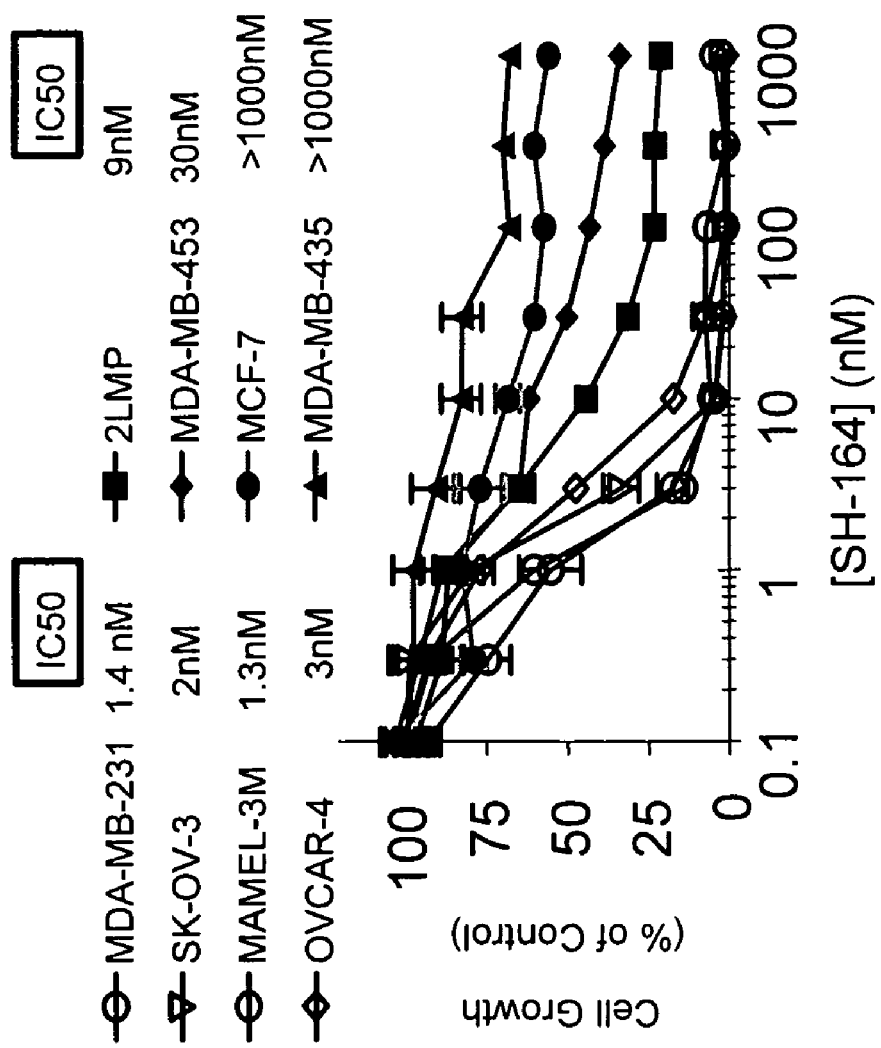
FIG. 2 is a graph showing the inhibition of cell growth in MDA-MB-231, MAMLE-3M, SK-OV-3 and OVCAR-4 cells by SH-164.

When tested against the MDA-MB-231 human breast cancer cell line and the MAMEL-3M melanoma cell line, SH-164 exhibited an $IC_{50}$ of 1.4 nM (FIG. 2). In addition, SH-164 is also a potent inhibitor in several other cancer cell lines (FIG. 2).

Example 15

Induction of Cell Death by Bivalent Smac Mimetics

Figure 3:
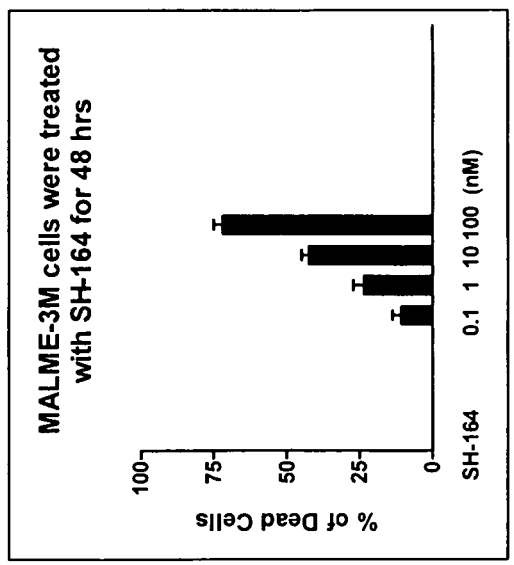
FIG. 3 is three graphs showing the induction of cell death in MDA-MB-231, MAMLE-3M, and OVCAR-4 cells by SH-164.
Figure 3:
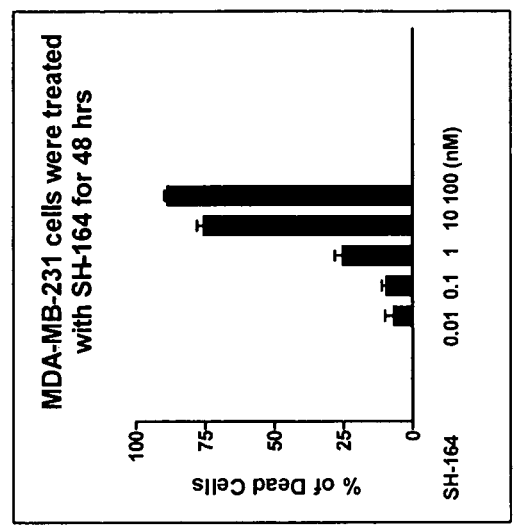
Figure 3:
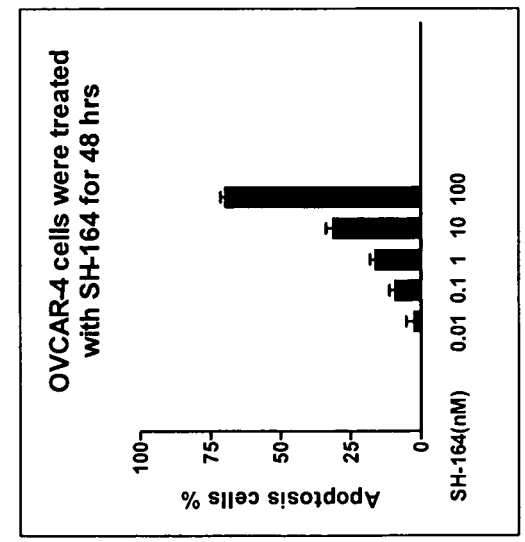

The ability of SH-164 to induce cell death in various cancer cell lines was tested using a Trypan blue cell viability assay. $0.3 \times 10^6$ cells were seeded in 6 well plates and incubated at 37° C. in an atmosphere of 95% air and 5% $CO_2$ without or with tested compound for 2 days. A 1:1 dilution of 0.4% Trypan blue (Invitrogen Corporation) was used to determine cell viability. SH-164 was shown to be an effective inducer of cell death when incubated with MDA-MB-231, MAMLE-3M, and OVCAR-4 cells (FIG. 3). In each case, SH-164 induced at least 70% cell death at a concentration of 100 nM.

Example 16

Figures 4A, 4B, 4C:
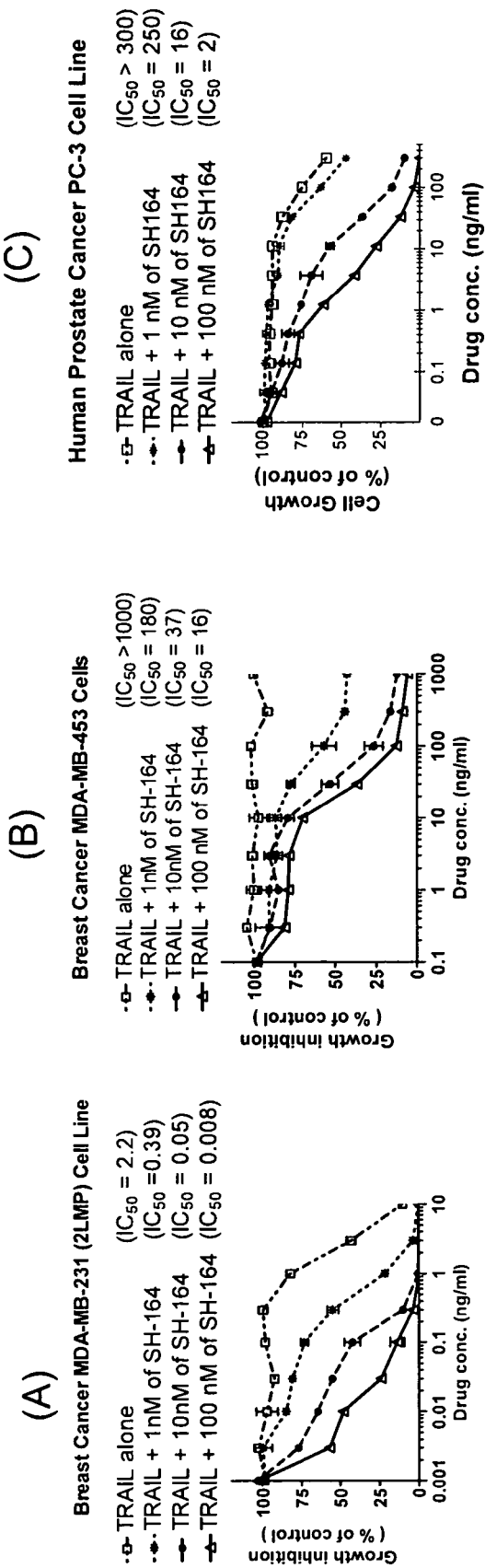
FIGS. 4A-4C are three graphs showing the inhibition of cell growth in MDA-MB-231 (A), MDA-MB-453 (B), and PC-3 (C) cells by SH-164 in combination with TRAIL.

Effect of Combinations of Bivalent Smac Mimetics and Other Agents on Cell Growth Inhibition To test the ability of bivalent Smac mimetics to sensitize cancer cells to the growth inhibiting effects of other agents, cell growth inhibition assays were carried out with various agents alone or in combination with increasing doses of bivalent Smac mimetics. Exposure of MDA-MB-231 (2LMP) breast cancer cells to TRAIL alone resulted in an $IC_{50}$ of 2.2 ng/ml (FIG. 4A). Combination of TRAIL and SH-164 lowered the $IC_{50}$ for TRAIL significantly, with TRAIL in the presence of 100 nM SH-164 having an $IC_{50}$ of 0.008 ng/ml. A similar result was seen with MDA-MB-453 breast cancer cells, where TRAIL alone had an $IC_{50}$ of >1000 ng/ml and the combination of TRAIL and 100 nM SH-164 had an $IC_{50}$ of 16 ng/ml (FIG. 4B). When PC-3 human prostate cancer cells were used, TRAIL alone had an $IC_{50}$ of >300 ng/ml while TRAIL in the presence of 100 nM SH-164 had an $IC_{50}$ of 2 ng/ml (FIG. 4C). SH-122 had a similar although less potent effect, with the combination of TRAIL and 1000 nM SH-122 having an $IC_{50}$ of 30 ng/ml. In contrast 500 nM SH-149 did not lower the $IC_{50}$ of TRAIL.

Figure 5:
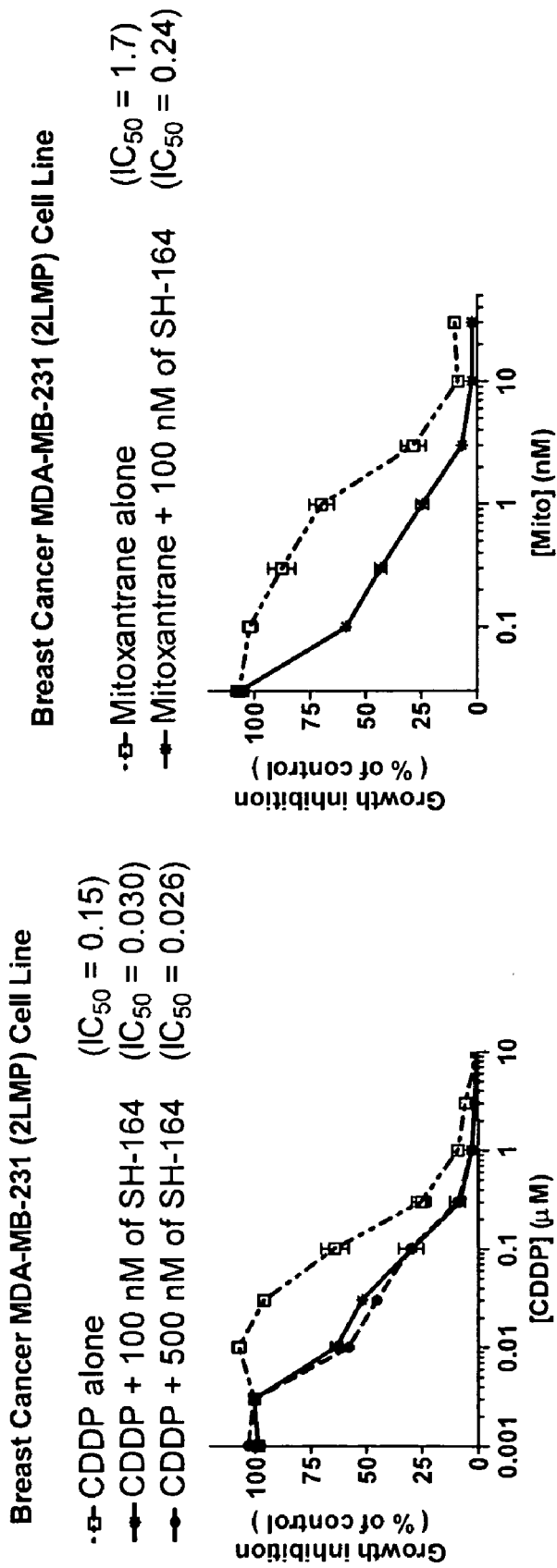
FIG. 5 is two graphs the inhibition of cell growth in MDA-MB-231 cells by SH-164 in combination with cisplatin or mitoxantrone.

SH-164 was also tested for its ability to enhance the growth inhibitory effects of the chemotherapeutic agents cisplatin and mitoxantrone. When tested on MDA-MB-231 (2LMP) human breast cancer cells, SH-164 at a concentration of 100 nM sensitized the cells to growth inhibition by both agents (FIG. 5). These data indicate that bivalent Smac mimetics are capable of sensitizing cells to the growth inhibitory effects of a variety of cancer-treating agents.

Example 17

Apoptosis Assay

Figure 6:
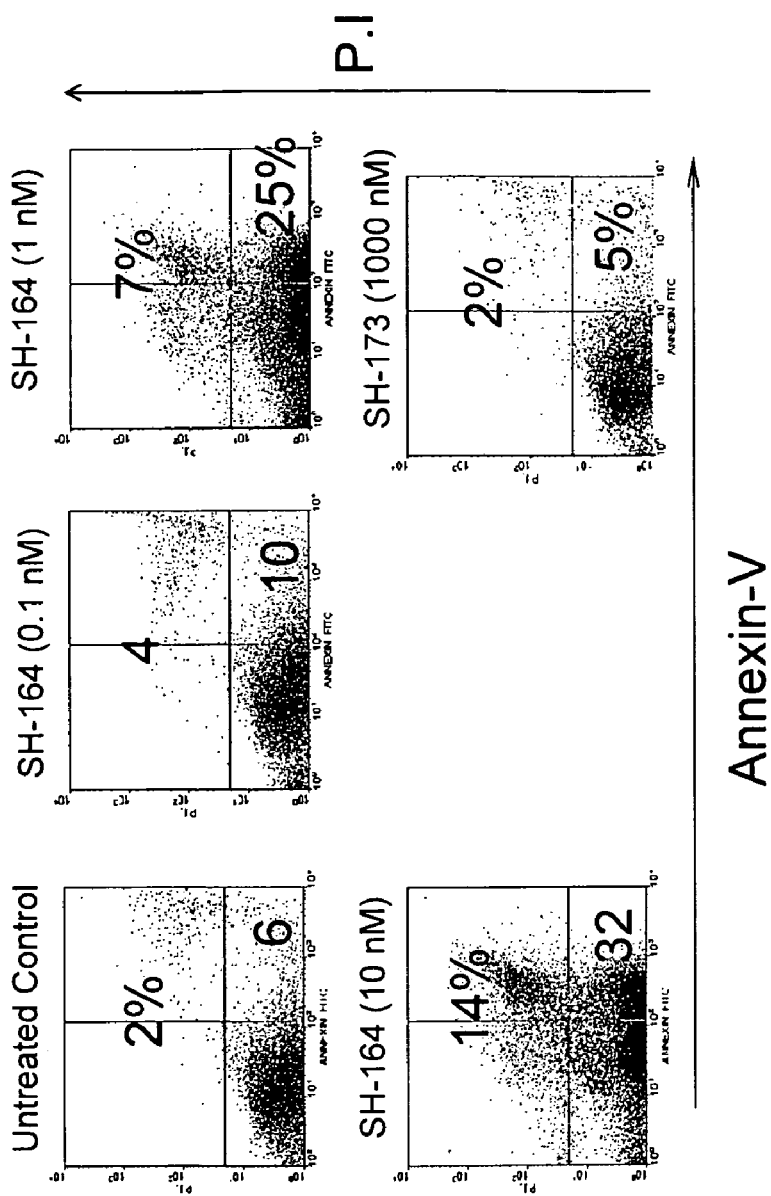
FIG. 6 is five panels showing induction of apoptosis by SH-164 in the MDA-MB-231 breast cancer cell line.

Analysis of apoptosis was performed using an apoptosis detection kit (BioVision Research Products, Mountain View, Calif.) according to the manufacturer's protocol. Briefly, cells were treated with Smac mimetics for 12 hours, harvested and washed with ice-cold PBS. Cells were stained with Annexin V-FITC and Propidium iodide (P.I.) for 15 minutes at room temperature in the dark and immediately analyzed by FACS calibur flow cytometer (Becton Dickinson, Erembodegem, Belgium). Cells that were stained Annexin V (+) and P.I. (−) were considered early-stage apoptotic cells. Cells that were stained annexin V (+) and P.I. (+) were considered late-stage apoptotic cells and cells that were stained annexin V (−) and P.I. (+) were considered necrotic cells (FIG. 6).

Example 18

Binding Affinities to XIAP and Activities in Cell Growth Inhibition

The binding affinities to XIAP and activities in cell growth inhibition of Smac mimetics are presented in Table 5.

TABLE 5

| Compound | Binding to XIAP $IC_{50}$ values [nM] | IC50 values (nM) In WST-assay (MDA-MB-231) | IC50 values (nM) In WST-assay SK-OV-3 |
|---|---|---|---|
| SH-142 | <50 | <100 | |
| SH-143 | <50 | | |
| SH-146 | <50 | | |
| SH-153 | <10 | <1000 | |
| SH-155 | <10 | <100 | <100 |
| SH-156 | <10 | <1000 | <1000 |
| SH-158 | <10 | <1000 | <1000 |
| SH-159 | <10 | <1000 | <1000 |
| SH-164 | <10 | <10 | <10 |
| SH-165 | <10 | <1000 | <1000 |
| SH-166 | <10 | <1000 | <1000 |
| SH-167 | <10 | <10 | <10 |
| SH-172 | <10 | <1000 | |
| SH-173 | >10,000 | >10000 | >10000 |
| SH-175 | <50 | <100 | <100 |
| SH-176 | <10 | <100 | |
| SH-177 | <10 | <100 | |
| SH-178 | <100 | <10,000 | |
| SH-179 | <100 | <10000 | |
| SH-180 | <100 | <1000 | <1000 |
| SH-181 | <100 | <10000 | |
| SH-182 | <100 | <10 | <10 |
| SH-183 | <100 | <10,000 | |
| SH-184 | <100 | <10 | <100 |
| SH-185 | <50 | <10 | <10 |
| SH-186 | <50 | <10 | <10 |
| SH-187 | >10000 | >10000 | >10000 |
| SH-188 | <100 | <100 | <100 |
| SH-189 | <100 | <100 | <100 |
| SH-190 | <100 | <10 | <10 |

TABLE 5-continued

| Compound | Binding to XIAP $IC_{50}$ values [nM] | IC50 values (nM) In WST-assay (MDA-MB-231) | IC50 values (nM) In WST-assay SK-OV-3 |
|---|---|---|---|
| SH-191 | <100 | <100 | <100 |
| SH-198 | <100 | <10 | <10 |
| SH-199 | <10 | <10 | <10 |
| SH200 | <10 | <100 | <100 |
| SH-201 | >10,000 | >1000 | >1000 |
| SH-202 | <100 | <10 | <10 |
| SH-206 | <1000 | <1000 | <1000 |
| YP-317 | <100 | <100 | |
| YP-343 | <100 | <100 | |
| YP-381 | <10 | <10 | <10 |
| YP-383 | <10 | <10 | <10 |
| YP-385 | <10 | <10 | <10 |
| SM-410 | <100 | <500 | <500 |

Example 19

Binding Affinities to IAP Proteins

SM-122 (referred to above as SH-122) is a monovalent, non-peptidic mimetic of the Smac AVPI peptide and SM-164 (referred to above as SH-164) as a bivalent Smac mimetic containing two SM-122 analogues tethered together by a chemical linker (Sun et al., *J. Am. Chem. Soc.* 129:15279 (2007)). SM-123 and SM-173 (referred to above as SH-173) are much less potent monovalent and bivalent control compounds, respectively (Sun *J. Am. Chem. Soc.* 129:15279 (2007)).

Figure 7:
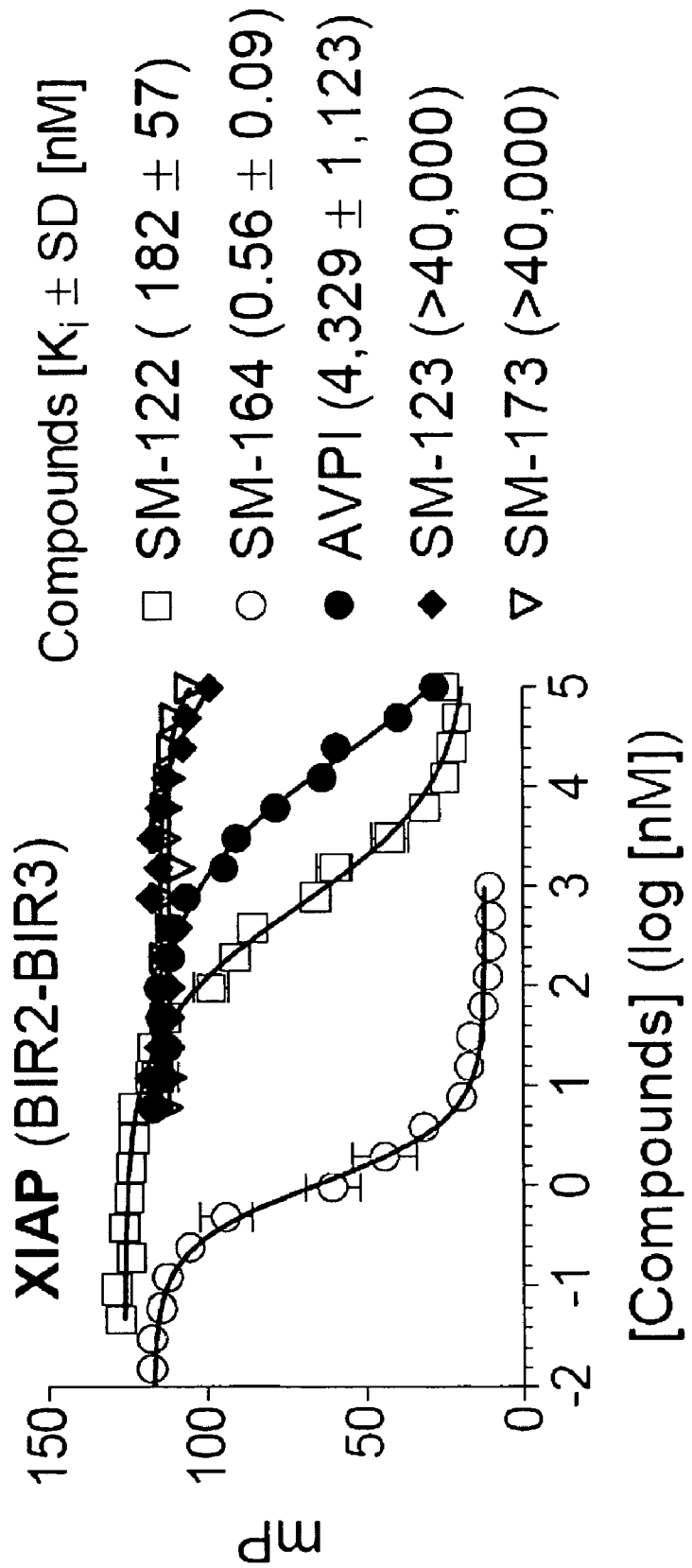
FIG. 7 is a line graph showing the binding affinity of Smac mimetics to XIAP (BIR2-BIR3) protein.
Figure 8:
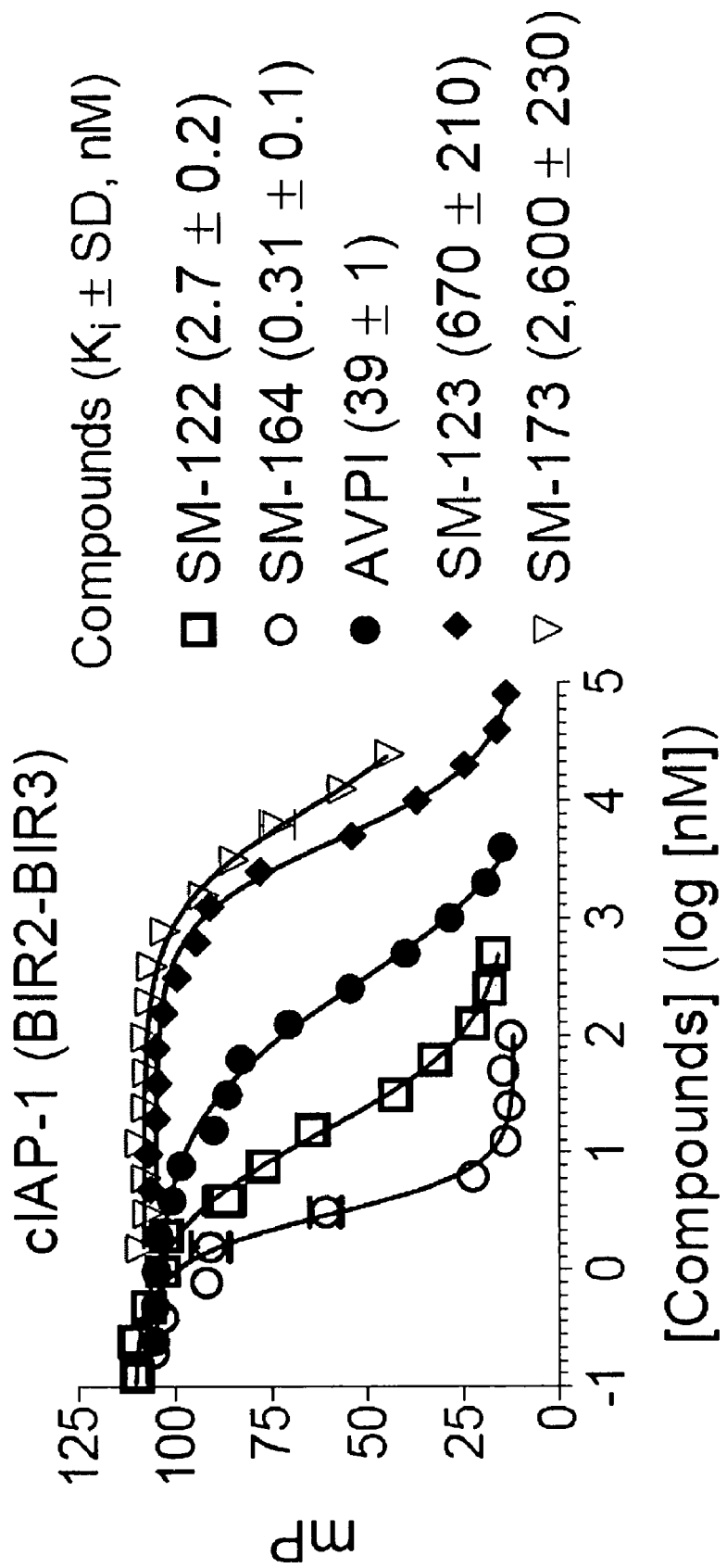
FIG. 8 is a line graph showing the binding affinity of Smac mimetics to cIAP-1 (BIR2-BIR3) protein.
Figure 9:
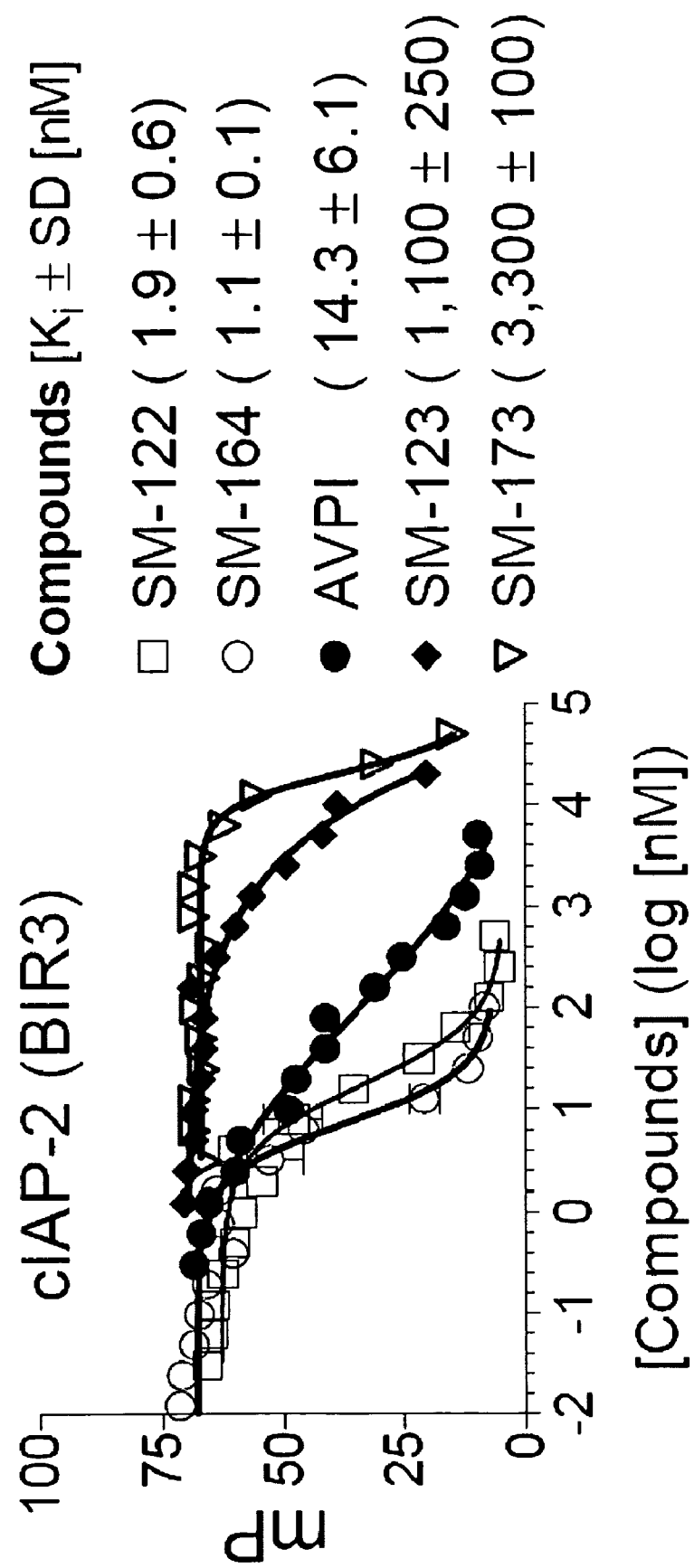
FIG. 9 is a line graph showing the binding affinity of Smac mimetics to cIAP-2 (BIR3) protein.

The binding affinities of SM-164 and SM-122 to XIAP, cIAP-1, and cIAP-2 proteins were determined using fluorescence-polarization based assays. SM-164 and SM-122 have $K_i$ values of 0.56 nM and 182 nM, respectively, to XIAP protein containing both BIR2 and BIR3 domains (FIG. 7). SM-164 and SM-122 have $K_i$ values of 0.31 nM and 2.7 nM, respectively, to cIAP-1 protein containing both BIR2 and BIR3 domains (FIG. 8). A soluble cIAP-2 protein containing both BIR2 and BIR3 domains could not be obtained. Therefore binding affinities of Smac mimetics to cIAP-2 BIR3-only protein were evaluated. SM-164 and SM-122 bind to cIAP-2 BIR3 protein with $K_i$ values of 1.1 nM and 1.9 nM, respectively (FIG. 9). Hence, bivalent SM-164 is 300 times more potent than the monovalent SM-122 for binding to XIAP, and is 9 times more potent than SM-122 to cIAP-1. SM-122 and SM-164 have similar high binding affinities to cIAP-2. The monovalent control compound, SM-123, is 100-1000 times less potent than SM-122 and SM-173 is 1000 times less potent than SM-164 to these IAP proteins (FIGS. 8-9).

Figure 10:
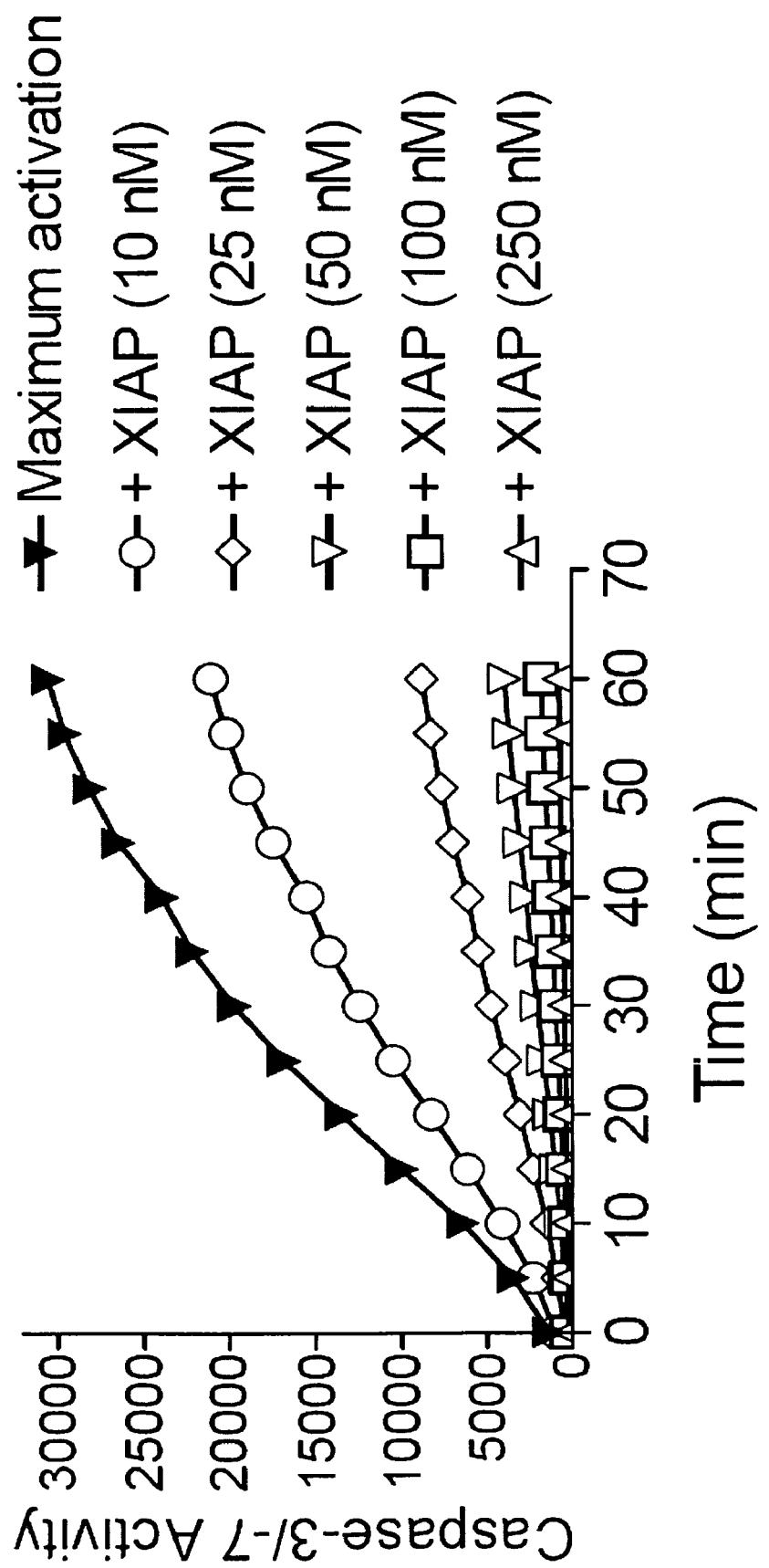
FIG. 10 is a line graph showing the inhibition of caspase-3/-7 activity by recombinant XIAP containing linker BIR2-BIR3.
Figure 11:
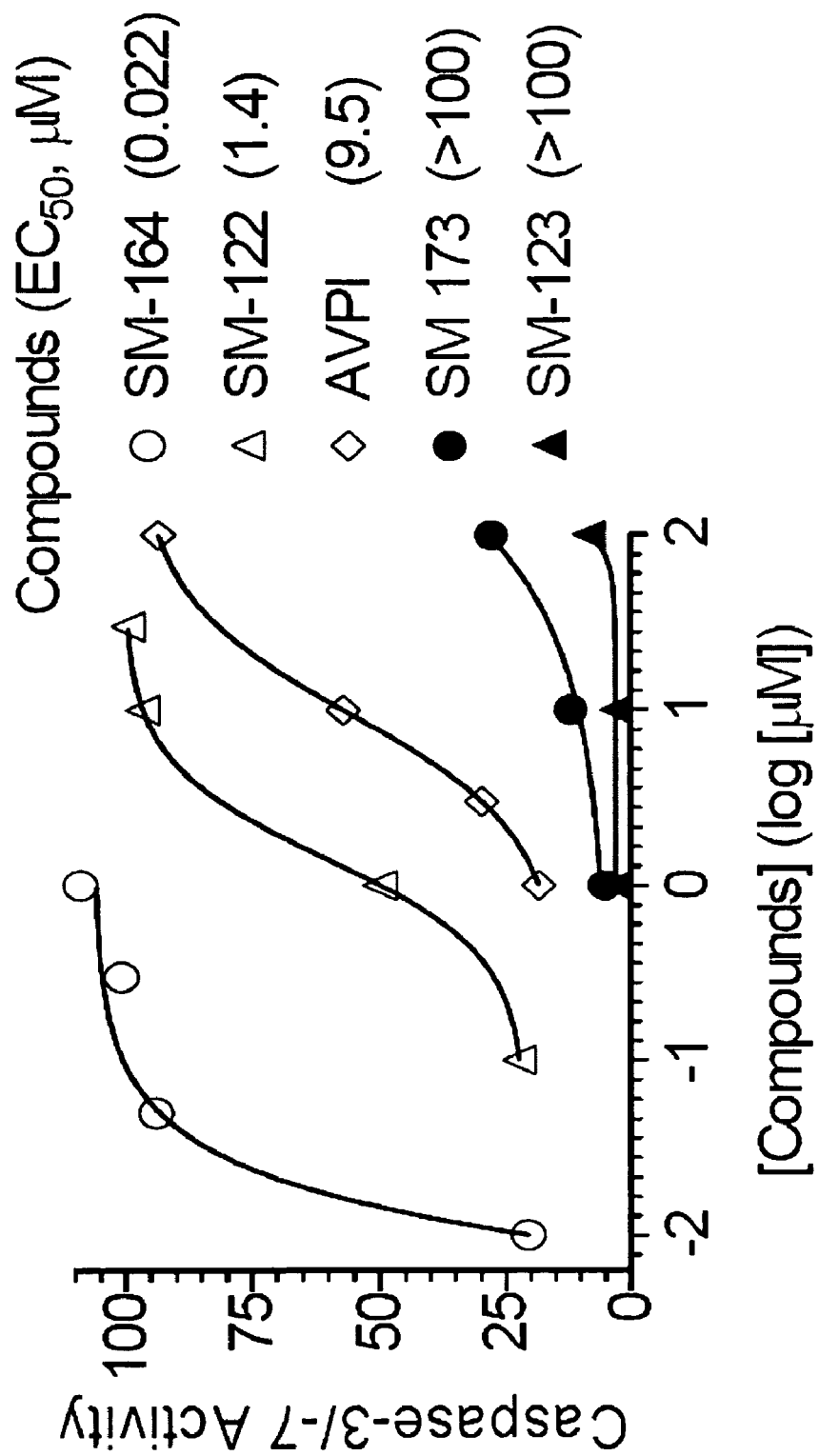
FIG. 11 is a graph showing the promotion of caspase-3/-7 activity by Smac mimetics.

Because XIAP functions as a potent antagonist of caspase-3/-7 (Riedl et al., *Cell* 104:791-800 (2001); Chai et al., *Cell* 104:769 (2001); Suzuki et al., *J. Biol. Chem.* 276:27058 (2001)), the ability of SM-164 and SM-122 to antagonize XIAP in cell-free functional assays was evaluated. Recombinant XIAP containing linker-BIR2-BIR3 (residues 120-356) effectively inhibited the activity of caspase-3/-7 in a dose-dependent manner and achieved complete inhibition at 50 nM (FIG. 10). Both SM-164 and SM-122 dose-dependently antagonized XIAP and promoted caspase activity but SM-164 was 60 times more potent than SM-122 (FIG. 11). SM-123 and SM-173 had minimal effect in this functional assay up to 100 μM (FIG. 11). Thus, these biochemical data show that the major difference between bivalent SM-164 and monovalent SM-122 is their potency in targeting XIAP. This is consistent with a previous study that SM-164 is >100 times more potent than SM-122 in competing off a biotinylated Smac mimetic to cellular XIAP in a pull-down assay (Sun et al., *J. Am. Chem. Soc.* 129:15279 (2007)).

Example 20

Induction of Caspase-3 and -8 Dependent Apoptosis in Cancer Cells

Smac mimetics were found to be effective in induction of apoptosis as single agents in a number of tumor cell lines. MDA-MB-231 breast cancer, SK-OV-3 ovarian cancer, and MALME-3M melanoma cell lines were selected as representative sensitive models for detailed studies.

Figure 12:
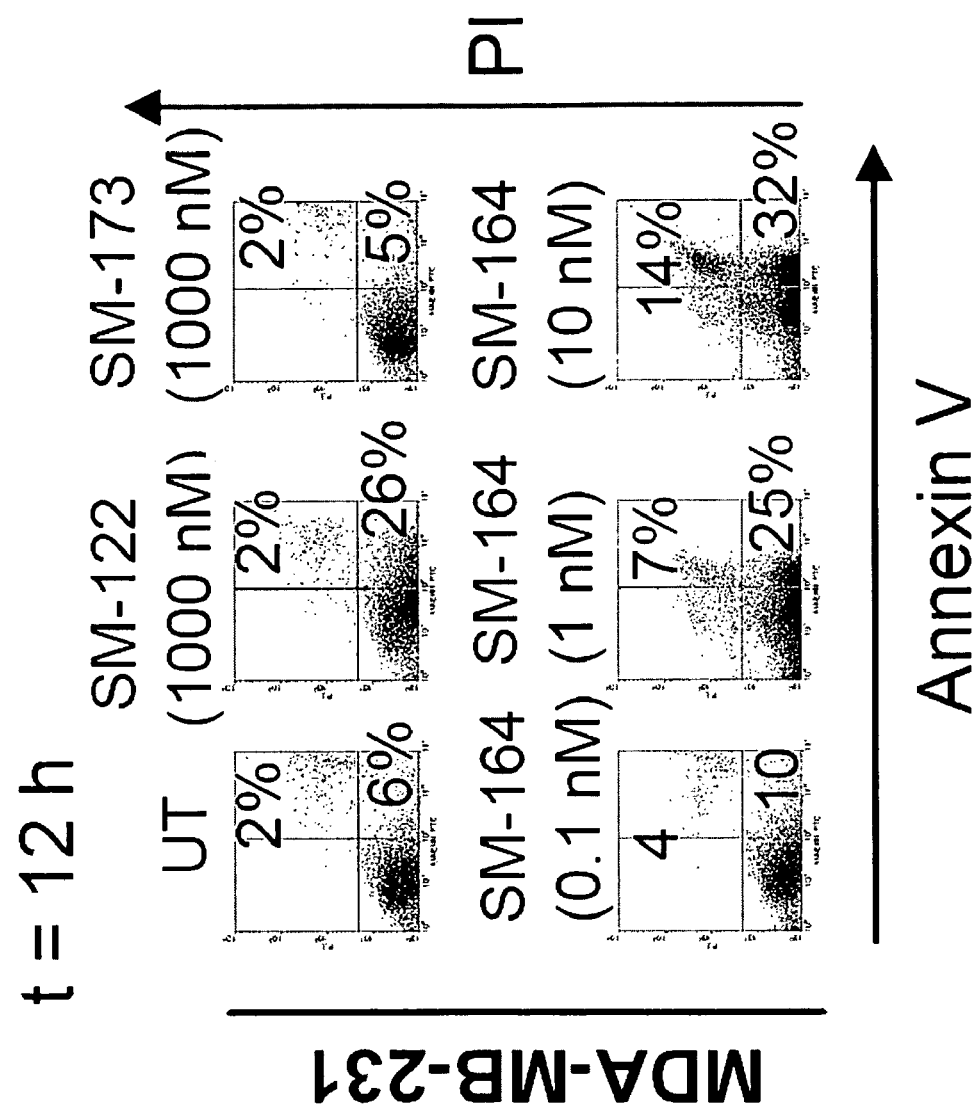
FIG. 12 is a series of six panels showing induction of apoptosis by Smac mimetics in the MDA-MB-231 breast cancer cell line.
Figure 13:
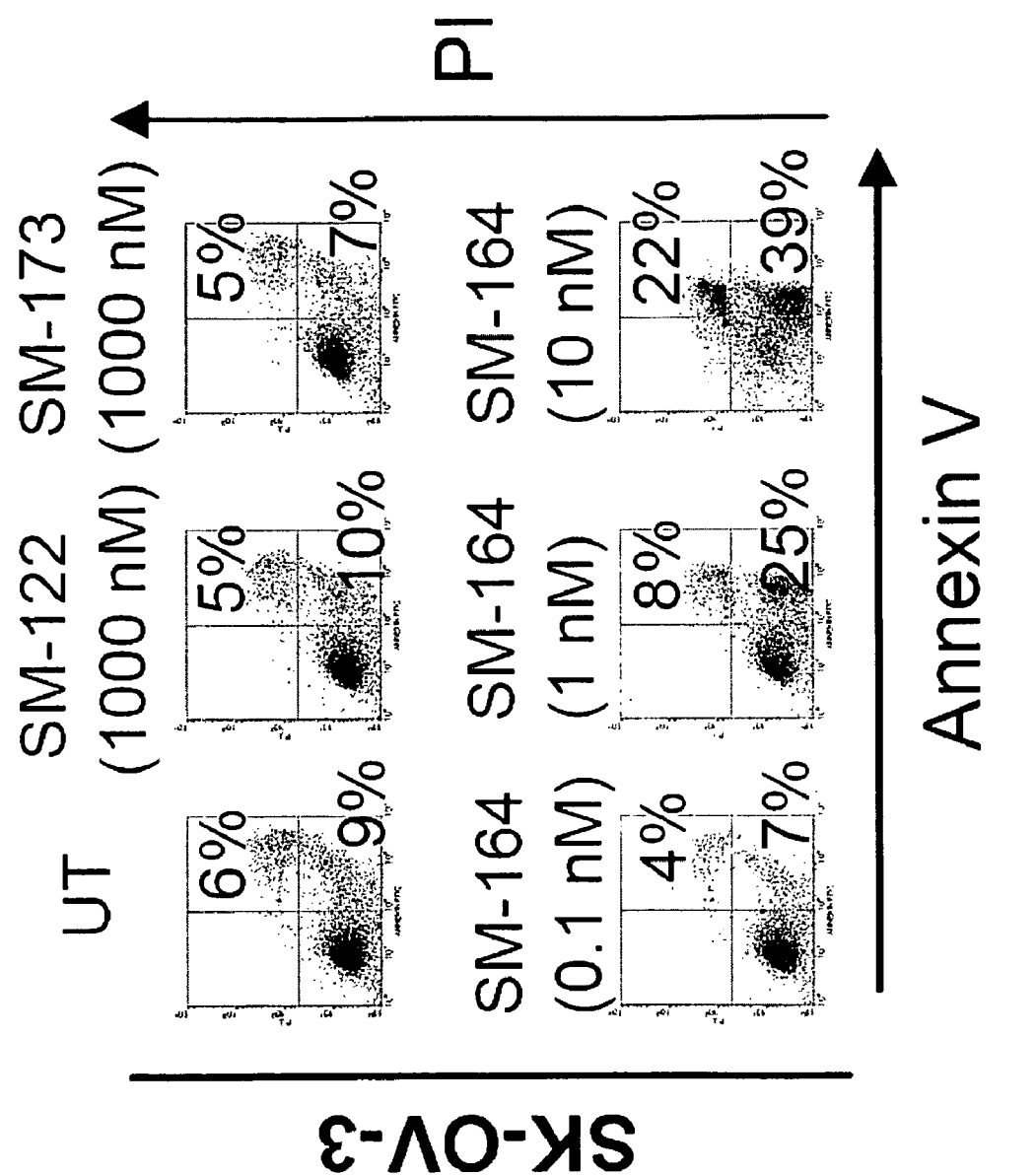
FIG. 13 is a series of six panels showing induction of apoptosis by Smac mimetics in the SK-OV-3 ovarian cancer cell line.
Figure 14:
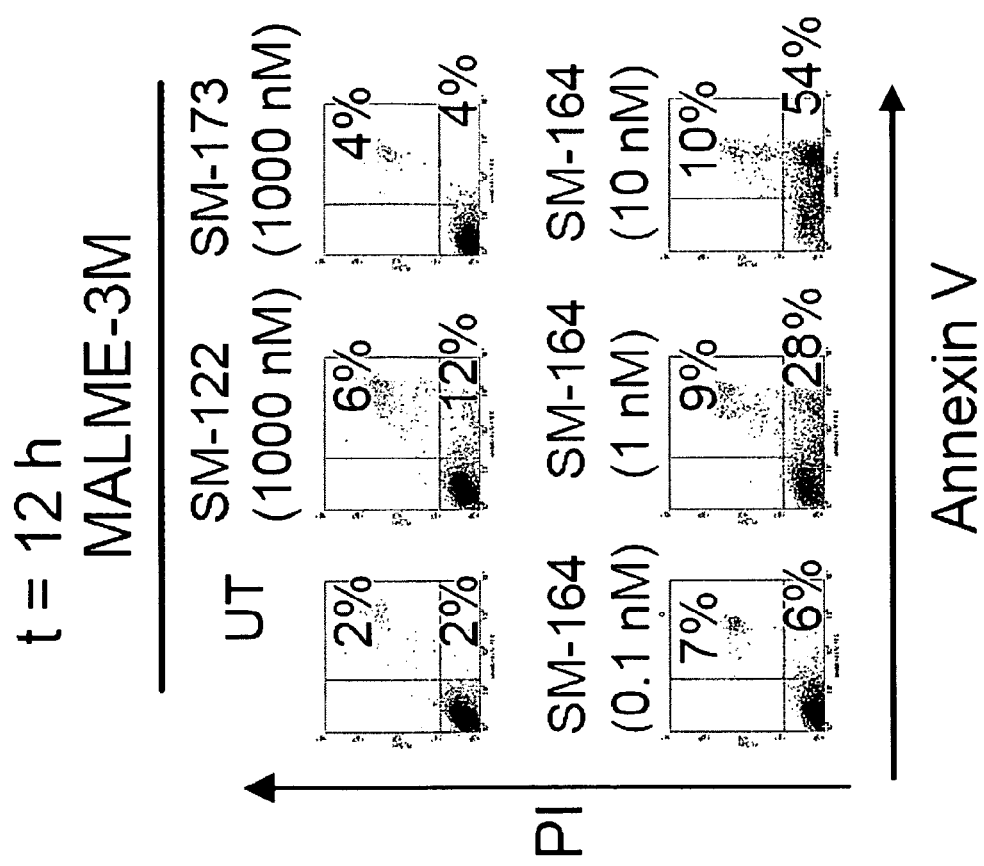
FIG. 14 is a series of six panels showing induction of apoptosis by Smac mimetics in the MALME-3M melanoma cell line.
Figure 15:
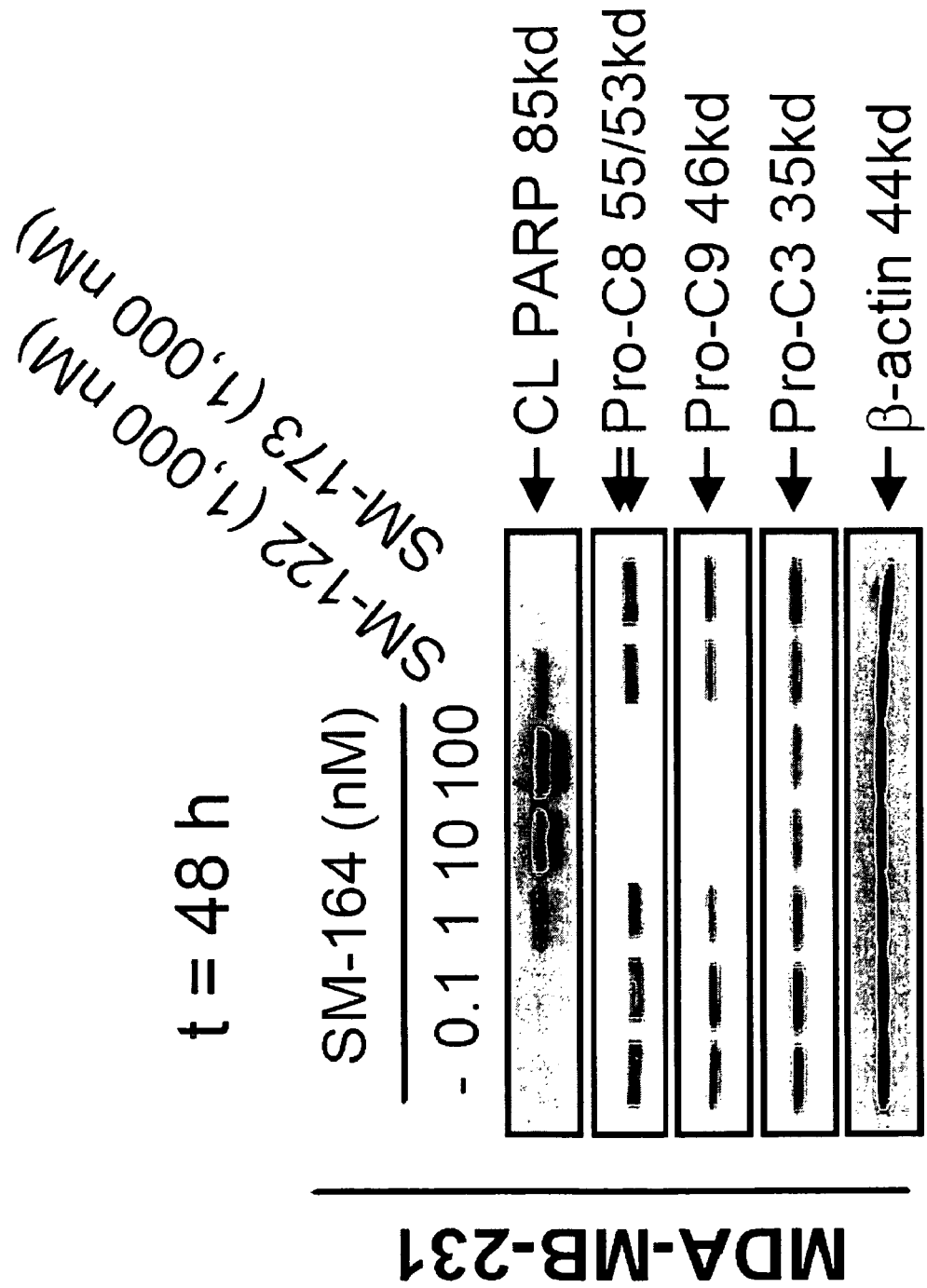
FIG. 15 is a series of five images showing SM-164 decreases levels of pro-caspase-3, -8, and -9 and increases levels of PARP in the MDA-MB-231 breast cancer cell line as measured by western blot analysis.
Figure 16:
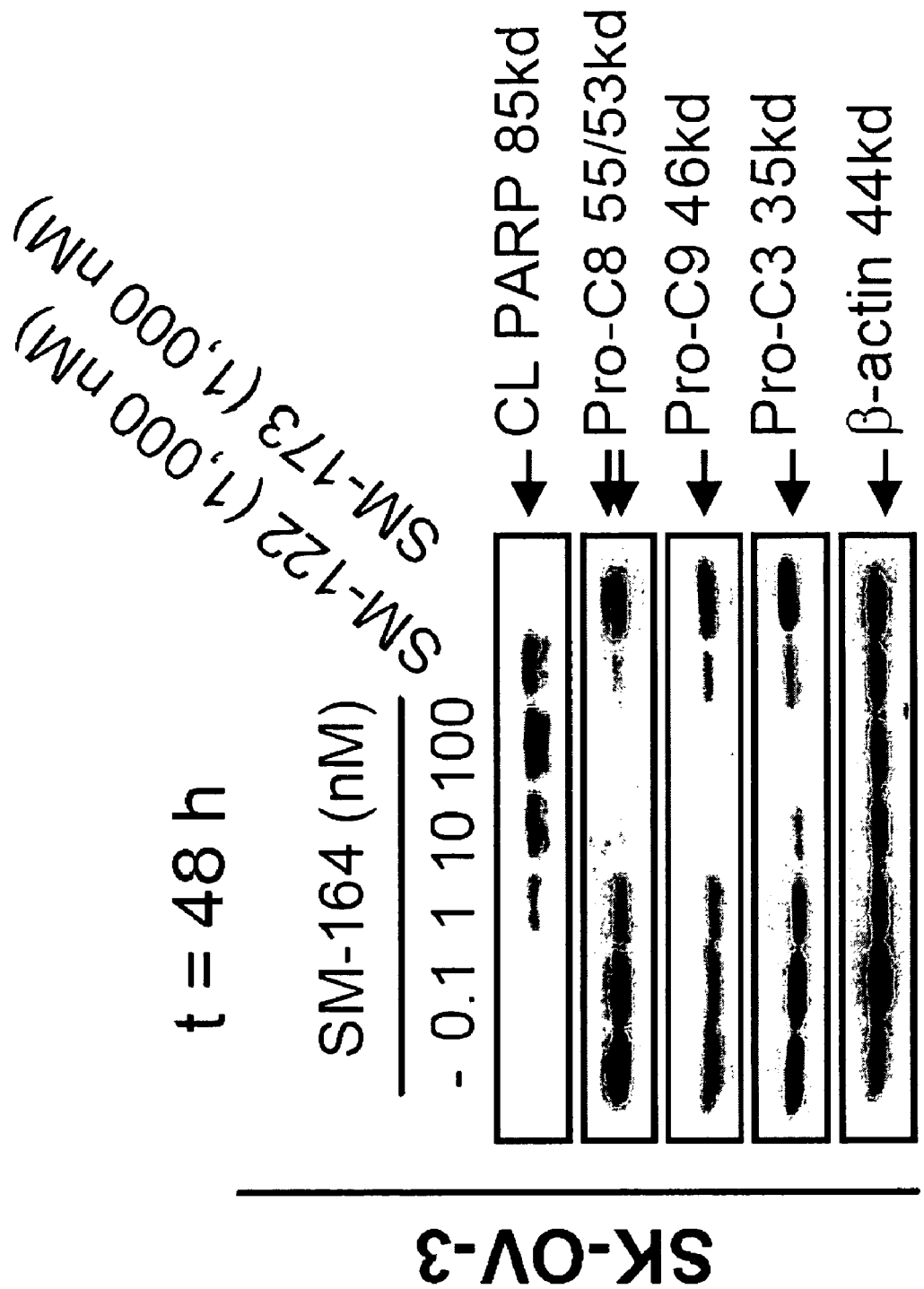
FIG. 16 is a series of five images showing SM-164 decreases levels of pro-caspase-3, -8, and -9 and increases levels of PARP in the SK-OV-3 ovarian cancer cell line as measured by western blot analysis.
Figure 17:
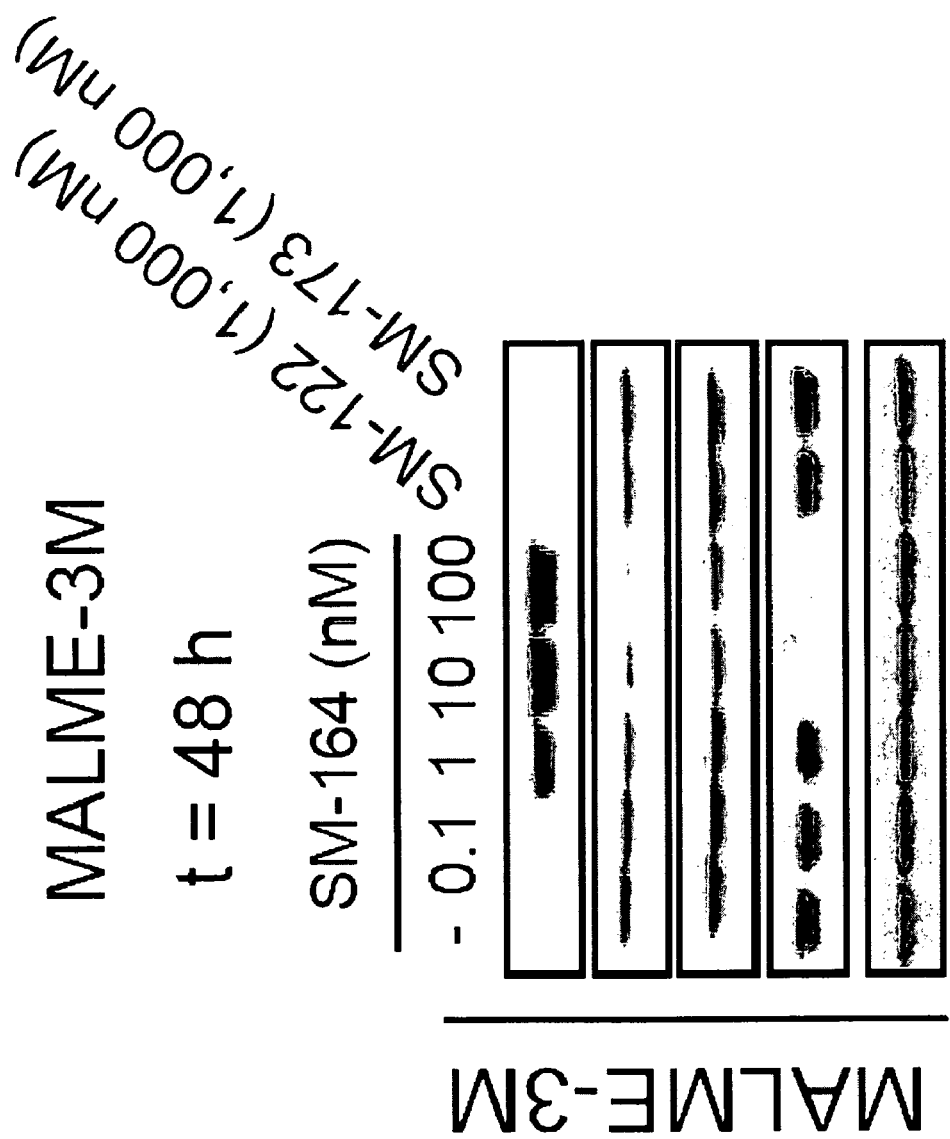
FIG. 17 is a series of five images showing SM-164 decreases levels of pro-caspase-3, -8, and -9 and increases levels of PARP in the MALME-3M melanoma cell line as measured by western blot analysis.

Both SM-164 and SM-122 induced apoptosis in each of these three cancer cell lines in a dose-dependent manner, but SM-164 was much more potent than SM-122. Treatment with SM-164 at 1 nM for 12 h induced 32%, 33%, and 37% of the MDA-MB-231, SK-OV-3 and MALME-3M cells to undergo apoptosis, respectively (FIGS. 12-14). Western blot analysis further showed that SM-164 at concentration as low as 1 nM markedly decreased the levels of pro-caspase-3, -8 and -9 and increased the levels of cleaved PARP in all the three cell lines (FIGS. 15-17). SM-164 at 1 nM was as effective as SM-122 at 1,000 nM in induction of cell death, caspase processing and PARP cleavage (FIGS. 15-17).

Figure 18:
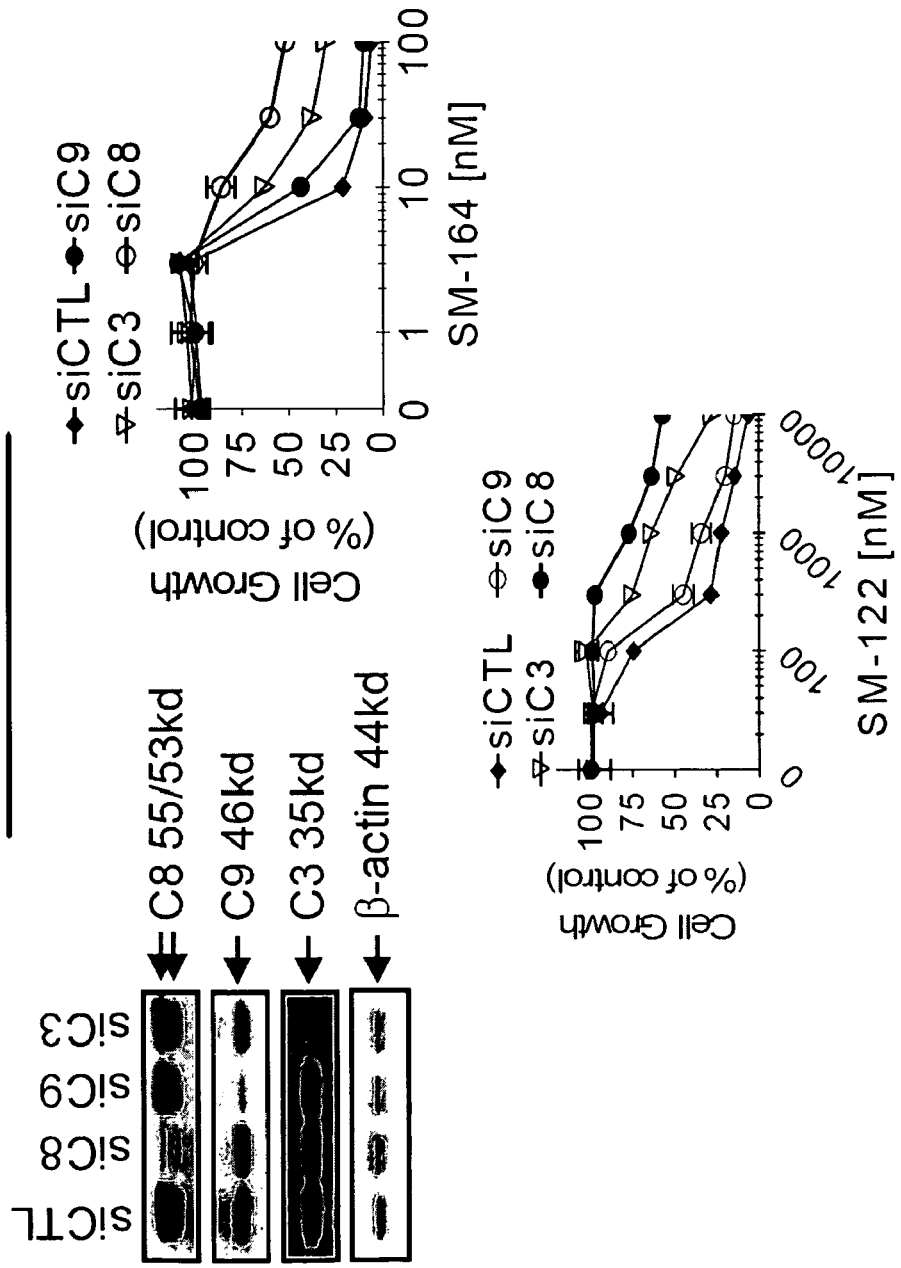
FIG. 18 is a series of four images and two line graphs showing knockdown of caspase-3, -8, and -9 attenuates the activity of Smac mimetics SM-122 and SM-164 and knockdown of caspase-9 has minimal effect on the activity of Smac mimetics SM-122 and SM-164 in the MDA-MB-231 breast cancer cell line.
Figure 19:
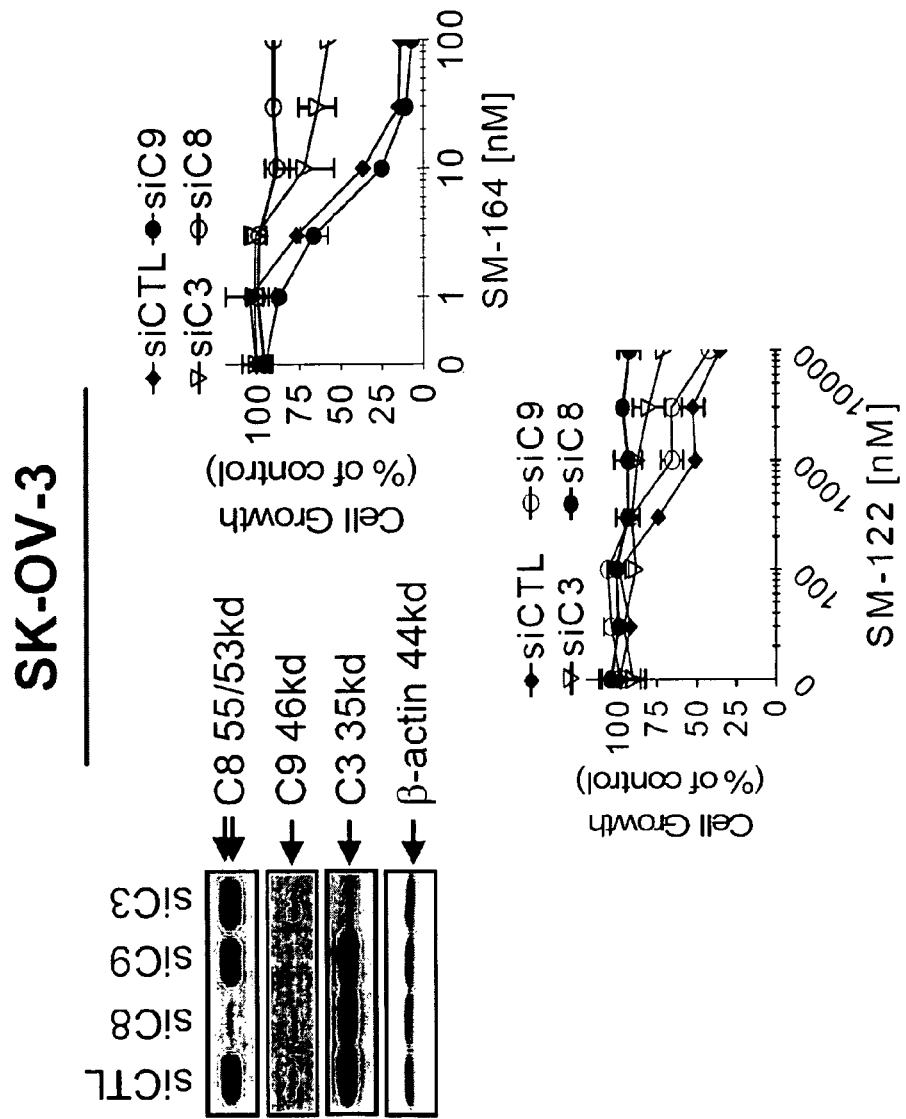
FIG. 19 is a series of four images and two line graphs showing knockdown of caspase-3, -8, and -9 attenuates the activity of Smac mimetics SM-122 and SM-164 and knockdown of caspase-9 has minimal effect on the activity of Smac mimetics SM-122 and SM-164 in the SK-OV-3 ovarian cancer cell line.

To examine the role of caspase-8, -3 and -9 in apoptosis induction by Smac mimetics, siRNA was employed against these caspases in MDA-MB-231 and SK-OV-3 cancer cell lines. Knockdown of caspase-3 and -8 markedly attenuated the activity of both SM-164 and SM-122, whereas knockdown of caspase-9 had a minimal effect (FIGS. 18-19). In addition, Z-IETD-FMK, a selective caspase-8 inhibitor, and Z-DEVD-FMK, a selective caspase-3/-7 inhibitor, markedly inhibited the activity of both Smac mimetics. Hence, although these three caspases are all processed, only caspase-8 and caspase-3 play a crucial role in apoptosis induction by Smac mimetics and caspase-9 appears to have a minimal role, consistent with a previous study (Petersen et al., *Cancer Cell* 12:445 (2007)).

Example 21

Induction of TNFα-Dependent Apoptosis

Figure 20:
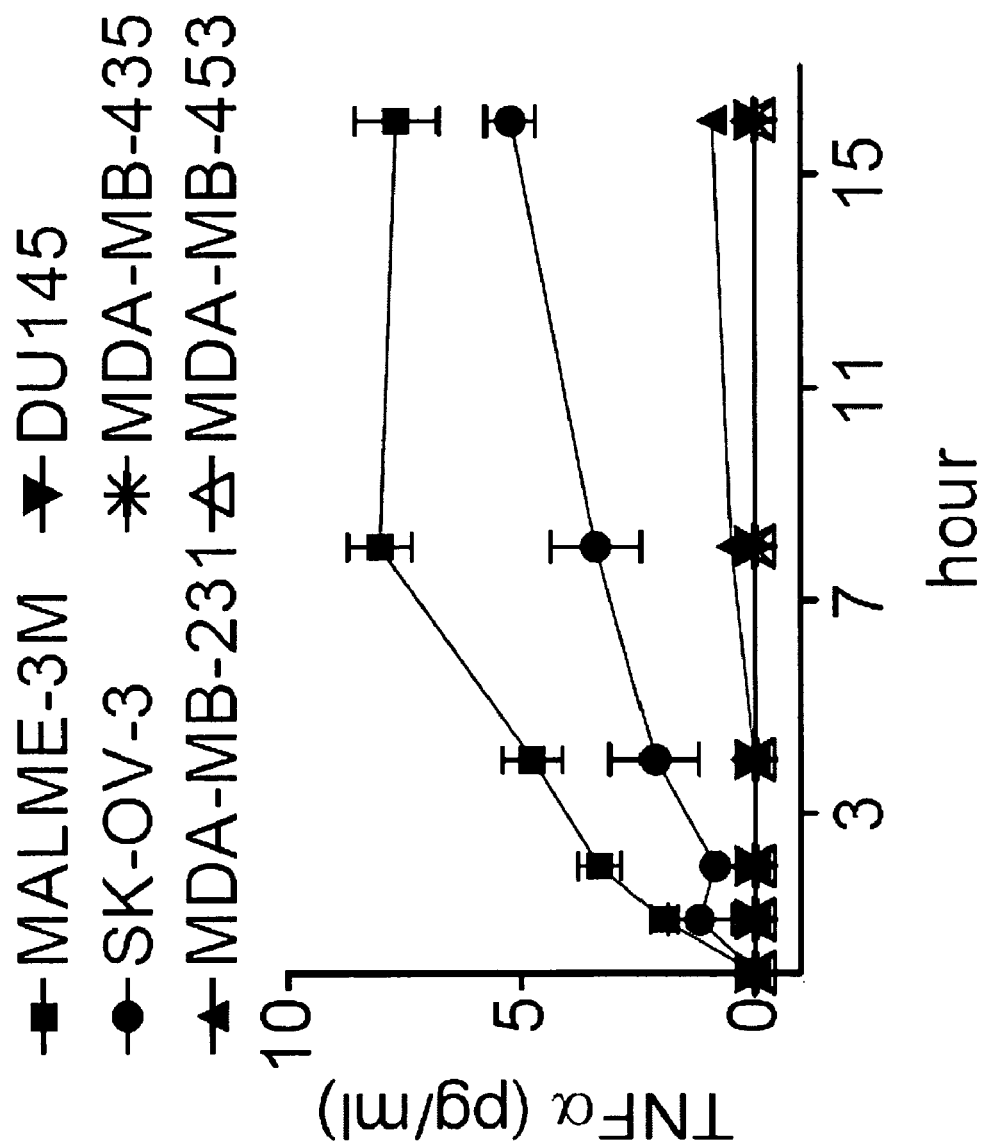
FIG. 20 is a line graph showing secretion of TNFα in various cancer cell lines in the absence of Smac mimetics.
Figure 21:
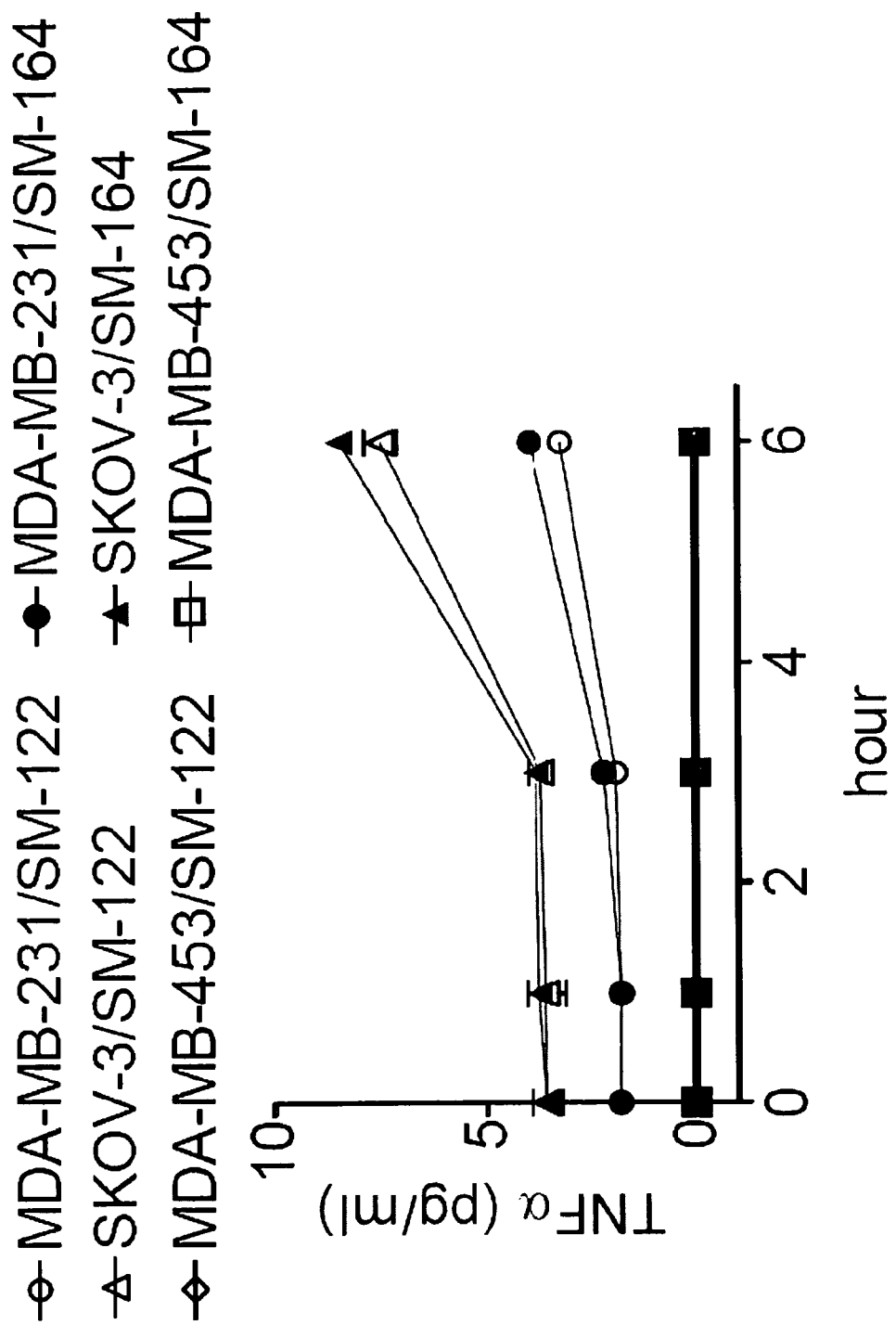
FIG. 21 is a line graph showing secretion of TNFα in various cancer cell lines enhanced by treatment with Smac mimetics SM-122 and SM-164.
Figure 22:
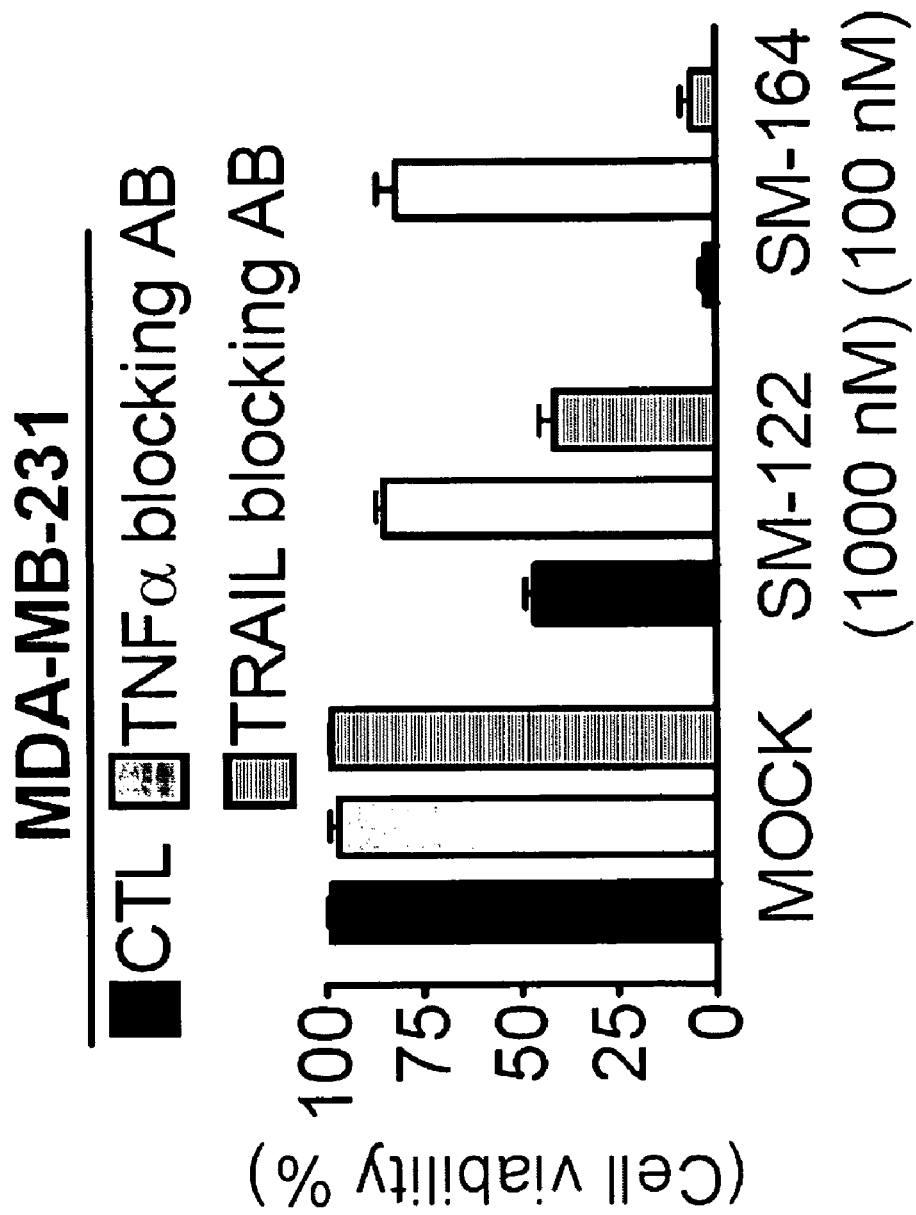
FIG. 22 is a bar graph showing cell death induction by Smac mimetics SM-122 and SM-164 is blocked by TNFα neutralizing antibody but not by a TRAIL neutralizing antibody in the MDA-MB-231 breast cancer cell line.
Figure 23:
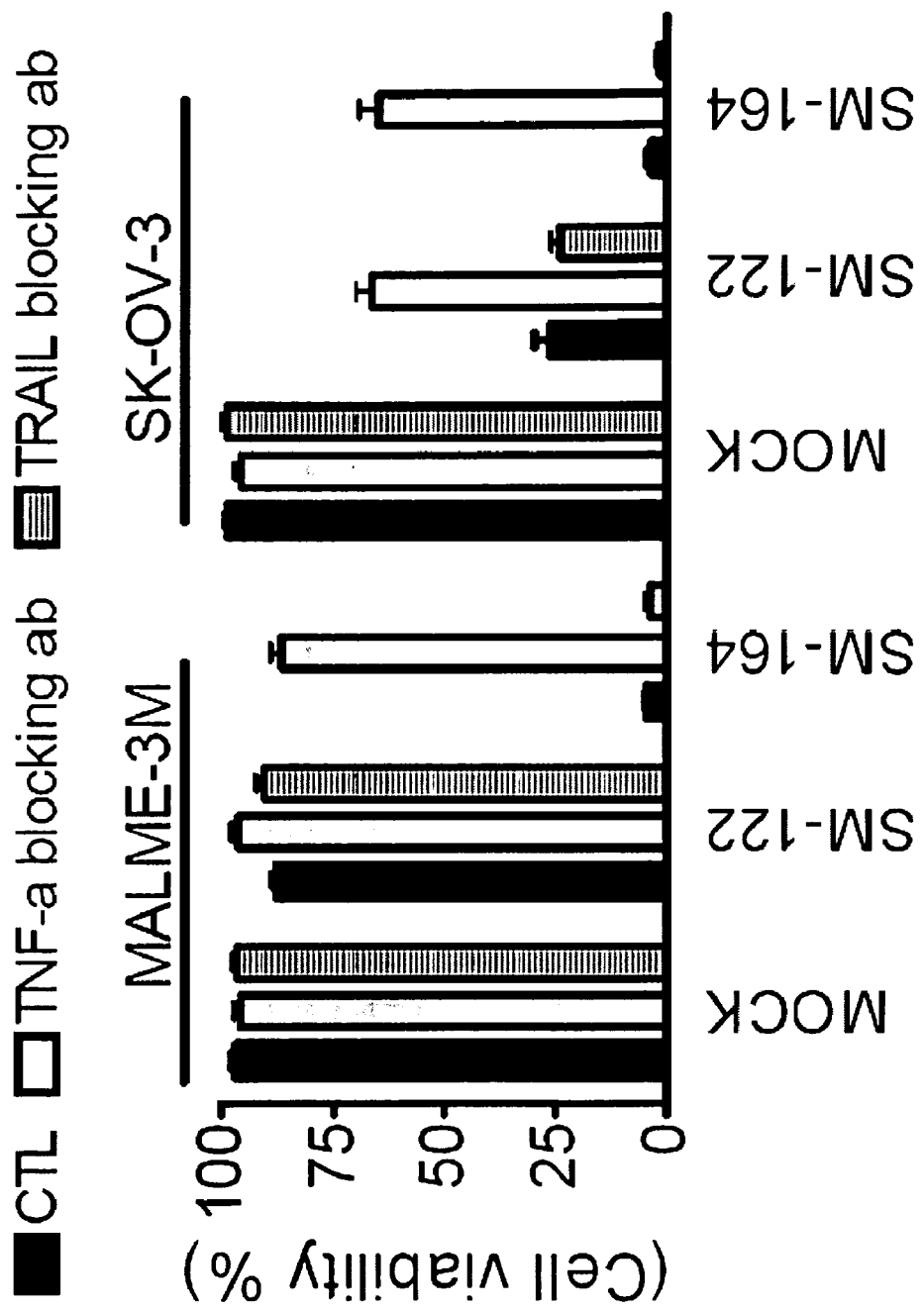
FIG. 23 is a bar graph showing cell death induction by Smac mimetics SM-122 and SM-164 is blocked by a TNFα neutralizing antibody but not by a TRAIL neutralizing antibody in the MALME-3M and SK-OV-3 cell lines.

Recent studies have shown that Smac mimetics induce apoptosis in tumor cells through a TNFα-dependent pathway (Varfolomeev et al., *Cell* 131:669 (2007); Vince et al., *Cell* 131:682 (2007); (Petersen et al., *Cancer Cell* 12:445 (2007)). Sensitive cancer cell lines secreted detectable levels of TNFα in the cell culture medium without Smac mimetic treatment (FIG. 20) and the secretion of TNFα was further enhanced by SM-164 and SM-122 (FIG. 21). Furthermore, cell death induction by SM-164 and SM-122 was effectively blocked by a TNFα, but not by a TRAIL, neutralizing antibody (FIGS. 22-23), indicating that apoptosis induction by both SM-164 and SM-122 is TNFα dependent.

Figure 24:
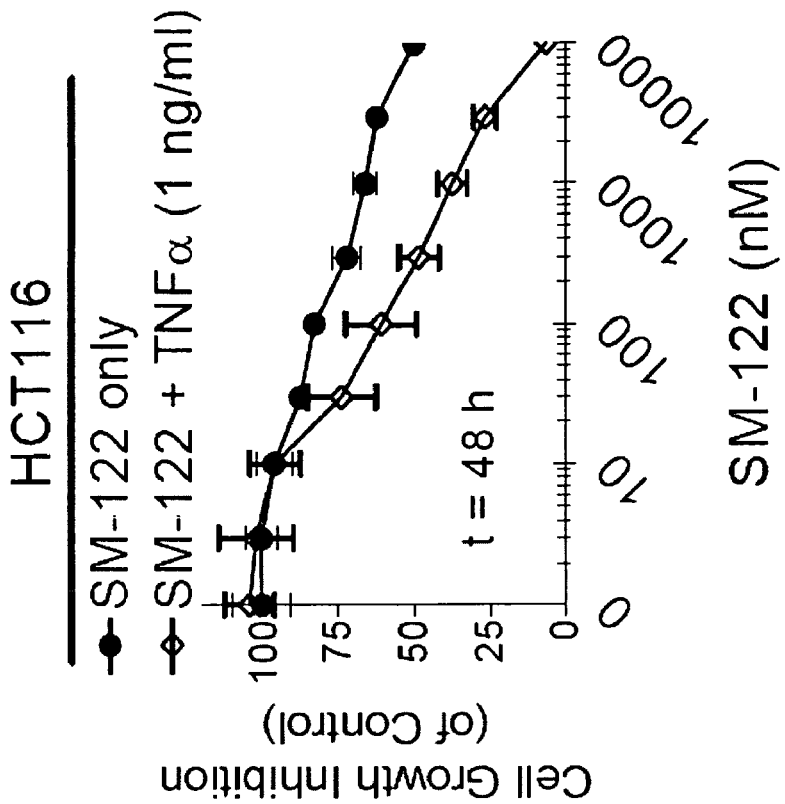
FIG. 24 is two line graphs showing exogenous TNFα enhances the activity of Smac mimetics SM-122 and SM-164 in the resistant cancer cell line HCT116.
Figure 24:
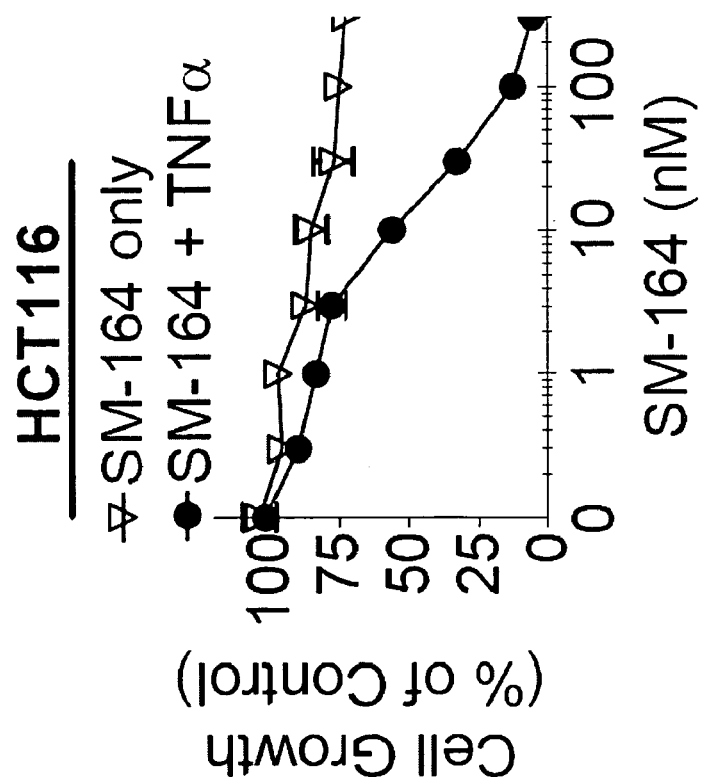
Figure 25:
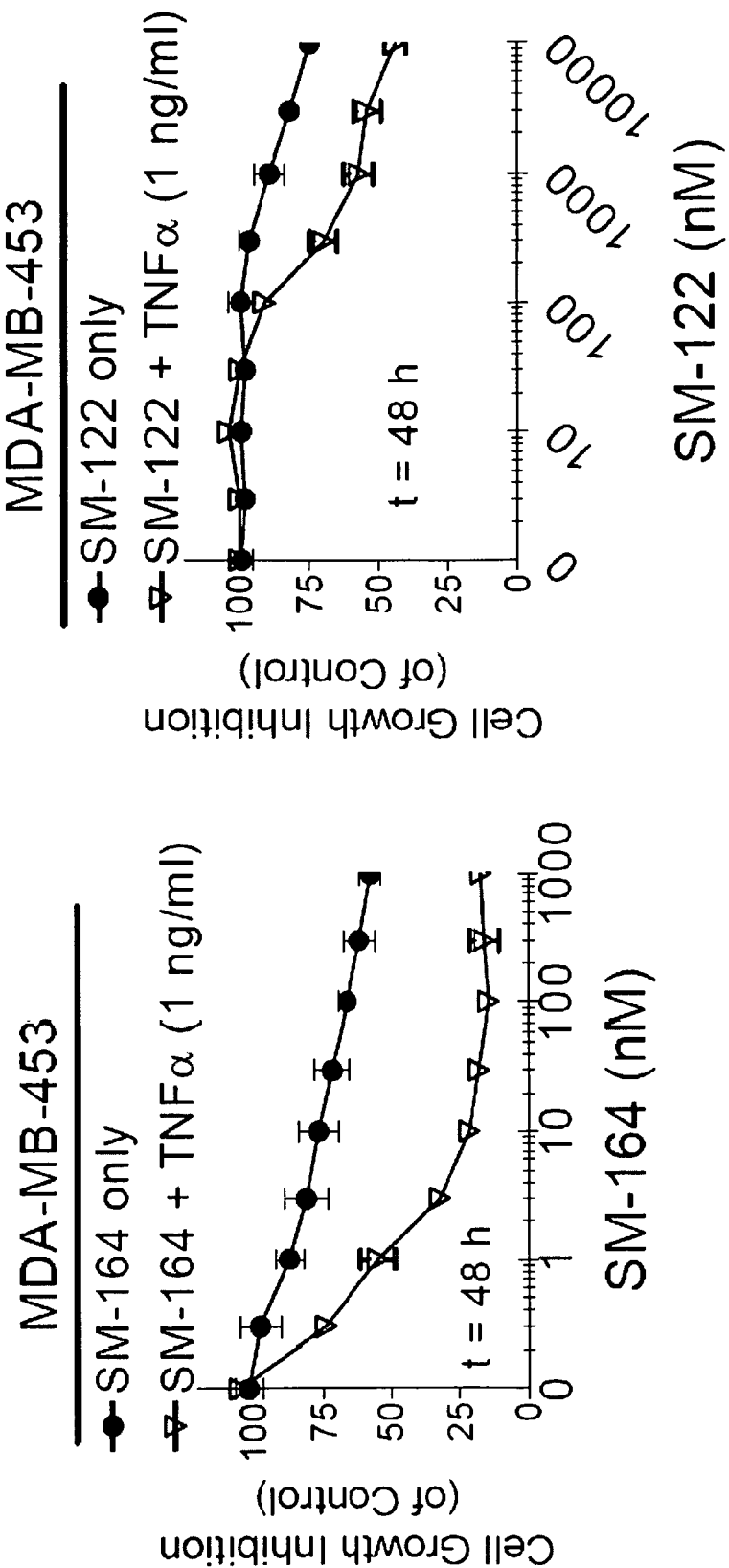
FIG. 25 two line graphs showing exogenous TNFα enhances the activity of Smac mimetics SM-122 and SM-164 in the resistant cancer cell line MDA-MD-453.
Figure 26:
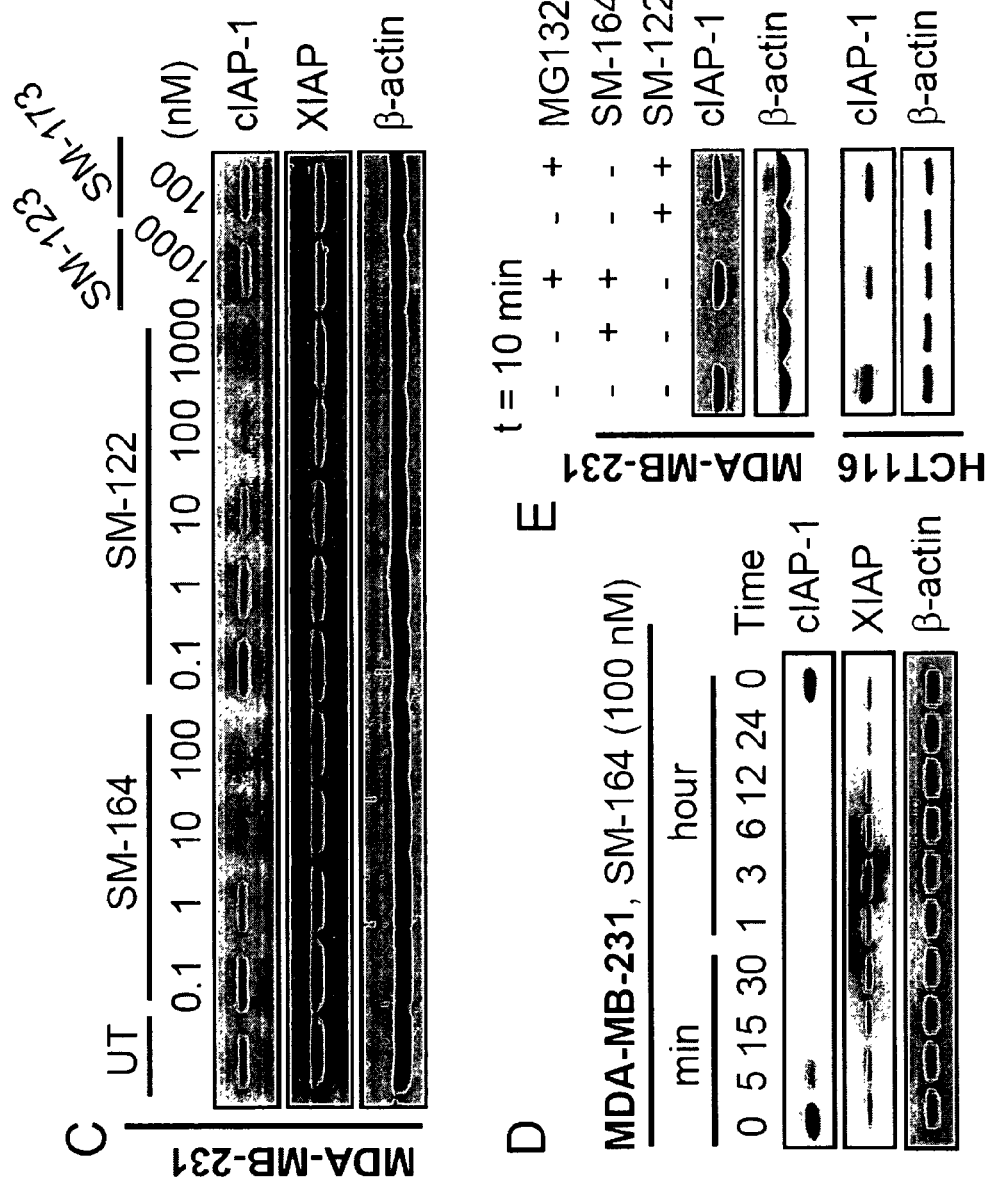
FIG. 26 includes a total of ten images showing that Smac mimetics SM-122 and SM-164 induce cIAP-1 degradation in MDA-MB-231 and HCT116 cell lines.
Figure 27:
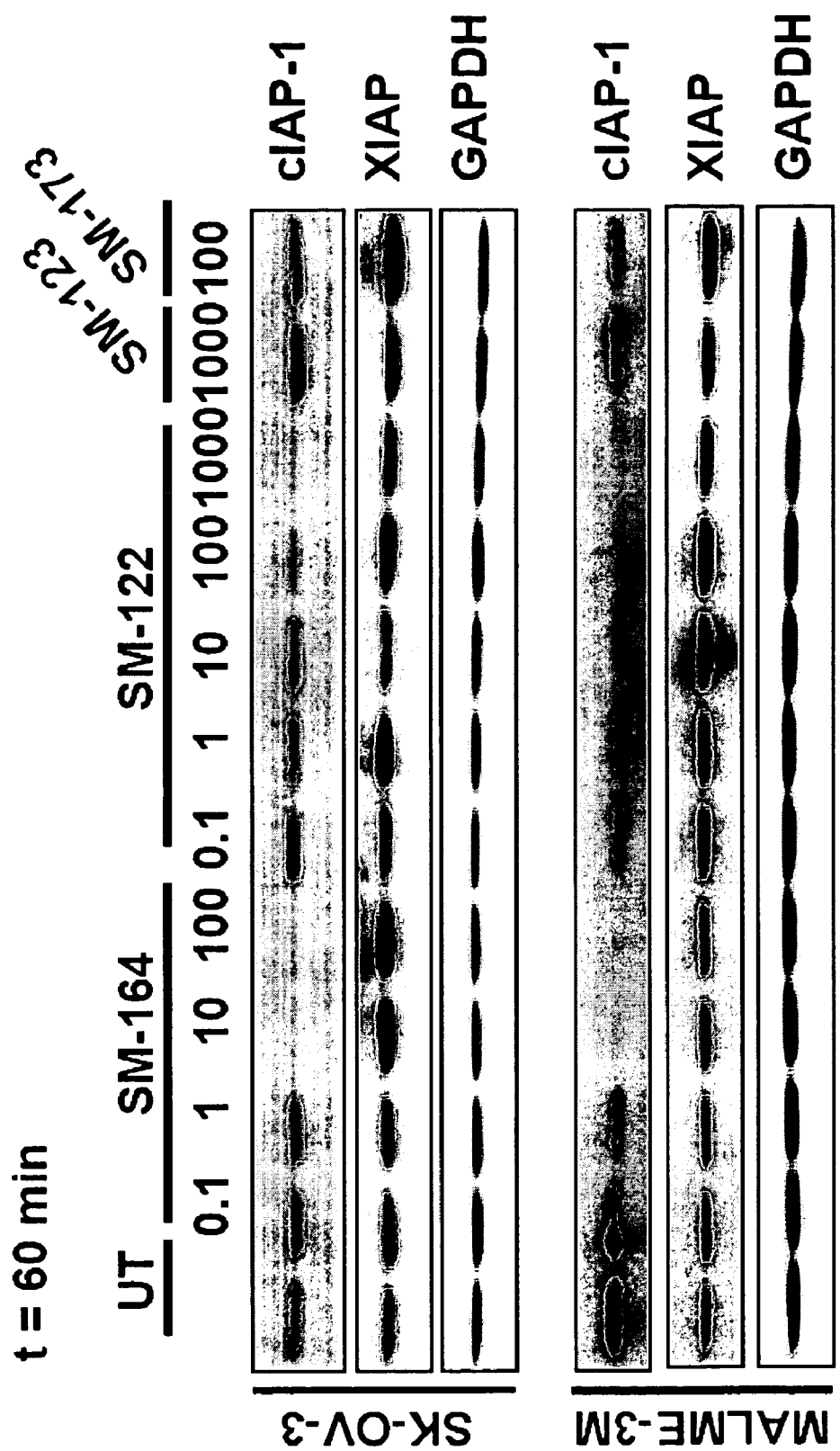
FIG. 27 is a series of six images showing that Smac mimetics SM-122 and SM-164 induce cIAP-1 degradation in SK-OV-3 and MALME-3M cell lines.
Figure 28:
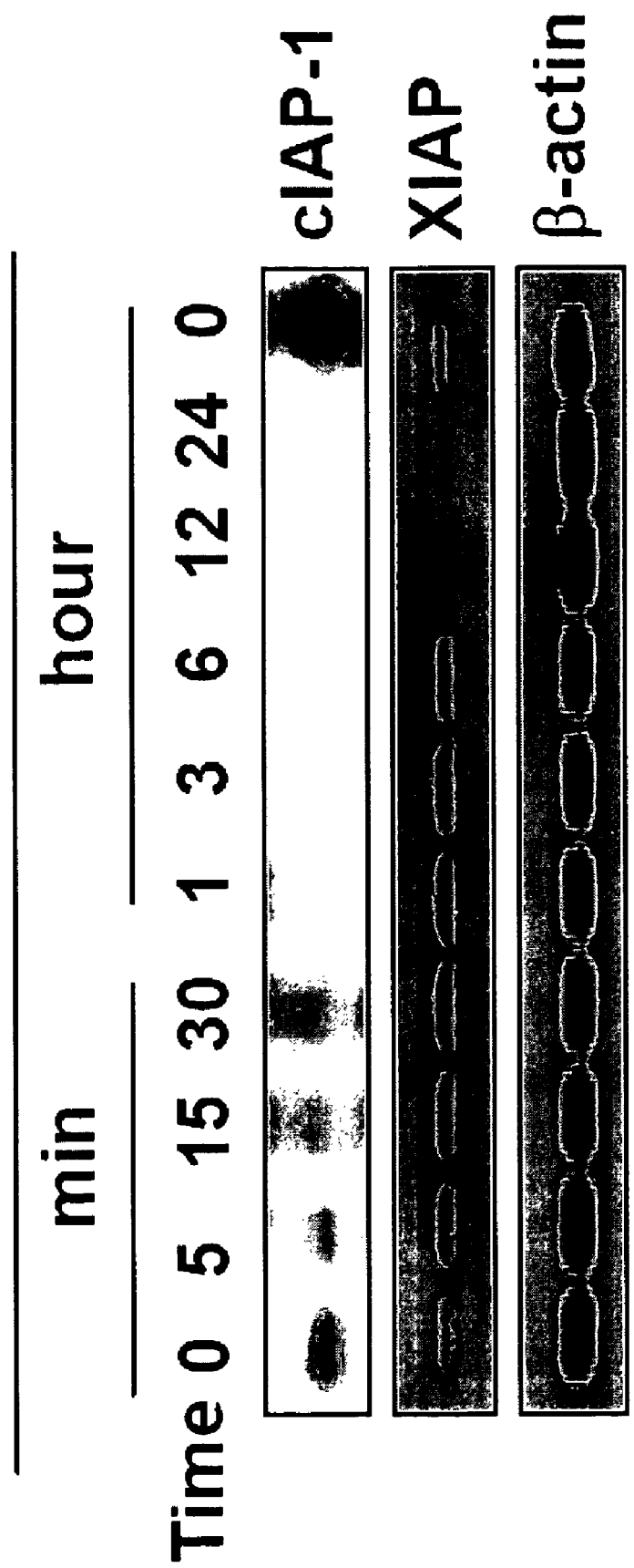
FIG. 28 is a series of three images showing that 100 nM of Smac mimetic SM-164 induces rapid cIAP-1 degradation in the SK-OV-3 cell line.
Figure 29:
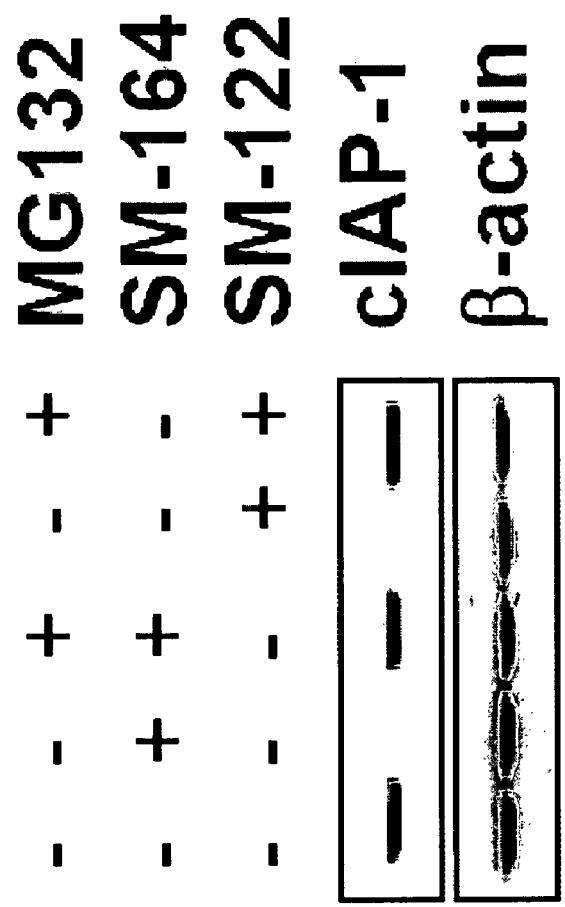
FIG. 29 is a series of two images showing that Smac mimetics SM-122 and SM-164 induce cIAP-1 degradation in the SK-OV-3 cell line in the absence of a proteasome inhibitor, MG-132.

To explore whether the resistance of cancer cells to Smac mimetics is due to the lack of secreted TNFα, the levels of secreted TNFα were examined. Secreted TNFα concentrations were determined in 200 µl of cell culture medium using the Quantikine HS Human TNFα ELISA kit (R&D Systems). The assay was performed according to the manufacturer's instructions. All resistant cancer cell lines tested, such as the MDA-MB-453 breast, DU-145 prostate and MDA-MB-435 melanoma cancer cell lines, had undetectable levels of TNFα in the cell culture medium (FIG. 20). Furthermore, both SM-164 and SM-122 failed to induce detectable levels of TNFα in these resistant cancer cell lines. However, addition of exogenous TNFα significantly enhanced the activity of these Smac mimetics, especially for SM-164, in resistant cancer cell lines, such as HCT116 and MDA-MB-453 cell lines (FIGS. 24-25). These data indicate that the secreted TNFα is essential for the activity of Smac mimetics as single agents.

Example 22

Induction of cIAP-1 Degradation in Cancer Cells

Consistent with previous studies (Varfolomeev et al., *Cell* 131:669 (2007); Vince et al., *Cell* 131:682 (2007); Petersen et al., *Cancer Cell* 12:445 (2007)), both SM-122 and SM-164 effectively and potently induced cIAP-1 degradation in sensitive cancer cell lines (FIGS. 26-29). SM-164 at 1 nM for 60 min reduced cIAP-1 markedly and at 10-100 nM to undetectable levels, and SM-122 effectively induced degradation of cIAP-1 at 10-100 nM. Induction of cIAP-1 degradation by both compounds was rapid, occurring within 5-10 min of drug treatment. SM-164 and SM-122 also induced rapid cIAP-1 degradation in resistant cancer cell lines. MG-132, a proteasome inhibitor, effectively blocked cIAP-1 degradation by SM-122 and SM-164 in both sensitive and resistant cancer cell lines indicating that cIAP-1 degradation by SM-122 and SM-164 is proteasome-mediated, consistent with the observation for other Smac mimetics (FIG. 29) (Varfolomeev et al., *Cell* 131:669 (2007); Vince J E, et al., *Cell* 131:682 (2007)). The levels of XIAP protein in MDA-MB-231 and SK-OV-3 cancer cell lines were also reduced upon treatment with SM-164. However, the reduction took place at 12-24 h time points, several hours after robust apoptosis induction, indicating degradation of XIAP is not required for the apoptosis induction by Smac mimetics.

Example 23 cIAP-1/2 Removal And Induction of TNFα-Dependent Apoptosis

SM-122 at 100 nM markedly decreased the levels of cIAP-1 and cIAP-2, but induced minimal apoptosis in each sensitive cell line at this concentration, suggesting that removal of cIAP-1/2 alone by Smac mimetics may not be sufficient for apoptosis induction.

Figure 30:
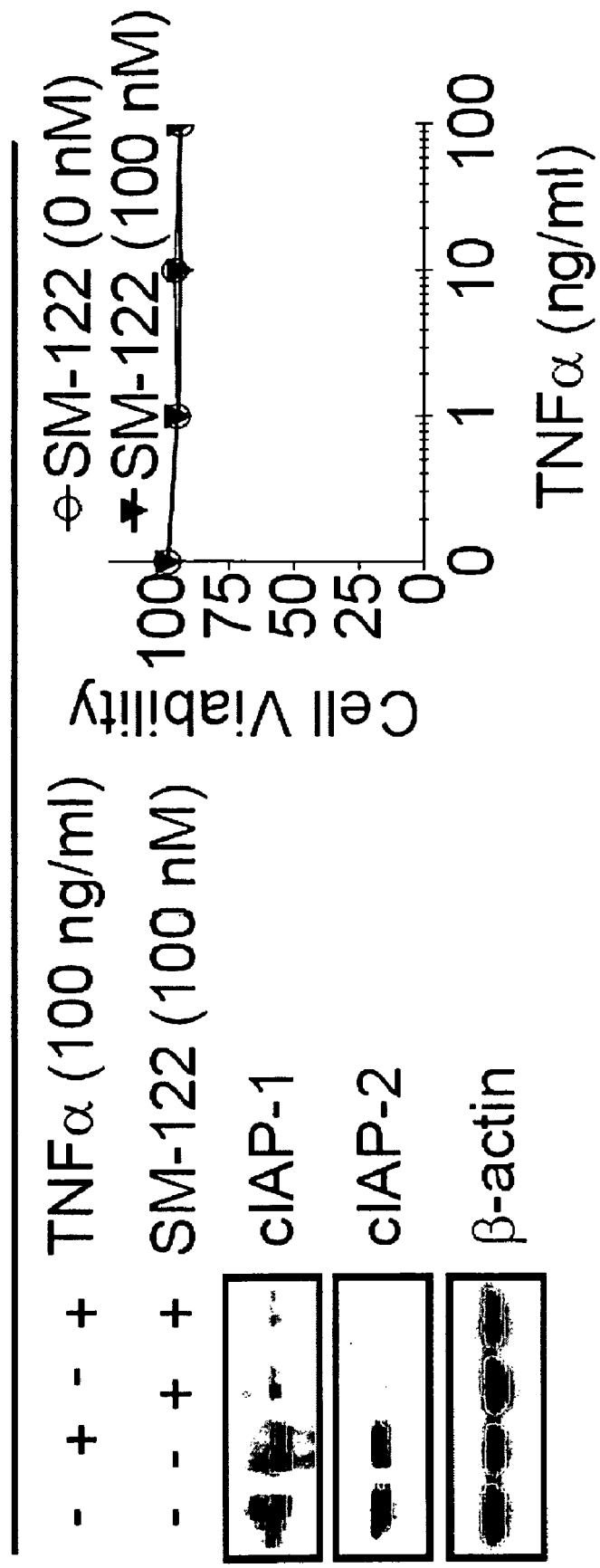
FIG. 30 is a series of three images and a line graph showing that 100 nM of Smac mimetic SM-122 decreases the levels of cIAP-1 and cIAP-2 and exogenous TNFα has minimal effect of cell killing by SM-122 in the MDA-MB-231 breast cancer cell line.
Figure 31:
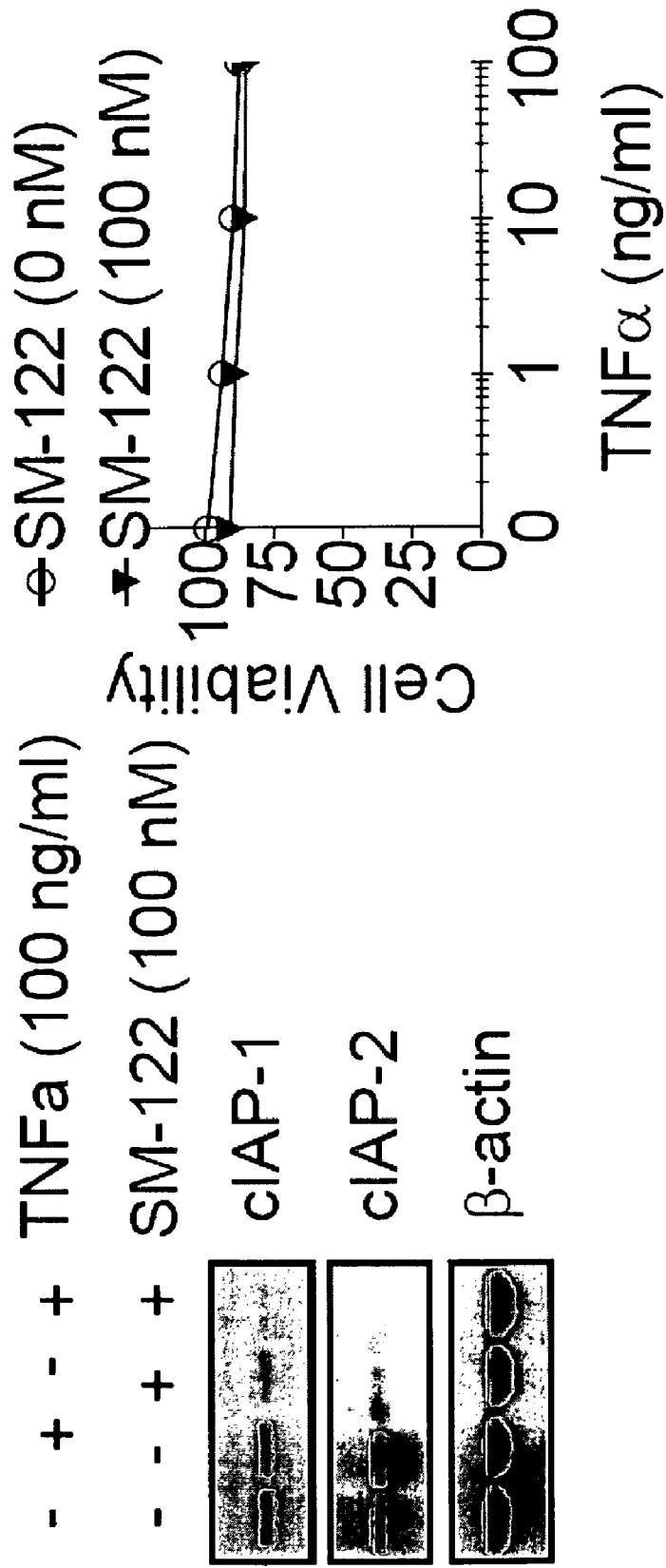
FIG. 31 is a series of three images and a line graph showing that 100 nM of Smac mimetic SM-122 decreases the levels of cIAP-1 and cIAP-2 and exogenous TNFα has minimal effect of cell killing by SM-122 in the SK-OV-3 ovarian cancer cell line.

To investigate whether the lack of apoptosis induction by SM-122 at 100 nM is due to insufficient levels of secreted TNFα, cells were treated with an excess amount of exogenous TNFα in combination with SM-122. Addition of exogenous TNFα only had minimal effect on cell killing by SM-122 (FIGS. 30-31) indicating that the lack of robust apoptosis induction by SM-122 at 100 nM is not simply due to an insufficient amount of secreted TNFα.

Figure 32:
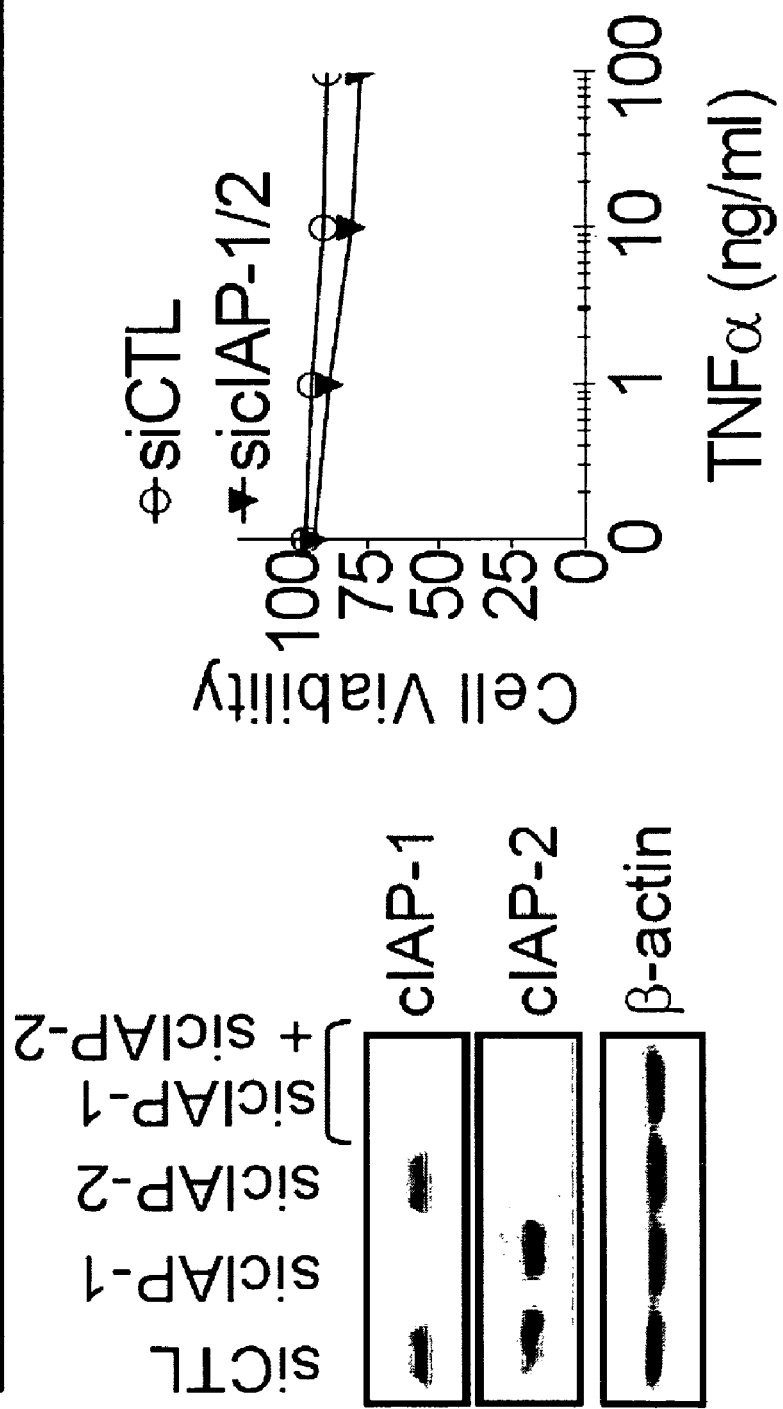
FIG. 32 is a series of three images and a line graph showing that knockdown of cIAP-1 or cIAP-2 by siRNA had little effect in cell death in the MDA-MB-231 cell line with or without exogenous TNFα.
Figure 33:
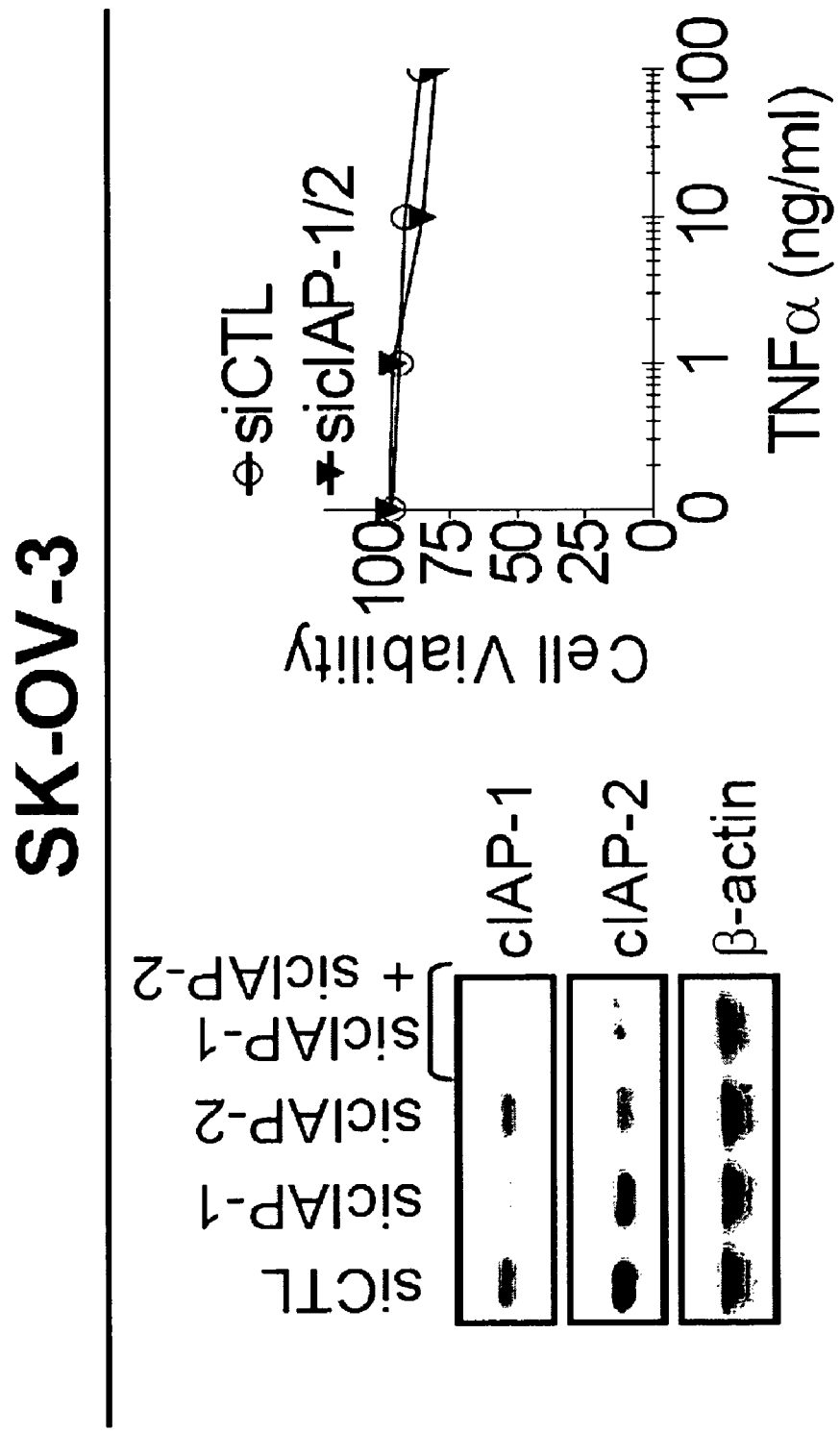
FIG. 33 is a series of three images and a line graph showing that knockdown of cIAP-1 or cIAP-2 by siRNA had little effect in cell death in the SK-OV-3 cell line with or without exogenous TNFα.

Furthermore, efficient knockdown of cIAP-1 or cIAP-2 by siRNA, individually or together, had little effect on cell death in the MDA-MB-231 and SK-OV-3 cell lines, with or without exogenous TNFα (FIGS. 32-33). Taken together, these data show that removal of cIAP-1/2 is not sufficient to achieve robust TNFα-dependent cell killing.

Example 24

XIAP as a Cellular Target for Smac Mimetics

Caspase-3 plays a crucial role in apoptosis induction by Smac mimetics (Petersen et al., *Cancer Cell* 12:445 (2007)).

Since XIAP binds to and inhibits caspase-3, it was reasoned that the inhibition of caspase-3 by XIAP must be relieved for efficient apoptosis induction by Smac mimetics and XIAP is a critical cellular target for Smac mimetics.

Figure 34:
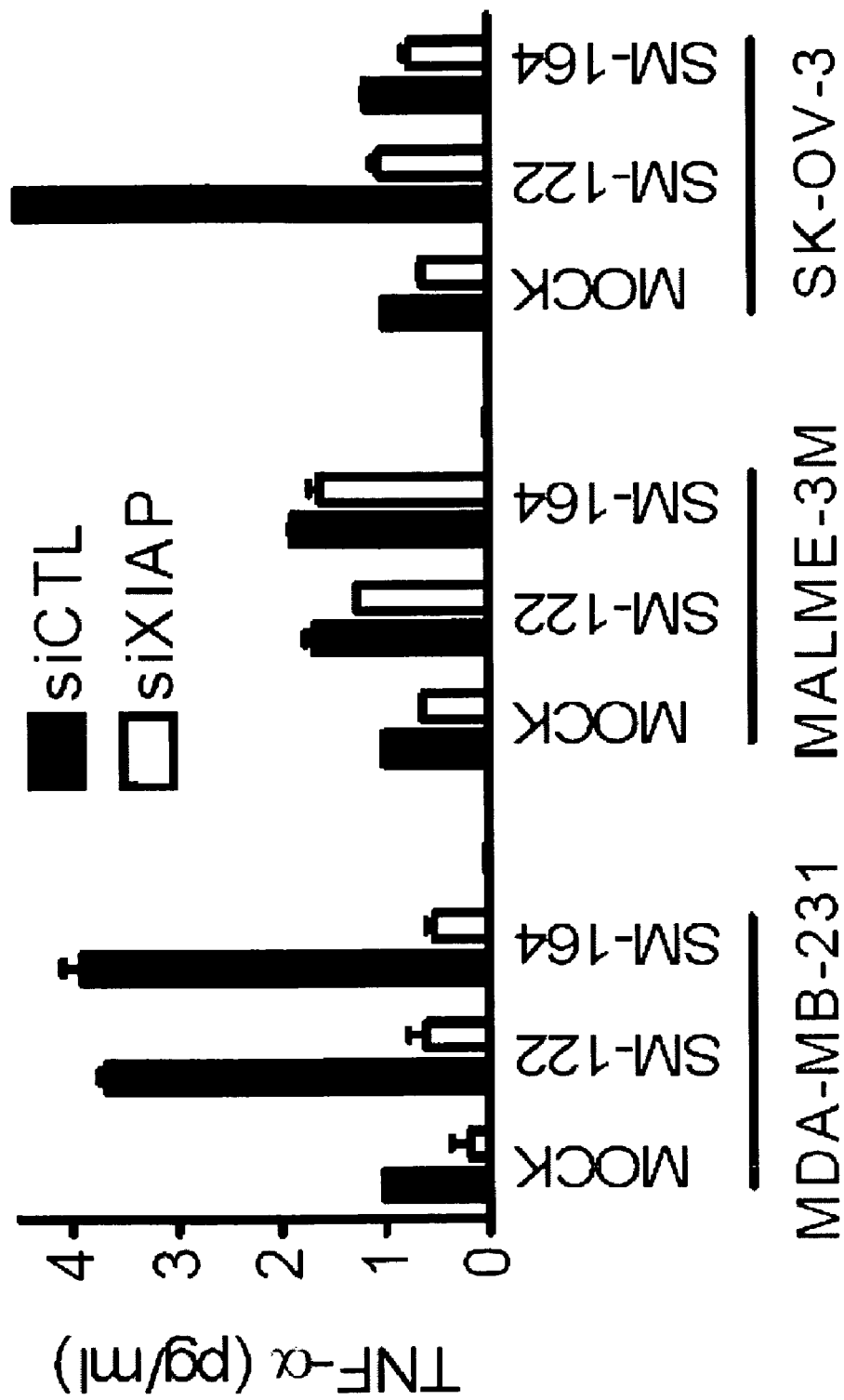
FIG. 34 is a bar graph showing TNFα production following knockdown with XIAP siRNA followed by treatment with Smac mimetics SM-122 and SM-164 in MDA-MB-231, MALME-3M, and SK-OV-3 cell lines.
Figure 35:
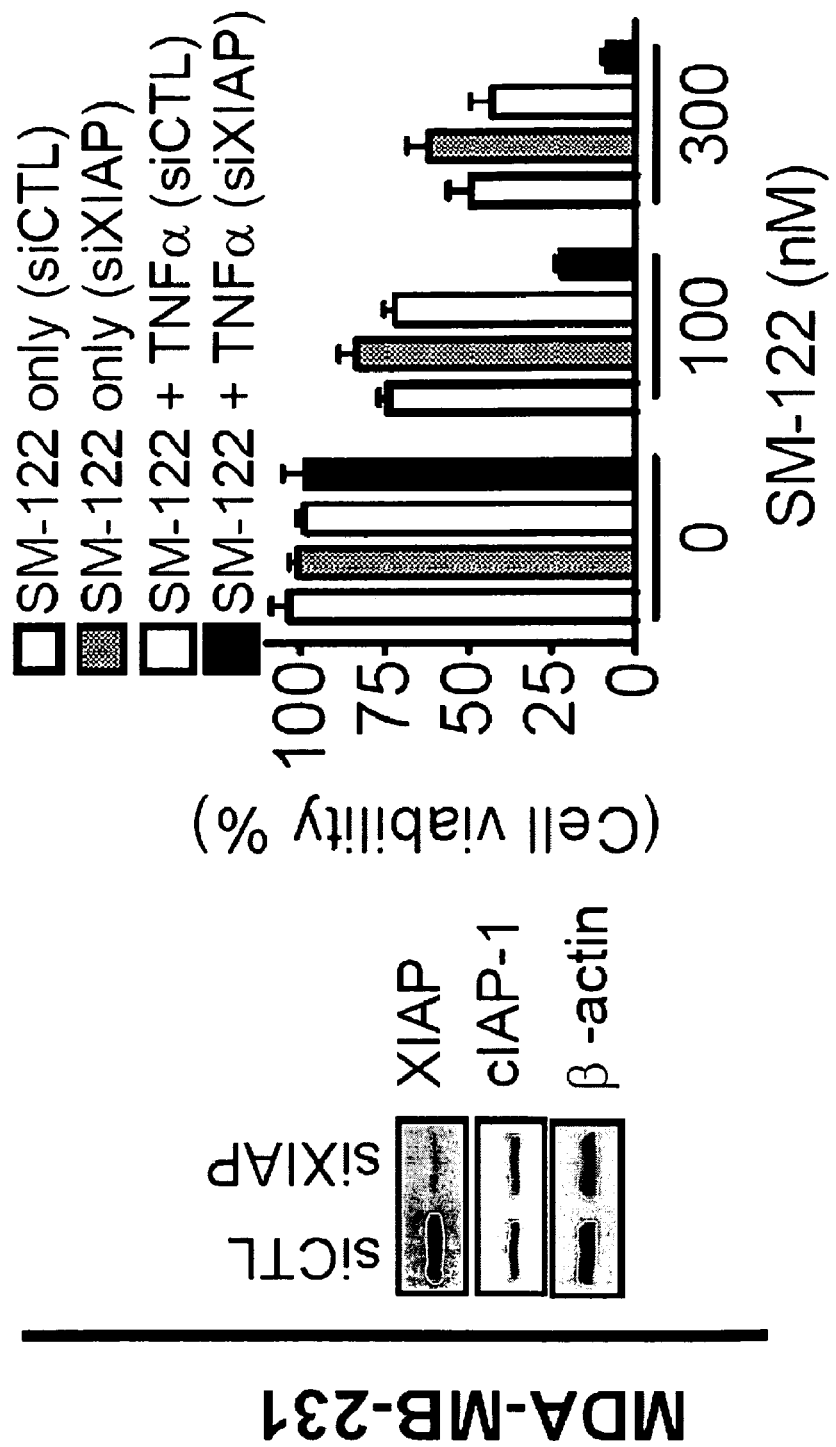
FIG. 35 is a series of three images and a bar chart showing knockdown of XIAP by siRNA sensitizes MDA-MB-231 cells to SM-122 in the presence of exogenous TNFα.
Figure 36:
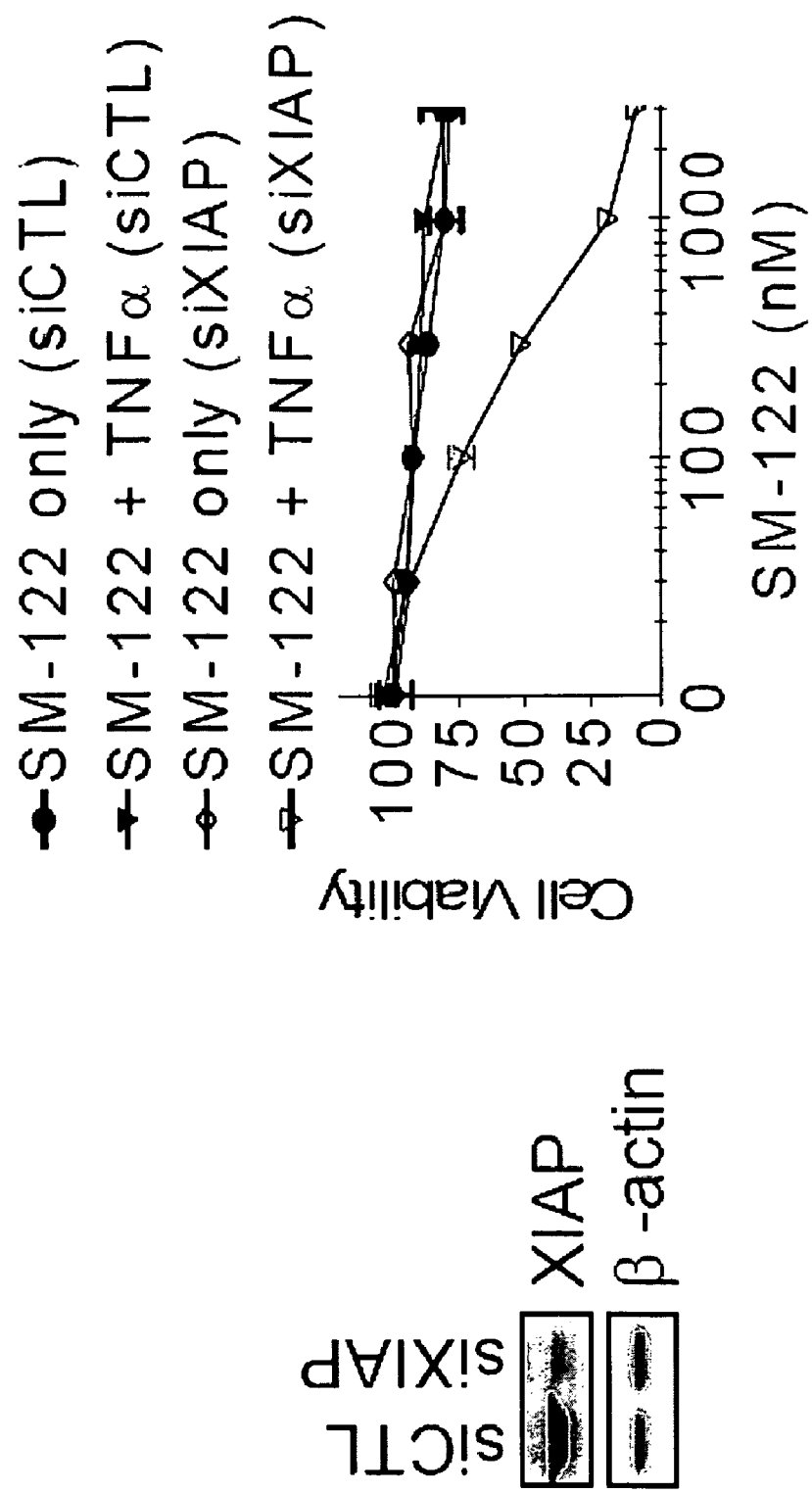
FIG. 36 is a series of two images and a line graph showing knockdown of XIAP by siRNA sensitizes MALME-3M cells to SM-122 in the presence of exogenous TNFα.
Figure 37:
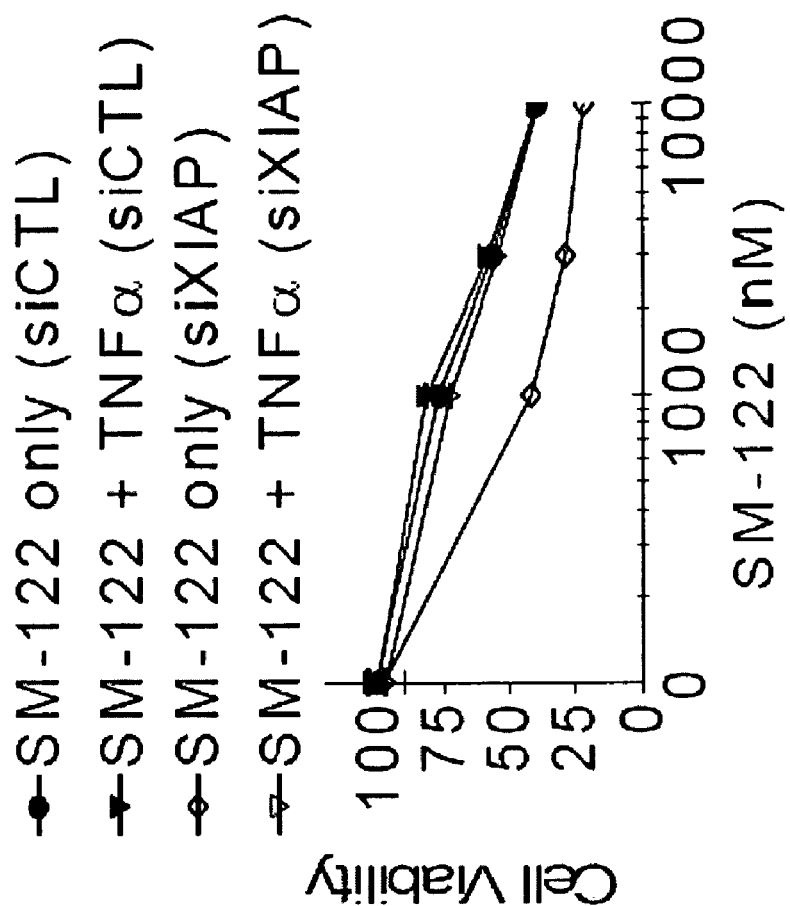
FIG. 37 is a series of two images and a line graph showing knockdown of XIAP by siRNA sensitizes SK-OV-3 cells to SM-122 in the presence of exogenous TNFα.
Figure 37:
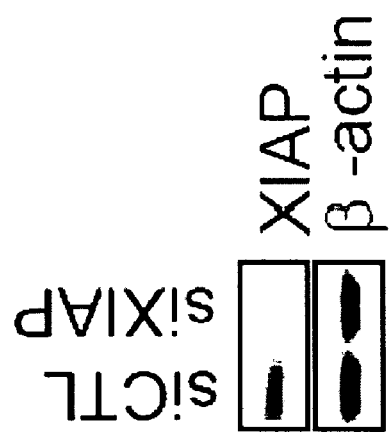
Figure 52:
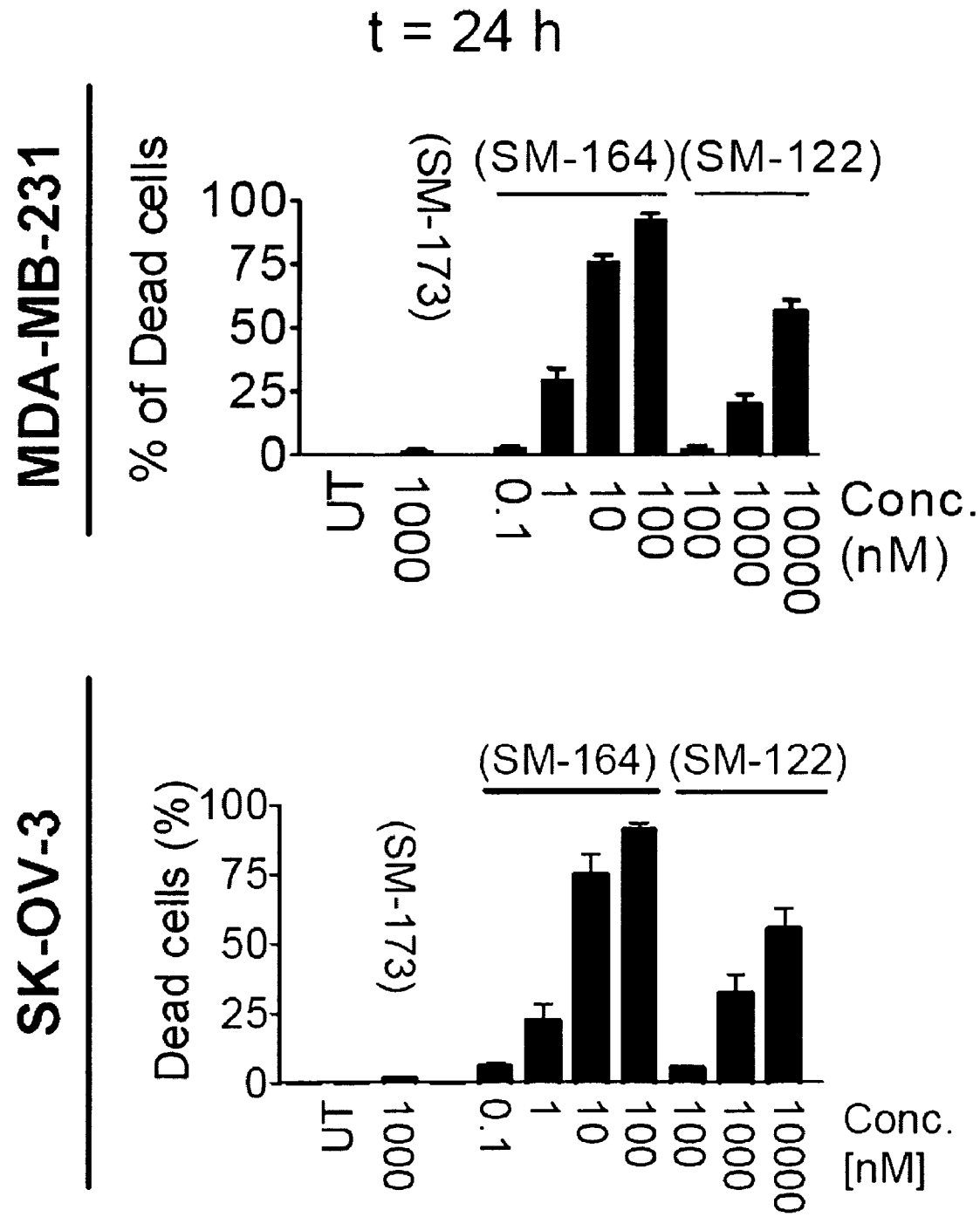
FIG. 52 is two bar graphs showing induction of cell death in MDA-MB-231 and SK-OV-3 cells by Smac mimetics SM-122 and SM-164.

To investigate the role of XIAP in apoptosis induction by Smac mimetics, XIAP was knocked down in sensitive cancer cell lines. Because XIAP knockdown attenuated the production and secretion of TNFα (FIG. 34) (Gaither et al., *Cancer Res.* 67:11493 (2007)), exogenous TNFα was added in these XIAP knockdown experiments. The results show that in all three cancer cell lines, efficient knockdown of XIAP by siRNA dramatically sensitized cancer cells to SM-122 in the presence of exogenous TNFα (FIGS. 35-37). For example, while SM-122 at 100 nM in combination with TNFα killed 25% of the MDA-MB-231 cells when control siRNA was used, the same combination killed 75% of the cells when XIAP was knocked down. These data show that degradation of cIAP-1/2 by SM-122 and down-regulation of XIAP by siRNA is highly effective in induction of TNFα-dependent apoptosis. These data further suggest that SM-122 at 100 nM effectively induced cIAP-1/2 degradation, but is ineffective in antagonizing cellular XIAP in these cancer cells, consistent with its relatively weak functional antagonism against XIAP. However, SM-122 at higher concentrations was still capable of inducing robust cell death in these sensitive cancer cell lines (FIG. 52), indicating that SM-122 can still effectively antagonize cellular XIAP but higher concentrations are needed, consistent with the functional data.

Figure 38:
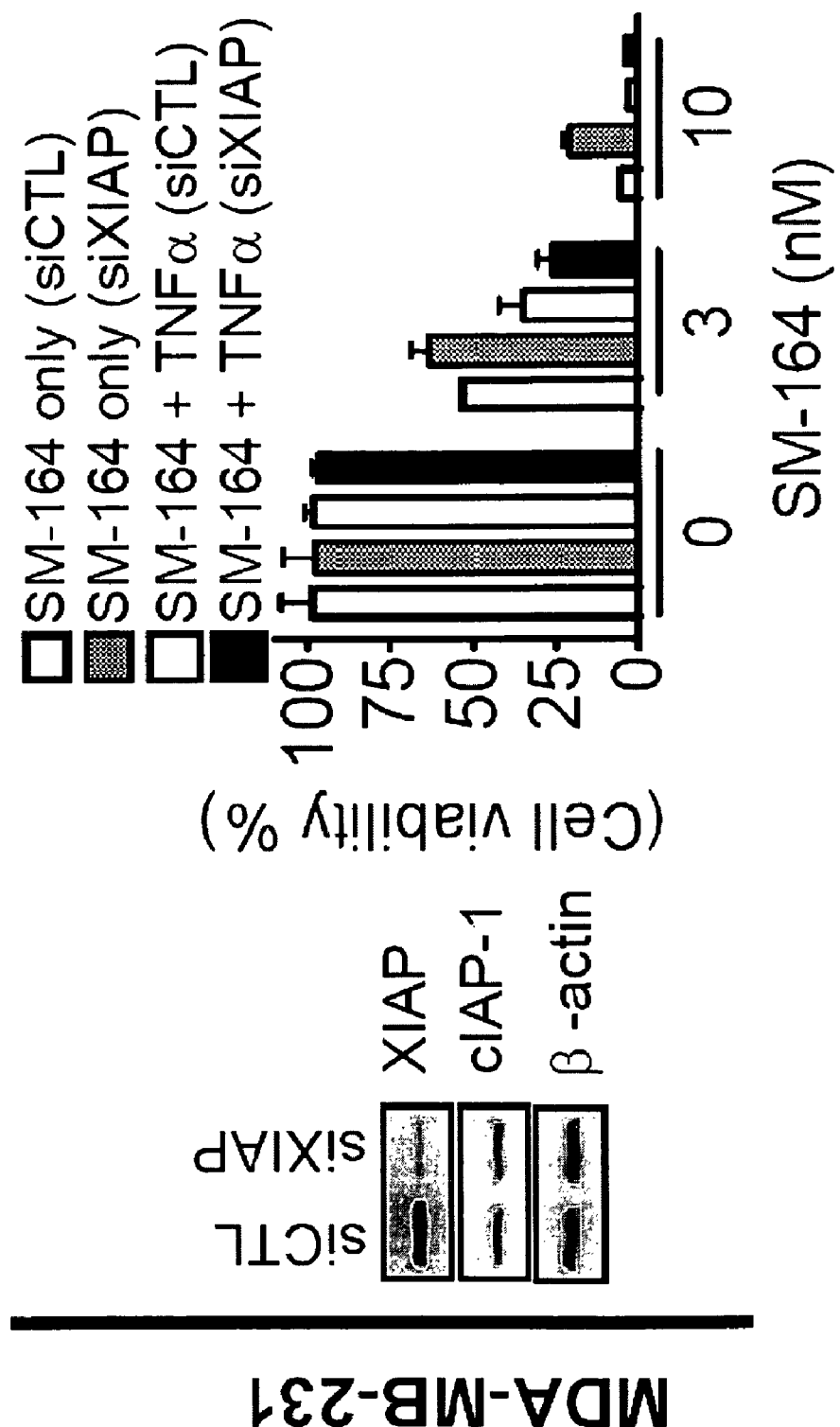
FIG. 38 is a series of three images and a bar chart showing knockdown of XIAP by siRNA sensitizes MDA-MB-231 cells to SM-164 in the presence of exogenous TNFα.
Figure 39:
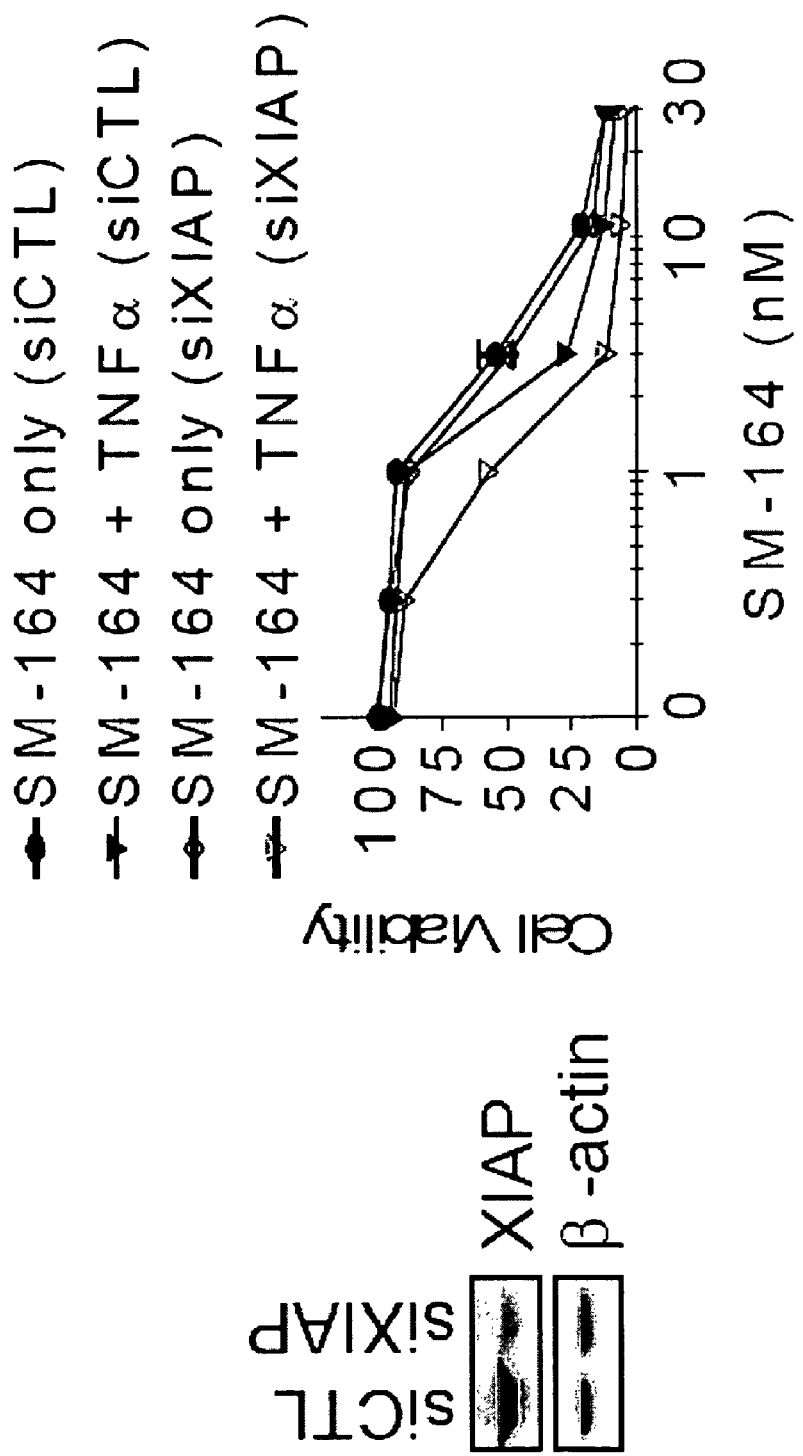
FIG. 39 is a series of two illustrations and a line graph showing knockdown of XIAP by siRNA sensitizes MALME-3M cells to SM-164 in the presence of exogenous TNFα.
Figure 40:
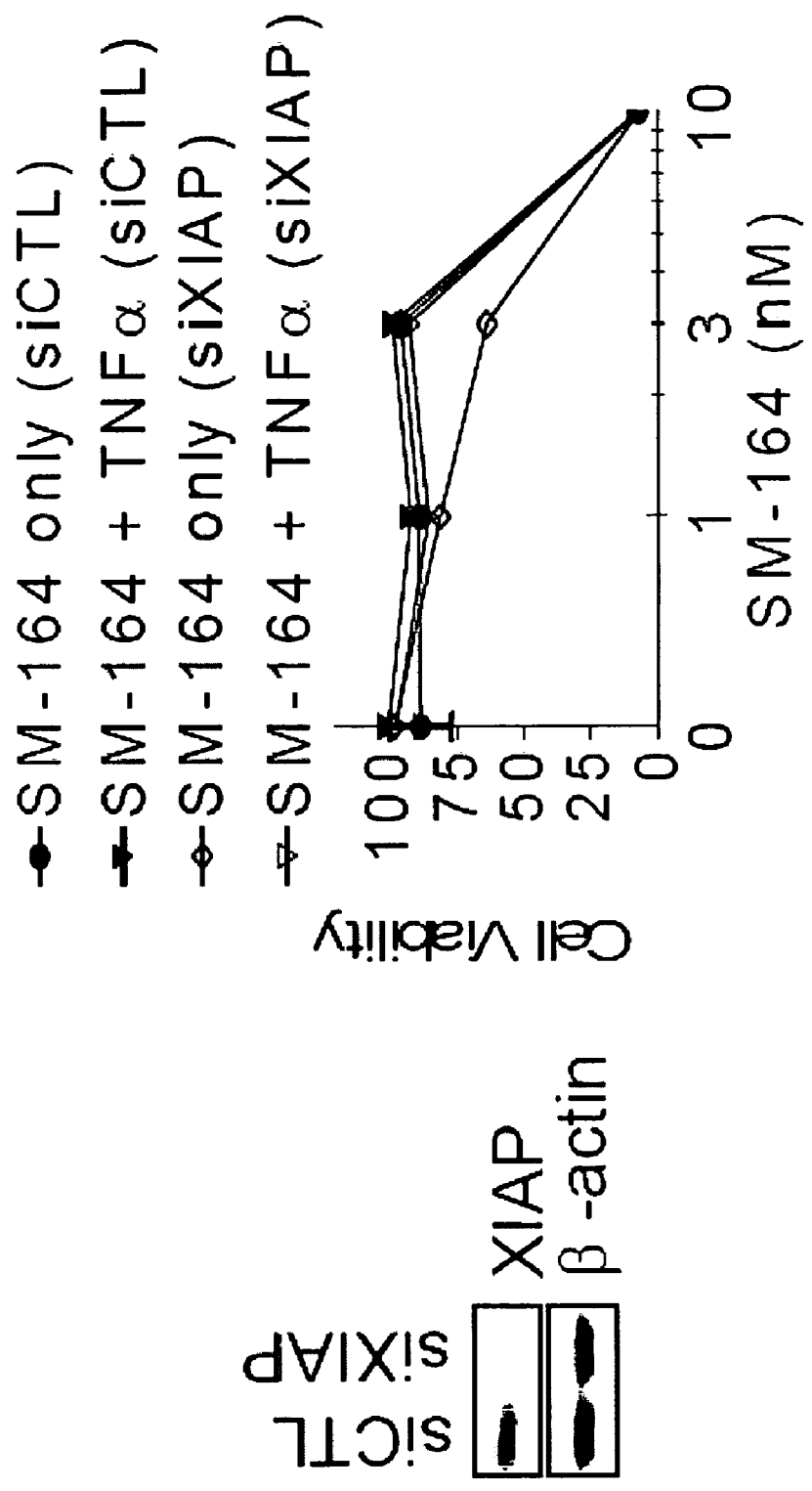
FIG. 40 is a series of two images and a line graph showing knockdown of XIAP by siRNA sensitizes SK-OV-3 cells to SM-164 in the presence of exogenous TNFα.

In contrast, SM-164 at 3 and 10 nM effectively induced cell death with or without TNFα in all these sensitive cancer cell lines (FIGS. 38-40). Furthermore, knockdown of XIAP only modestly sensitized the cancer cells to SM-164 in the presence of exogenous TNFα in these sensitive cancer cell lines. These data suggest that SM-164 at these concentrations not only efficiently induces marked cIAP-1 degradation, but also effectively antagonizes cellular XIAP. This is consistent with binding and functional data that indicates SM-164 binds to XIAP with a high affinity and is a potent antagonist of XIAP.

Example 25

Figure 41:
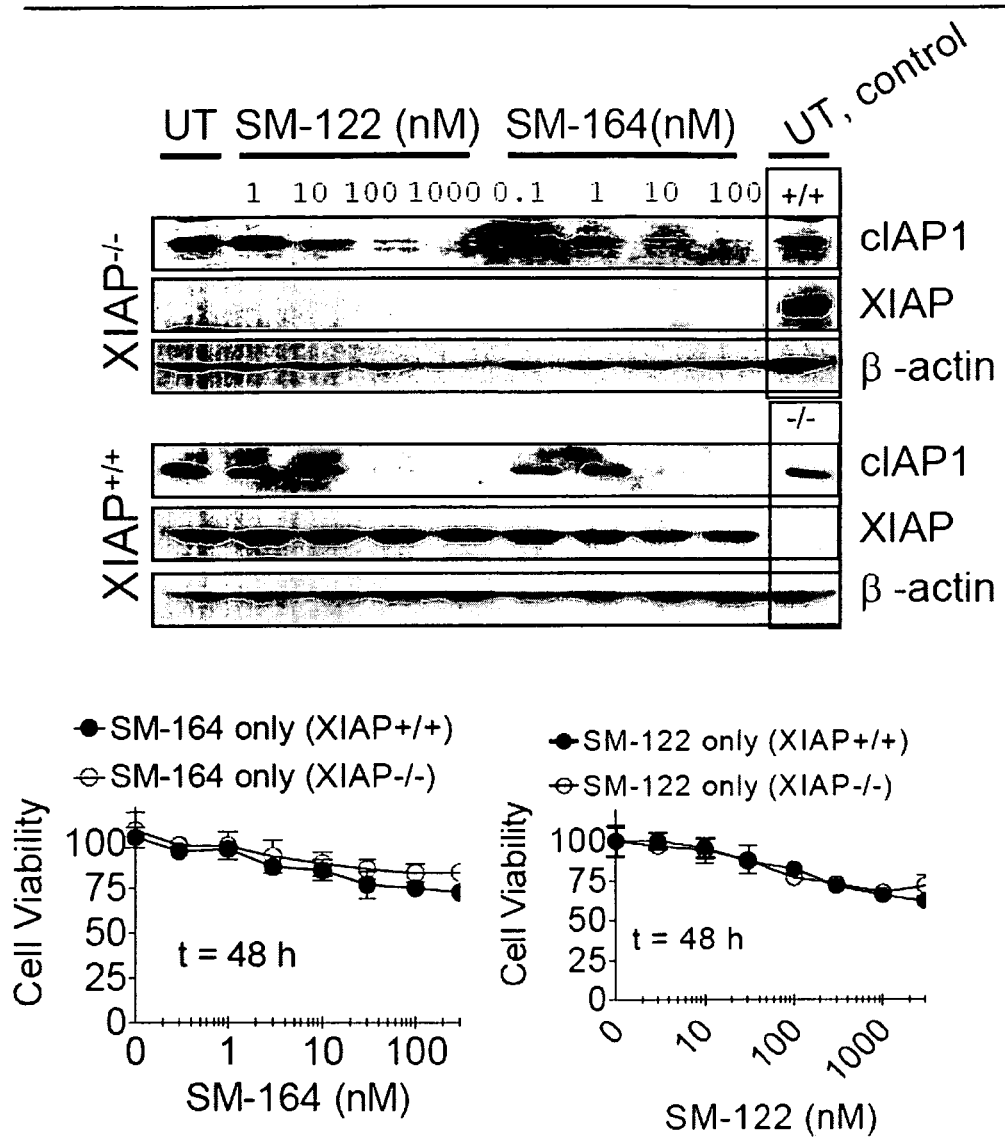
FIG. 41 is a series of six images and two line graphs showing the degradation of cIAP-1 by Smac mimetics SM-122 and SM-164 in the HCT116 cell line.
Figure 42:
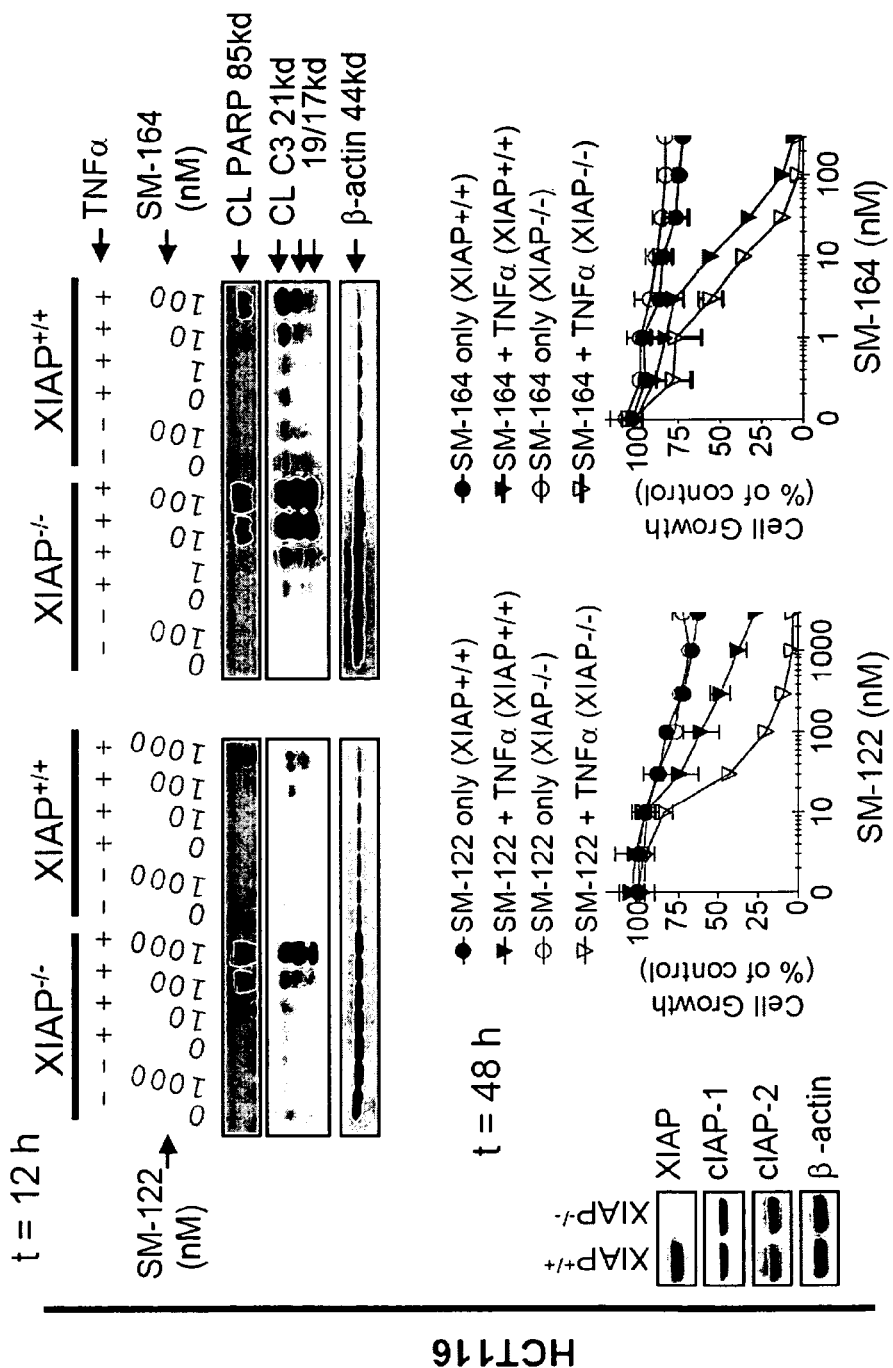
FIG. 42 includes a total of 10 images and two line graphs showing caspase-3 activation, PARP cleavage, and inhibition of cell growth by Smac mimetics SM-122 and SM-164 in combination with TNFα in the HCT116 cell line.

Knockout of XIAP Sensitizes Cancer Cells to Smac Mimetics for TNFα-Dependent Apoptosis Induction To complement the siRNA experiments and to more precisely define the role of XIAP in TNFα-dependent apoptosis induction by Smac mimetics, HCT116 XIAP$^{+/+}$ and XIAP$^{-/-}$ isogenic cell lines were used in further studies (Cummins et al., *Cancer Res.* 64:3006 (2004)). Since both these cell lines were resistant to SM-122 and SM-164 as a single agent (FIG. 41), the role of XIAP using Smac mimetics in combination with TNFα was investigated. SM-122 at 100-1,000 nM effectively induced cIAP-1 degradation in both cell lines (FIG. 41). The combination of SM-122 at 100-1,000 nM with exogenous TNFα had a modest effect in induction of caspase-3 activation, PARP cleavage and cell growth inhibition in the HCT-116 XIAP$^{+/+}$ cell line (FIG. 42). In contrast, the same combination was highly effective in the isogenic XIAP$^{-/-}$ cell line in induction of robust caspase-3 activation and strong PARP cleavage and in inhibition of cell growth (FIG. 42). These data show that XIAP strongly attenuates TNFα-dependent apoptosis induction by SM-122 in the HCT116 cells and knockout of XIAP dramatically sensitizes the cells to SM-122 in combination with TNFα.

SM-164 effectively induced cIAP-1 degradation at 10-100 nM in both cell lines (FIG. 41). The combination of SM-164 at these concentrations with TNFα was effective in induction of caspase-3 activation, PARP cleavage and in inhibition of cell growth in the XIAP$^{+/+}$ cell line (FIG. 42). Although knockout of XIAP sensitized the HCT116 cells to SM-164 in combination with TNFα, the effect was much less than that observed with the combination of SM-122 with TNFα (FIG. 42).

Example 26

Figure 43:
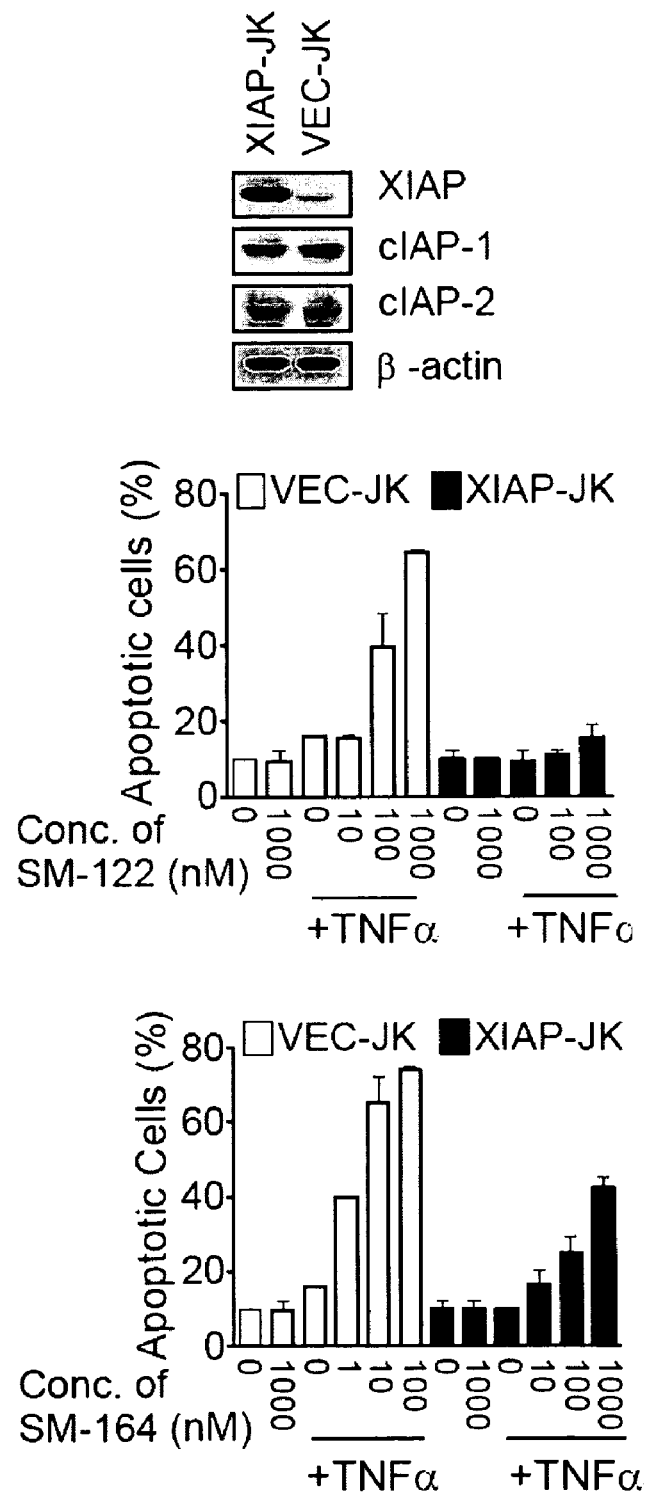
FIG. 43 is a series of four images and two bar graphs showing the VEC-JK cell line is sensitive and the XIAP-JK cell line was resistant to Smac mimetics SM-122 and SM-164 in combination with TNFα.
Figure 44:
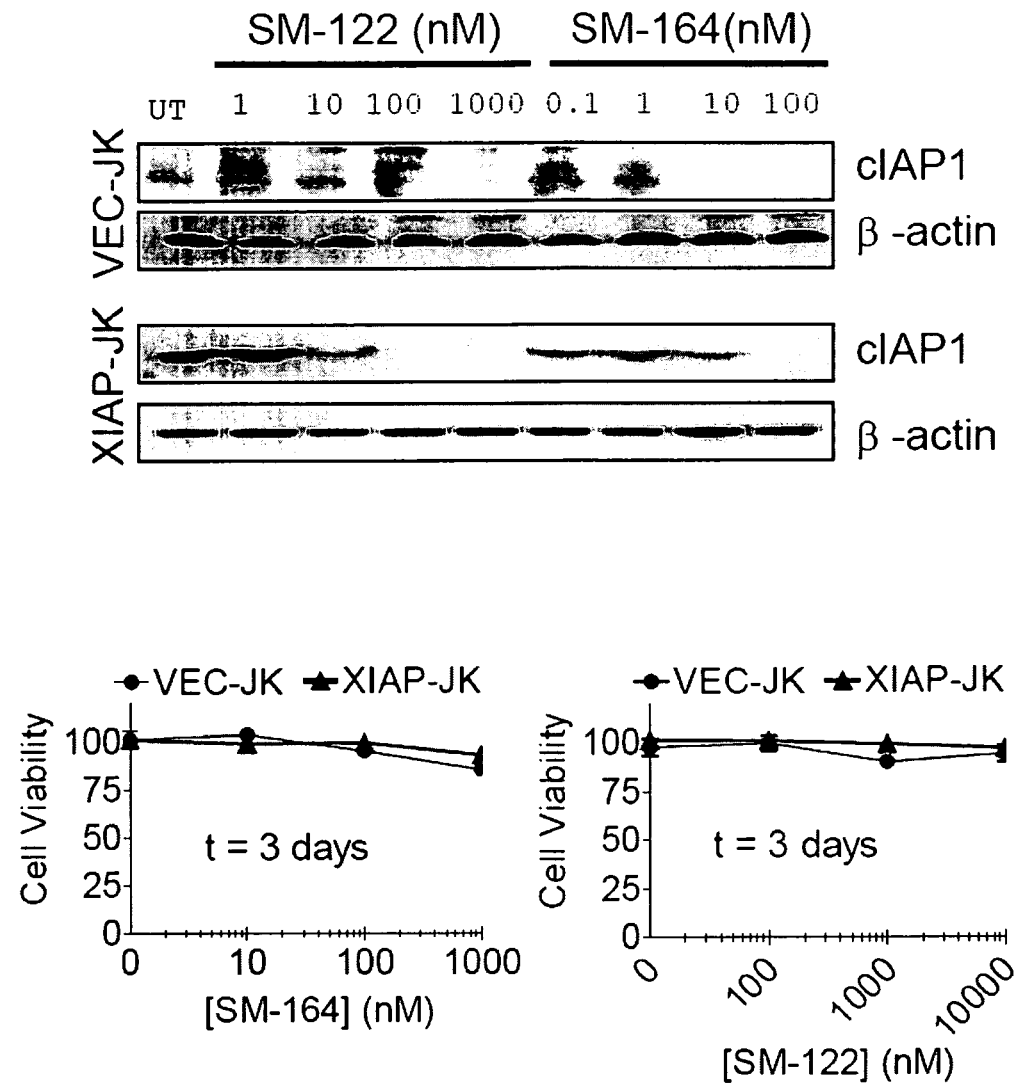
FIG. 44 is a series of four images and two line graphs showing the degradation of cIAP-1 by Smac mimetics SM-122 and SM-164 in Jurkat cell lines.

Overexpression of XIAP Renders Cancer Cells Resistant to TNFα-Dependent Apoptosis Induction by Smac Mimetics The effect of XIAP overexpression in cancer cells on TNFα-dependent apoptosis induction by Smac mimetics was investigated. Since stable transfection of XIAP in those sensitive cancer cell lines was unsuccessful, the previously well-characterized XIAP stably transfected Jurkat leukemia cell line (XIAP-JK) and its vector control cell line (VEC-JK) were employed (Wilkinson et al., *Mol. Cell. Biol.* 24:7003 (2004)). The VEC-JK cell line with low expression of XIAP was sensitive to SM-122 or SM-164 in combination with TNFα (FIG. 43). In contrast, the XIAP-JK cell line with high levels of XIAP expression became extremely resistant to the combination of SM-122 with TNFα. For instance, while SM-122 at 100 and 1,000 nM efficiently and rapidly degraded cIAP-1 in XIAP-JK cells (FIG. 44), it was ineffective in induction of apoptosis in combination with TNFα (FIG. 43). Moreover, although the combination of SM-164 with TNFα was capable of inducing apoptosis in the XIAP-JK cell line, it was much less effective than in the VEC-JK cell line. These data show that overexpression of XIAP effectively attenuates TNFα-dependent apoptosis induction by both SM-164 and SM-122 but with a stronger effect on SM-122.

Collectively, the data obtained using complementary approaches provide strong evidence that XIAP plays a key role in attenuating apoptosis induction by Smac mimetics. Since bivalent SM-164 is a more potent antagonist of XIAP than monovalent SM-122, it exhibits much stronger potency than SM-122 in TNFα dependent apoptosis induction.

Example 27

Degradation of cIAP-1 and In Vivo Antitumor Activity of Smac Mimetics

Figure 45:
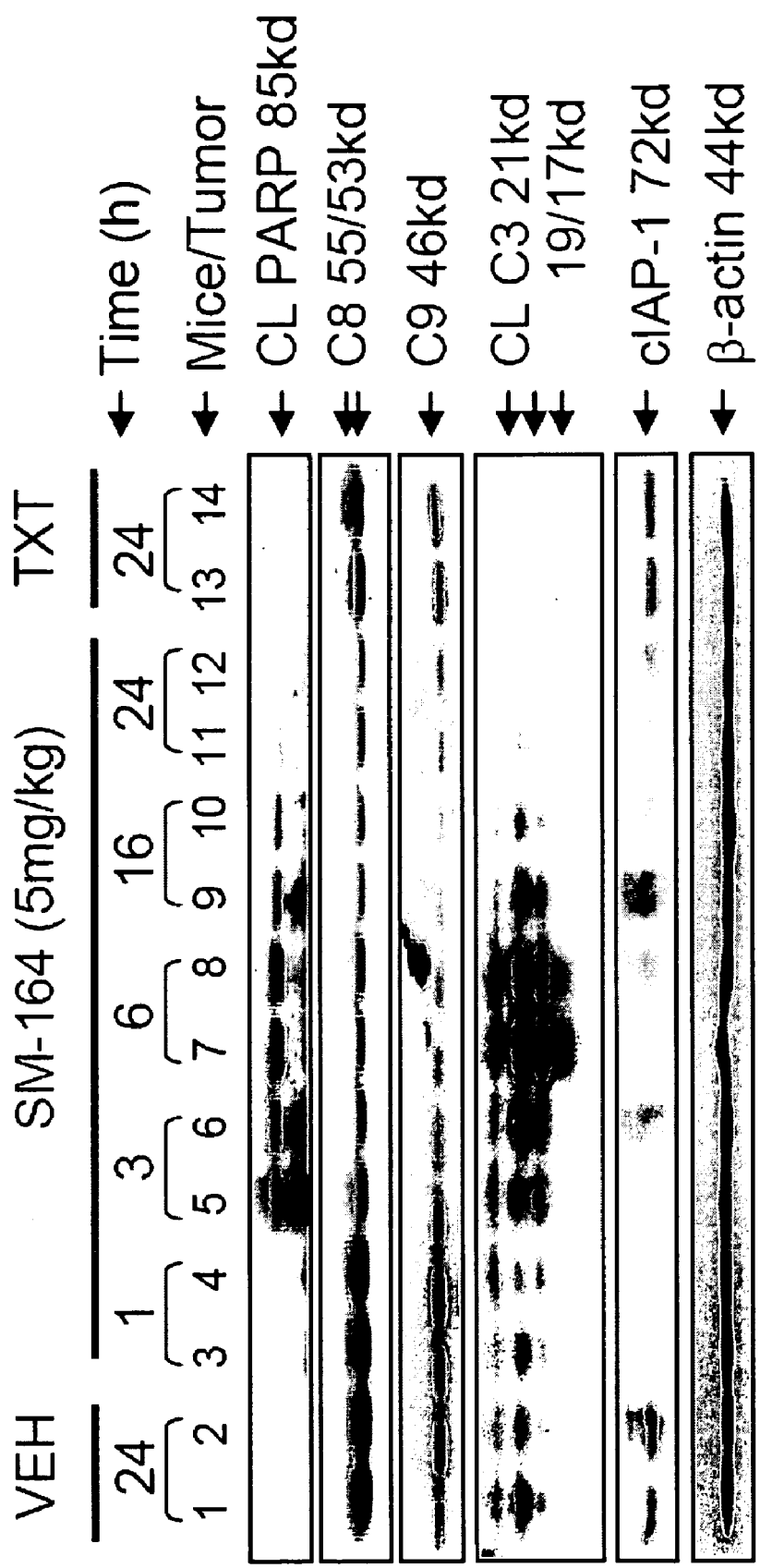
FIG. 45 is a series of six images showing the degradation of c-IAP, activation of caspase-3, -8, and -9, and cleavage of PARP by Smac mimetic SM-164 in MDA-MB-231 xenograft tissues in mice.
Figure 46:
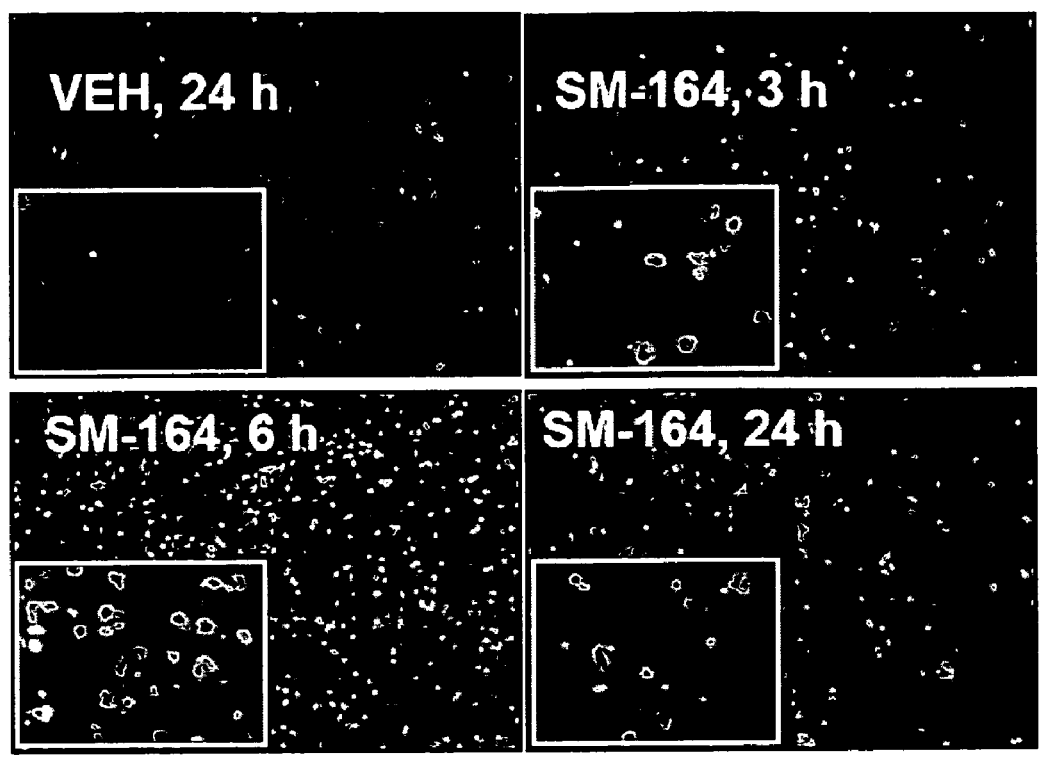
FIG. 46 is a series of four images and a bar graph showing SM-164 induces strong apoptosis in tumor tissues as measured using a TUNEL assay.
Figure 46:
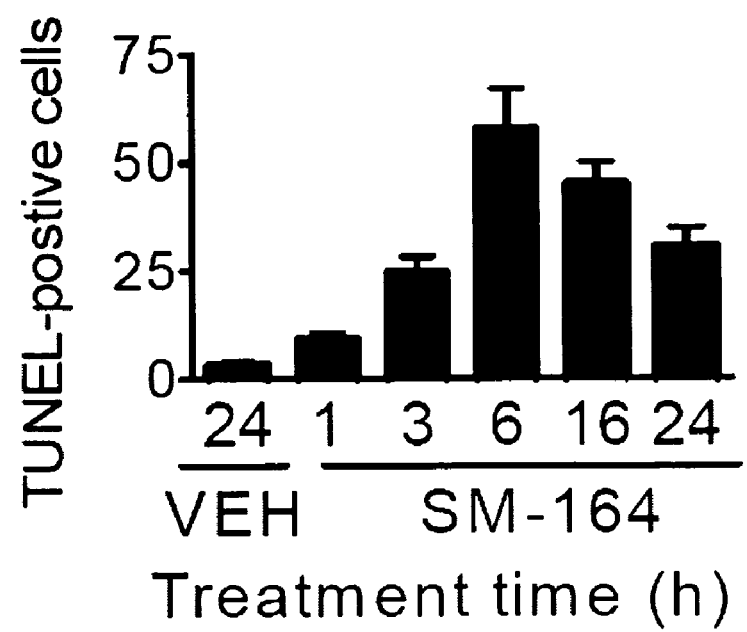
Figure 47:
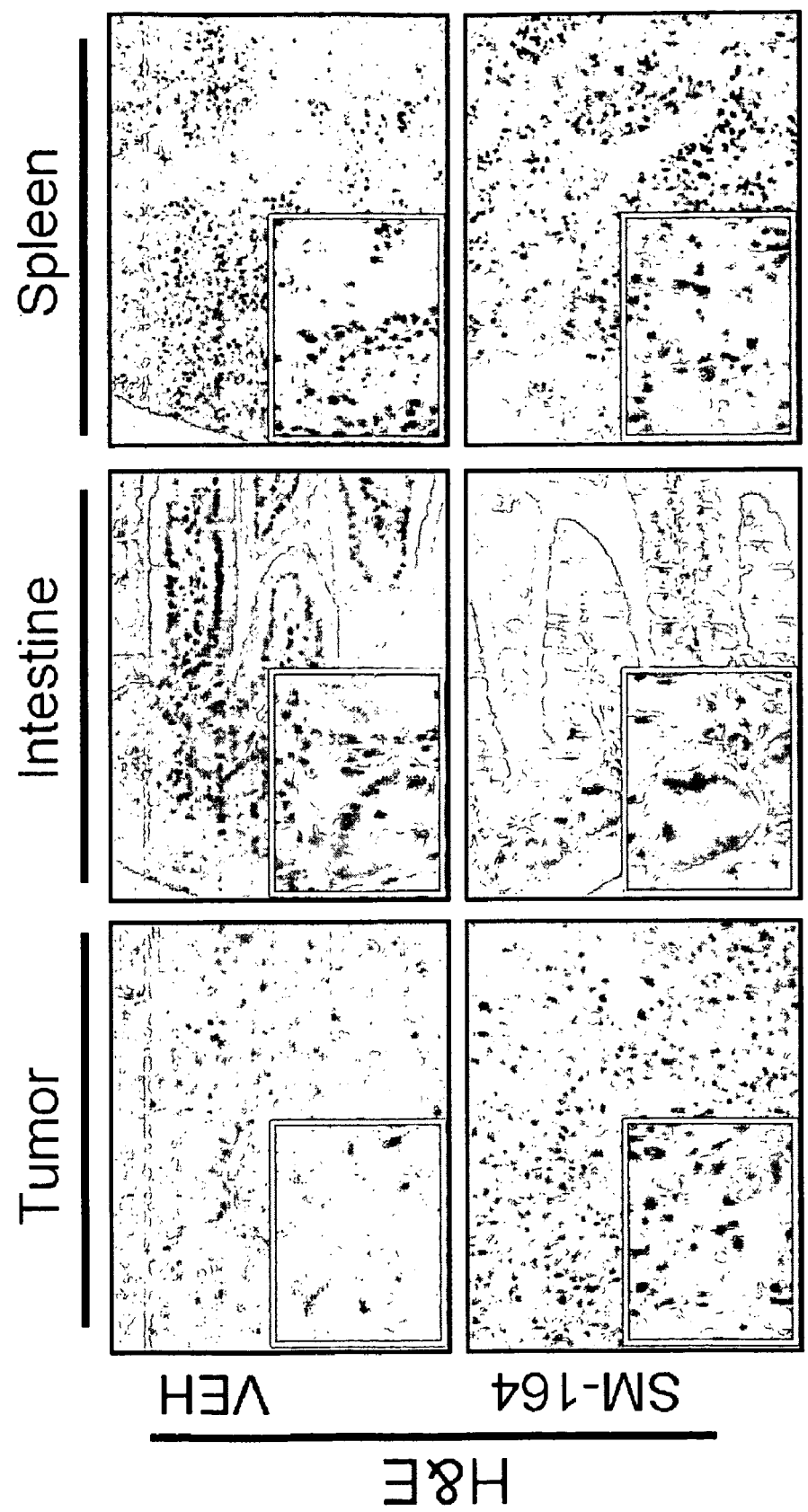
FIG. 47 is a series of six images showing Smac mimetic SM-164 causes damage to xenograft tumor tissues but no effect on normal tissues in mice as measured by H&E staining.
Figure 48:
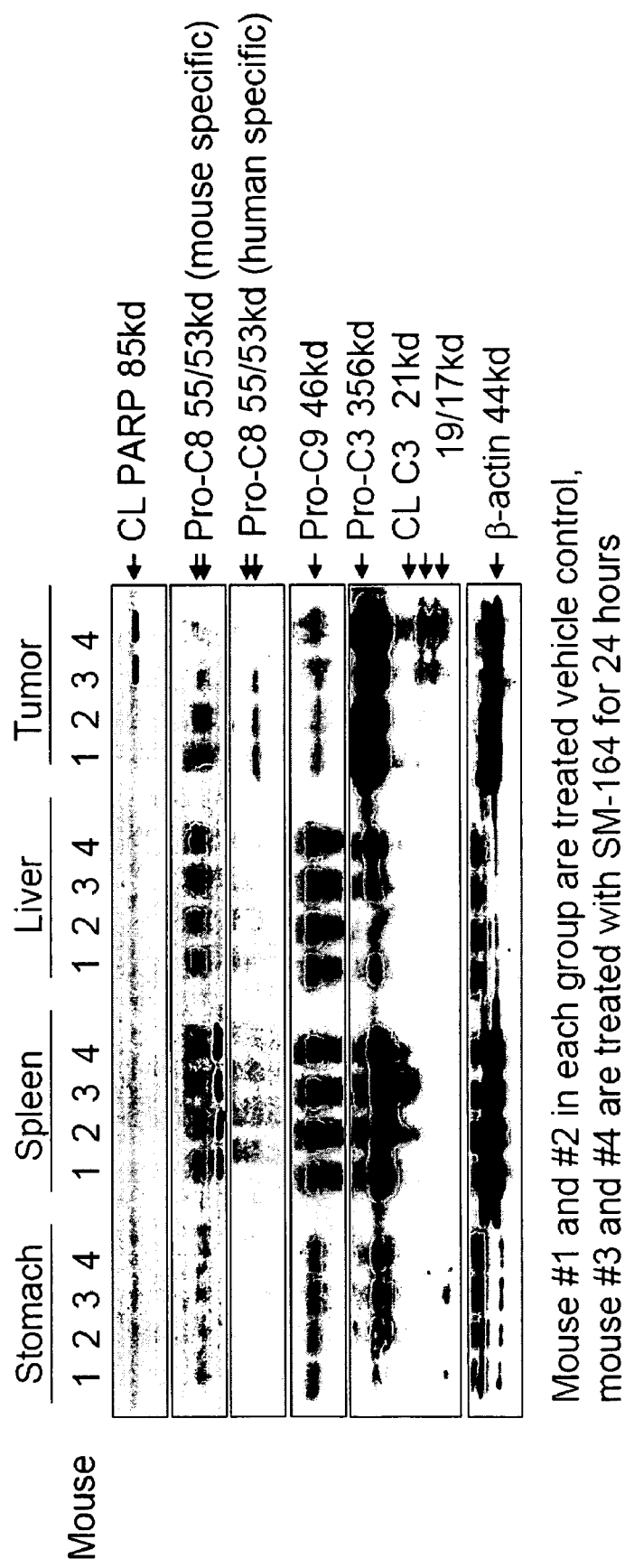
FIG. 48 is a series of six images showing Smac mimetic SM-164 has no effect on normal tissues in mice.
Figure 49:
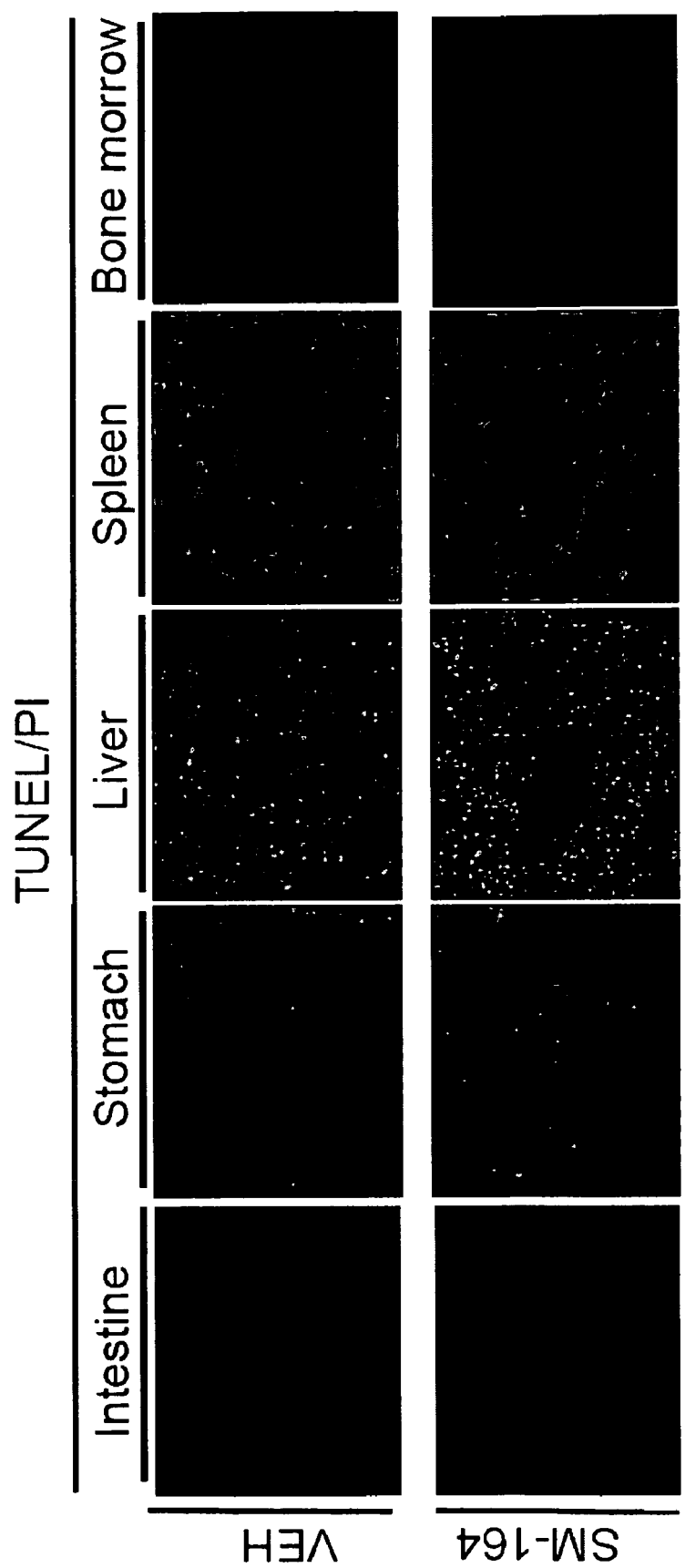
FIG. 49 is a series of ten images showing Smac mimetic SM-164 has no effect on normal tissues in mice.

To further investigate its therapeutic potential and in vivo mechanism, SM-164 was evaluated in the MDA-MB-231 xenograft model in mice. SM-164 induced rapid cIAP-1 degradation and apoptosis in the MDA-MB-231 xenograft tumor tissues (FIG. 45). A single dose of SM-164 at 5 mg/kg decreased the level of cIAP-1 protein within 1 h and the effect lasted for at least 24 h. Robust activation of caspase-8, -9, and -3 and cleavage of PARP were observed at the 3 h time point, and persisted for 24 h. Apoptosis was examined by TUNEL staining using the In situ Cell Death Detection Kit (Roche Applied Science). To determine apoptosis in xenograft tumor and normal mouse tissues, severe combined immunodeficient (SCID) mice bearing established tumor were treated with Smac mimetics. Tissues were harvested and TUNEL staining was performed on formaldehyde-fixed, paraffin-embedded tissues. Paraffin-embedded tissue sections, mounted on slides, were deparaffinized and rehydrated by washing in a descending series of alcohol solutions (100%, 95%, 70% and 50%) and PBS. Antigen retrieval was performed by the microwave oven method using a commercially available antigen retrieval buffer (Covance Research Products, Inc.). Tissue sections were blocked with 3% BSA and 20% normal bovine serum in PBS for 30 min at room temperature (RT) to block unspecific binding sites. Tissue sections were incubated in 100 µl of TUNEL mixture [TUNEL mixture=10 µl of Enzyme solution (Vial 1)+90 µl of Label solution (Vial 2)] for 60 min at RT. Tissue section incubated in 90 µl of Label solution (Vial 2), instead of TUNEL mixture was used as negative control. Tissue section preincubated in DNase I recombination in 3000 U/ml of PBS, 1 mg/ml BSA for 10 min RT, followed by incubation with TUNEL mixture was used as positive control. Tissues slides were rinsed with PBS 5 min ×3, and stained with Propidium iodide and mounted and observed under a fluorescent microscope. The TUNEL assay shows that SM-164 induces strong apoptosis in tumor tissues as early as the 3 h time point, and more than 50% of tumor cells are TUNEL positive at the 6 h time point (FIG. 46), consistent with the strong caspase processing and PARP cleavage at this time point (FIG. 45). The strong apoptosis induction by SM-164 was still evident at the 24 h time point. Hematoxylin and eosin (H&E) staining shows that SM-164 causes profound damage to tumor tissues (FIG. 47). In contrast to the strong apoptosis induction and damage in xenograft tumor tissues, SM-164 has no effect on all the normal mouse tissues examined, including highly proliferative tissues such as the small intestine, stomach, liver and spleen (FIGS. 47-49).

Using the MDA-MB-231 xenograft model, SM-122 was also examined for its ability to induce cIAP-1 degradation and apoptosis in tumor tissues in vivo. Administration of a single dose of SM-122 at 100 mg/kg iv, a near maximum tolerated dose, effectively induces cIAP-1 degradation in tumor tissues but has minimal effect on PARP cleavage. Hence, these in vivo data further indicate that cIAP-1 degradation is not sufficient for apoptosis induction.

Figure 50:
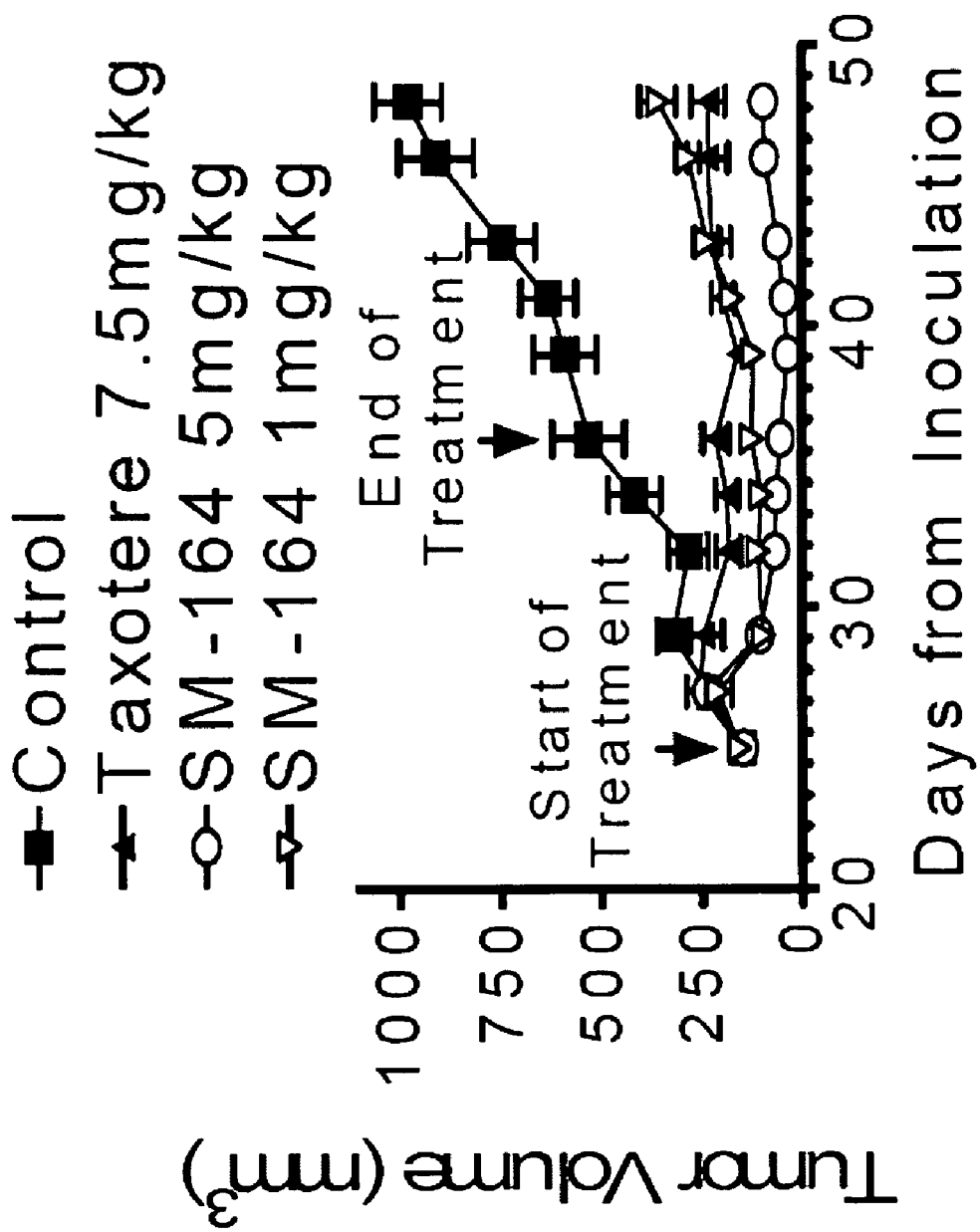
FIG. 50 is a line graph showing inhibition of tumor growth by Smac mimetic SM-164 in the MDA-MB-231 xenograft model in mice.
Figure 51:
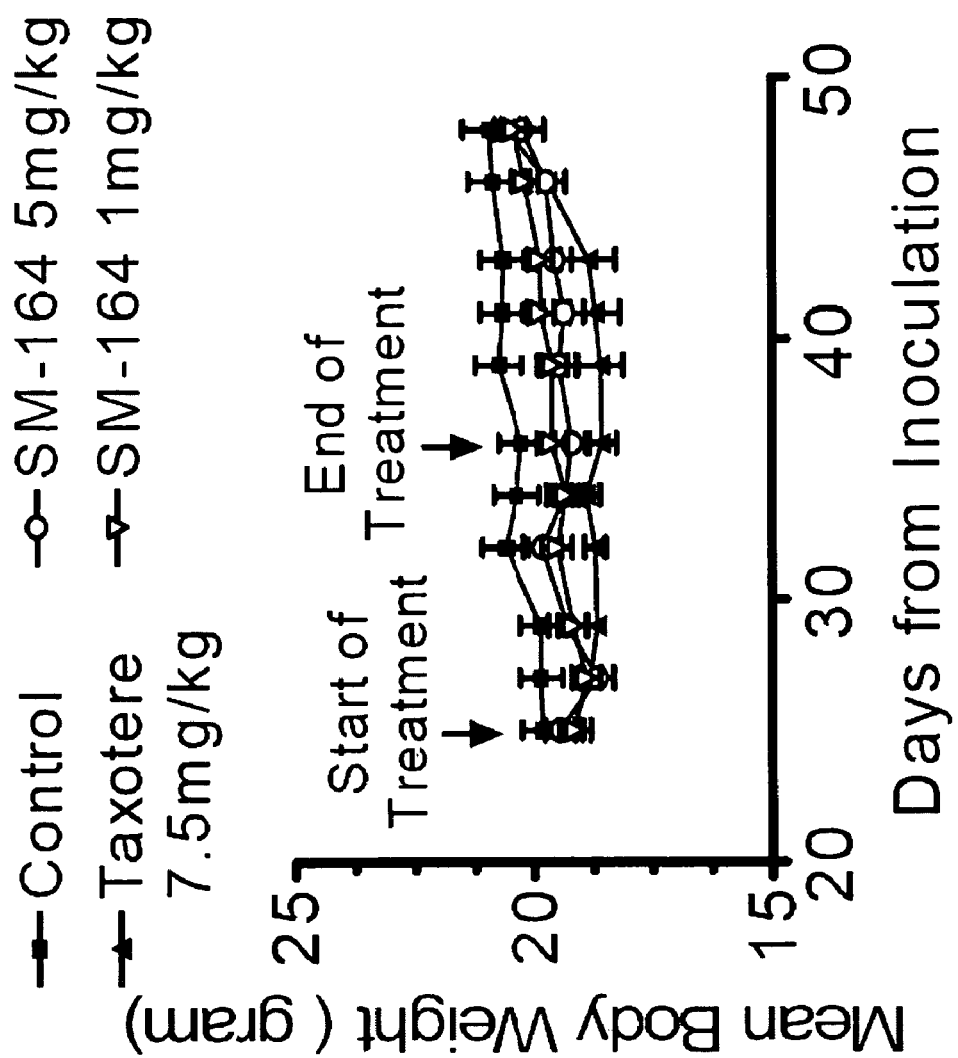
FIG. 51 is a line graph showing weight loss of mice treated with Smac mimetic SM-164.

SM-164 was evaluated for its ability to inhibit tumor growth. Consistent with its potent activity in apoptosis induction in xenograft tumor tissues, SM-164 is highly effective in inhibition of tumor growth and capable of achieving tumor regression in the MDA-MB-231 xenograft model (FIG. 50). Treatment with SM-164 at 1 mg/kg completely inhibits tumor growth during the treatment. Treatment with SM-164 at 5 mg/kg reduces the tumor volume from 147±54 mm³ at the beginning of the treatment (day 25) to 54±32 mm³ at the end of the treatment (day 36), a reduction of 65%. The strong antitumor activity by SM-164 is long lasting and not transient. Importantly, no significant weight loss or other sign of toxicity is observed for mice treated with SM-164 at 1 or 5 mg/kg (FIG. 51). Treatment with taxotere (TXT) at 7.5 mg/kg is effective in inhibition of tumor growth, as compared to the control treatment, but failed to achieve tumor regression. SM-164 at 5 mg/kg is statistically more effective than TXT at the end of the treatment (p<0.01) or when the tumor size in the control group reached 750 mm³ (p<0.02). Taken together, these data show that SM-164 has strong in vivo antitumor activity at non-toxic dose-schedules.

In summary, cIAP-1/2 and XIAP are crucial and independent blockades that need to be concurrently removed by Smac mimetics for efficient TNFα-dependent apoptosis to proceed. By concurrently targeting cIAP-1/2 and XIAP, SM-164 is an effective inducer of apoptosis in vitro and in vivo. Furthermore, SM-164 is selectively toxic to tumor cells versus normal cells in vitro and to tumor tissues versus normal tissues in vivo.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. The compound having formula XIII:

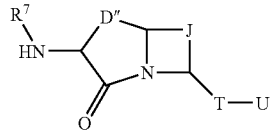

XIII wherein:

D" is $(CR^1R^2)_n$—$R^{5c}$—$(CR^3R^4)_m$;

J is selected from the group consisting of optionally substituted alkylenyl and $(CR^1R^2)_p$—$R^{5b}$—$(CR^3R^4)_q$;

T is selected from the group consisting of C=O, C=S, C=NR¹, S, O, NR¹, CR¹R², optionally substituted carbocyclic, optionally substituted heterocyclic, optionally substituted aryl and optionally substituted heteroaryl;

U is selected from the group consisting of hydrogen, NR¹R², OR¹, SR¹, optionally substituted alkyl and optionally substituted aryl;

n, m, p and q are independently selected from 0-5;

each R¹, R², R³ and R⁴ are independently selected from the group consisting of hydrogen, optionally substituted alkyl, optionally substituted carbocyclic, optionally substituted heterocyclic, optionally substituted aryl and optionally substituted heteroaryl;

$R^{5c}$ is selected from the group consisting of NR¹, NCOR⁸ and NCO₂R⁸;

$R^{1a}$ and $R^{2a}$ are independently selected from the group consisting of hydrogen, hydroxy, azido, optionally substituted alkyl, optionally substituted carbocyclic, optionally substituted heterocyclic, optionally substituted aryl and optionally substituted heteroaryl;

$R^{5b}$ is selected from the group consisting of O, S, NR¹, CR¹R², C=O, C=S and C=NR¹;

R⁷ is selected from the group consisting of hydrogen, CO₂R$^{7a}$ and COCH(R$^{7b}$)N(R$^{7c}$)CO₂R$^{2a}$;

R$^{7a}$ is selected from the group consisting of optionally substituted alkyl, optionally substituted carbocyclic, optionally substituted heterocyclic, optionally substituted aryl and optionally substituted heteroaryl;

R$^{7b}$ is optionally substituted C₁₋₃ alkyl;

R$^{7c}$ is selected from the group consisting of hydrogen and optionally substituted alkyl;

and,

R⁸ is selected from the group consisting of optionally substituted alkyl, optionally substituted carbocyclic, optionally substituted heterocyclic, optionally substituted aryl and optionally substituted heteroaryl.

2. The compound of claim 1, wherein R$^{7a}$ is t-butyl.

3. The compound of claim 1, wherein n is 1, m is 2, $R^{5c}$ is NCO₂R⁸ and R⁸ is benzyl.

4. The compound of claim 1, selected from the group consisting of:

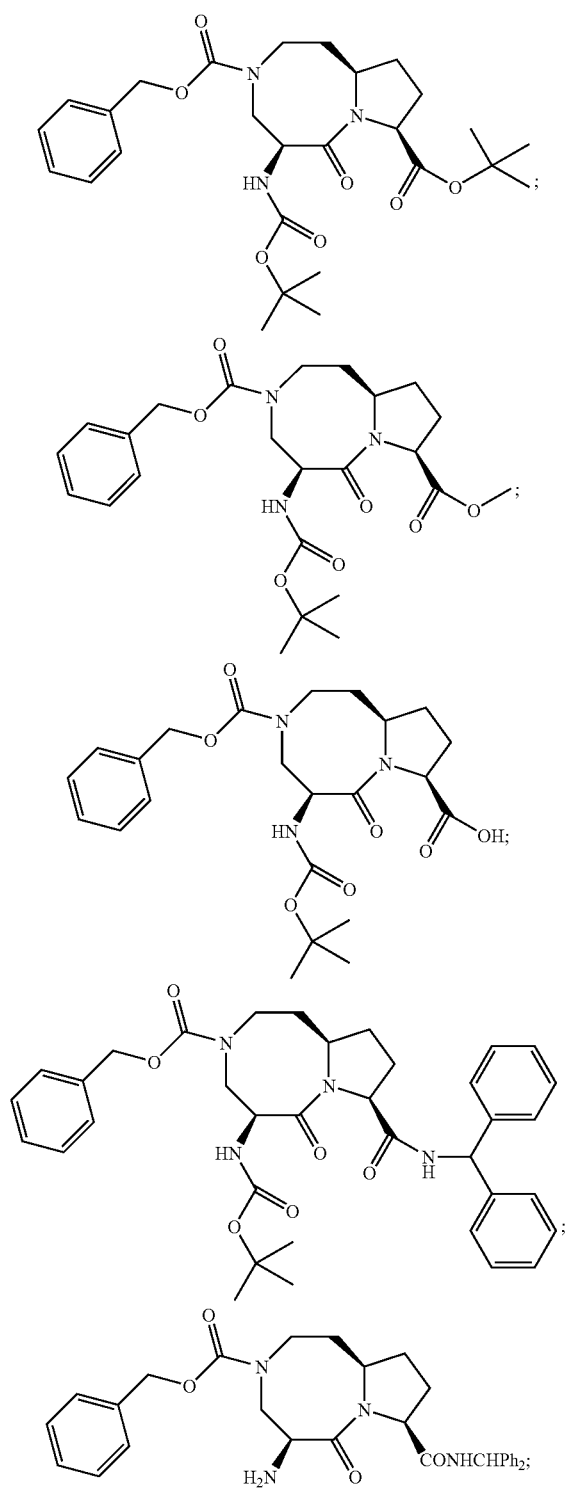
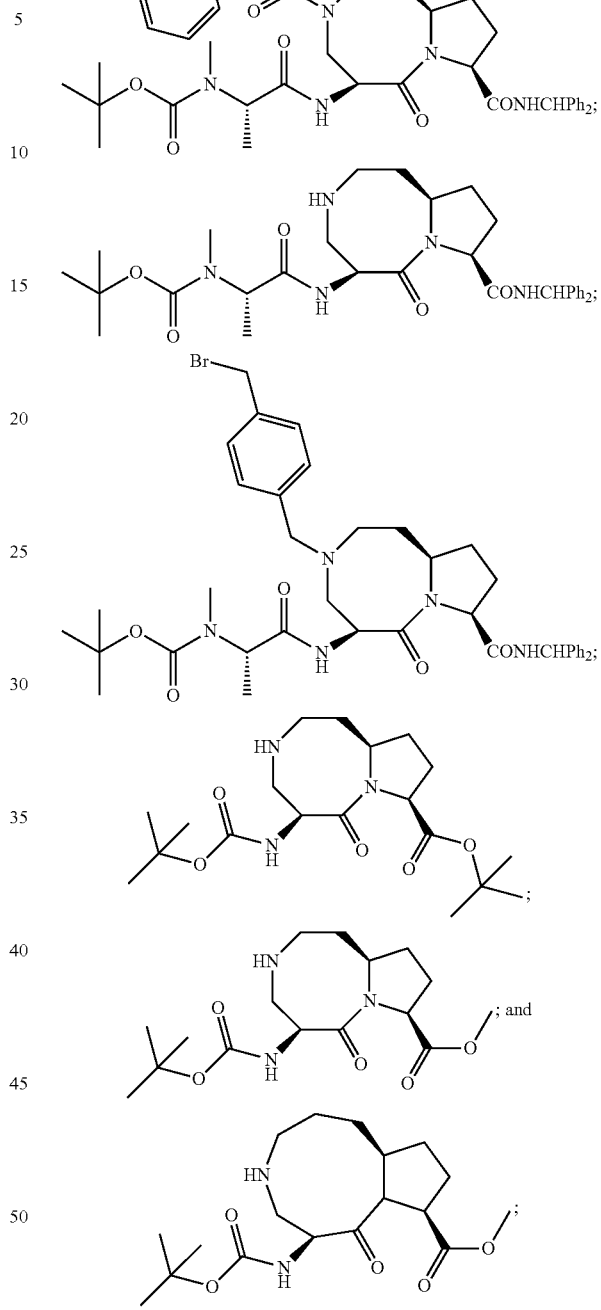

UNITED STATES PATENT AND TRADEMARK OFFICE
CERTIFICATE OF CORRECTION

PATENT NO. : 8,202,902 B2
APPLICATION NO. : 12/270374
DATED : June 19, 2012
INVENTOR(S) : Shaomeng Wang et al.

It is certified that error appears in the above-identified patent and that said Letters Patent is hereby corrected as shown below:

Column 138, lines 47-48 should read:

--$R^7$ is selected from the group consisting of hydrogen, $CO_2R^{7a}$ and $COCH(R^{7b})N(R^{7c})CO_2R^{7a}$;--

Column 140, lines 47-54 should read:

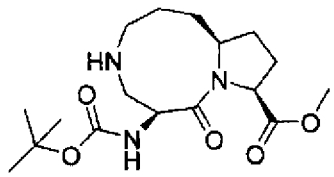

--                                   --

Signed and Sealed this
Thirty-first Day of July, 2012

David J. Kappos
*Director of the United States Patent and Trademark Office*